(12) United States Patent
Anderson et al.

(10) Patent No.: US 8,088,574 B2
(45) Date of Patent: Jan. 3, 2012

(54) POLY(A) POLYMERASE

(75) Inventors: Richard A. Anderson, Cross Plains, WI (US); Michael L. Gonzales, Davis, CA (US); David L. Mellman, Madison, WI (US); Chunhua Song, Madison, WI (US); Christy Ann Barlow, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 331 days.

(21) Appl. No.: 12/182,922

(22) Filed: Jul. 30, 2008

(65) Prior Publication Data

US 2009/0263375 A1     Oct. 22, 2009

Related U.S. Application Data

(60) Provisional application No. 60/953,116, filed on Jul. 31, 2007, provisional application No. 61/030,169, filed on Feb. 20, 2008.

(51) Int. Cl.
*C12Q 1/68*     (2006.01)
*C07K 14/00*     (2006.01)

(52) U.S. Cl. ............................................. 435/6; 530/350
(58) Field of Classification Search ....... 435/6; 530/350
See application file for complete search history.

(56) References Cited

U.S. PATENT DOCUMENTS

2003/0083272 A1 *   5/2003   Wiederholt et al. ............. 514/44

FOREIGN PATENT DOCUMENTS

WO     WO 03009814 A2 *   2/2003

OTHER PUBLICATIONS

Johnson, EE. et al. Gene silencing reveals a specific function of hVps34 phosphatidylinosito 3-kinase in late versus early endosomes. J. Cell Science, vol. 119, pp. 1219-1232, 2006.*

Alam et al., "How Many Transcription Factors Does It take to Turn on the Heme Oxygenase-1 Gene?", *Am J Respir Cell Mol Biol*, vol. 36, 2007 (pp. 166-174).

Dong et al., "Heme Oxygenase-1 in Tissue Pathology", *American Journal of Pathology*, vol. 156, No. 5, May 2000 (pp. 1485-1488).

Gilbert et al., "Elongator Interactions with Nascent mRNA Revealed by RNA Immunoprecipitation", *Molecular Cell*, vol. 14, May 21, 2004 (pp. 457-464).

James et al., "Genomic Libraries and a Host Strain Designed for Highly Efficient Two-Hybrid Selection in Yeast", *Genetics*, vol. 144, Dec. 1996 (pp. 1425-1436).

Kyriakopoulou et al., "A Novel Nuclear Human Poly(A) Polymerase (PAP), PAPγ", *The Journal of Biological Chemistry*, vol. 276, No. 36, Sep. 7, 2001 (pp. 33504-33511).

Stevenson et al., "The Cid I family of non-canonical poly(A) polymerases", *Yeast*, vol. 23, 2006 (pp. 991-1000).

Trippe et al., "Identification, cloning, and functional analysis of the human U6 snRNA-specific terminal uridylyl transferease", *RNA*, vol. 12, 2006 (pp. 1494-1504).

Sixth Annual MCP Research Training Symposium, University of Wisconsin—Madison, Oct. 3, 2006, select abstracts, 10 pgs.

Mellman et al., "Star-PAP is a Non-Canonical Poly(A) Polymerase that Functions in a Nuclear Phosphoinositide Signalling Pathway with PIPKIa for the Efficient 3'-End Formation of Select mRNAs", poster as presented for the 6th Annual MCP Research Training Symposium, University of Wisconsin-Madison, Oct. 3, 2006, 10 pgs.

Mellman et al., "A Novel Phosphatidylinositol 4,5-Bisphosphate Regulated Poly(A) Polymerase is Required for Efficient 3' Processing of Select mRNA", power point presentation as presented by David L. Mellman to the RNA society in May 2007, 30 pgs.

* cited by examiner

*Primary Examiner* — Prabha Chunduru
(74) *Attorney, Agent, or Firm* — Foley & Lardner LLP

(57) ABSTRACT

The present invention relates to novel poly(A) polymerases and their use in the treatment of diseases, disorders and conditions. More specifically, the poly(A) polymerases of the present invention include polymerases which are directly modulated by components of the phosphoinositide signaling pathway. Such components may include phosphatidylinositol phosphate kinases and phosphoinositide second messengers.

4 Claims, 69 Drawing Sheets

FIGURE 3

GSX₁₀DxD

| | | | |
|---|---|---|---|
| hGld2 | SRLFLVGS | SLNGFGTRSSDGD | -LCLVVK |
| STAR-PAP | CVVHPFGS | SINSFDVHGCDLD | -LFLDLG |
| PAPα | GKIFTFGS | YRLGVHTKGADIDA | LCVAPR |
| Cid13 | IKTSLFGS | TQSLLASNASDID | -LCIITD |
| Trf4p | ADLHVFGS | FATDLYLPGSDID | --CVVNS |
|  |  | * | * |

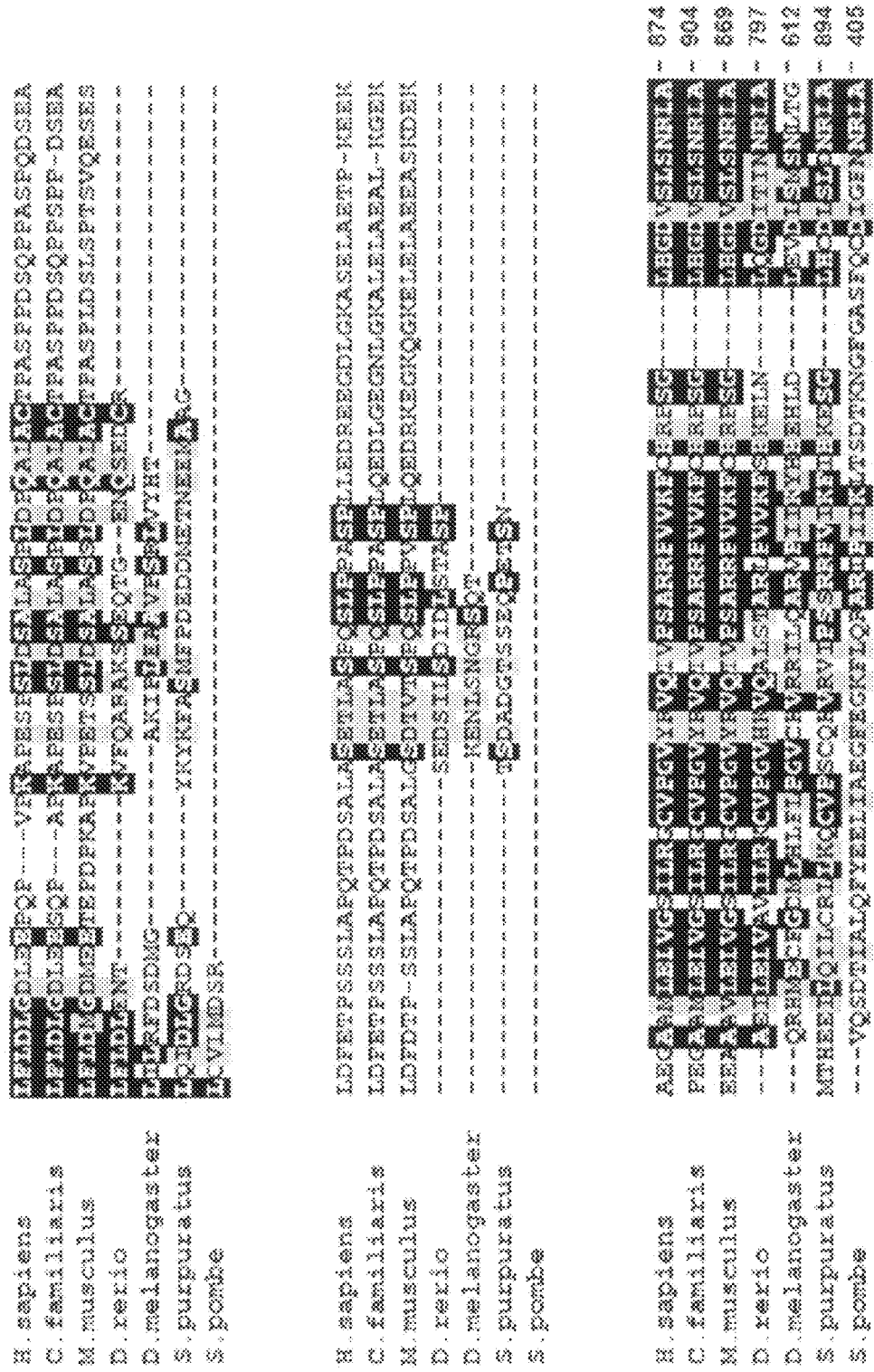

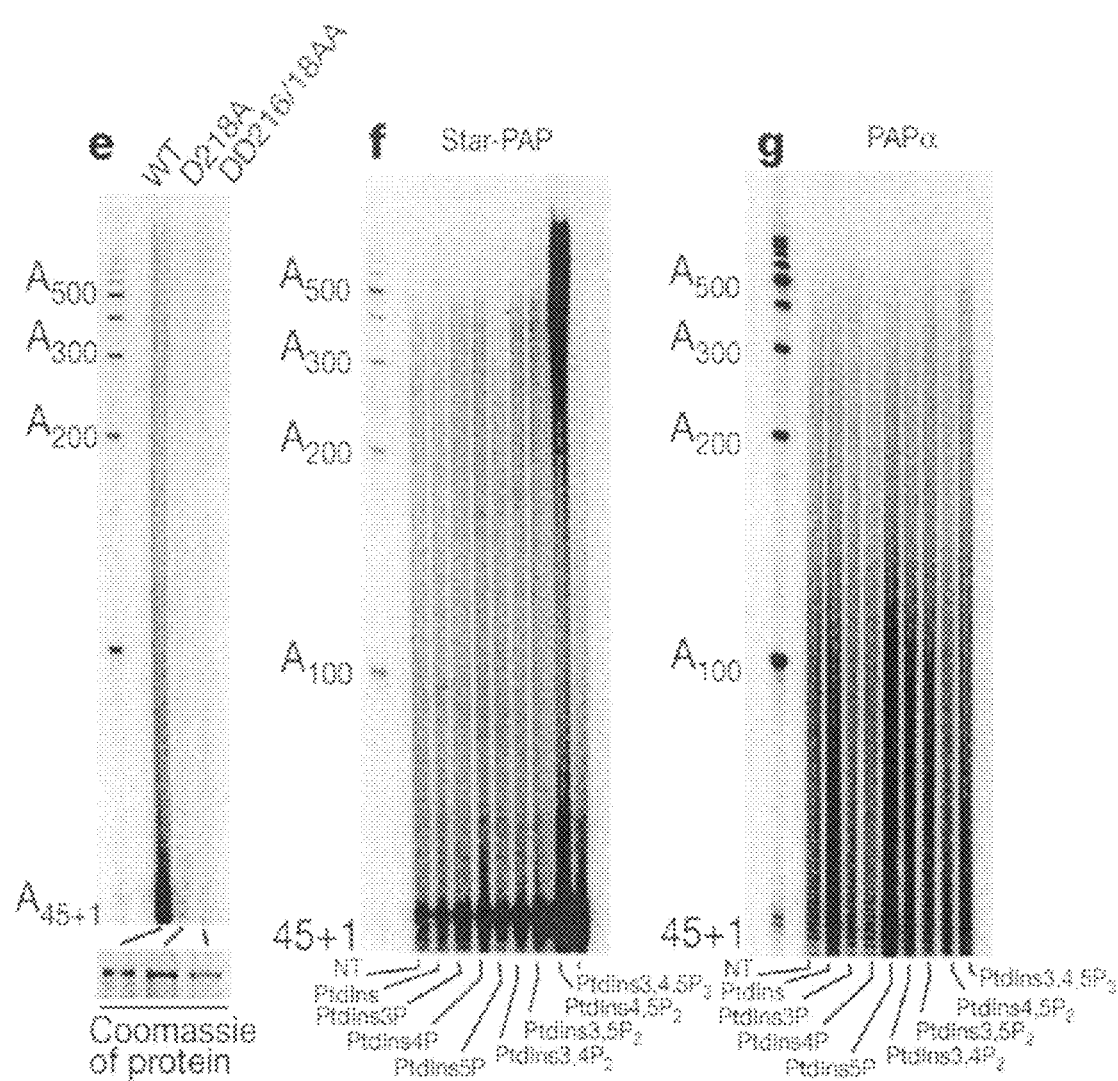
FIGURE 8 con't.

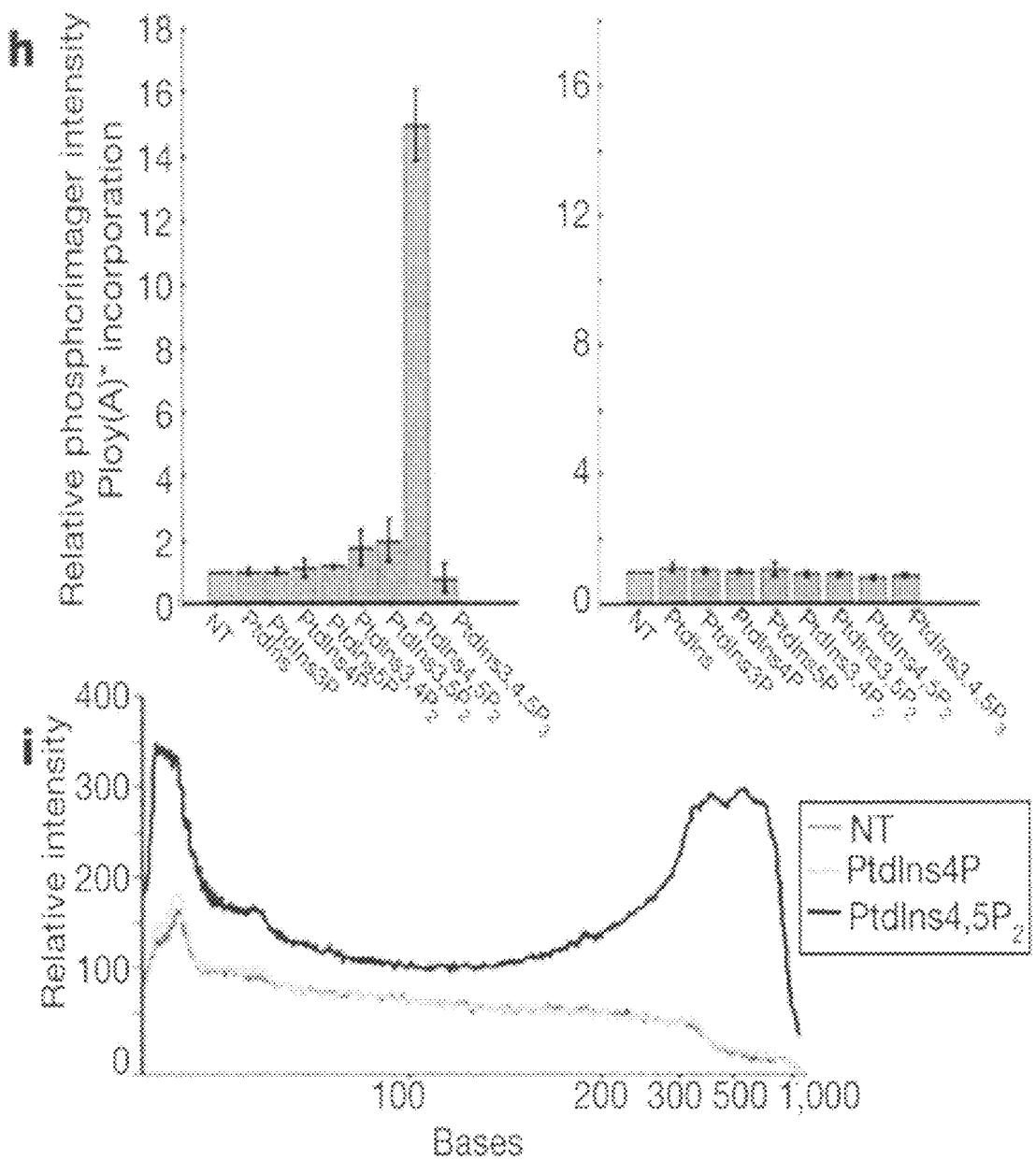
FIGURE 8 con't.

FIGURE 10

Table 1

| probe ID | gene ID | cell processes/functions | fold | gene name |
|---|---|---|---|---|
| 203665_at | NM_002133.1 | heme metabolism | -5.8 | heme oxygenase (decycling) 1 (HMOX1) |
| 219270_at | NM_024111.1 | cation transport | -5.8 | cation transport regulator-like1 (CHAC1) |
| 204035_at | NM_003469.2 | protein secretion | -4.7 | secretogranin II (chromogranin C) (SCG2) |
| 203952_at | NM_007348.1 | regulation of transcription | -4.5 | activating transcription factor 6 (ATF6) |
| 232689_at | FLJ13747 | hypothetical protein | -4.0 | hypothetical protein LOC284561 |
| 205047_s_at | NM_001673.1 | asparagine biosynthesis | -3.7 | asparagine synthetase (ASNS) |
| 233737_s_at | AK023548.1 | hypothetical protein | -3.4 | hypothetical protein LOC284561 |
| 206103_at | NM_005052.1 | small GTPase / signal transduction | -3.3 | ras-related C3 botulinum toxin substrate 3 (Rac3) |
| 223666_at | BC002724.1 | transport/ signal transduction | -3.3 | Sorting nexin 5 |
| 209230_s_at | AF135266.1 | apoptosis/ cell growth | -3.2 | p8 protein homolog (COM1) |
| 235640_at | AI763196 | unkown | -3.0 | Transcribed locus |
| 231840_x_at | NM_003426.1 | hypothetical protein | -2.8 | hypothetical protein LOC90624 |
| 205881_at | NM_003426.1 | regulation of transcription, | -2.8 | zinc finger protein 74 (Cos52) |
| 235579_at | AA679858 | unkown | -2.6 | unknown |
| 236738_at | AW057589 | unkown | -2.7 | Similar to LOC166075 |
| 203438_at | AF031036.1 | signal transduction in response to nutrient | -2.6 | stanniocalcin 2 (STC2) |
| 203439_s_at | AF055460.1 | signal transduction in response to nutrient | -2.2 | stanniocalcin 2 (STC2) |
| 229758_at | AW168771 | regulation of transcription | -2.5 | tigger transposable element derived 5 |
| 1555788_a_at | AF250311.1 | transcription corepressor | -2.6 | SKIP3 |
| 231269_at | AU153330 | regulation of transcription | -2.6 | activating signal cointegrator 1 complex subunit 3 (ASCC3) |
| 205156_s_at | U78180.1 | ion transport (Na, Ca) | -2.4 | amiloride-sensitive cation channel 2, neuronal (ACCN2) |
| 208712_at | M73554.1 | regulation of cell cycle progress | -2.5 | cyclin D1 (CCND1) |
| 218772_x_at | FLJ10493 | unknown function | -2.5 | transmembrane protein 38B (TMEM38B) |
| 202131_s_at | NM_003831.1 | chromosome segregation | -2.4 | RIO kinase 3 (RIOK3) |
| 218145_at | NM_021158.1 | regulation of transcription, | -2.5 | tribbles homolog 3 (Drosophila) (TRIB3) |
| 217127_at | AL354872 | amino acid biosynthesis | -2.5 | cystathionase (cystathionine gamma-lyase) (CTH) |
| 202319_at | NM_015571.1 | proteolysis/ubiquitin cycle | -2.3 | SUMO-1-specific protease |
| 235762_at | AI458566 | sensory perception of taste | -2.5 | taste receptor, type 2, member 14 |
| 225767_at | AI825833 | unknown | -2.4 | PIHUB6 salivary proline-rich protein precursor PRB1 |
| 236273_at | AW269499 | unknown | -2.4 | neuroblastoma breakpoint family, member 1 |
| 1554020_at | BC010091.1 | RNA processing | -2.4 | Bicaudal D (Drosophila) homolog 1 |
| 232160_s_at | AL137262.1 | protein modification/ubiquitin cycle | -2.4 | TNFAIP3 interacting protein 2 |

FIGURE 10 (cont.)

Table 2

| probe ID | gene ID | cell processes/functions | fold | gene name |
|---|---|---|---|---|
| 218340_s_at | FLJ10808 | transcription regulation | -2.3 | ubiquitin-activating enzyme E1-like 2 (UBEIL2) |
| 207219_at | LOC65243 | regulation of transcription | -2.4 | zinc finger protein 643 (ZNF643) |
| 231367_s_at | AW300131 | hypothetical protein | -2.3 | hypothetical protein LOC647131 |
| 225446_at | AI638279 | unknown function | -2.3 | bromodomain and WD repeat domain containing 1 |
| 213283_s_at | BG285616 | regulation of transcription, | -2.4 | sal (Drosophila)-like 2 (SALL2) |
| 220892_s_at | NM_021154.1 | L-serine biosynthesis | -2.4 | phosphoserine aminotransferase1 (PSAT1) |
| 236219_at | AI452512 | unknown | -2.3 | EST clone |
| 214453_s_at | NM_006417.1 | immune response | -2.1 | interferon-induced protein 44 (IFI44) |
| 242224_at | R40111 | unknown function | -2.2 | G patch domain containing 2 |
| 244531_at | BE501279 | electron transport/proton transport | -2.4 | Nicotinamide nucleotide transhydrogenase |
| 228106_at | FLJ11752 | unknown | -2.3 | tropomyosin1, non-muscle isoform |
| 222735_at | FLJ10493 | unknown | -2.3 | transmembrane protein 38B (TMEM38B), |
| 1557192_at | FLJ25311 | hypothetical protein | -2.3 | chromosome 1 open reading frame 136 (C1orf136) |
| 235760_at | AI421972 | unknown | -2.3 | NSD1 protein (M.musculus) |
| 217966_s_at | AF288391.1 | transport | -2.3 | chromosome 1 open reading frame 24 (C1 or F24) |
| 225864_at | AL039862 | unknown function | -2.4 | family with sequence similarity 84, member B |
| 203926_x_at | NM_001687.1 | ion transport ATP synthesis | -2.2 | ATP synthase/H+ transporting/mitochondrial F1 complex,D |
| 228980_at | NM_001017368 | ubiquitin cycle, apoptosis | -2.2 | ring finger and FYVE-like domain containing 1 (RFFL) |
| 235443_at | BG284827 | generation of precursor | -2.2 | Creatine kinase, mitochondrial 2 (sarcomeric) |
| 224786_at | AL133580.1 | unknown function | -2.2 | short coiled-coil protein |
| 235736_at | BF000047 | unknown mRNA | -2.2 | Homo sapiens, clone IMAGE:5167600, |
| 242996_at | AI341686 | protein biosynthesis/regulation of translation | -2.1 | mitochondrial peptide chain release factor 1 precursor |
| 223453_s_at | BC005096.1 | immune response | -2.1 | DKFZP564J0863 protein |
| 208713_at | NM_007040.1 | RNA processing response to virus | -2.2 | heterogeneous nuclear ribonucleoprotein U-like 1(HNRPUL1) |
| 216713_at | AL049325.1 | small GTPase mediated signal transduction | -2.2 | ankyrin repeat containing (KRIT1) |
| 229865_at | AW058617 | unknown function | -2.2 | fibronectin type III domain containing 3B |
| 229371_at | BF940010 | transport, phosphate transport | -2.2 | Solute carrier family 20 (phosphate transporter), member 2 |
| 226269_at | BF002104 | neurite differentiation/signal transduction | -2.2 | Ganglioside-induced differentiation-associated protein 1 |
| 241946_at | BF184089 | unknown function | -2.2 | zinc finger, DHHC-type containing 21 (ZDHHC21) |

FIGURE 10 (cont.)

Table 3

| probe ID | gene ID | cell processes/functions | fold | gene name |
|---|---|---|---|---|
| 213764_s_at | AW665892 | extracellular matrix/structural constituent | 5.5 | PEG3 (paternally expressed 3) |
| 209283_at | AF007162.1 | protein folding/muscle contraction | 4.0 | crystallin, alpha B |
| 213765_at | AW665892 | extracellular matrix/structural constituent | 3.5 | PEG3 |
| 227062_at | AU155361 | noncoding RNA | 3.0 | trophoblast-derived noncoding RNA |
| 226793_at | LOC283267 | hypothetical protein | 3.5 | hypothetical protein |
| 209758_s_at | U37283.1 | extracellular matrix/structural constituent | 3.3 | microfibril-associated glycoprotein-2 MAGP-2 |
| 214247_s_at | AU148057 | electron transport/development | 3.3 | dickkopf homolog 3 (Xenopus laevis) |
| 226868_at | BF977231 | carbohydrate biosynthesis | 3.2 | glycosyltransferase 8 domain containing 3 |
| 229256_at | AV724329 | carbohydrate and glucose metabolism | 3.2 | phosphoglucomutase 2-like 1 |
| 229065_at | BF968270 | unknown | 3.2 | solute carrier family 35, member F3 |
| 211354_s_at | U52913.1 | energy reserve metabolism | 3.2 | leptin receptor |
| 225239_at | FLJ26120 | unknown function | 2.6 | CDNA FLJ26120 fis, clone SYN00419 |
| 235342_at | AI808090 | protease inhibition | 2.9 | sparc/osteonectin, cwcv and kazal-like domains proteoglycan |
| 241722_x_at | BF724558 | unknown | 2.9 | Transcribed locus |
| 209765_at | AF311317.1 | proteolysis | 2.7 | ADAM metallopeptidase domain 19 (meltrin beta) |
| 241755_at | AI961429 | electron transport/oxidative phosphorylation | 2.9 | Ubiquinol-cytochrome c reductase core protein II |
| 213075_at | AL050002.1 | unknown function | 2.8 | olfactomedin-like 2A |
| 234989_at | AV699657 | noncoding RNA | 2.3 | trophoblast-derived noncoding RNA |
| 214500_at | AF044286.1 | nucleosome assembly | 2.7 | H2A histone family, member Y |
| 209189_at | BC004490.1 | regulation of transcription | 2.5 | v-fos FBJ murine osteosarcoma viral oncogene homolog |
| 226189_at | BF513121 | cell adhesion | 2.6 | integrin, beta 8 |
| 242398_x_at | AA605121 | ion transport/ATP synthesis | 2.6 | ATP synthase/H+ transporting/mitochondrial F0 complex,B1 |
| 209031_at | AL519710 | immune response | 2.6 | immunoglobulin superfamily, member 4 |
| 227623_at | FLJ30478 | hypothetical protein | 2.5 | CDNA FLJ30478 fis, clone BRAWH1000167 |
| 229553_at | AA736452 | carbohydrate/glucose metabolism | 2.4 | phosphoglucomutase 2-like 1 |
| 235016_at | AL118571 | unknown function | 2.4 | receptor accessory protein 3 |
| 219529_at | AF102166.1 | ion transport/chloride transport | 2.4 | chloride intracellular channel 3 (CLIC3) |
| 238127_at | AI479082 | cell growth/signal transduction | 2.5 | Growth arrest-specific 6 |
| 219450_at | FLJ11017 | hypothetical protein | 2.4 | chromosome 4 open reading frame 19 |
| 226609_at | N22751 | cell adhesion | 2.4 | discoidin, CUB and LCCL domain containing 1 |
| 230722_at | AI377043 | regulation of transcription | 2.4 | Basonuclin 2 |
| 207174_at | AF001462.1 | extracellular matrix | 2.4 | glypican 5 (GPC5) |
| 235739_at | AA523939 | regulation of transcription | 2.4 | Nuclear receptor subfamily 4, group A, member 2 |

FIGURE 10 (cont.)

Table 4

| probe ID | gene ID | cell processes/functions | fold | gene name |
|---|---|---|---|---|
| 235739_at | AA523939 | regulation of transcription | 2.4 | Nuclear receptor subfamily 4, group A, member 2 |
| 214605_x_at | NM_005279.1 | G-protein coupled receptor signaling | 2.3 | G protein-coupled receptor 1 |
| 227546_x_at | FLJ20608 | regulation of mitosis/proteolysis | 2.4 | aurora kinase A interacting protein 1 |
| 206907_at | NM_003811.1 | apoptosis/ immune response | 2.3 | tumor necrosis factor (ligand) superfamily, member 9 |
| 241899_at | LOC285989 | hypothetical protein | 2.5 | hypothetical protein LOC285989 |
| 213935_at | AF007132.1 | proteolysis/aromatic compound metabolism | 2.3 | abhydrolase domain containing 5 (ABHD5) |
| 214954_at | BF977837 | cell adhesion | 2.2 | sushi domain containing 5 |
| 208747_s_at | M18767.1 | immune response/proteolysis | 2.5 | complement subcomponent C1s, alpha- and beta-chains |
| 218923_at | NM_004388.1 | carbohydrate metabolism/chitin catabolism | 2.3 | chitobiase, di-N-acetyl- |
| 232720_at | AL353746 | unknown function | 2.3 | Leucine rich repeat neuronal 6C |
| 223854_at | AF131761.1 | cell adhesion/synaptic transmission | 2.3 | protocadherin-3 (pcdh3) |
| 205792_at | AF083500.1 | cell growth/ cell adhesion | 2.3 | WNT1 inducible signaling pathway protein 2 (WISP2) |
| 212488_at | N30339 | phosphate transport/cell adhesion | 2.4 | collagen, type V, alpha 1 |
| 212489_at | AI983428 | phosphate transport/cell adhesion | 2.3 | collagen, type V, alpha 1 |
| 235904_at | AL135700 | metabolism | 2.3 | UDP glycosyltransferase 3 family, polypeptide A1 |
| 229337_at | AW274034 | ubiquitin cycle | 2.3 | ubiquitin specific peptidase 2 |
| 209483_at | AF338650.1 | cell adhesion | 2.2 | PDZ domain-containing protein AIPC (AIPC) |
| 203504_s_at | NM_005502.1 | lipid metabolism/transport | 2.3 | ATP-binding cassette, sub-family A (ABCA1) |
| 223391_at | BE880703 | unknown function | 2.2 | sphingosine-1-phosphatase |
| 201681_s_at | AB011155.1 | regulation of cell cycle/proliferation | 2.2 | discs, large (Drosophila) homolog 5 (DLG5) |
| 1553768_a_at | MGC46341 | cell adhesion | 2.2 | discoidin, CUB and LCCL domain containing 1(DCBLD1) |
| 242307_at | LOC285989 | regulation of transcription | 2.3 | hypothetical protein LOC285989 |
| 235350_at | AI935586 | hypothetical protein | 2.2 | Chromosome 4 open reading frame 19 |
| 244091_at | AI560305 | cell adhesion | 2.2 | Cadherin 13, H-cadherin (heart) |
| 231175_at | AI560305 | hypothetical protein | 2.2 | chromosome 6 open reading frame 65 |
| 204435_at | NM_014778.1 | transport | 2.2 | nucleoporin like 1(NUPL1) |
| 233506_at | FLJ21531 | unknown | 2.2 | Full length insert cDNA clone ZB81B12 |
| 227919_at | FLJ14241 | unknown function | 2.2 | UCA1 protein |
| 202903_at | AF182291.1 | nuclear mRNA splicing, mRNA processing | 2.1 | U6 snRNA-associated Sm-like protein |

FIGURE 14
A
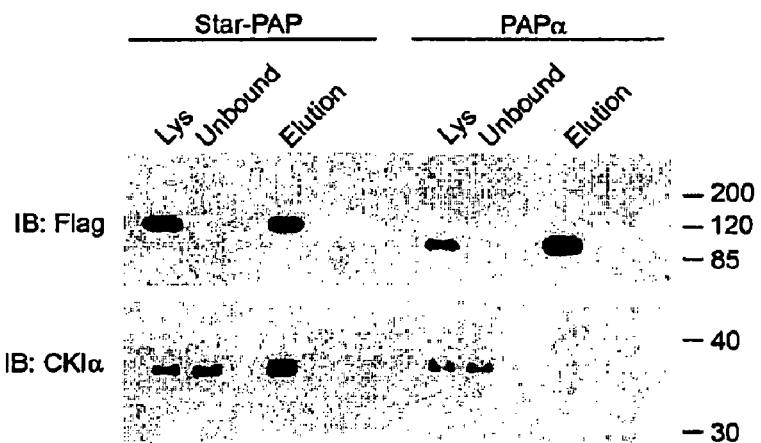
B
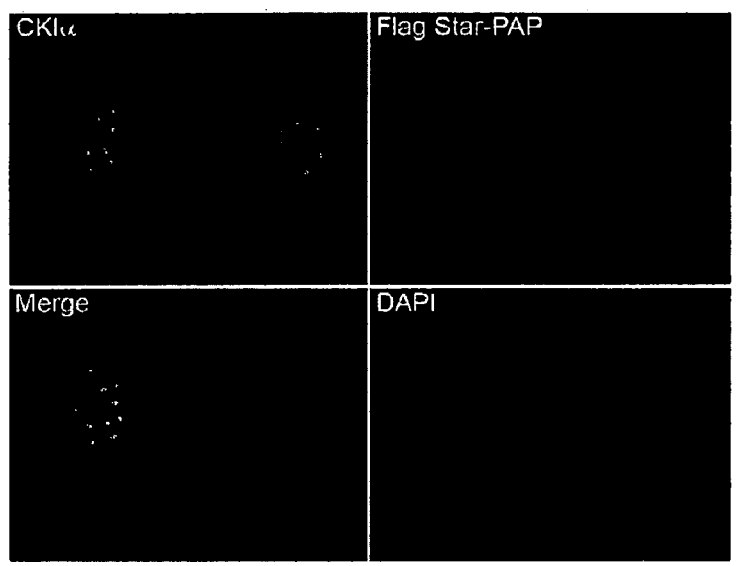
C
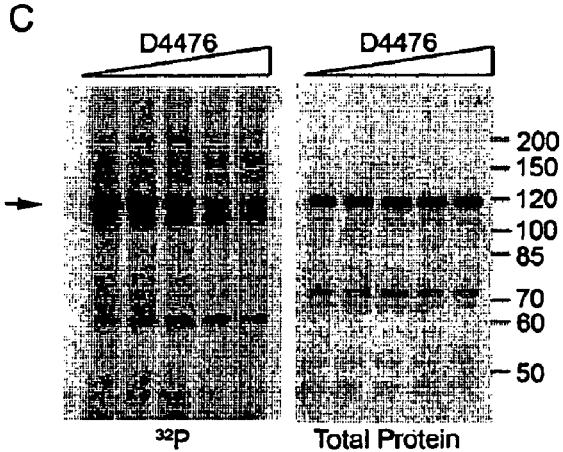
D
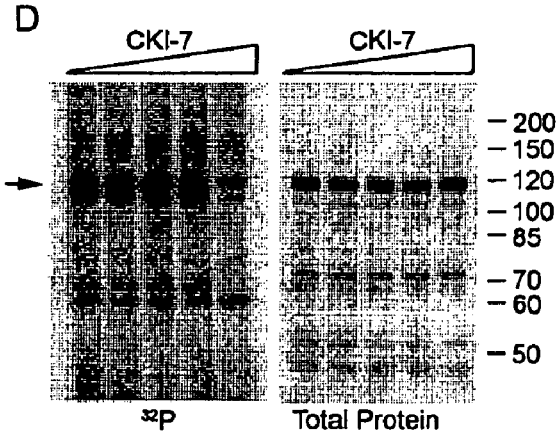

FIGURE 15
A.
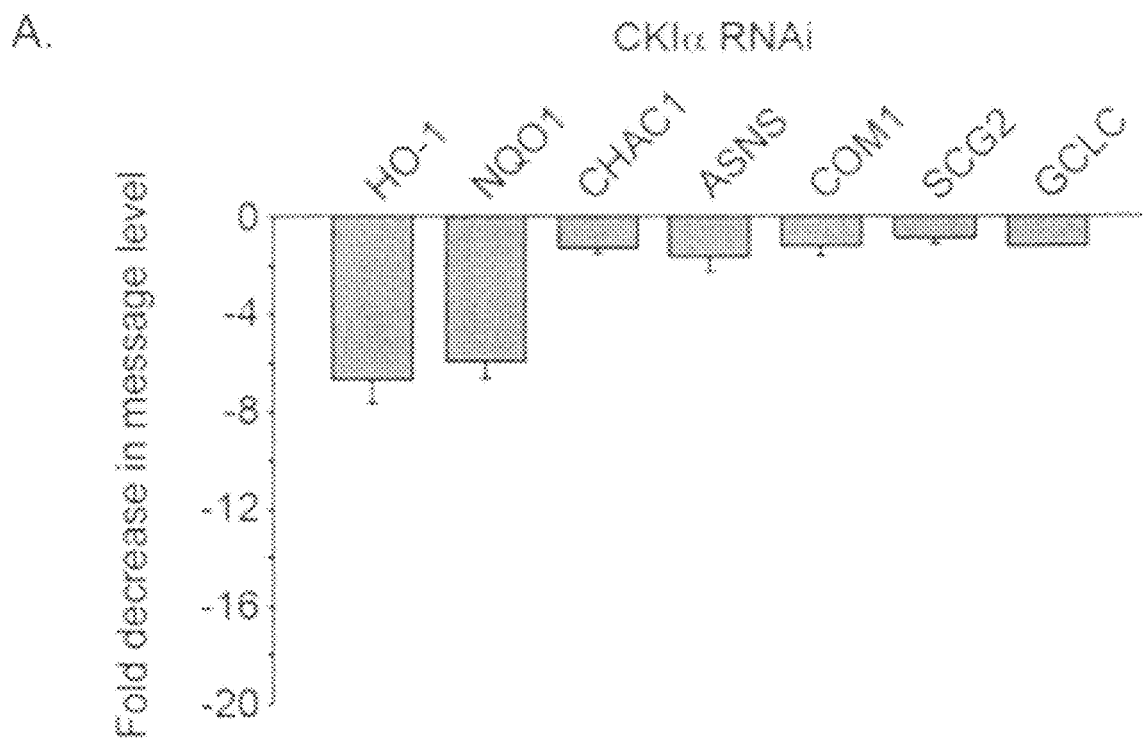
B.
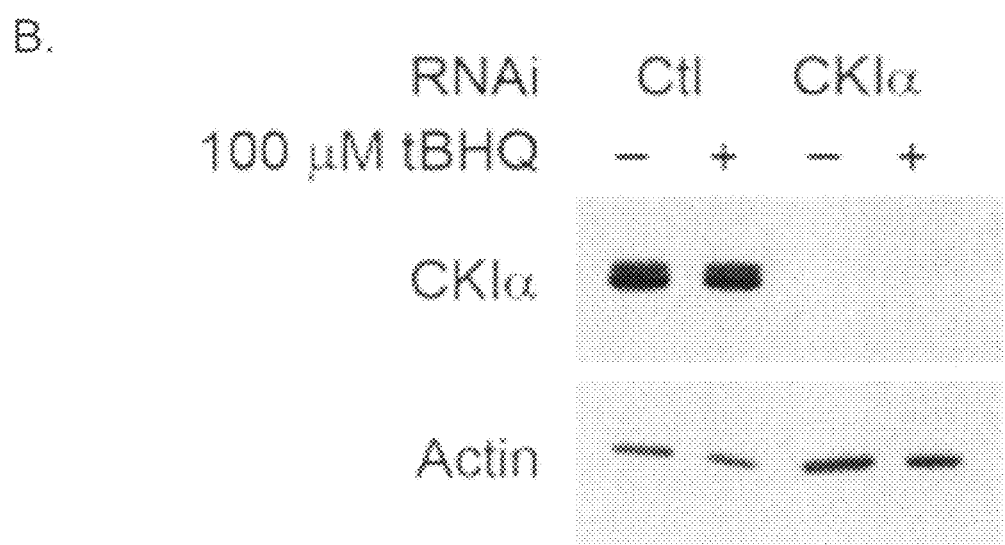

FIGURE 15 con't.
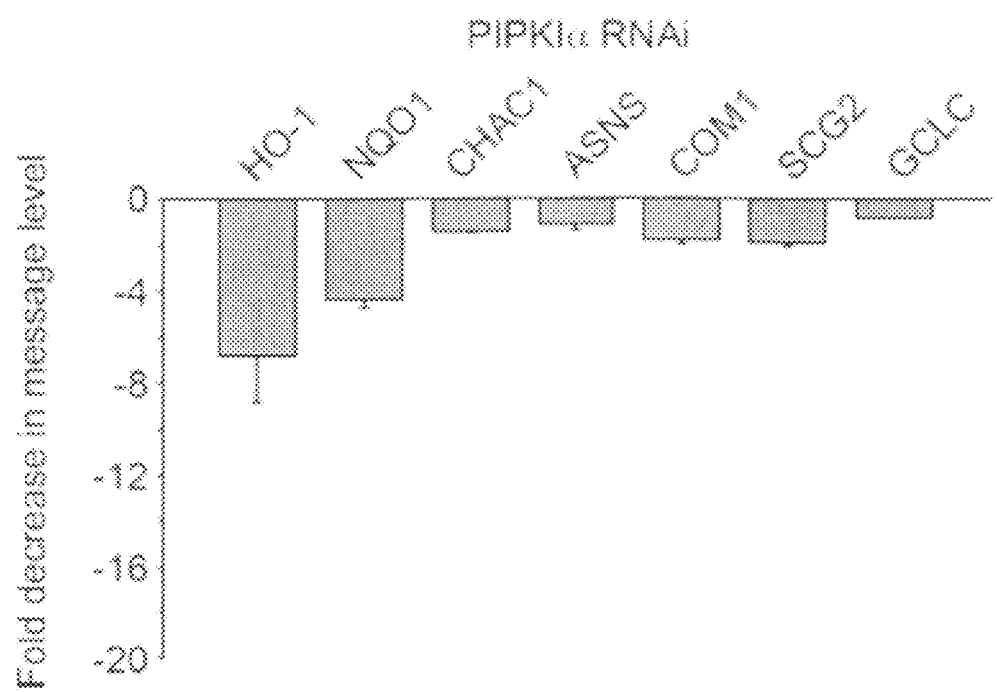
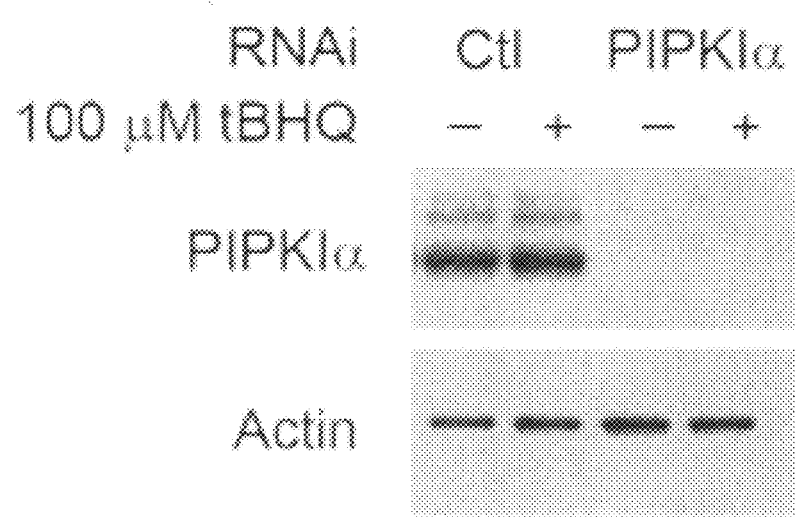

FIGURE 15 con't.
E.
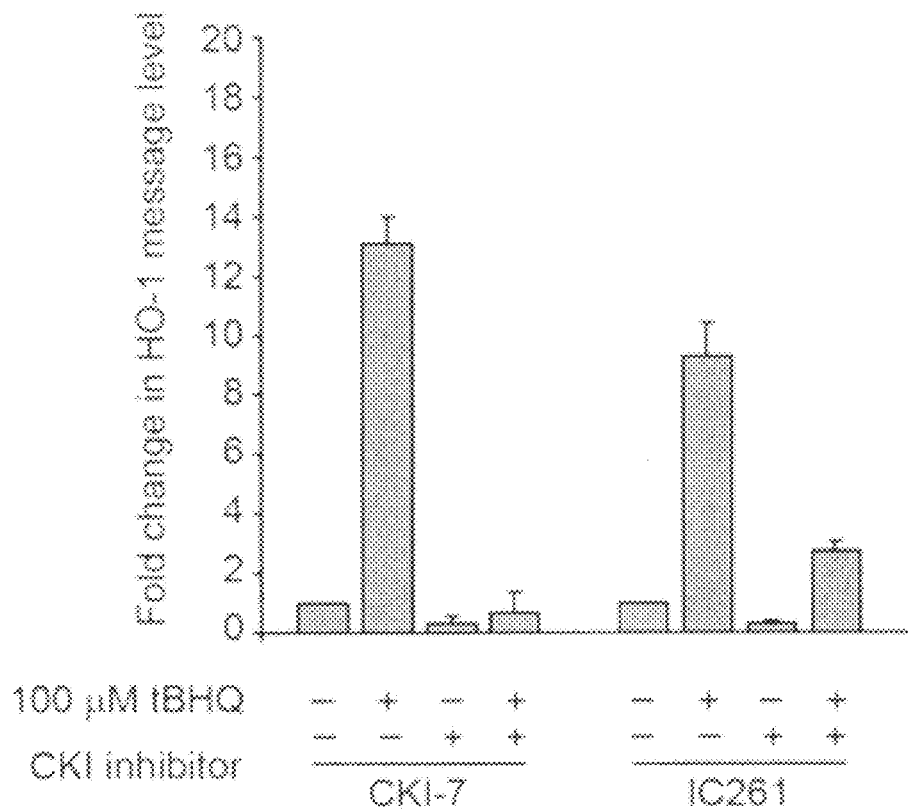
F.
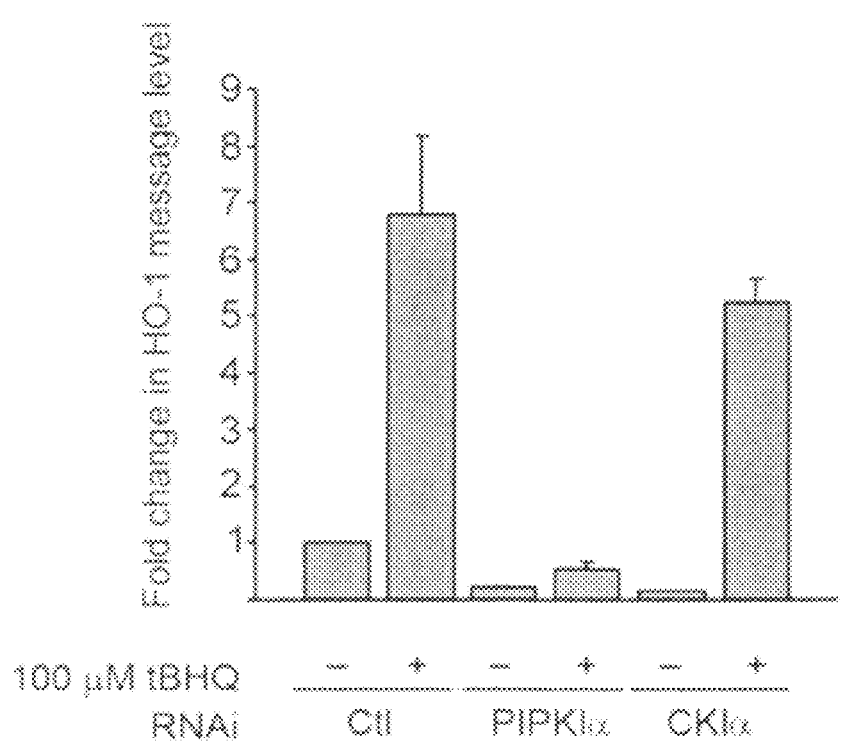

FIGURE 18

Supplemental Table 1 mRNAs showing statistically significant decreases in expression after Star-PAP siRNA treatment.

| Gene Name | Gene ID | Fold Change Star-PAP KD | Fold Change PIPKIα KD | Probe ID |
|---|---|---|---|---|
| Detoxification and Antioxidative Stress | | | | |
| Heme oxygenase (decycling) 1 | HO-1 | -8.93 | -1.32 | 203665_at |
| NAD(P)H dehydrogenase, quinone 1 | NQO1 | -4.29 | -3.38 | 201468_s_at |
| Aldehyde dehydrogenase 1 family, member A3 | ALDH1A3 | -4.23 | -1.19 | 203180_at |
| NADH dehydrogenase (ubiquinone) Fe-S protein 1, 75kDa (NADH-coenzyme Q reductase) | NDUFS1 | -3.68 | -5.99 | 236356_at |
| Apolipoprotein E | APOE | -3.31 | -1.80 | 203382_s_at |
| Isocitrate dehydrogenase 2 (NADP+), mitochondrial | IDH2 | -3.25 | -1.01 | 210046_s_at |
| Microsomal glutathione S-transferase 3 | MGST3 | -2.47 | -1.11 | 201403_s_at |
| Scavenger receptor class A, member 3 | SCARA3 | -2.25 | -1.54 | 219416_at |
| Aldehyde dehydrogenase 2 family (mitochondrial) | ALDH2 | -2.15 | -1.20 | 201425_at |
| Aldo-keto reductase family 1, member A1 (aldehyde reductase) | AKR1A1 | -2.13 | -1.07 | 201900_s_at |
| NADH dehydrogenase (ubiquinone) Fe-S protein 3, 30kDa (NADH-coenzyme Q reductase) | NDUFS3 | -2.07 | 1.41 | 229535_at |
| Catalase | CAT | -2.07 | 1.06 | 201432_at |
| Thioredoxin reductase 1 | TXNRD1 | -2.05 | -2.25 | 231292_at |

FIGURE 18 (cont.)

| | | | | |
|---|---|---|---|---|
| Peroxiredoxin 1 | PRDX1 | -2.02 | -1.15 | 208680_at |
| Glutathione S-transferase kappa 1 | GSTK1 | -2.02 | -1.84 | 217751_at |
| Aldo-keto reductase family 1, member C3 (3-alpha hydroxysteroid dehydrogenase, type II) | AKR1C3 | -1.94 | -4.03 | 209160_at |
| Thioredoxin domain containing 11 | TXNDC11 | -1.93 | -1.24 | 223325_at |
| Glutathione S-transferase theta 2 | GSTT2 | -1.89 | 1.421 | 205439_at |
| Nudix (nucleoside diphosphate linked moiety X)-type motif 21 | NUDT21 | -1.88 | -2.11 | 224830_at |
| Hydroxyacylglutathione hydrolase | HAGH | -1.85 | -1.13 | 205012_s_at |
| Thioredoxin domain containing 5 | TXNDC5 | -1.85 | -2.49 | 243405_at |
| Transaldolase 1 | TALDO1 | -1.82 | -1.02 | 201463_s_at |
| Aldo-keto reductase family 7, member A2 (aflatoxin aldehyde reductase) | AKR7A2 | -1.69 | -1.23 | 202139_at |
| Glutathione S-transferase A4 | GSTA4 | -1.67 | 1.748 | 202967_at |
| 3' Processing Factors | | | | |
| Polypyrimidine tract binding protein 2 | PTBP2 | -7.19 | -7.04 | 1554614_a_at |
| RNA binding motif protein 25 | RBM25 | -2.87 | -1.43 | 236613_at |
| PCF11, cleavage and polyadenylation factor subunit, homolog (S. cerevisiae) | PCF11 | -2.14 | -1.95 | 227622_at |
| Cytoplasmic polyadenylation element binding protein 1 | CPEB1 | -1.92 | -1.34 | 219578_s_at |
| Cytoplasmic polyadenylation element binding protein 3 | CPEB3 | -1.79 | 1.85 | 205773_at |
| Cleavage and polyadenylation specific factor 6, 68kDa | CPSF6 | -1.75 | -1.01 | 202470_s_at |

FIGURE 18 (cont.)

| | | | | |
|---|---|---|---|---|
| Poly(A)-specific ribonuclease (deadenylation nuclease) | PARN | -1.74 | -2.02 | 203905_at |
| DEAD (Asp-Glu-Ala-Asp) box polypeptide 17 | DDX17 | -1.68 | -1.69 | 208719_s_at |
| Others | | | | |
| Cyclin A1 | CCNA1 | -11.36 | -6.02 | 205899_at |
| Amyloid beta (A4) precursor-like protein 1 | APLP1 | -4.31 | -2.38 | 209462_at |
| Ankyrin repeat domain 1 (cardiac muscle) | ANKRD1 | -3.65 | -11.236 | 206029_at |
| Protein kinase C and casein kinase substrate in neurons 1 | PACSIN1 | -3.56 | -4.55 | 227053_at |
| Integrin, beta 1 (fibronectin receptor, beta polypeptide, antigen CD29 includes MDF2, MSK12) | ITGB1 | -2.77 | -2.96 | 1561042_at |
| Kruppel-like factor 10 | KLF10 | -2.79 | -1.94 | 202393_s_at |
| Cyclin E2 | CCNE2 | -2.64 | -3.65 | 211814_s_at |
| Sorting nexin 10 | SNX10 | -2.60 | -1.77 | 218404_at |
| Ras-related C3 botulinum toxin substrate 3 (rho family, small GTP binding protein Rac3) | RAC3 | -2.53 | -1.64 | 206103_at |
| BCL2/adenovirus E1B 19kDa interacting protein 3 | BNIP3 | -2.25 | -2.66 | 201849_at |
| Kruppel-like factor 7 (ubiquitous) | KLF7 | -2.04 | -2.11 | 1555420_a_at |
| Protein kinase C and casein kinase substrate in neurons 3 | PACSIN3 | -2.04 | -1.06 | 218744_s_at |
| Kruppel-like factor 5 (intestinal) | KLF5 | -1.96 | -1.33 | 209211_at |
| SH3 and multiple ankyrin repeat domains 3 | SHANK3 | -1.96 | -1.34 | 227923_at |
| Kruppel-like factor 9 | KLF9 | -1.86 | -1.15 | 230636_s_at |
| Kruppel-like factor 12 | KLF12 | -1.69 | 1.066 | 208467_at |

FIGURE 18 (cont.)

Supplemental Table 2 mRNAs showing statistically significant increases in expression after Star-PAP siRNA treatment.

| Gene Name | Gene ID | Fold Change Star-PAP KD | Fold Change PIPKIα KD | Probe ID |
|---|---|---|---|---|
| Detoxification and Antioxidative Stress | | | | |
| NADH dehydrogenase (ubiquinone) flavoprotein 3, 10kDa | NDUFV3 | 3.02 | 2.50 | 226209_at |
| Methylenetetrahydrofolate dehydrogenase (NADP+ dependent) 2, methenyltetrahydrofolate cyclohydrolase | MTHFD2 | 2.83 | 2.13 | 201761_at |
| Transketolase (Wernicke-Korsakoff syndrome) | TKT | 2.74 | 1.54 | 228205_at |
| Methylenetetrahydrofolate dehydrogenase (NADP+ dependent) 2-like | MTHFD2L | 2.24 | 1.80 | 220346_at |
| NAD(P) dependent steroid dehydrogenase-like | HSPC105 | 2.10 | 1.30 | 229522_at |
| Glucose-6-phosphate dehydrogenase | G6PD | 2.10 | 3.50 | 202275_at |
| Thioredoxin domain containing 2 (spermatozoa) | TXNDC2 | 2.01 | 1.25 | 224168_at |
| 3′ Processing Factors | | | | |
| Poly(A) polymerase gamma | PAPOLG | 2.63 | 3.06 | 222273_at |
| Splicing factor 3B, 14 kDa subunit | SF3B14 | 2.59 | 2.39 | 223416_at |
| La ribonucleoprotein domain family, member 1 | LARP1 | 2.53 | 1.57 | 210966_x_at |
| Splicing factor 3a, subunit 2, 66kDa | SF3A2 | 2.36 | 1.47 | 209381_x_at |
| DEAD (Asp-Glu-Ala-Asp) box polypeptide 52 | DDX52 | 2.15 | 2.48 | 212834_at |
| SLU7 splicing factor homolog (S. cerevisiae) | SLU7 | 2.07 | 1.30 | 227990_at |

FIGURE 18 (cont.)

| | | | | |
|---|---|---|---|---|
| Polypyrimidine tract binding protein 1 | PTBP1 | 2.05 | 2.24 | 211270_x_at |
| Others | | | | |
| Ribosomal protein L31 | RPL31 | 23.06 | 9.41 | 241017_at |
| Ribosomal protein L23 | RPL23 | 5.52 | 3.47 | 214744_s_at |
| Activating transcription factor 6 | ATF6 | 4.71 | 3.42 | 231927_at |
| Nuclear factor (erythroid-derived 2)-like 2 | NFE2L2 | 4.01 | 3.29 | 1567014_s_at |
| Sorting nexin 17 | SNX17 | 3.06 | 3.62 | 200991_s_at |
| Sorting nexin 13 | SNX13 | 2.01 | 2.25 | 1553148_a_at |

FIGURE 19 con't.
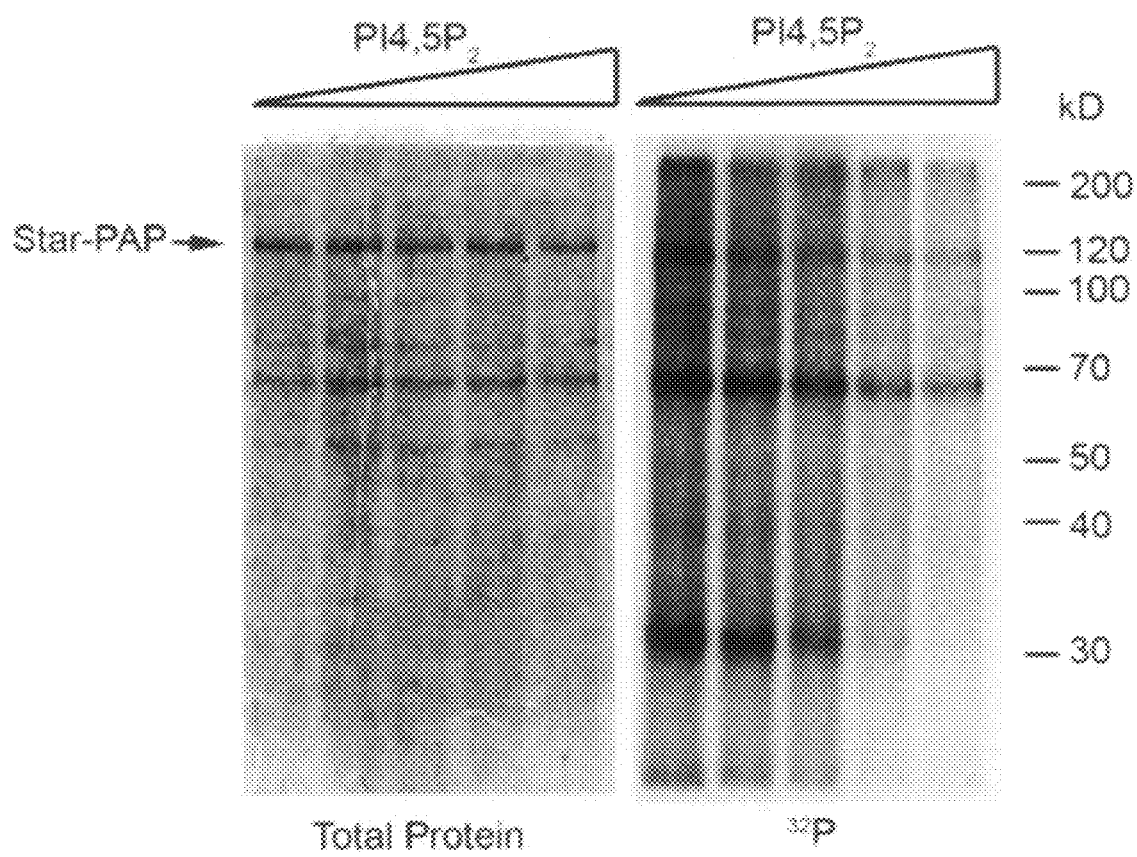

FIGURE 23
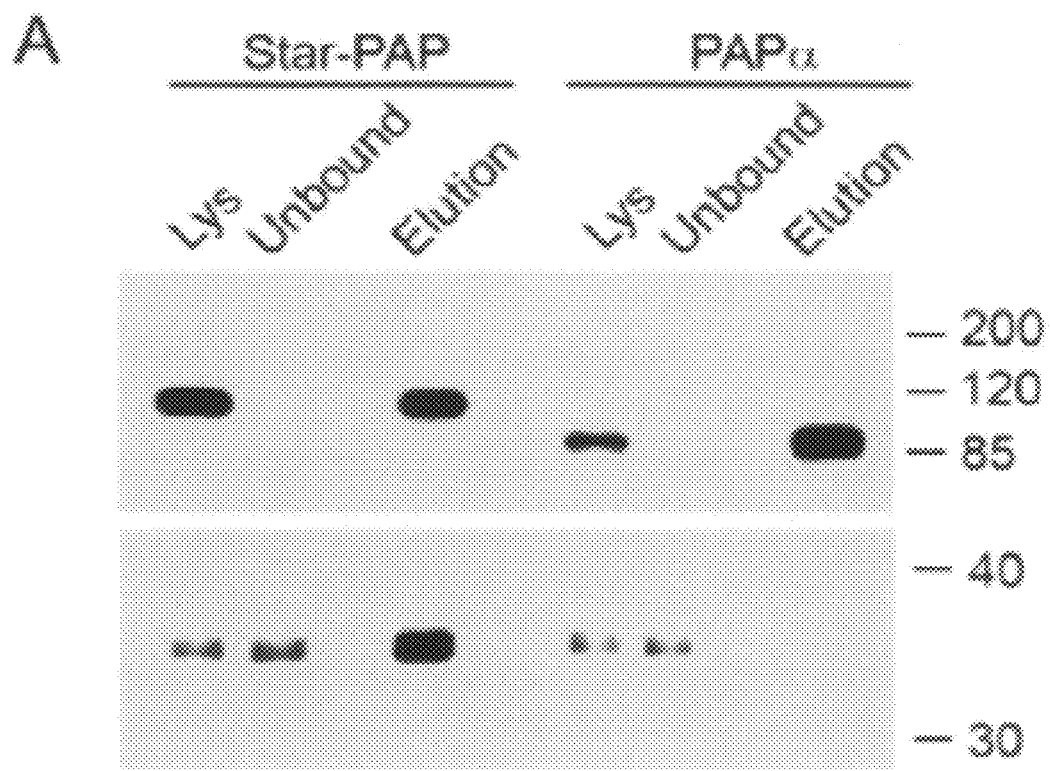
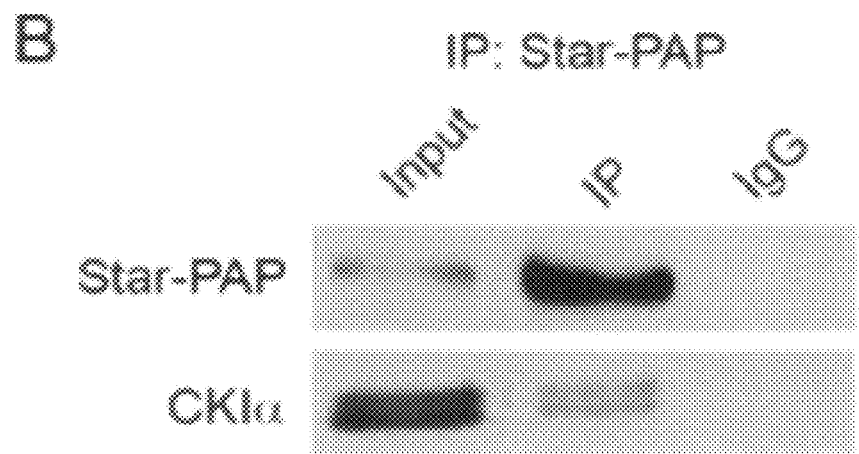

FIGURE 23 con't.
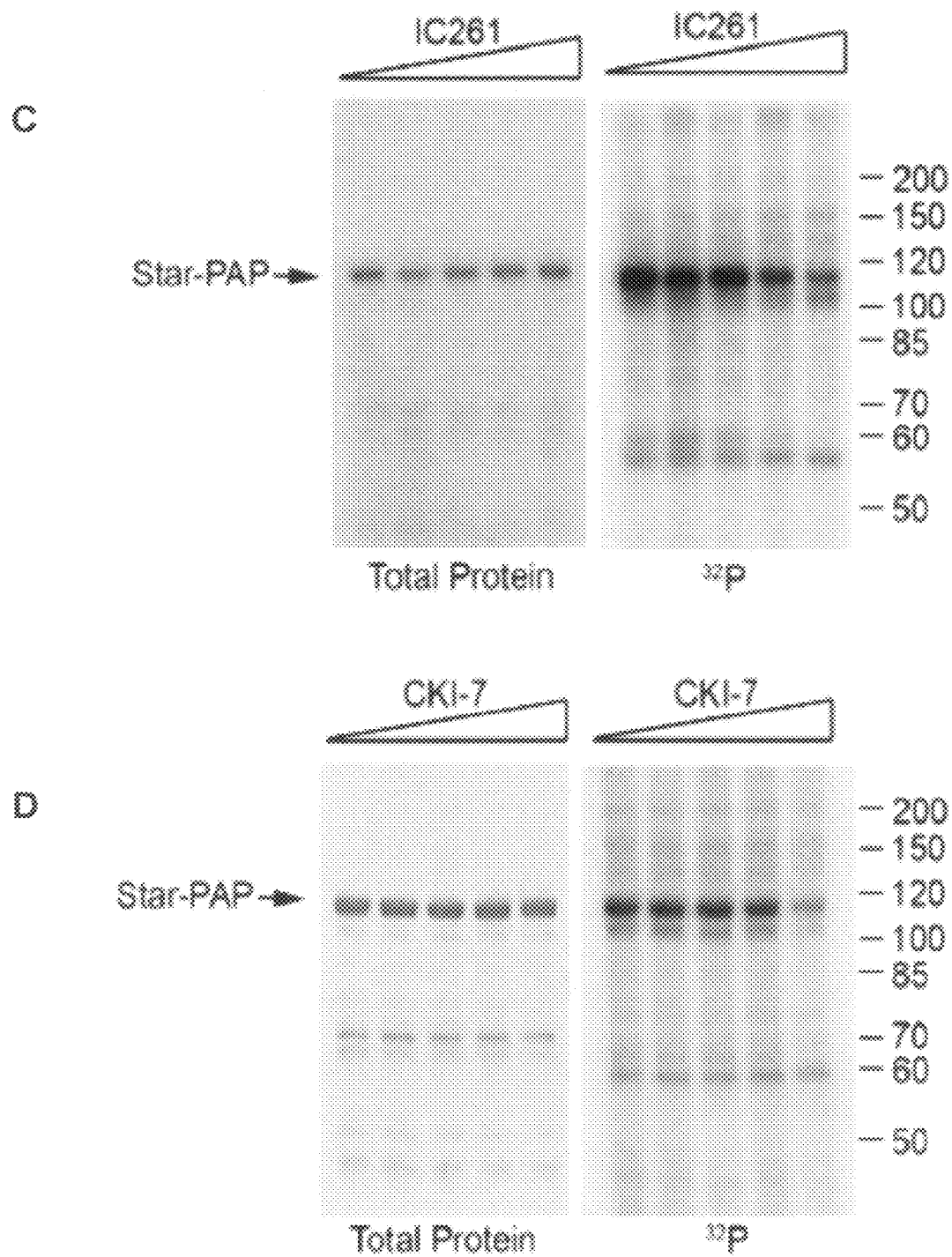

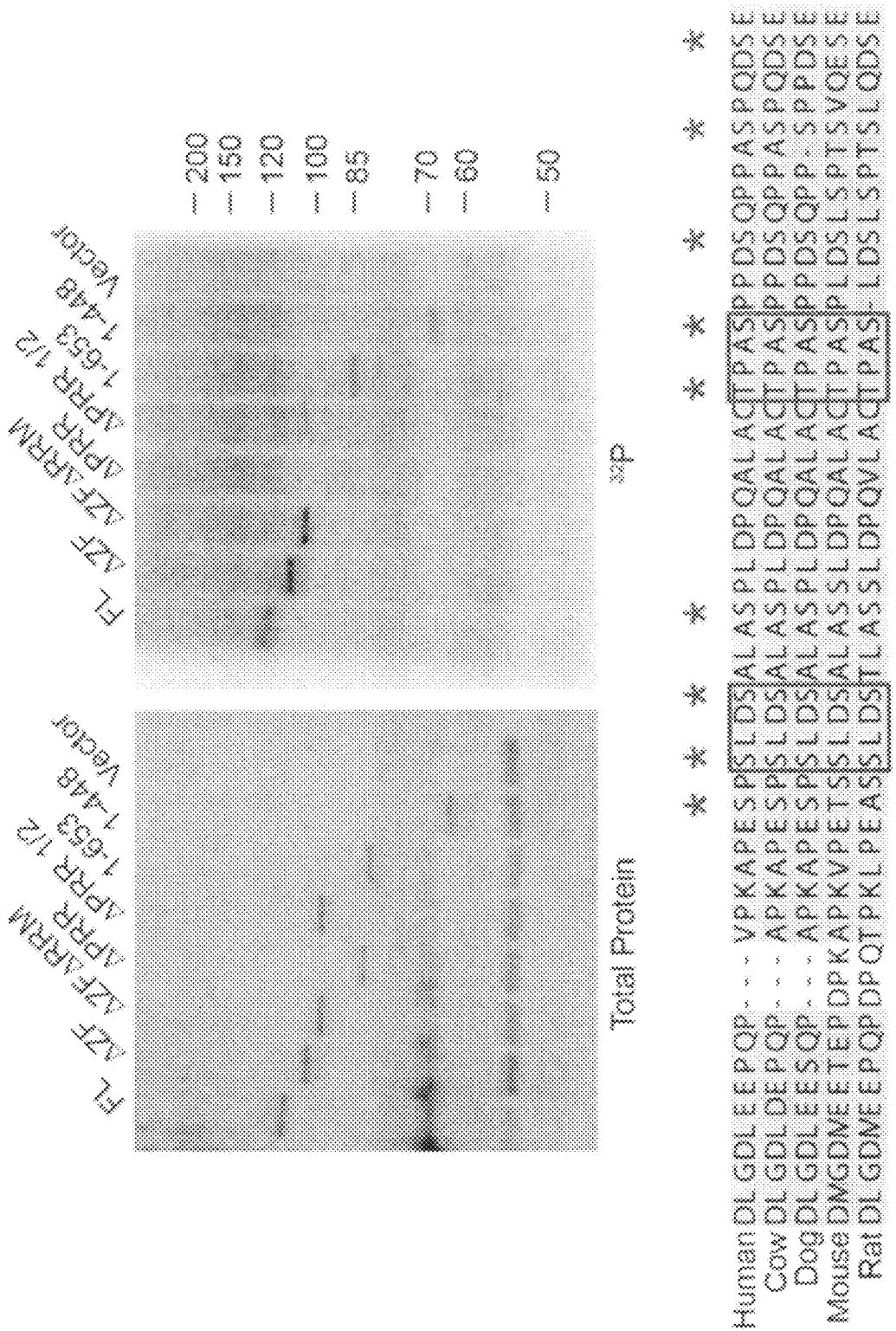
FIGURE 24 con't.

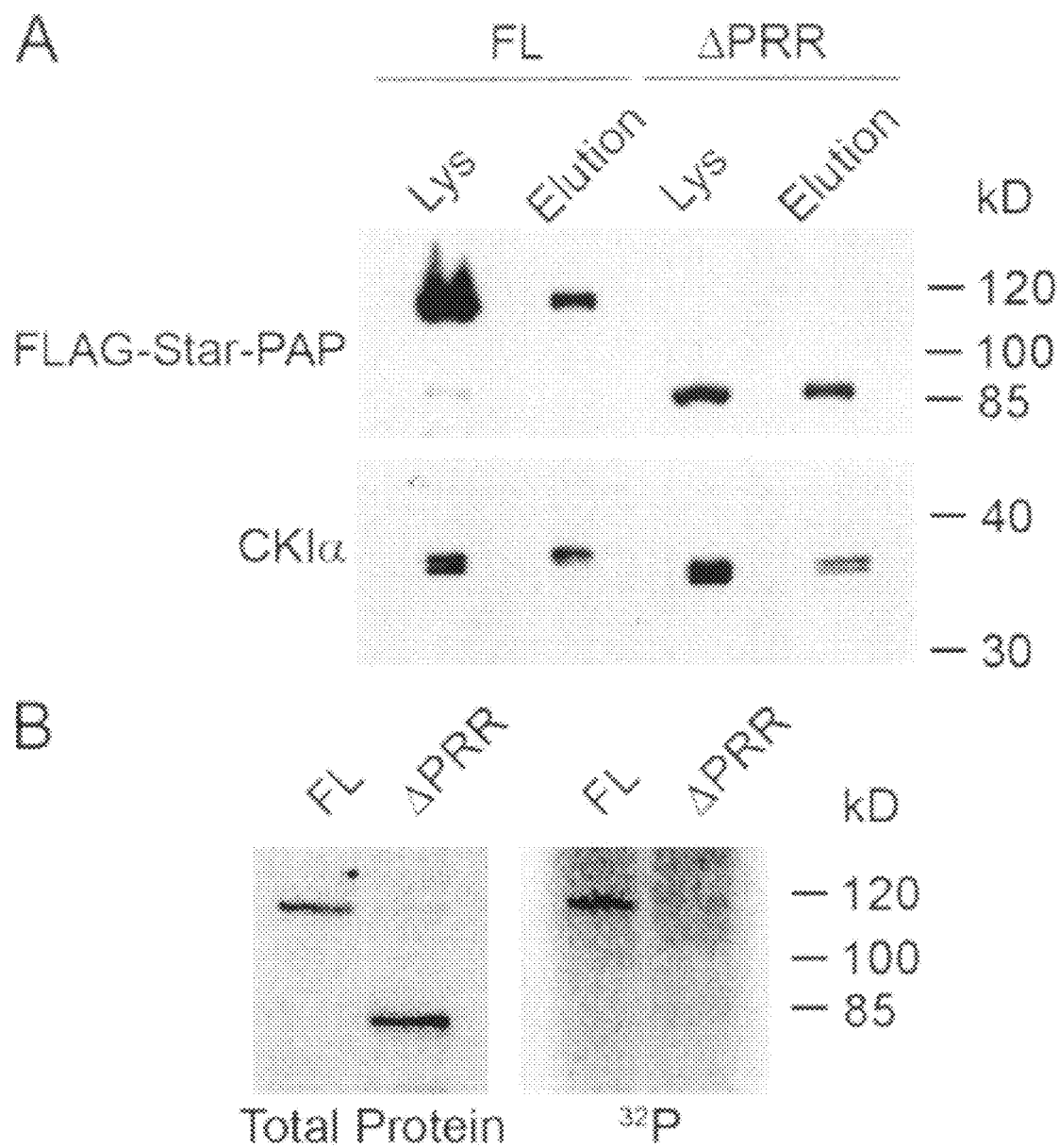

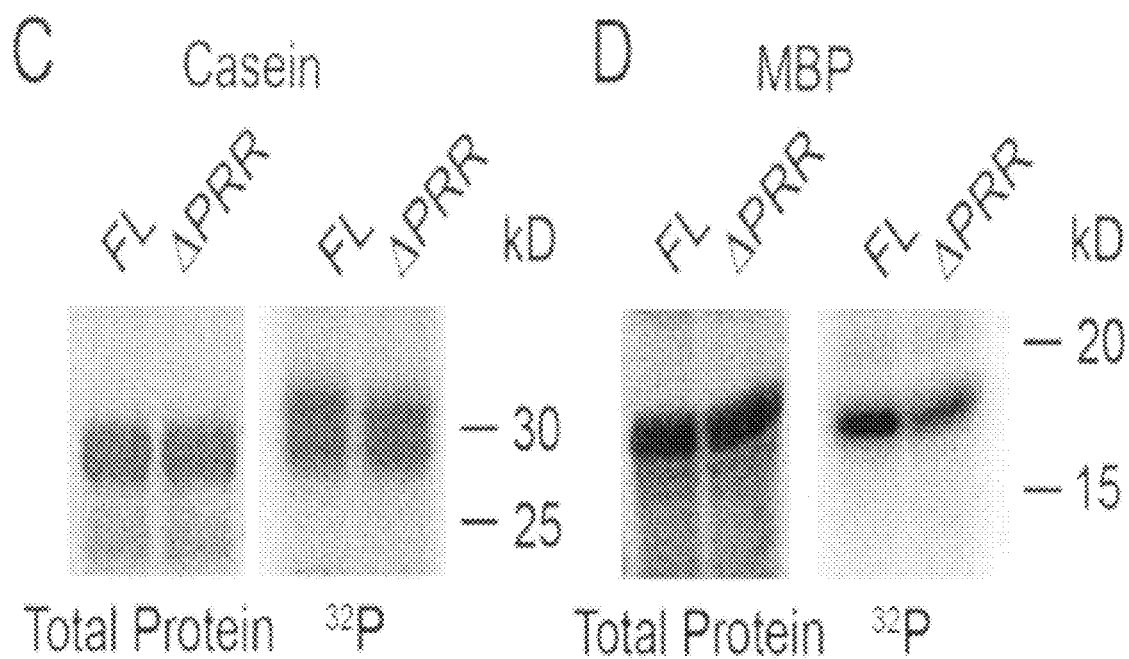
FIGURE 25 con't.

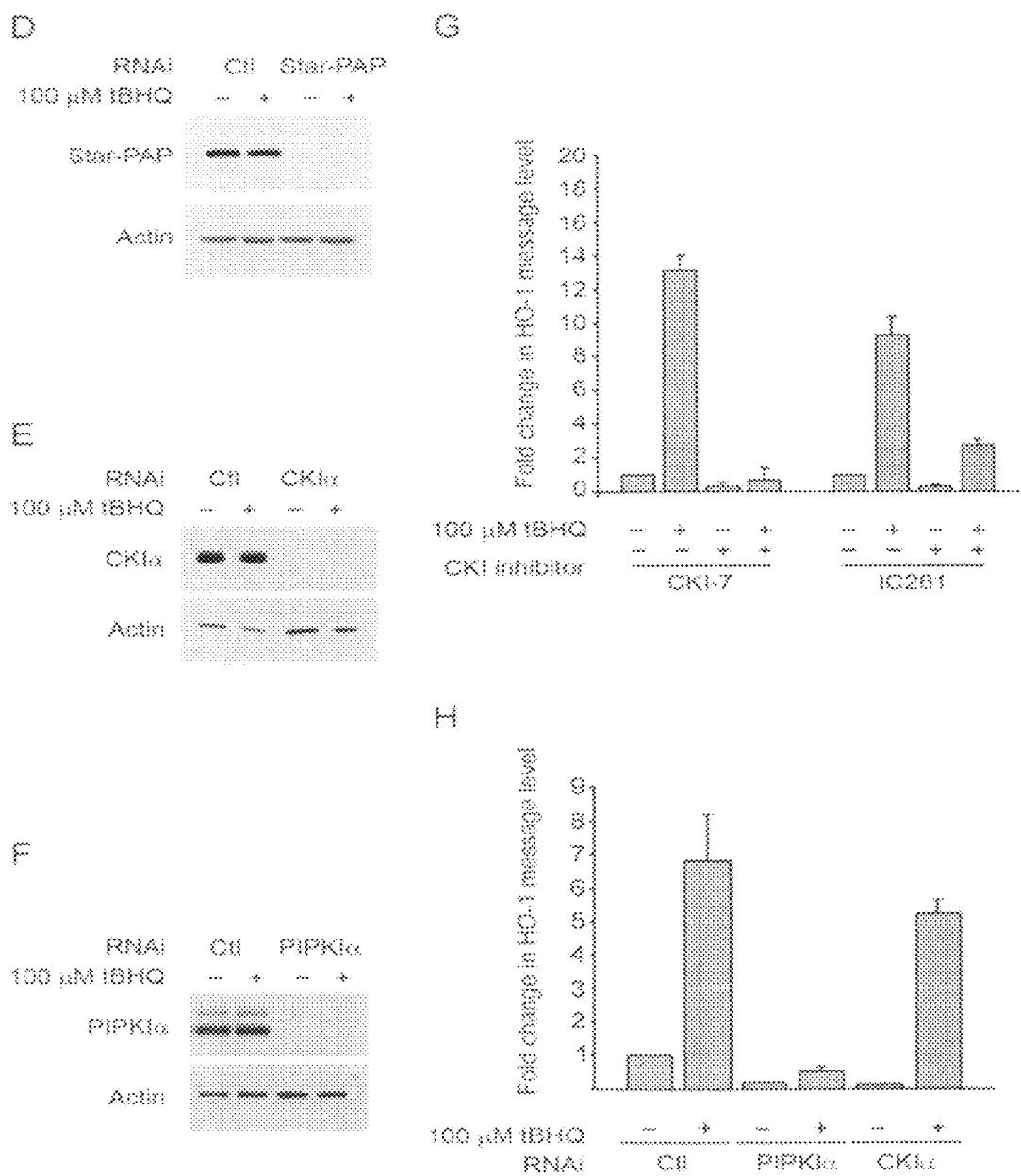
FIGURE 26 con't.

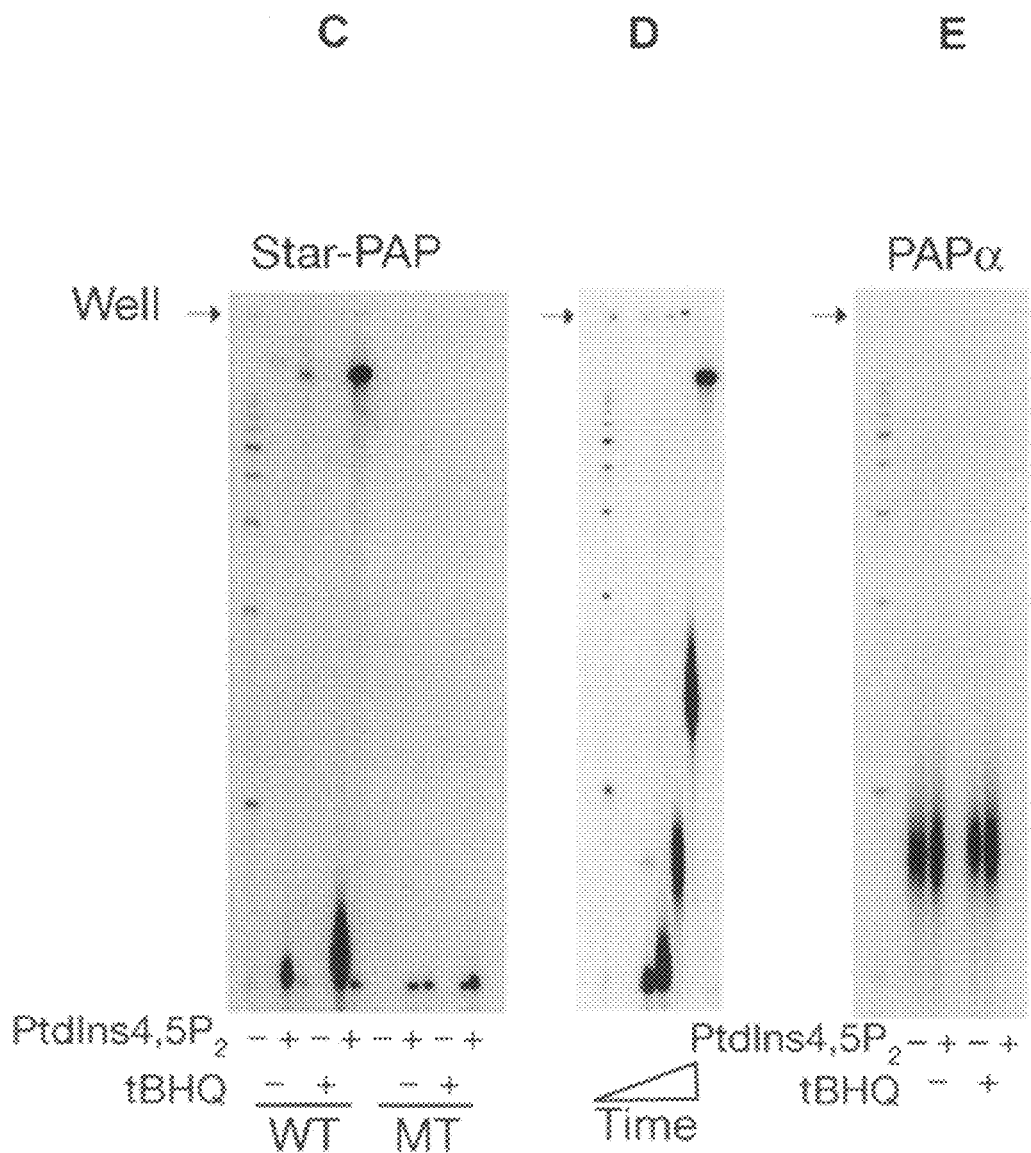
FIGURE 27 con't.

FIGURE 28

SEQ ID NO: 1) Star-PAP cDNA Seq:
>gi|12383073|ref|NM_022830.1| Homo sapien

GAAGTGGGTTCCGGTGGTGGCAGAGGTGCTTGTGTTTTGTCGGTACAGGAGAGTCGCTATGGCGGCGGT
GGATTCGGATGTCGAATCGCTGCCGCGTGGGGGGTTCCGCTGCTGCCTCTGCCACGTTACTACAGCCAAC
CGACCCAGCCTTGATGCCCACTTGGGAGGCAGAAAGCACCGGCACCTGGTAGAACTACGAGCTGCGAGAA
AGGCCCAGGGACTTCGAAGTGTGTTTGTCAGTGGCTTTCCCAGGGGTGTGGATTCTGCTCAGCTCTCTGA
GTACTTCCTAGCATTTGGGCCTGTGGCCAGTGTTGTCATGGACAAGGACAAGGGAGTGTTTGCCATTGTG
GAGATGGGGGACGTGGGTGCTCGAGAGGCTGTCTTGTCACAGTCCCAGCACAGCCTGGGAGGACATCGCC
TGCGTGTCCGCCCACGGGAGCAGAAGGAGTTCCAGAGCCCGGCCTCCAAATCCCCCAAAGGAGCGGCCCC
CGACAGTCACCAGCTGGCCAAAGCGCTAGCTGAGGCTGCAGACGTGGGGGCACAAATGATAAAGCTTGTG
GGGCTGAGGGAGTTGTCCGAGGCCGAGCGGCAGCTTCGCAGCCTAGTGGTGGCCCTGATGCAGGAGGTCT
TCACAGAGTTCTTCCCTGGCTGTGTGGTCCACCCTTTTGGCTCTTCCATAAATAGCTTCGATGTCCATGG
CTGTGATCTTGACCTCTTCTTGGATCTGGGTGACTTGGAAGAGCCCCAGCCAGTCCCAAAGGCTCCAGAA
TCTCCATCGCTGGACTCGGCCCTGGCTTCCCCACTGGACCCTCAAGCCCTGGCCTGCACCCCAGCTTCCC
CTCCAGATTCACAACCTCCTGCTTCTCCCCAGGATTCTGAAGCCCTGGACTTTGAAACCCCTTCCTCCTC
CCTGGCGCCCCAAACTCCGGACTCTGCCTTGGCCTCCGAGACCCTTGCTTCTCCCCAGTCTCTGCCTCCA
GCTTCACCACTGCTAGAGGACAGGGAAGAGGGGGACCTGGGGAAGGCCTCGGAACTAGCAGAGACCCCAA
AGGAGGAGAAAGCAGAGGGGGCAGCAATGCTGGAGCTGGTGGGATCCATTCTCCGGGGCTGTGTCCCTGG
GGTGTATCGAGTCCAAACTGTGCCCTCTGCCCGGCGCCCTGTGGTCAAGTTCTGTCATCGGCCTTCAGGT
CTCCACGGTGATGTCTCCCTCAGTAACCGGCTGGCCCTGCATAACTCCCGTTTCCTGAGTCTCTGCTCTG
AGCTGGATGGTCGAGTCCGGCCCCTCGTGTACACCCTCCGCTGCTGGGCTCAGGGTCGGGGGCTGTCAGG
GAGTGGCCCCCTTCTCAGTAACTACGCCCTGACCTTGCTGGTGATCTATTTCTTCAGACCAGGGACCCT
CCTGTGTTGCCCACTGTGTCCCAGCTCACCCAGAAAGCAGGAGAGGGGAACAGGTGGAAGTCGATGGCT
GGGACTGCAGTTTCCCCAGGGATGCCTCAAGACTGGAGCCCAGCATAAATGTGGAGCCCCTCAGTTCCCT
GCTAGCCCAGTTCTTCTCCTGTGTATCTTGTTGGGATCTTCGTGGCTCCCTGCTGTCCCTGCGGGAGGGT
CAGGCACTGCCTGTGGCAGGGGCCTGCCTTCTAATCTCTGGGAGGGTCTGCGCCTTGGCCCCCTGAATC
TCCAGGACCCTTTTGACCTGAGTCACAATGTCGCAGCCAATGTGACCAGCCGGGTGGCTGGGCGCCTACA
GAACTGCTGCCGAGCAGCAGCCAATTACTGCCGAAGCCTCCAGTACCAGCGCCGTTCCTCCCGGGGTCGG
GACTGGGGGCTGCTCCCTCTTCTGCAGCCCAGCTCCCCCAGCTCCCTGCTCTCTGCTACGCCGATCCCTT
TACCCCTTGCACCCTTCACCCAGCTCACTGCTGCCCTGGTGCAGGTATTCAGGGAAGCACTGGGGTGCCA
TATGAACAGGCAACCAAGAGAACGCGGTCAGAAGGAGGTGGAACTGGGGAGTCCTCTCAGGGAGGGACA
AGCAAAAGACTCAAAGTAGATGGACAGAAAAACTGCTGTGAGGAGGGGAAAGAGGAGCAGCAGGGATGTG
CAGGGGACGGTGGGGAAGACAGGGTAGAAGAGATGGTTATAGAGGTTGGAGAGATGGTGCAGGACTGGGC
CATGCAGAGCCCTGGGCAGCCAGGGGACCTGCCCCTGACCACTGGAAAGCATGGAGCCCCTGGAGAAGAG
GGGCAGCCCAGCCACGCAGCCCTGGCAGAGCGGGGGCCCAAGGGACATGAGGCAGCCCAAGAATGGTCTC
AGGGTGAGGCAGGGAAGGGGGCATCCCTGCCCTCCTCAGCGAGCTGGCGCTGTGCCTTGTGGCACCGAGT

FIGURE 28 (CONT.)

```
GTGGCAAGGGCGGCGGCGAGCCCGTAGACGCTTGCAGCAGCAAACCAAGGAGGGAGCTGGAGGTGGCGCT
GGCACAAGAGCAGGGTGGCTGGCGACTGAGGCTCAGGTCACCCAGGAGCTGAAAGGACTGAGTGGTGGCG
AAGAGAGGCCAGAAACTGAGCCCCTGCTGAGCTTTGTGGCGTCTGTCTCCCCGGCTGACCGAATGCTCAC
TGTGACCCCGCTCCAGGATCCCCAAGGCCTGTTCCCTGATCTCCATCATTTCTTACAGGTTTTCCTCCCT
CAAGCAATTCGACATCTCAAGTGAAGACATGGCCCCTGAAGGGCAATAAAGCTGCTAGTTTATTAATACA
AAAAAAAAAAAAAAAAA
```

FIGURE 29

SEQ ID NO: 2) Star-PAP Amino Acid Seq:
>gi|12383074|ref|NP_073741.1| RNA binding motif protein 21 [Homo sapiens]
MAAVDSDVESLPRGGFRCCLCHVTTANRPSLDAHLGGRKHRHLVELRAARKAQGLRSVFVSGFPRGVDSA
QLSEYFLAFGPVASVVMDKDKGVFAIVEMGDVGAREAVLSQSQHSLGGHRLRVRPREQKEFQSPASKSPK
GAAPDSHQLAKALAEAADVGAQMIKLVGLRELSEAERQLRSLVVALMQEVFTEFFPGCVVHPFGSSINSF
DVHGCDLDLFLDLGDLEEPQPVPKAPESPSLDSALASPLDPQALACTPASPPDSQPPASPQDSEALDFET
PSSSLAPQTPDSALASETLASPQSLPPASPLLEDREEGDLGKASELAETPKEEKAEGAAMLELVGSILRG
CVPGVYRVQTVPSARRPVVKFCHRPSGLHGDVSLSNRLALHNSRFLSLCSELDGRVRPLVYTLRCWAQGR
GLSGSGPLLSNYALTLLVIYFLQTRDPPVLPTVSQLTQKAGEGEQVEVDGWDCSFPRDASRLEPSINVEP
LSSLLAQFFSCVSCWDLRGSLLSLREGQALPVAGGLPSNLWEGLRLGPLNLQDPFDLSHNVAANVTSRVA
GRLQNCCRAAANYCRSLQYQRRSSRGRDWGLLPLLQPSSPSSLLSATPIPLPLAPFTQLTAALVQVFREA
LGCHIEQATKRTRSEGGGTGESSQGGTSKRLKVDGQKNCCEEGKEEQQGCAGDGGEDRVEEMVIEVGEMV
QDWAMQSPGQPGDLPLTTGKHGAPGEEGQPSHAALAERGPKGHEAAQEWSQGEAGKGASLPSSASWRCAL
WHRVWQGRRRARRRLQQQTKEGAGGGAGTRAGWLATEAQVTQELKGLSGGEERPETEPLLSFVASVSPAD
RMLTVTPLQDPQGLFPDLHHFLQVFLPQAIRHLK

FIGURE 30

SEQ ID NO: 3) Canonical PAPa cDNA Seq:

>gi|47834324|ref|NM_032632.3| Homo sapiens poly(A) polymerase alpha (PAPOLA), mRNA

```
GAACGTTGCTGTGGTAGCGCTCGGGCGCCATGTTAGGACGAAGGGGAAGGAGGAGAAGCGCTTAAAGCGG
CGGGAGCGGTGCGGGAGAGGGGTTGGACCCAGGGCTGAGGCAGGCCCCCCCCTCCCTCCCGCCTCAGTGG
ATCATGCCCAGGCGGCAGCGGCGGCGGTTGCGGGGGGGAAGTGACTGGGCGGTGCCGGCGCCGGAGACG
ATGCCGTTTCCAGTTACAACACAGGGATCACAACAAACACAACCGCCACAGAAGCACTATGGCATTACTT
CTCCTATCAGCTTAGCAGCCCCAAGGAGACTGACTGCGTACTTACACAGAAACTAATTGAGACATTGAA
ACCCTTTGGGGTTTTTGAAGAGGAAGAGGAACTGCAGCGCAGGATTTTAATTTTGGGAAAACTAAATAAC
CTGGTAAAAGAGTGGATACGAGAAATCAGTGAAAGCAAGAATCTTCCACAATCTGTAATTGAAAATGTTG
GAGGAAAAATTTTTACATTTGGATCTTACAGATTAGGAGTGCATACAAAAGGTGCTGATATTGATGCGTT
GTGTGTTGCACCAAGACATGTTGATCGAAGTGACTTTTTCACCTCATTCTATGATAAGTTGAAATTACAG
GAAGAAGTAAAAGATTTAAGAGCTGTTGAAGAGGCATTCGTACCAGTTATTAAACTCTGTTTTGATGGGA
TAGAGATTGATATTTTGTTTGCAAGATTAGCACTGCAGACAATTCCTGAAGATTTGGATCTACGAGATGA
CAGTCTGCTAAAAAATTTAGATATAAGATGTATAAGAAGTCTTAACGGTTGCAGGGTAACCGATGAAATT
TTACATCTAGTACCAAACATTGACAACTTCAGGTTAACTCTGAGAGCTATCAAACTATGGGCCAAACGCC
ACAACATCTATTCCAATATATTAGGTTTCCTCGGTGGTGTTTCCTGGGCTATGCTAGTAGCAAGAACTTG
CCAGCTTTATCCAAATGCAATAGCATCAACTCTTGTACATAAATTTTTCTTGGTATTTTCTAAATGGGAA
TGGCCAAATCCAGTGCTATTGAAACAGCCTGAAGAATGCAATCTTAATTTGCCTGTATGGGACCCAAGGG
TAAACCCCAGTGATAGGTACCATCTTATGCCTATAATTACACCAGCATACCCACAACAGAACTCCACGTA
CAATGTGTCCGTTTCAACACGGATGGTCATGGTTGAGGAGTTTAAACAAGGTCTTGCTATCACAGATGAA
ATTTTGCTGAGTAAGGCAGAGTGGTCCAAACTTTTTGAAGCTCCAAACTTCTTTCAAAAGTACAAGCATT
ATATTGTACTTCTAGCAAGTGCACCAACAGAAAAACAACGCCTGGAATGGGTGGGCTTGGTGGAATCAAA
AATCCGAATCCTGGTTGGAAGCTTGGAGAAGAATGAATTTATTACACTGGCTCATGTGAATCCCCAGTCA
TTTCCAGCACCCAAAGAAAATCCCGACAAGGAAGAATTTCGCACGATGTGGGTGATTGGGTTAGTGTTTA
AAAAAACAGAAAACTCTGAAAACCTCAGTGTTGATCTCACCTATGATATTCAGTCTTTCACAGATACAGT
TTATAGGCAAGCAATAAACAGCAAGATGTTTGAGGTGGATATGAAAATTGCTGCAATGCATGTAAAAAGA
AAGCAACTCCATCAACTACTACCTAATCATGTGCTTCAGAAAAAGAAAAAGCATTCAACAGAAGGTGTCA
AATTGACAGCTCTCAATGACAGCAGCCTCGACTTGTCTATGGACAGTGATAACAGCATGTCTGTGCCTTC
ACCTACTAGTGCTACGAAGACCAGTCCATTGAACAGTTCTGGCAGCTCTCAGGGCAGAAACAGTCCTGCT
CCAGCTGTAACAGCAGCATCTGTGACCAACATACAGGCTACTGAAGTTTCTGTGCCACAAGTAAATTCCA
GTGAAAGCTCAGGGGGTACATCGAGTGAAAGCATTCCTCAAACTGCCACACAACCAGCCATTTCTCCACC
ACCAAAGCCTACGGTCTCCAGAGTTGTTTCTTCAACACGTCTGGTAAACCCACCACCTAGATCTTCAGGA
AATGCAGCAACTTCAGGAAATGCAGCAACAAAAATACCTACTCCTATAGTAGGAGTCAAGAGGACATCCT
CACCTCATAAAGAAGAGAGTCCCAAGAAAACCAAAACAGAAGAGGATGAAACAAGTGAAGATGCTAACTG
```

FIGURE 30 (CONT.)

```
TCTTGCTTTGAGTGGACATGATAAAACAGAAGCAAAGGAACAACTTGATACAGAGACAAGTACAACTCAA
TCAGAAACTATTCAGACAGCGGCTTCTCTGTTGGCCTCTCAGAAAACATCCAGTACAGACCTTTCTGATA
TCCCTGCTCTCCCTGCAAATCCTATTCCTGTTATCAAGAATTCAATAAAACTGAGATTGAATCGGTAAAA
ACAACCTCAGGGGTCCATAAACAATATCTGCCAACTCAACCTGTTGTCTTCAAATGCTAAAAAGGAGAA
TGGAGGGTACAAGACTAGACATGACTGAAATGGATTTGGGTTTTTTGGTGACCTCCCTTACTGGGCTAAT
CAGCACTTGATCGGAAGTCCAGGTTAGTATGTGAAGCCAGGAGTACTATTATTATTGTGTTAGCAACAGT
TGCATTAACTATTTCAAAAATTACTGCCTTTAAAAAAAACAACCTCAAGCTATATTTGTATTCATAATTG
ACATCTGGATTGGGTTTATGTTTGATGCATTGTTTGGAAAATTTGCAATACAAACTGGCATAAGAATTAC
TTATTCTGATGATGCACTTTTATGTATTTTTCATTAGAAAGTAGAACTAATTTTAGATTTTCAGCTTGAT
GGATTTTCAGTTTTTCCTGAAGAATTTTCTTTACCATTAGTCTTCAAATTGGATACTGTTGTGCAGTGGT
GTACTGTTATACTTCAGAGAAAGGGTAAGAGTACATCTAGTTCAGTTCCTATGAGGTAGCTGTAACCCTT
AAAAATGAAACGTCAACTCTAGGGTACATTTGACATTGAAAGAATAGTTAGGAAATAACTTGGTTTTGAT
AGGGTCATGATTAAGAAATGATATATTGGTTTTATTTATGGAATTGTTTTATAGTGCATACAAATCAGCG
ATCAGCCAGCAAATATTTTTCTTTGAGCTTGTGAAAGCTCTGTGTTCTTTTGCCTTCAATCTGTTGTCTT
CAAAACAAACAAACAAAAAAAGCTTCTTGCGCCTTTCCCTCCCCTGTTTTCTTCCTTTTTCTTTTTGCTT
GTATGCACAAGGTAGGACTTACTTCGTAAGAAACAAAATGCCAGTATTTTCTTAAGCCATGATGTGAAAC
CAATGACCCTGTGACCACATGGCACAGAACACTAAATTTTGGTCCCATGGCTGAAACTTGAGGGTGACTA
AAAGTAATGCCTGTGAAACATGATATCTATCTGGGATGGCCATTTGATCTCTAAAAGGAATTTTGTACAC
TCCACAGAACTCCTATCTATAGTAAAATTGATTTTCAGTTTTAAATGTGGGCAAAAAGGCATTTTCTCCA
AGATTTTAAAACTAATTCTTATTTTTAAATGGTTTACCAAAATTTGTCAGTACATTTTACGTGTAGAAGC
ATTTTAAAAATCATTTCTAGCAAGCACTTGACATCTAGTCAGCTCTCTACTCCTTTATTTTGTTTTATCA
AAAGATTAAGAGCTCCTTTCTTTGAATAAAATAATTTCTCATAATTAAGCAGTAGAAGATCTATCTTCAC
AAAGTATGAGGGATGCCAGATGTTGATAAACTTACTCTTTCTGAATCTGGACAAAGTCGACTTAACAGAT
TTTTCTGATGAGCATGTTTTATGAATCCTCCATTGTGCTCCATTCTATCACATGTGCATTTTTCATGTTA
AACTGCAATTACTTAATCTCTTCCCCTATCCTTCTAAATTAATTTTCTGAAGTTGGAGTGTAGTCTTTTC
CCCCTTAGGCTATGCATTAATCGAAGCTTTCTTTTCACCATGACTTTATAATGTCTAGTAAACAATATTT
CTACTTCCCACATCTTTGCTTTACACAGTCACCTTGCCCTTCCTTCCACCACCGAAGAAAAAGATGGTC
ATACTAACAGGTGAAATGTACAAGGTGTCTGTGTGTTTTGTGTAGCTTCAGAGTTAGATTGAAATTACCA
GGCACAGATTTAGTCTTGTCATTTTGTTTACACATTGGGGAAAACAATTCAGTTTATTAAACGTTTCATG
TAACTGCACCCAAGTTTTGCCAAGCTGGAAACTTGGACCTTTTCTGTGTAGTGACTTTTTAATTATAGTT
TTCATAACCTGGAGATCAGACTGTTGCTTTCGCATGATGTATGTAGTGTCTCATGACTGGAGTTTGCTTT
GTTTTATAGTATCTGTACTCCTTGTATTTTTCAAGAGCTATTTTGTAAACAGATGATGTATTTCTCCATT
GAAAACACAATAAAAAAAAAACAGCACAAAAAAAAAAAAAAAAAAAAAAAAAAAAAAA
```

FIGURE 31

SEQ ID NO: 4) Canonical PAPa Amino Acid Seq:
>gi|32490557|ref|NP_116021.2| poly(A) polymerase alpha [Homo sapiens]
MPFPVTTQGSQQTQPPQKHYGITSPISLAAPKETDCVLTQKLIETLKPFGVFEEEEELQRRILILGKLNN
LVKEWIREISESKNLPQSVIENVGGKIFTFGSYRLGVHTKGADIDALCVAPRHVDRSDFFTSFYDKLKLQ
EEVKDLRAVEEAFVPVIKLCFDGIEIDILFARLALQTIPEDLDLRDDSLLKNLDIRCIRSLNGCRVTDEI
LHLVPNIDNFRLTLRAIKLWAKRHNIYSNILGFLGGVSWAMLVARTCQLYPNAIASTLVHKFFLVFSKWE
WPNPVLLKQPEECNLNLPVWDPRVNPSDRYHLMPIITPAYPQQNSTYNVSVSTRMVMVEEFKQGLAITDE
ILLSKAEWSKLFEAPNFFQKYKHYIVLLASAPTEKQRLEWVGLVESKIRILVGSLEKNEFITLAHVNPQS
FPAPKENPDKEEFRTMWVIGLVFKKTENSENLSVDLTYDIQSFTDTVYRQAINSKMFEVDMKIAAMHVKR
KQLHQLLPNHVLQKKKKHSTEGVKLTALNDSSLDLSMDSDNSMSVPSPTSATKTSPLNSSGSSQGRNSPA
PAVTAASVTNIQATEVSVPQVNSSESSGGTSSESIPQTATQPAISPPPKPTVSRVVSSTRLVNPPPRSSG
NAATSGNAATKIPTPIVGVKRTSSPHKEESPKKTKTEEDETSEDANCLALSGHDKTEAKEQLDTETSTTQ
SETIQTAASLLASQKTSSTDLSDIPALPANPIPVIKNSIKLRLNR

FIGURE 32

SEQ ID NO: 5) PIPKIa cDNA Seq
>gi|4505814|ref|NM_003557.1| Homo sapiens phosphatidylinositol-4-phosphate 5-
kinase, type I, alpha (PIP5K1A), mRNA
ATTAACAGGCCGTGGTTAGGAAGGACGGAGAAGGGGCGTTCGCTCCTTTGGGACTTTTCATGCCTCGTTT
TTTTTTCAGATGTGGCTTGGTCTGGGCGCAAGGTCCCAGCAGCCAGCTTAAGCTTACTCTTCTGTGAAAG
GGGAAAGTATCCCCTGTGGAAAGCGGTTAAACTTGTGGAGGGGGTGCGGGACGTGAGTTCTTCCCCATGC
CAGGCGAATGGTGTGGCCTTGAGCTGGTCCAGGAGCCGGCTCGACGTGTCTGAGGGAGGCCCGGAGGGGG
CGGGGAGGTGGCCCACAGAACGCGGGTTCTGTAAAGAGACGTTGGGAAGATTCGATTCCGAGAAGAGGAA
GAACCGGATTGAAAGAGAGCCAGGCCGCTGAGGGGGAGGGGGCTGCTAAGATGGCGTCGGCCTCCTCCGG
GCCGTCGTCTTCGGTCGGTTTTTCATCCTTTGATCCCGCGGTCCCTTCCTGTACCTTGTCCTCAGCATCT
GGAATCAAGAGACCCATGGCATCTGAGGTGCCTTATGCCTCTGGCATGCCCATCAAGAAAATAGGCCATA
GAAGTGTTGATTCCTCAGGAGAGACAACATATAAAAAGACAACCTCATCAGCCTTGAAAGGTGCCATCCA
GTTAGGCATTACCCACACTGTGGGGAGCCTGAGTACCAAACCAGAGCGTGATGTCCTCATGCAAGATTTC
TACGTGGTTGAGAGTATCTTCTTTCCCAGTGAAGGGAGCAACCTGACCCCTGCTCATCACTACAATGACT
TTCGTTTCAAGACCTATGCACCTGTTGCCTTCCGCTACTTCGGGGAGCTATTTGGTATCCGGCCCGATGA
TTACTTGTATTCCCTCTGCAGTGAGCCGCTGATTGAACTCTGTAGCTCTGGAGCTAGTGGTTCCCTATTC
TATGTGTCCAGCGACGATGAGTTCATTATTAAGACAGTCCAACATAAAGAGGCGGAATTTCTGCAGAAGC
TGCTTCCAGGATACTACATGAACCTCAACCAGAACCCTCGGACTTTGCTGCCTAAATTCTATGGACTGTA
CTGTGTGCAGGCAGGTGGCAAGAACATTCGGATTGTGGTGATGAACAATCTTTTACCAAGATCGGTAAAA
ATGCATATCAAATATGACCTCAAAGGCTCAACCTACAAACGGCGGGCTTCCCAGAAAGAGCGAGAGAAGC
CTCTTCCCACATTTAAAGACCTAGACTTCTTACAAGACATCCCTGATGGTCTTTTTTTGGATGCTGACAT
GTACAACGCTCTCTGTAAGACCCTGCAGCGTGACTGTTTGGTGCTGCAGAGCTTCAAGATAATGGATTAC
AGCCTCTTGATGTCAATCCATAATATAGATCATGCACAACGAGAGCCCTTAAGCAGTGAAACACAGTACT
CAGTTGATACTCGAAGACCGGCCCCCCAAAAGGCTCTGTATTCCACAGCCATGGAATCCATCCAGGGAGA
GGCTCGACGGGGTGGTACCATGGAGACTGATGACCATATGGGTGGCATCCCTGCCCGGAATAGTAAAGGG
GAAAGGCTTCTGCTTTATATTGGCATCATTGACATTCTACAGTCTTACAGGTTTGTTAAGAAGTTGGAGC
ACTCTTGGAAAGCCCTGGTACATGACGGAGACACTGTCTCAGTGCATCGCCCAGGCTTCTACGCTGAACG
GTTCCAGCGCTTCATGTGCAACACAGTATTTAAGAAGATTCCCTTGAAGCCTTCTCCTTCCAAAAAGTTT
CGGTCTGGCTCATCTTTCTCTCGGCGAGCAGGCTCCAGTGGCAACTCCTGCATTACTTACCAGCCATCGG
TCTCTGGGGAACACAAGGCACAAGTGACAACAAAGGCAGAAGTGGAGCCAGGCGTTCACCTTGGTCGTCC
TGATGTTTTACCTCAGACTCCACCTTTGGAGGAAATCAGTGAGGGCTCGCCTATTCCTGACCCCAGTTTC
TCACCTCTAGTTGGAGAGACTTTGCAAATGCTAACTACAAGTACAACCTTGGAAAAGCTTGAAGTTGCAG
AGTCAGAGTTCACCCATTAAGCGCAAAGCCTCAGAAGACCTGGAACAAGATTCTGCCATCTCTGTGATCC
CAAGATGTCAGCCCTTGCCCCAGCAATGCTGAATTTTCTTCTACTTGGTCATCAAAAAAGGAGTGTAATA
GAAGTGAGGGGAGCTGCTCCTCCATCTTCTTCCTGAAGAAGAACCTTCTCTCCTTCCTCTTCCTCATGAA

FIGURE 32 (CONT.)

```
TGGGCCTTAGTGCCTCAGAGAGTTGAGGACCGCAGCATCCCCTCCACTCCAGAGTTGGGTGGTACGGATT
TTCAACTGGCCAACCCTTTGCCTCCACTATTGAATTTTTTTCAGACCCCCATTCTTCATGCTGGAAATGG
GATTGCTGGACTTGGCAGCTTTCTTTCCCCTCGTCTTTGACTAGGAACCGGACTCTTAATTTCCTCAGGA
CAGACTAGCTGGCACATTATCCCTACCTTAGTTCTTTCTCTCTGACTCCTGGAAGAATACTCCTGTAATC
TCTGTAAAGGTTTTTGGGGGATAAGGGTGTTTAACCACCTCCCAGCTTTCTTCTTCTTTTTTTTTCTGA
AAAAAGGAAAAGCACACAGCACACAATTTCAAGCCATTTTCAGATCAGAACTCCAGAAGTGTTGACAAG
ATGCCTATTCGTAGAGTTCCCTCAGAAGAGCCATGGTGTTTATGAAGAGAAGAGTAGTGATTGCTCTGCC
AGAAGCAGCTCCTCTTTAAACTCCTCCTCTCTTGATGAATTTCTTAAGGCTGAAGGAATGAAGAGAGTGG
GACATGGGGTAATCTTTATCCCTTTTGTTAAAACAGGAGGCAGCCATGGGCTGGGAGATCATAGCCCTTC
CTAGGCAGAATCCTGTTCACTGCCAGGCTATAGTAATTATTACTATTTTGCAATTTGAAATATATTCTGG
TTGTTTTTCTAAATGTGAAGACTTACCAAATGAATTTTAGATCATTCTCCAGAGGAGATTTTTTTTGCTC
TTCTCATCTTTTCCAACAGTGTTCTCCTGTTTGTGGAGCTAAGGTAAAGAGGGGACACTTCTGTCTGTTT
AACAGACAGTCCATATCTGTGAGGCCAGCAAATATTTTCTTAAACTCATGGGGAGACAGCAGATTCTTGC
CTTGGTGAGGTCATTGCTGTGCCATATGTCCTACCCCCCTGTCTTCATGCAGGGAAGTTGGAAATGGGGG
CTACATATGCCCTCTCCTCCCCGTCTACAAGAGTTGTGGTTTTCCATCTGATCCTTCCACTCTTGTCAGG
GGAAGAAGGGGGCCTGGTATCTCAGGCAGATTGTTGAATTCCTGTTCTATCCCTTCTCTATCCCACCCTG
CCTTGATAATATGTTAGCCCATACCCCAAATAACTGTCTATATTAGACACCCCAGCCAGTTTCTGGCTG
CCTGTCTTTGCTGCCATGTTTTTTACAAGAAGGAAAGAATTCTTGCTATTTTTTTTCATAATTTACTAT
TTATGATGTATTTAAGTGTTTTATTAAGGACAGAGTTCTGTTAGGGGTGGGAGGGAATATTTGAGGGAGG
GCTGGGTCTTAGGGAAAGGAATGGGGAAGCAACATTTTTATTAAGTGTTACTATTTGCCTCTACTTTGTA
TTGTTCAGAAATGGCAAATACAATATAAAAGTGATATATGGTTTTAATGTAATAAACTTTAATGAGTTAT
TTA
```

FIGURE 33

```
SEQ ID NO: 6) PIPKIa Amino Acid Seq
>gi|4505815|ref|NP_003548.1| phosphatidylinositol-4-phosphate 5-kinase, type
I, alpha [Homo sapiens]
MASASSGPSSSVGFSSFDPAVPSCTLSSASGIKRPMASEVPYASGMPIKKIGHRSVDSSGETTYKKTTSS
ALKGAIQLGITHTVGSLSTKPERDVLMQDFYVVESIFFPSEGSNLTPAHHYNDFRFKTYAPVAFRYFREL
FGIRPDDYLYSLCSEPLIELCSSGASGSLFYVSSDDEFIIKTVQHKEAEFLQKLLPGYYMNLNQNPRTLL
PKFYGLYCVQAGGKNIRIVVMNNLLPRSVKMHIKYDLKGSTYKRRASQKEREKPLPTFKDLDFLQDIPDG
LFLDADMYNALCKTLQRDCLVLQSFKIMDYSLLMSIHNIDHAQREPLSSETQYSVDTRRPAPQKALYSTA
MESIQGEARRGGTMETDDHMGGIPARNSKGERLLLYIGIIDILQSYRFVKKLEHSWKALVHDGDTVSVHR
PGFYAERFQRFMCNTVFKKIPLKPSPSKKFRSGSSFSRRAGSSGNSCITYQPSVSGEHKAQVTTKAEVEP
GVHLGRPDVLPQTPPLEEISEGSPIPDPSFSPLVGETLQMLTTSTTLEKLEVAESEFTH
```

FIGURE 34

SEQ ID NO: 7) HO-1 cDNA Seq
>gi|4504436|ref|NM_002133.1| Homo sapiens heme oxygenase (decycling) 1 (HMOX1), mRNA TCAACGCCTGCCTCCCCTCGAGCGTCCTCAGCGCAGCCGCCGCCCGCGGAGCCAGCACGAACGAGCCCAG
CACCGGCCGGATGGAGCGTCCGCAACCCGACAGCATGCCCCAGGATTTGTCAGAGGCCCTGAAGGAGGCC
ACCAAGGAGGTGCACACCCAGGCAGAGAATGCTGAGTTCATGAGGAACTTTCAGAAGGGCCAGGTGACCC
GAGACGGCTTCAAGCTGGTGATGGCCTCCCTGTACCACATCTATGTGGCCCTGGAGGAGGAGATTGAGCG
CAACAAGGAGAGCCCAGTCTTCGCCCCTGTCTACTTCCCAGAAGAGCTGCACCGCAAGGCTGCCCTGGAG
CAGGACCTGGCCTTCTGGTACGGGCCCGCTGGCAGGAGGTCATCCCCTACACACCAGCCATGCAGCGCT
ATGTGAAGCGGCTCCACGAGGTGGGGCGCACAGAGCCCGAGCTGCTGGTGGCCCACGCCTACACCCGCTA
CCTGGGTGACCTGTCTGGGGGCCAGGTGCTCAAAAAGATTGCCCAGAAAGCCCTGGACCTGCCCAGCTCT
GGCGAGGGCCTGGCCTTCTTCACCTTCCCCAACATTGCCAGTGCCACCAAGTTCAAGCAGCTCTACCGCT
CCCGCATGAACTCCCTGGAGATGACTCCCGCAGTCAGGCAGAGGGTGATAGAAGAGGCCAAGACTGCGTT
CCTGCTCAACATCCAGCTCTTTGAGGAGTTGCAGGAGCTGCTGACCCATGACACCAAGGACCAGAGCCCC
TCACGGGCACCAGGGCTTCGCCAGCGGGCCAGCAACAAAGTGCAAGATTCTGCCCCGTGGAGACTCCCA
GAGGGAAGCCCCCACTCAACACCCGCTCCCAGGCTCCGCTTCTCCGATGGGTCCTTACACTCAGCTTTCT
GGTGGCGACAGTTGCTGTAGGGCTTTATGCCATGTGAATGCAGGCATGCTGGCTCCCAGGGCCATGAACT
TTGTCCGGTGGAAGGCCTTCTTTCTAGAGAGGGAATTCTCTTGGCTGGCTTCCTTACCGTGGGCACTGAA
GGCTTTCAGGGCCTCCAGCCCTCTCACTGTGTCCCTCTCTCTGGAAAGGAGGAAGGAGCCTATGGCATCT
TCCCCAACGAAAAGCACATCCAGGCAATGGCCTAAACTTCAGAGGGGGCGAAGGGGTCAGCCCTGCCCTT
CAGCATCCTCAGTTCCTGCAGCAGAGCCTGGAAGACACCCTAATGTGGCAGCTGTCTCAAACCTCCAAAA
GCCCTGAGTTTCAAGTATCCTTGTTGACACGGCCATGACCACTTTCCCCGTGGGCCATGGCAATTTTTAC
ACAAACCTGAAAAGATGTTGTGTCTTGTGTTTTTGTCTTATTTTGTTGGAGCCACTCTGTTCCTGGCTC
AGCCTCAAATGCAGTATTTTTGTTGTGTTCTGTTGTTTTTATAGCAGGGTTGGGGTGGTTTTTGAGCCAT
GCGTGGGTGGGGAGGGAGGTGTTTAACGGCACTGTGGCCTTGGTCTAACTTTTGTGTGAAATAATAAACA
ACATTGTCTG

FIGURE 35

SEQ ID NO: 8) HO-1 Amino Acid Seq
>gi|4504437|ref|NP_002124.1| heme oxygenase (decyclizing) 1 [Homo sapiens]
MERPQPDSMPQDLSEALKEATKEVHTQAENAEFMRNFQKGQVTRDGFKLVMASLYHIYVALEEEIERNKE
SPVFAPVYFPEELHRKAALEQDLAFWYGPRWQEVIPYTPAMQRYVKRLHEVGRTEPELLVAHAYTRYLGD
LSGGQVLKKIAQKALDLPSSGEGLAFFTFPNIASATKFKQLYRSRMNSLEMTPAVRQRVIEEAKTAFLLN
IQLFEELQELLTHDTKDQSPSRAPGLRQRASNKVQDSAPVETPRGKPPLNTRSQAPLLRWVLTLSFLVAT
VAVGLYAM

FIGURE 36

SEQ ID NO: 9) NQO1 cDNA Seq

>gi|70995356|ref|NM_000903.2| Homo sapiens NAD(P)H dehydrogenase, quinone 1 (NQO1), transcript variant 1, mRNA CCGCCCTTGTAGGCTGTCCACCTCAAACGGGCCGGACAGGATATATAAGAGAGAATGCACCGTGCACTAC
ACACGCGACTCCCACAAGGTTGCAGCCGGAGCCGCCCAGCTCACCGAGAGCCTAGTTCCGGCCAGGGTCG
CCCCGGCAACCACGAGCCCAGCCAATCAGCGCCCCGGACTGCACCAGAGCCATGGTCGGCAGAAGAGCAC
TGATCGTACTGGCTCACTCAGAGAGGACGTCCTTCAACTATGCCATGAAGGAGGCTGCTGCAGCGGCTTT
GAAGAAGAAAGGATGGGAGGTGGTGGAGTCGGACCTCTATGCCATGAACTTCAATCCCATCATTTCCAGA
AAGGACATCACAGGTAAACTGAAGGACCCTGCGAACTTTCAGTATCCTGCCGAGTCTGTTCTGGCTTATA
AAGAAGGCCATCTGAGCCCAGATATTGTGGCTGAACAAAAGAAGCTGGAAGCCGCAGACCTTGTGATATT
CCAGTTCCCCCTGCAGTGGTTTGGAGTCCCTGCCATTCTGAAAGGCTGGTTTGAGCGAGTGTTCATAGGA
GAGTTTGCTTACACTTACGCTGCCATGTATGACAAAGGACCCTTCCGGAGTAAGAAGGCAGTGCTTTCCA
TCACCACTGGTGGCAGTGGCTCCATGTACTCTCTGCAAGGGATCCACGGGGACATGAATGTCATTCTCTG
GCCAATTCAGAGTGGCATTCTGCATTTCTGTGGCTTCCAAGTCTTAGAACCTCAACTGACATATAGCATT
GGGCACACTCCAGCAGACGCCCGAATTCAAATCCTGGAAGGATGGAAGAAACGCCTGGAGAATATTTGGG
ATGAGACACCACTGTATTTTGCTCCAAGCAGCCTCTTTGACCTAAACTTCCAGGCAGGATTCTTAATGAA
AAAAGAGGTACAGGATGAGGAGAAAAACAAGAAATTTGGCCTTTCTGTGGGCCATCACTTGGGCAAGTCC
ATCCCAACTGACAACCAGATCAAAGCTAGAAAATGAGATTCCTTAGCCTGGATTTCCTTCTAACATGTTA
TCAAATCTGGGTATCTTTCCAGGCTTCCCTGACTTGCTTTAGTTTTTAAGATTTGTGTTTTTCTTTTTCC
ACAAGGAATAAATGAGAGGGAATCGACTGTATTCGTGCATTTTTGGATCATTTTTAACTGATTCTTATGA
TTACTATCATGGCATATAACCAAAATCCGACTGGGCTCAAGAGGCCACTTAGGGAAAGATGTAGAAAGAT
GCTAGAAAAATGTTCTTTAAAGGCATCTACACAATTTAATTCCTCTTTTTAGGGCTAAAGTTTTAGGGTA
CAGTTTGGCTAGGTATCATTCAACTCTCCAATGTTCTATTAATCACCTCTCTGTAGTTTATGGCAGAAGG
GAATTGCTCAGAGAAGGAAAAGACTGAATCTACCTGCCCTAAGGGACTTAACTTGTTTGGTAGTTAGCCA
TCTAATGCTTGTTTATGATATTTCTTGCTTTCAATTACAAAGCAGTTACTAATATGCCTAGCACAAGTAC
CACTCTTGGTCAGCTTTTGTTGTTTATATACAGTACACAGATACCTTGAAAGGAAGAGCTAATAAATCTC
TTCTTTGCTGCAGTCATCTACTTTTTTTTTAATTAAAAAAAATTTTTTTTGAAGCAGTCTTGCTCTGTT
ACCCAGGCTGGAGTGCAGTGGTGTGATCTCGGCTCACTGCAACCTCTGCCTCCCAGGTTCCAGCAATTCT
CCTGCCTCAGCCTCCCTAGTAGCTGGGATGACAGGCGCCTGCCATCATGCCTGACTAATTTTTGTATTTT
TAGTAGAGACGGCGTTTCACCATGTTGGCCAGGCTGGTCTCAAACTCCTGACCTCAGGTGATCCGCCTAC
CTCAGCCTCCCAAAGTGCTGGGATTACAGGCGTGATCCACCACACCTGGCCCTTGCAATCTTCTACTTTA
AGGTTTGCAGAGATAAACCAATAAATCCACACCGTACATCTGCAATATGAATTCAAGAAAGGAAATAGTA
CCTTCAATACTTAAAAATAGTCTTCCACAAAAAATACTTTATTTCTGATCTATACAAATTTTCAGAAGGT
TATTTTCTTTATCATTGCTAAACTGATGACTTACTATGGGATGGGGTCCAGTCCCATGACCTTGGGGTAC
AATTGTAAACCTAGAGTTTTATCAACTTTGGTGAACAGTTTTGGCATAATAGTCAATTTCTACTTCTGGA

FIGURE 36 (CONT.)

```
AGTCATCTCATTCCACTGTTGGTATTATATAATTCAAGGAGAATATGATAAAACACTGCCCTCTTGTGGT
GCATTGAAAGAAGAGATGAGAAATGATGAAAAGGTTGCCTGAAAAATGGGAGACAGCCTCTTACTTGCCA
AGAAAATGAAGGGATTGGACCGAGCTGGAAAACCTCCTTTACCAGATGCTGACTGGCACTGGTGGTTTTT
GCTCTCGACAGTATCCACAATAGCTGACGGCTGGGTGTTTCAGTTTGAAAATATTTTGTTGCCTTCATCT
TCACTGCAATTTTGTGTAAATTTCTCAAAGATCTGAATTAAATAAATAAAATTCATTTCTACAGACCCAC
AAAAAAAAAA
```

FIGURE 37

SEQ ID NO: 10) (NQO1) >gi|4505415|ref|NP_000894.1| NAD(P)H menadione oxidoreductase 1, dioxin-inducible isoform a [Homo sapiens]

MVGRRALIVLAHSERTSFNYAMKEAAAAALKKKGWEVVESDLYAMNFNPIISRKDITGKL
KDPANFQYPAESVLAYKEGHLSPDIVAEQKKLEAADLVIFQFPLQWFGVPAILKGWFERV
FIGEFAYTYAAMYDKGPFRSKKAVLSITTGGSGSMYSLQGIHGDMNVILWPIQSGILHFC
GFQVLEPQLTYSIGHTPADARIQILEGWKKRLENIWDETPLYFAPSSLFDLNFQAGFLMK
KEVQDEEKNKKFGLSVGHHLGKSIPTDNQIKARK

FIGURE 38

```
SEQ ID NO: 11.) (CKIαL) >uc003lqw.1 (CSNK1A1L) length=3149
CCTTTCCCAGAGTGCTCTGCGCCGTGAAGAAGCGGCTCCCGGGGACTGGGGGCATTTTGTGTTGGCTGGAGCTGGAG
TAACAAGATGGCGTCGTCCGCGGAGTGACAGGGGTCCCTCTGGGCCGGAGCCGGCGGCAGTGGTGGCAGCGGTATCG
CCGCCCTAGCTCACCGCGCCCCTTTTCCAGCCCGCGACGTCGCCGCGCAAGCGAGGCAGCGGCGGCCGCCGAGAAAC
AAGTGGCCCAGCCTGGTAACCGCCGAGAAGCCCTTCACAAACTGCGGCCTGGCAAAAAGAAACCTGACTGAGCGGCG
GTGATCAGGTTCCCCTCTGCTGATTCTGGGCCCCGAACCCCGGTAAAGGCCTCCGTGTTCCGTTTCCTGCCGCCCTC
CTCCGTAGCCTTGCCTAGTGTAGGAGCCCCGAGGCCTCCGTCCTCTTCCCAGAGGTGTCGGGGCTTGGCCCCAGCCT
CCATCTTCGTCTCTCAGGATGGCGAGTAGCAGCGGCTCCAAGGCTGAATTCATTGTCGGAGGGAAATATAAACTGGT
ACGGAAGATCGGGTCTGGCTCCTTCGGGGACATCTATTTGGCGATCAACATCACCAACGGCGAGGAAGTGGCAGTGA
AGCTAGAATCTCAGAAGGCCAGGCATCCCCAGTTGCTGTACGAGAGCAAGCTCTATAAGATTCTTCAAGGTGGGGTT
GGCATCCCCCACATACGGTGGTATGGTCAGGAAAAAGACTACAATGTACTAGTCATGGATCTTCTGGGACCTAGCCT
CGAAGACCTCTTCAATTTCTGTTCAAGAAGGTTCACAATGAAAACTGTACTTATGTTAGCTGACCAGATGATCAGTA
GAATTGAATATGTGCATACAAAGAATTTTATACACAGAGACATTAAACCAGATAACTTCCTAATGGGTATTGGGCGT
CACTGTAATAAGTGTTTAGAATCTCCAGTGGGGAAGAGGAAAAGAAGCATGACTGTTAGTACTTCTCAGGACCCATC
TTTCTCAGGATTAAACCAGTTATTCCTTATTGATTTTGGTTTGGCCAAAAAGTACAGAGACAACAGGACAAGGCAAC
ACATACCATACAGAGAAGATAAAAACCTCACTGGCACTGCCCGATATGCTAGCATCAATGCACATCTTGGTATTGAG
CAGAGTCGCCGAGATGACATGGAATCATTAGGATATGTTTTGATGTATTTTAATAGAACCAGCCTGCCATGGCAAGG
GCTAAAGGCTGCAACAAAGAAACAAAAATATGAAAAGATTAGTGAAAAGAAGATGTCCACGCCTGTTGAAGTTTTAT
GTAAGGGGTTTCCTGCAGAATTTGCGATGTACTTAAACTATTGTCGTGGGCTACGCTTTGAGGAAGCCCCAGATTAC
ATGTATCTGAGGCAGCTATTCCGCATTCTTTTCAGGACCCTGAACCATCAATATGACTACACATTTGATTGGACAAT
GTTAAAGCAGAAAGCAGCACAGCAGGCAGCCTCTTCCAGTGGGCAGGGTCAGCAGGCCCAAACCCCCACAGGCAAGC
AAACTGACAAAACCAAGAGTAACATGAAAGGTTTCTAAGCATGAATTGAGGAACAGAAGAAGCAGAGCAGATGATCG
GAGCAGCATTTGTTTCTCCCCAAATCTAGAAATTTTAGTTCATATGTACACTAGCCAGTGGTTGTGGACAACCATTT
ACTTGGTGTAAAGAACTTAATTTCAGTATAAACTGACTCTGGGCAGCATTGGTGATGCTGTATCCTGAGTTGTAGCC
TCTGTAATTGTGAATATTAACTGAGATAGTGAAACATGGTGTCCGGTTTTCTATTGCATTTTTTCAAGTGGAAAAGT
TAACTAAATGGTTGACACACAAAAATTGGTGGAGAAATTGTGCATATGCCAATTTTTTGTTAAAACCTTTTGTTTTG
AACTATACTGCTTTGAGATCTCATTTCAGAAGAACGGCATGAACAGTCTTCAGCCACAGTTGTGATGGTTGTTAAAT
GCTCACAATTGTGCATTCTTAGGGTTTTTCCATCCCTGGGGTTTGCAAGTTGTTCACTTAAAACATTCTTAAAATGG
TTGGCTTCTTGTCTGCAAGCCAGCTGATATGGTAGCAACCAAAGATTCCAGTGTTTGAGCATATGAAAGACTCTGCC
TGCTTAATTGTGCTAGAAATAACAGCATCTAAAGTGAAGACTTAAGAAAAACTTAGTGACTACTAGATTATCCTTAG
GACTCTGCATTAACTCTATAATGTTCTTGGTATTAAAAAAAAAAGCATATTTGTCACAGAAATTTAGTTAACATCTTA
CAACTGAACATGTATGTATGTTGCTTAGATAAATGTAATCACTGTAAACATCTATATGATCTGGGATTTTGTTTTTA
TTTTGAAATGGGAGCTTTTTTGTTTACAAGTTCATTAAAAACTAAAAACTGTTTCTGTAAGGAAATGAGATTTTTTT
TAAACAACAAAAAATGCCTTGCTGACTCACTATTAAATAAAAATCTCCCCAATTTTTTGATAGACTACTTCAAGCCA
TTTGTTACATGGTATTCCTTTGCAAGTCAATTTAGGTTTCGTGTTATAACTTTTCCTCTTTTTTTAAGAAAAATGAA
```

FIGURE 38 (CONT.)

```
AAAAGTAATTCTTTTGTCTGAAGGGGAAAGGCATTCTTTCATTTTTTTCTTTTTTTTTTTTTTTTTATGACTTGC
AGGCACAATATCTAGTACTGCAACTGCCAGAACTTGGTATTGTAGCTGCTGCCCGCTGACTAGCAGCTGGACTGATT
TTGAATAAAAATGAAAGCATTAAAGGGTTTCCCTACAAAACATTTTTCTTTAAAATACTTTTGAAATGGCTATAAGC
AGTTGACTTTCACCCTTGGAGAGCATCACACTGTGTGAGGTTCAGTGATTGTTGACCCTCCCCAGCCCCTCCTGCTT
CTTTAAGTTATCTGTGTGCGTGCGCTTCCTCTCAATCTTCTTTGCACGCTCATTTCTTTTTCTCTGACCCATGAGAA
AGGAAAACTTACTGATGATAATTTTTAAATAGTGTAATTTATTCATTTATAGCATGTCAGGATAAATTAAAAGAACA
TTTGTCTGGAAATGCTGCCGGGAGCCTATTGTGTAAATGTAGGTATTTTGTAAAATAACCTTGAAATTG
```

FIGURE 39

```
SEQ ID NO: 12.) (CKIαL) >uc003lqw.1 (CSNK1A1L) length=365
MASSSGSKAEFIVGGKYKLVRKIGSGSFGDIYLAINITNGEEVAVKLESQKARHPQLLYESKLYKILQGGVGIPHIR
WYGQEKDYNVLVMDLLGPSLEDLFNFCSRRFTMKTVLMLADQMISRIEYVHTKNFIHRDIKPDNFLMGIGRHCNKCL
ESPVGKRKRSMTVSTSQDPSFSGLNQLFLIDFGLAKKYRDNRTRQHIPYREDKNLTGTARYASINAHLGIEQSRRDD
MESLGYVLMYFNRTSLPWQGLKAATKKQKYEKISEKKMSTPVEVLCKGFPAEFAMYLNYCRGLRFEEAPDYMYLRQL
FRILFRTLNHQYDYTFDWTMLKQKAAQQAASSSGQGQQAQTPTGKQTDKTKSNMKGF
```

FIGURE 40

SEQ ID NO: 13.), (CKIαS) >uc003lqx.1 (CSNK1A1S) length=3065
CCTTTCCCAGAGTGCTCTGCGCCGTGAAGAAGCGGCTCCCGGGGACTGGGGGCATTTTGTGTTGGCTGGAGCTGGAG
TAACAAGATGGCGTCGTCCGCGGAGTGACAGGGGTCCCTCTGGGCCGGAGCCGGCGGCAGTGGTGGCAGCGGTATCG
CCGCCCTAGCTCACCGCGCCCCTTTTCCAGCCCGCGACGTCGCCGCGCAAGCGAGGCAGCGGCGGCCGCCGAGAAAC
AAGTGGCCCAGCCTGGTAACCGCCGAGAAGCCCTTCACAAACTGCGGCCTGGCAAAAAGAAACCTGACTGAGCGGCG
GTGATCAGGTTCCCCTCTGCTGATTCTGGGCCCCGAACCCCGGTAAAGGCCTCCGTGTTCCGTTTCCTGCCGCCCTC
CTCCGTAGCCTTGCCTAGTGTAGGAGCCCCGAGGCCTCCGTCCTCTTCCCAGAGGTGTCGGGGCTTGGCCCCAGCCT
CCATCTTCGTCTCTCAGGATGGCGAGTAGCAGCGGCTCCAAGGCTGAATTCATTGTCGGAGGGAAATATAAACTGGT
ACGGAAGATCGGGTCTGGCTCCTTCGGGGACATCTATTTGGCGATCAACATCACCAACGGCGAGGAAGTGGCAGTGA
AGCTAGAATCTCAGAAGGCCAGGCATCCCCAGTTGCTGTACGAGAGCAAGCTCTATAAGATTCTTCAAGGTGGGGTT
GGCATCCCCCACATACGGTGGTATGGTCAGGAAAAAGACTACAATGTACTAGTCATGGATCTTCTGGGACCTAGCCT
CGAAGACCTCTTCAATTTCTGTTCAAGAAGGTTCACAATGAAAACTGTACTTATGTTAGCTGACCAGATGATCAGTA
GAATTGAATATGTGCATACAAAGAATTTTATACACAGAGACATTAAACCAGATAACTTCCTAATGGGTATTGGGCGT
CACTGTAATAAGTTATTCCTTATTGATTTTGGTTTGGCCAAAAAGTACAGAGACAACAGGACAAGGCAACACATACC
ATACAGAGAAGATAAAAACCTCACTGGCACTGCCCGATATGCTAGCATCAATGCACATCTTGGTATTGAGCAGAGTC
GCCGAGATGACATGGAATCATTAGGATATGTTTTGATGTATTTTAATAGAACCAGCCTGCCATGGCAAGGGCTAAAG
GCTGCAACAAAGAAACAAAAATATGAAAAGATTAGTGAAAAGAAGATGTCCACGCCTGTTGAAGTTTTATGTAAGGG
GTTTCCTGCAGAATTTGCGATGTACTTAAACTATTGTCGTGGGCTACGCTTTGAGGAAGCCCCAGATTACATGTATC
TGAGGCAGCTATTCCGCATTCTTTTCAGGACCCTGAACCATCAATATGACTACACATTTGATTGGACAATGTTAAAG
CAGAAAGCAGCACAGCAGGCAGCCTCTTCCAGTGGGCAGGGTCAGCAGGCCCAAACCCCCACAGGCAAGCAAACTGA
CAAAACCAAGAGTAACATGAAAGGTTTCTAAGCATGAATTGAGGAACAGAAGAAGCAGAGCAGATGATCGGAGCAGC
ATTTGTTTCTCCCCAAATCTAGAAATTTTAGTTCATATGTACACTAGCCAGTGGTTGTGGACAACCATTTACTTGGT
GTAAAGAACTTAATTTCAGTATAAACTGACTCTGGGCAGCATTGGTGATGCTGTATCCTGAGTTGTAGCCTCTGTAA
TTGTGAATATTAACTGAGATAGTGAAACATGGTGTCCGGTTTTCTATTGCATTTTTTCAAGTGGAAAAGTTAACTAA
ATGGTTGACACACAAAAATTGGTGGAGAAATTGTGCATATGCCAATTTTTTGTTAAAACCTTTTGTTTTGAACTATA
CTGCTTTGAGATCTCATTTCAGAAGAACGGCATGAACAGTCTTCAGCCACAGTTGTGATGGTTGTTAAATGCTCACA
ATTGTGCATTCTTAGGGTTTTTCCATCCCTGGGGTTTGCAAGTTGTTCACTTAAAACATTCTTAAAATGGTTGGCTT
CTTGTCTGCAAGCCAGCTGATATGGTAGCAACCAAAGATTCCAGTGTTTGAGCATATGAAAGACTCTGCCTGCTTAA
TTGTGCTAGAAATAACAGCATCTAAAGTGAAGACTTAAGAAAAACTTAGTGACTACTAGATTATCCTTAGGACTCTG
CATTAACTCTATAATGTTCTTGGTATTAAAAAAAAAGCATATTTGTCACAGAAATTTAGTTAACATCTTACAACTGA
ACATGTATGTATGTTGCTTAGATAAATGTAATCACTGTAAACATCTATATGATCTGGGATTTTGTTTTTATTTTGAA
ATGGGAGCTTTTTTGTTTACAAGTTCATTAAAAAACTAAAAACTGTTTCTGTAAGGAAATGAGATTTTTTTAAACAA
CAAAAAATGCCTTGCTGACTCACTATTAAATAAAAATCTCCCCAATTTTTTGATAGACTACTTCAAGCCATTTGTTA
CATGGTATTCCTTTGCAAGTCAATTTAGGTTTCGTGTTATAACTTTTCCTCTTTTTTTAAGAAAAATGAAAAAAGTA
ATTCTTTTGTCTGAAGGGGAAAGGCATTCTTTCATTTTTTTCTTTTTTTTTTTTTTTTTATGACTTGCAGGCACA

FIGURE 40 (CONT.)

ATATCTAGTACTGCAACTGCCAGAACTTGGTATTGTAGCTGCTGCCCGCTGACTAGCAGCTGGACTGATTTTGAATA
AAAATGAAAGCATTAAAGGGTTTCCCTACAAAACATTTTTCTTTAAAATACTTTTGAAATGGCTATAAGCAGTTGAC
TTTCACCCTTGGAGAGCATCACACTGTGTGAGGTTCAGTGATTGTTGACCCTCCCCAGCCCCTCCTGCTTCTTTAAG
TTATCTGTGTGCGTGCGCTTCCTCTCAATCTTCTTTGCACGCTCATTTCTTTTTCTCTGACCCATGAGAAAGGAAAA
CTTACTGATGATAATTTTTAAATAGTGTAATTTATTCATTTATAGCATGTCAGGATAAATTAAAAGAACATTTGTCT
GGAAATGCTGCCGGGAGCCTATTGTGTAAATGTAGGTATTTTGTAAAATAACCTTGAAATTG

FIGURE 41

SEQ ID NO: 14.) (CKIαS) >uc003lqx.1 (CSNK1A1S) length=337
MASSSGSKAEFIVGGKYKLVRKIGSGSFGDIYLAINITNGEEVAVKLESQKARHPQLLYESKLYKILQGGVGIPHIR
WYGQEKDYNVLVMDLLGPSLEDLFNFCSRRFTMKTVLMLADQMISRIEYVHTKNFIHRDIKPDNFLMGIGRHCNKLF
LIDFGLAKKYRDNRTRQHIPYREDKNLTGTARYASINAHLGIEQSRRDDMESLGYVLMYFNRTSLPWQGLKAATKKQ
KYEKISEKKMSTPVEVLCKGFPAEFAMYLNYCRGLRFEEAPDYMYLRQLFRILFRTLNHQYDYTFDWTMLKQKAAQQ
AASSSGQGQQAQTPTGKQTDKTKSNMKGF

FIGURE 42

SEQ ID NO: 15.) (CKIα) >uc003lqv.1 (CSNK1A1) length=2544 (truncated variant...)
CAGCTTTTCACTTCTTCTTGTAGTCGCGACTTGGAGTTTTGCTAATGTCTCCCTCCTTTCCTAAGTGACATTGAATC
CGTAGGGATGTTGATGCCATCATCCCCTCTTTCCCCTGCAGGAAGTGGCAGTGAAGCTAGAATCTCAGAAGGCCAGG
CATCCCCAGTTGCTGTACGAGAGCAAGCTCTATAAGATTCTTCAAGGTGGGGTTGGCATCCCCCACATACGGTGGTA
TGGTCAGGAAAAAGACTACAATGTACTAGTCATGGATCTTCTGGGACCTAGCCTCGAAGACCTCTTCAATTTCTGTT
CAAGAAGGTTCACAATGAAAACTGTACTTATGTTAGCTGACCAGATGATCAGTAGAATTGAATATGTGCATACAAAG
AATTTTATACACAGAGACATTAAACCAGATAACTTCCTAATGGGTATTGGGCGTCACTGTAATAAGTTATTCCTTAT
TGATTTTGGTTTGGCCAAAAAGTACAGAGACAACAGGACAAGGCAACACATACCATACAGAGAAGATAAAAACCTCA
CTGGCACTGCCCGATATGCTAGCATCAATGCACATCTTGGTATTGAGCAGAGTCGCCGAGATGACATGGAATCATTA
GGATATGTTTTGATGTATTTTAATAGAACCAGCCTGCCATGGCAAGGGCTAAAGGCTGCAACAAAGAAACAAAAATA
TGAAAAGATTAGTGAAAAGAAGATGTCCACGCCTGTTGAAGTTTTATGTAAGGGGTTTCCTGCAGAATTTGCGATGT
ACTTAAACTATTGTCGTGGGCTACGCTTTGAGGAAGCCCCAGATTACATGTATCTGAGGCAGCTATTCCGCATTCTT
TTCAGGACCCTGAACCATCAATATGACTACACATTTGATTGGACAATGTTAAAGCAGAAAGCAGCACAGCAGGCAGC
CTCTTCCAGTGGGCAGGGTCAGCAGGCCCAAACCCCCACAGGTTTCTAAGCATGAATTGAGGAACAGAAGAAGCAGA
GCAGATGATCGGAGCAGCATTTGTTTCTCCCCAAATCTAGAAATTTTAGTTCATATGTACACTAGCCAGTGGTTGTG
GACAACCATTTACTTGGTGTAAAGAACTTAATTTCAGTATAAACTGACTCTGGGCAGCATTGGTGATGCTGTATCCT
GAGTTGTAGCCTCTGTAATTGTGAATATTAACTGAGATAGTGAAACATGGTGTCCGGTTTTCTATTGCATTTTTTCA
AGTGGAAAAGTTAACTAAATGGTTGACACACAAAAATTGGTGGAGAAATTGTGCATATGCCAATTTTTTGTTAAAAC
CTTTTGTTTTGAACTATACTGCTTTGAGATCTCATTTCAGAAGAACGGCATGAACAGTCTTCAGCCACAGTTGTGAT
GGTTGTTAAATGCTCACAATTGTGCATTCTTAGGGTTTTTCCATCCCTGGGGTTTGCAAGTTGTTCACTTAAAACAT
TCTTAAAATGGTTGGCTTCTTGTCTGCAAGCCAGCTGATATGGTAGCAACCAAAGATTCCAGTGTTTGAGCATATGA
AAGACTCTGCCTGCTTAATTGTGCTAGAAATAACAGCATCTAAAGTGAAGACTTAAGAAAAACTTAGTGACTACTAG
ATTATCCTTAGGACTCTGCATTAACTCTATAATGTTCTTGGTATTAAAAAAAAAGCATATTTGTCACAGAAATTTAG
TTAACATCTTACAACTGAACATGTATGTATGTTGCTTAGATAAATGTAATCACTGTAAACATCTATATGATCTGGGA
TTTTGTTTTTATTTTGAAATGGGAGCTTTTTTGTTTACAAGTTCATTAAAAACTAAAAACTGTTTCTGTAAGGAAAT
GAGATTTTTTTAAACAACAAAAAATGCCTTGCTGACTCACTATTAAATAAAAATCTCCCCAATTTTTTGATAGACT
ACTTCAAGCCATTTGTTACATGGTATTCCTTTGCAAGTCAATTTAGGTTTCGTGTTATAACTTTTCCTCTTTTTTTA
AGAAAAATGAAAAAAGTAATTCTTTTGTCTGAAGGGGAAAGGCATTCTTTCATTTTTTTCTTTTTTTTTTTTTTTTT
TTATGACTTGCAGGCACAATATCTAGTACTGCAACTGCCAGAACTTGGTATTGTAGCTGCTGCCCGCTGACTAGCAG
CTGGACTGATTTTGAATAAAAATGAAAGCATTAAAGGGTTTCCCTACAAAACATTTTTCTTTAAAATACTTTTGAAA
TGGCTATAAGCAGTTGACTTTCACCCTTGGAGAGCATCACACTGTGTGAGGTTCAGTGATTGTTGACCCTCCCCAGC
CCCTCCTGCTTCTTTAAGTTATCTGTGTGCGTGCGCTTCCTCTCAATCTTCTTTGCACGCTCATTTCTTTTTCTCTG
ACCCATGAGAAAGGAAAACTTACTGATGATAATTTTTAAATAGTGTAATTTATTCATTTATAGCATGTCAGGATAAA
TTAAAAGAACATTTGTCTGGAAATGCTGCCGGGAGCCTATTGTGTAAATGTAGGTATTTTGTAAAATAACCTTGAAA
TTG

FIGURE 43

SEQ ID NO: 16.) >uc003lqv.1 (CSNK1A1) length=236
MDLLGPSLEDLFNFCSRRFTMKTVLMLADQMISRIEYVHTKNFIHRDIKPDNFLMGIGRHCNKLFLIDFGLAKKYRD
NRTRQHIPYREDKNLTGTARYASINAHLGIEQSRRDDMESLGYVLMYFNRTSLPWQGLKAATKKQKYEKISEKKMST
PVEVLCKGFPAEFAMYLNYCRGLRFEEAPDYMYLRQLFRILFRTLNHQYDYTFDWTMLKQKAAQQAASSSGQGQQAQ
TPTGF

POLY(A) POLYMERASE

CROSS-REFERENCE TO RELATED PATENT APPLICATIONS

This application claims the benefit of U.S. Provisional Application No. 60/953,116, filed Jul. 31, 2007, and U.S. Provisional Application No. 61/030,169, filed Feb. 20, 2008, both of which are incorporated herein by reference in their entirety.

GOVERNMENT SUPPORT

The invention was made with United States government support awarded by the following agency: NIH GM051968. The United States government has certain rights in this invention.

FIELD OF THE INVENTION

The invention relates generally to novel poly(A) polymerases. More specifically, the invention relates to poly(A) polymerases whose activity can be directly modulated by components of the phosphatidylinositol signaling pathways, including phosphatidylinositol phosphate kinases and the phosphoinositide second messengers generated by the kinases.

BACKGROUND OF THE INVENTION

The following discussion of the background is merely provided to aid the reader in understanding the invention and is not admitted to describe or constitute prior art to the invention.

Phosphatidylinositol based signaling pathways play crucial roles in the regulation of cell processes at the plasma membrane and in the nucleus. Two components of such pathways include phosphatidylinositol phosphate kinases and the phosphoinositide second messengers generated by these kinases.

In mammalian cells, there are two types of phosphatidylinositol phosphate kinases: Type I and Type II. Both types generate phosphoinositide second messengers. There are at least three isoforms of type I phosphatidylinositol phosphate kinase ("PIPKI") termed α, β, and γ. All are differentially expressed spatially and temporally, thereby providing a mechanism of control of second messenger generation. Of the three type I PIP kinases, only PIPKIα targets to nuclear speckles, structures within the nucleus of mammalian cells that are enriched in pre-messenger RNA splicing factors.

The Type I PIPKIs, including PIPKIα, are the major producers of a second messenger named phosphatidylinositol-4, 5-bisphosphate ("PI4,5$P_2$"). PI4,5$P_2$ is a phospholipid which plays a role in the regulation of many cellular signaling pathways, and though it is maintained at relatively constant levels in cells, it is hypothesized that small local changes in the spatial and temporal synthesis of PI4,5$P_2$ defines its role as a second messenger. PI4,5$P_2$ is present in the nucleus of mammalian cells, and was found to co-immunoprecipitate with snRNPs, the hyperphosphorylated form of RNA Pol II, and snRNAs, suggesting that PI4,5$P_2$, and thus PIPKIα, may play a role in the processing of mRNA.

Accordingly, due to the importance of PIPKIα and the second messenger PI4,5$P_2$ in numerous cellular pathways, identification of nuclear proteins that are directly modulated by these molecules was undertaken to better understand the control of nuclear functions, including protein expression and message regulation.

SUMMARY OF THE INVENTION

The compositions, methods and kits described herein relate to novel poly(A) polymerases, termed phosphatidylinositol phosphate regulated poly(A) polymerases or "PIP-PAPs." Like known poly(A) polymerases, PIP-PAPs add adenosyl residues to the 3' end of polynucleotides. Unlike other known poly(A) polymerases, the activity of PIP-PAPs may be directly modulated by components of the phosphatidylinositol based signaling pathways including phosphoinositides second messengers such as PI4,5$P_2$ and/or phosphatidylinositol phosphate kinase ("PIP kinase"), such as PIPKIα. These proteins are useful in that they provide a novel nuclear regulatory mechanism and thereby a new means to control and regulate protein expression. These PIP-PAPs provide a means to regulate or control nucleic acid polyadenylation in vitro and in vivo. Thus, in various aspects the present invention provides compositions, including polynucleotides encoding PIP-PAPs, polypeptides having PIP-PAP activity, and antibodies that bind PIP-PAPs, methods of making and using the compositions, and kits comprising the compositions. One exemplary PIP-PAP, termed Speckle Targeting and PIPKIα Regulated Poly(A) Polymerase or "Star-PAP" is shown in SEQ ID NO: 1 and SEQ ID NO: 2 (FIG. 28 and FIG. 29).

In accordance with one aspect of the invention there are provided isolated polynucleotides encoding novel PIP-PAP polypeptides and their homologues, wherein the polypeptides have a poly(A) polymerase activity which is directly modulated by a second messenger of the phosphatidylinositol signaling pathway. Other embodiments may include isolated polynucleotides encoding variants of the novel PIP-PAP polypeptides and fragments of the novel PIP-PAP polypeptides. In still other embodiments, complements to such polynucleotides are provided.

In some embodiments, the polynucleotide sequence may encode a polypeptide sequence having at least about 50%, at least about 60%, at least about 70%, at least about 80%, at least about 90% or at least about 95% sequence identity to SEQ ID NO: 2. In other embodiments, a polynucleotide sequence encodes the polypeptide of SEQ ID NO: 2. In still other embodiments the polynucleotide includes SEQ ID NO: 1. In yet further embodiments, the polynucleotide sequence may have at least about 50%, at least about 60%, at least about 70%, at least about 80%, at least about 90% or at least about 95% sequence identity to SEQ ID NO: 1.

Compositions described herein may also include polynucleotides encoding fragments, domains or functional fragments of the novel PIP-PAPs such as Star-PAP. In other embodiments, complements of such fragments are provided. By way of example, but not by way of limitation, such fragments may include polynucleotides encoding the polypeptides of the poly(A) polymerase function of Star-PAP, and/or the PIPKIα binding domain function of Star-PAP, and/or a zinc finger domain of Star-PAP. Also provided are polynucleotides encoding variants of such fragments and protein fusions including such fragments. Protein fusions may be used, for example, to expedite protein purification, to alter protein solubility, or to generate antibodies.

In still other embodiments, fragments of Star-PAP include functional domains of the full-length molecule. By way of example, but not by way of limitation, fragments of Star-PAP include the following: amino acids 1-547; amino acids 1-328;

amino acids 557-874; amino acids 16-46; amino acids 56-128; amino acids 197-221 and amino acids 357-447 (together or individually); amino acids 229-310; amino acids 575-587; amino acids 640-643 and 659-662.

In some embodiments, the polynucleotide may be a DNA molecule and may act as a primer or a probe; in other embodiments, the polynucleotide may be an RNA molecule. In some embodiments, the polynucleotide may function as an siRNA or as an antisense molecule. In some embodiments, the polynucleotide may include one or more detectable labels, such as fluorescent or radioactive labels.

In some embodiments, a polynucleotide encoding a PIP-PAP or fragment thereof may be contained in a vector such as an expression vector. Expression vectors may contain control sequences to which the polynucleotide is operably linked; accordingly, in some embodiments, the control sequence may direct the production of a polypeptide in a host cell. In still other embodiments, the vector may be introduced into an isolated host cell. The host cell may be prokaryotic or eukaryotic, and may include bacterial cells, yeast cells, mammalian cells and plant cells. In particular embodiments, *Escherichia coli* cells are used.

In some aspects of the present invention there are provided methods for producing a polypeptide encoding a PIP-PAP or a fragment or a variant thereof. In some embodiments, cells containing an expression vector carrying a polynucleotide encoding the PIP-PAP or a fragment or variant thereof may be cultured under conditions suitable for expression of the polypeptide. In such embodiments, the polynucleotide encoding the polypeptide may be operably linked to a promoter sequence. Additionally, the polypeptide so produced may be isolated. In particular embodiments, the expressed polypeptide may be SEQ ID NO: 2 or a fragment or a variant thereof; in other embodiments, the polynucleotide encoding the PIP-PAP may be SEQ ID NO: 1 or a fragment or a variant thereof.

Other aspects relate to polypeptide sequences encoding PIP-PAPs such as Star-PAP or functional fragments thereof. In some embodiments, the polypeptide has poly(A) polymerase activity which can be directly modulated (e.g., enhanced) by a component of the phosphatidylinositol signaling pathway; exemplary components may include phosphoinositide second messengers such as PI4,5P$_2$ or may include PIP kinases such as PIPKIα. In some embodiments, the phosphatidylinositol pathway component may directly interact with and bind the PIP-PAP. In further embodiments, the polypeptide may have an amino acid sequence which has at least about 50%, at least about 60%, at least about 70%, at least about 80%, at least about 90% or at least about 95% sequence identity with SEQ ID NO: 2. In some embodiments, the polypeptide is Star-PAP, as shown in SEQ ID NO: 2.

In some embodiments, variants of Star-PAP may include amino acid substitutions, deletions and insertions. In some embodiments, variants or fragments of Star-PAP maintain at least some level of function found in the non-variant form (e.g., poly(A) polymerase function or PIPKIα binding function). In some embodiments, variants include 1-5 amino acid substitutions; in other embodiments, variants include 6-10 amino acid substitutions. In still other embodiments, variants include 10-20 amino acid substitutions. In further embodiments, variants include 20 or more amino acid substitutions.

In some embodiments, the Star-PAP polypeptide, a variant or a fragment thereof may be linked to a heterologous polypeptide, a detectable maker or both. Heterologous polypeptides and detectable markers may be used, for example, to aid in purification, protein identification, solubility, or protein targeting, for example, within the body or within a cell.

Some aspects of the present invention relate to antibodies capable of specifically binding to a PIP-PAP, PIP-PAP variants, or a fragments thereof. In some embodiments, the antibody is a monoclonal antibody that specifically binds to a polypeptide of SEQ ID NO: 2, or to a polypeptide having at least about 50%, at least about 60%, at least about 70%, at least about 80%, at least about 90% or at least about 95% sequence identity to SEQ ID NO: 2 or a fragment thereof. In other embodiments, the antibody is a polyclonal antibody that specifically binds to an amino acid sequence having at least about 50%, at least about 60%, at least about 70%, at least about 80%, at least about 90% or at least about 95% sequence identity to SEQ ID NO 2, or a fragment thereof. In still other embodiments, the antibody binds to a chimeric peptide, wherein the chimeric peptide includes all or a fragment of SEQ ID NO: 2, or a variant of SEQ ID NO: 2. In some embodiments, the antibody is a chimeric antibody, an antibody fragment (e.g., a Fab, F(ab')2, Fv and single chain), a human antibody, or a humanized antibody.

In some aspects, the novel PIP-PAP, such as Star-PAP is used in vitro to polyadenylate a target nucleic acid. For example, in some embodiments, Star-PAP is combined in vitro with at least the following components: a target polynucleotide sequence, ATP, and a Star-PAP polypeptide (e.g., as shown in SEQ ID NO: 2), a variant or a fragment thereof, under polyadenylation conditions. In some embodiments, PI4,5P$_2$ (also termed "PtdIns4,5P$_2$") is added to the polyadenylation reaction. In some embodiments, a Star-PAP fragment is used. In other embodiments, a Star-PAP variant is used. For example, in some embodiments, a polypeptide lacking the zinc finger domain is used. In yet other embodiments, the Star-PAP polypeptide, fragment or variant is linked to a heterologous polypeptide.

In other aspects, a method for determining Star-PAP targets is provided. For example, Star-PAP, a variant or fragment thereof is expressed in a bacterial or mammalian test cell. Messenger RNA from the test cell is isolated and compared with the same messenger RNA isolated from a control cell. In some aspects, the level or amount of one or more messenger RNAs is compared between the test cell and the control cell. In other aspects, the level or amount of uncleaved pre-messenger RNA is compared (for one or more specific messenger RNAs) between the test cell and control cell.

In some aspects, methods for modulating the activity of a PIP-PAP, such as Star-PAP, are provided. In some embodiments, methods to modulate the poly(A) polymerase activity of Star-PAP are provided. Such methods include contacting a cell expressing Star-PAP with one or more of an antibody that specifically binds SEQ ID NO: 2, a variant or a fragment thereof, and/or an siRNA that specifically binds to SEQ ID NO: 1 or a portion of SEQ ID NO: 1. In embodiments, the antibody can be a polyclonal, monoclonal, a Fab fragment, a F(ab')2 fragment, a FV fragment, a single chain antibody, a chimeric antibody, a human antibody, a humanized antibody, or a combination of these antibodies. In some embodiments, the cell is a mammalian cell. In other embodiments, the cell is a bacterial cell. In some embodiments, Star-PAP expression or activity is greater in the subject cell than in a normal cell of the same cell type.

Further aspects include methods for identifying agents which modulate the activity of a PIP-PAP such as Star-PAP, or fragments or variants thereof. In some embodiments, the methods include exposing a PIP-PAP, for example, Star-PAP, to a test agent and determining whether the agent modulates Star-PAP activity, or the activity of a Star-PAP fragment or variant.

In some embodiments, the poly(A) polymerase activity of Star-PAP, a Star-PAP fragment or variant is evaluated for modulation. Thus, in some embodiments, the modulation of Star-PAP activity is evaluated in the presence of a polyadenylation target.

In other embodiments, the ability of PIPKIα to bind Star-PAP, a Star-PAP fragment or variant is evaluated for modulation. In some embodiments, a fragment of PIPKIα (e.g., amino acids 440-562 of PIPKIα) is used to evaluate modulation of Star-PAP/PIPKIα binding.

Other aspects relate to methods to identify agents which modulate (e.g., inhibit or enhance) a PIP-PAP, such as Star-PAP, binding to a PIP kinase, such as PIPKIα. In some embodiments, the methods include contacting Star-PAP with a test agent in the presence of PIPKIα and determining whether the test agent modulates the binding of PIPKIα to Star-PAP. In other embodiments, the ability of PIPKIα to bind Star-PAP, a Star-PAP fragment or variant is evaluated for modulation. In some embodiments, a fragment of PIPKIα (e.g., amino acids 440-562 of PIPKIα) is used to evaluate the modulation of Star-PAP/PIPKIα binding in the presence of a test agent. In further embodiments, a fragment of PIPKIα and a fragment of Star-PAP may be used. In some embodiments, the methods are performed in vitro; in other embodiments, the methods are performed in vivo.

In some embodiments, the modulation of Star-PAP activity, or the activity of a fragment or variant of Star-PAP, is evaluated in the presence of a phosphoinositide second messenger such as PI4,5P$_2$. In some embodiments, the method is be performed in vivo; in other embodiments, the method is be performed in vitro.

Other aspects include methods to screen for agents which bind to a PIP-PAP such as Star-PAP, a fragment of Star-PAP, or variants thereof. In some methods, a polypeptide comprising a PIP-PAP such as Star-PAP or a fragment or a variant thereof may be combined, under suitable conditions, with one or more test agents. Binding of the test agent to the PIP-PAP (such as Star-PAP) may then be detected.

In other embodiments the activity of Star-PAP may be determined by evaluating the level of expression (e.g., mRNA level) of one or more Star-PAP targets. Exemplary Star-PAP targets include but are not limited to prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). In particular embodiments, HO-1 mRNA levels may be evaluated to determine whether an agent modulates the activity of Star-PAP. In other embodiments, NQO1 levels may be evaluated to determine whether an agent modulates the activity of Star-PAP. In still other embodiments, CHAC1 levels may be evaluated to determine whether an agent modulates the activity of Star-PAP. Such methods may be performed in vivo or in vitro. An example of such an assay method is presented below along with two compounds that modulate HO-1 and NQO1 expression via Star-PAP and protein kinase CKI.

Star-PAP activity may be tested in the presence or absence of a PIP kinase, such as PIPKIα, or in the presence or absence of a phosphoinositide, for example, PI4,5P$_2$.

Other aspects of the invention include methods of treating a disease or characterized by HO-1 over-expression or over-activity in a patient. In some embodiments, the method includes: administering to the patient a therapeutic compound which down-modulates Star-PAP expression, activity, or both, thereby decreasing the amount of HO-1. In some embodiments the therapeutic compound includes an siRNA which hybridizes to SEQ ID NO: 1 or to a portion of SEQ ID NO: 1; in other embodiments, the therapeutic compound includes an antibody.

Still other aspects of the invention include methods of treating a disease or disorder characterized by enhanced HO-1 expression or activity in a patient. In some embodiments, the method includes: administering to the patient a therapeutic compound which further enhances Star-PAP expression, activity or both, thereby increasing the amount of HO-1.

Still other aspects of the invention includes methods of treating a disease or disorder characterized by aberrant expression of a gene in a patient. In some embodiments, the method includes administering to the patient a therapeutic compound which modulates Star-PAP expression, activity, or both, thereby modulating expression of the gene. In some embodiments, the gene is one or more of the following: prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene ("WHSC1"), microfibrillar associated protein 5 ("MFAP5"), β-crystalline A ("β-CryA"), NAD(P)H dehydrogenase, quinine 1 ("NQO1"), glutamate cysteine ligase catalytic subunit ("GCLC"), glutathione S-transferase A4 ("GSTA4"), glutamate-cysteine ligase, modifier subunit ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). In other embodiments, the gene is one or more of the genes presented in the tables of FIG. 10 and FIG. 18.

Other aspects of the invention described herein include kits. The kits may include one or more oligonucleotides which can hybridize under stringent conditions to one or more of the following: 1) a polynucleotide encoding a polypeptide of SEQ ID NO: 2; 2) a polynucleotide sequence encoding a polypeptide having at least about 50%, at least about 60%, at least about 70%, at least about 80%, at least about 90% or at least about 95% sequence identity to SEQ ID NO: 2; 3) a polynucleotide degenerate to (2) due to the genetic code; 4) a polynucleotide sequence of SEQ ID NO: 1; 5) a polynucleotide sequence having at least about at least about 50%, at least about 60%, at least about 70%, at least about 80%, at least about 90% or at least about 95% sequence identity to SEQ ID NO: 1; 6) a polynucleotide degenerate to (4) or (5) due to the genetic code. Oligonucleotides may be DNA or RNA, and in some embodiments, the oligonucleotides may include one or more labels such as fluorophores or radioactive labels.

In other embodiments, the kit may include an antibody capable of specifically binding to Star-PAP, fragments, fusions, or variants thereof. In some embodiments, the antibody may be a polyclonal antibody or a monoclonal antibody that specifically binds to an amino acid sequence having at least about 50%, at least about 60%, at least about 70%, at least about 80%, at least about 90% or at least about 95% sequence identity to SEQ ID NO: 2 or a fragment thereof. In further embodiments, the antibody may be a monoclonal or a polyclonal antibody that specifically binds to an amino acid sequence of SEQ ID NO: 2.

Kits may also include test reaction reagents, control reagents, instruction for performing test reactions and instructions for interpreting test results.

In other aspects, the novel PIP-PAPs may be used to treat, detect, monitor and determine a prognosis for a disease, condition or a disorder. In some embodiments, the disease, condition or disorder may be characterized by aberrant expression of one or more of the following: prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene ("WHSC1"), microfibrillar associated protein 5 ("MFAP5"), β-crystalline A ("β-CryA"), NAD(P)H dehydrogenase, quinine 1 ("NQO1"), glutathione S-transferase A4 ("GSTA4"), glutamate cysteine ligase catalytic subunit ("GCLC"), glutamate-cysteine ligase, modifier subunit ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). In particular embodiments a disease, condition or disorder may be characterized by aberrant expression of one or more of the following: HO-1 and NQO1. In further embodiments, the disease, disorder or condition may be associated with oxidative damage, oxidative stress, and inflammation. In some embodiments, such disease, condition or disorder may be treated by increasing levels or activity of a PIP-PAP in a subject, e.g., by providing to the subject a therapeutic amount of a PIP-PAP, such as Star-PAP or providing an agent which up-modulates the expression or activity of a PIP-PAP such as Star-PAP. In other embodiments, such disease, condition or disorder may be treated by decreasing levels or activity of a PIP-PAP in a subject. In some embodiments, the mammal is a human, and the disease, condition or disorder is characterized by an increase in the level or activity of heme oxygenase (decycling). By way of example, but not by way of limitation, such disease, disorder or condition may include: neurodegenerative diseases such as Alzheimer's Disease and Parkinson's, cardiovascular disease such as atherosclerosis, inflammatory bowel disease, complications of sickle cell disease, graft-host rejection, septic shock, and Crohn's disease. In still other embodiments, the disease, condition or disorder may be characterized by an increase or decrease in the level or activity of NAD(P)H dehydrogenase, quinine 1.

In some embodiments, treatment may include decreasing the expression or activity of a PIP-PAP in a subject suffering or at risk of suffering from the disease, condition or disorder. In other embodiments, the treatment may include increasing the expression or activity of a PIP-PAP in the subject. In particular embodiments, the PIP-PAP is Star-PAP.

BRIEF DESCRIPTION OF THE DRAWINGS

FIG. 3 shows a ClustalW sequence alignment of the amino acid sequence of the nucleotidyl transferase motif of five known poly(A) polymerases and Star-PAP. The ** indicate amino acids which were altered to generate the polymerase mutant D216/218A. FIG. 3 discloses SEQ ID NOS 49-54, respectively, in order of appearance.

FIG. 7B shows an immunoprecipitation (IP) of Star-PAP from HEK-293 cells, followed by western blot analysis (IB) for PIPKIα, CPSF-73 and RNA PolII (8WG16). FIG. 7C shows an immunoprecipitation of symplekin from HEK 293 cells followed by western blot analysis for Star-PAP and SPSF-100. FIG. 7D shows PIP kinase activity of purified PAP complexes using PtdIns4P as substrate. Lyso, PtdIns4,5P$_2$ degradation product in which the inositol headgroup is lacking one acyl chain.

FIGS. 8A-I shows the characterization of the Star-PAP poly(A) polymerase activity and specific stimulation of Star-PAP activity by the lipid messenger PI4,5P$_2$. FIG. 8A shows the activity of His-Star-PAP (0-1.25 μM) towards A$_{15}$ RNA primer (SEQ ID NO: 17). Anti-T7 western blot (bottom) demonstrates protein levels. FIG. 8B shows the effects of cordycepin triphosphate on His-Star-PAP activity. FIG. 8C shows Star-PAP activity towards all four rNTPs. FIG. 8D shows oligo(dT)/RNase H treatment of Star-PAP generated RNA-product. FIG. 8E) shows effect on mutations of conserved catalytic residues in Star-PAP. Coomassie blue stain demonstrates protein levels. FIGS. 8F and G show the effects of 50 μM inositol phospholipid micelles on His-Star-PAP (8F) or PAPα (1 μM) (8G) activity. NT, non-treated vehicle-only control. FIG. 8H shows the incorporation of α$^{32}$-P ATP into poly(A)$^+$ products larger than A$_{200}$ (SEQ ID NO: 18) in the presence of phosphoinositide micelles by Star-PAP and PAPα from 8F and 8G (n=3). Error bars represent s.e.m. I, Relative distributions of poly(A)$^+$ products from non-treated (NT), PtdIns4P-treated and PtdIns4,5P$_2$-treated Star-PAP from 8F.

FIG. 9A) show a dot plot of signal intensities (logarithmic scale) of gene chip features in wild-type (x-axis) vs. Star-PAP siRNA knockdown (y-axis) (Affymetrix MAS 5.0 software). Arrows denote dots corresponding to features whose levels showed the largest changes in microarray as well as by RT-PCR. Insert: Star-PAP protein levels in the two sets of HeLa cells treated with controls siRNA (control) or Star-PAP siRNA (Star-PAP) used for microarray analysis.

FIG. 10 shows supplemental tables 1-4 listing the 120 mRNAs that show a statistically significant change in expression level upon Star-PAP knockdown.

FIG. 14 shows the CKIα is associated with the Star-PAP complex and phosphorylates Star-PAP. (A) Star-PAP and PAPα complexes were separated by SDS-PAGE, transferred to nitrocellulose and probed with anti-flag and -CKIα antibodies. (B) NRK cells were transfected with flag-Star-PAP, allowed to express for 24 h and fixed for immunoflouresence. Cells were stained with anti-flag (red) and -CKIα (green) to determine subcellular localization. Nuclei are indicated by staining with DAPI. Purified flag-Star-PAP complex was incubated with 0, 0.1, 1.0, 10, or 100 μM D4476 (C) or CKI-7 (D) for 45 min on ice prior to initiation of the kinase reaction by ATP. CKIα can directly phosphorylate Star-PAP in vitro on the proline rich insert region. A series of Star-PAP truncations and deletion mutations were created, purified from mammalian cells as FALG fusion proteins by immunoprecipitation and subject to in vitro kinase assays. CKIα was able to phosphorylate all truncation mutations except those which lacked the first half of the proline rich region (AAs 223-274) that splits the catalytic domain of Star-PAP. This region contains nine serine and threonine residues conserved across mammalian species. Included in this are two consensus CKIα sites and a number of acidic residues that could contribute to additional CKIα phosphorylation sites. (Data not shown).

FIG. 15 shows that CKIα and PIPKIα are required for the maintenance of specific Star-PAP messages. (A) Quantitative real-time PCR analysis of the levels of Star-PAP dependent messages showing fold decreases in CKIα siRNA treated cells vs. control siRNA treatment. (B and D) Western blot of CKIα and PIPKIα knockdown in HEK293 cells using siRNA. Western blots are representative of the three independent experiments used in B and C. (C) Quantitative real-time PCR analysis of the levels of Star-PAP dependent messages showing fold decreases in PIPKIα siRNA treated cells vs. control siRNA treatment. (E) Quantitative real-time PCR analysis of the levels of Star-PAP dependent messages showing that CKI specific inhibitors CKI-7 and IC261 reduce HO-1. These are lead compounds for modulation of the Star-PAP complex function. (F) Quantitative real-time PCR analysis of HO-1 message levels from CKIα or PIPKIα knockdown cells treated with 100 μM tBHQ or DMSO (control) for four hours. Quantitative real-time PCR results are

FIG. 18 shows supplemental tables 1-2 listing mRNAs showing statistically significant increases in expression after Star-PAP siRNA treatment. FIG. 18 discloses DEAD peptide as SEQ ID NO: 68.

FIG. 23 shows results of immunoprecipitation assays indicating interaction between Star-PAP and CKIα. (A) FLAG purified Star-PAP and PAPα complexes were separated by SDS-PAGE, transferred to nitrocellulose and probed with anti-FLAG and -CKIα antibodies. (B) Endogeneous Star-PAP was immunoprecipitated from HEK 293 cells. The resulting precipitates were immunoblotted with Star-PAP and CKIα specific antibodies. A non-specific IgG immunoprecipitation was used as a control. (C) Purified FLAG-Star-PAP complex was incubated with 0, 0.1, 1.0, or 100 µM IC261 ($IC_{50}$ 11 µM). (D) Purified FLAG-Star-PAP complex was incubated with 0, 0.1, 1.0, or 100 CKI-7 ($IC_{50}$~6.0 µM) prior to initiation of the kinase reaction by ATP. Arrow indicates Star-PAP protein.

FIG. 25 illustrates that kinase activity and CKIα remain associated with Star-PAP when the proline rich region is deleted. (A) Full length and ΔPRR FLAG-Star-PAP complexes were expressed and purified from HEK 293 cells. The cell lysate (Lys) and the eluted FLAG affinity purified complex are shown. Purified complexes were separated by SDS-PAGE and immunoblotted with anti-FLAG and anti-CIKIα antibodies. Full length and ΔPRR Flag-Star-PAP purified complexes were tested for associated kinase activity towards themselves (B) or 100 µg/ml Casein (C) or 100 µg/ml MBP (D) using in vitro protein kinase assays.

FIG. 28 shows the Star-PAP nucleic acid sequence.
FIG. 29 shows the Star-PAP amino acid sequence.
FIG. 30 shows the canonical PAPα nucleic acid sequence.
FIG. 31 shows the canonical PAPα amino acid sequence.
FIG. 32 shows the PIPKIα nucleic acid sequence.
FIG. 33 shows the PIPKIα amino acid sequence.
FIG. 34 shows the HO-1 nucleic acid sequence.
FIG. 35 shows the HO-1 amino acid sequence.
FIG. 36 shows the NQO1 nucleic acid sequence.
FIG. 37 shows the NQO1 amino acid sequence.
FIG. 38 shows the CNK1A1L nucleic acid sequence.
FIG. 39 shows the CSNK1A1L amino acid sequence.
FIG. 40 shows the CSNK1A1S nucleic acid sequence.
FIG. 41 shows the CSNK1A1S amino acid sequence.
FIG. 42 shows the CSNK1A1 nucleic acid sequence.
FIG. 43 shows the CSNK1A1 amino acid sequence.

DETAILED DESCRIPTION

Figure 1:
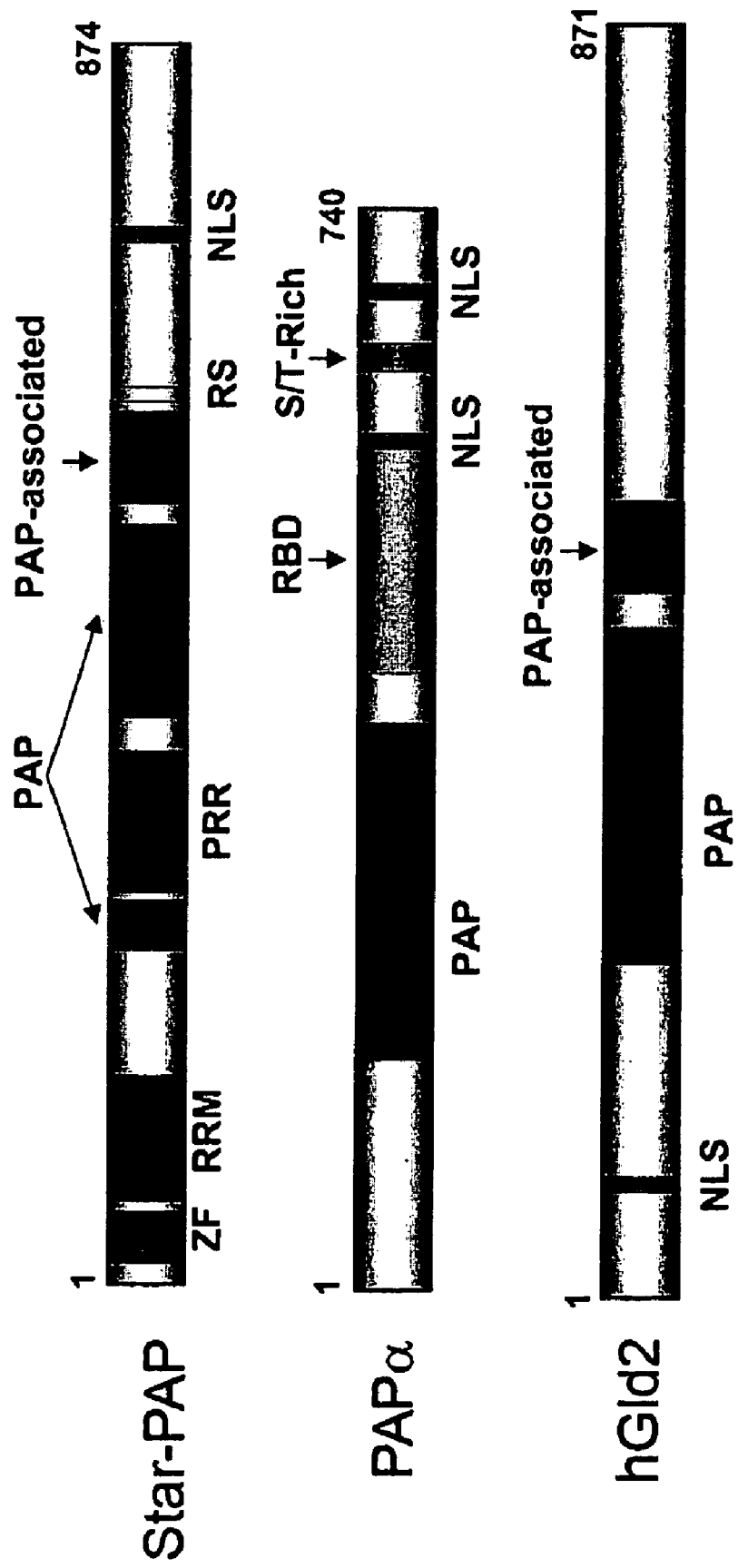
FIG. 1 shows a schematic of Star-PAP, PAPα and hGld2 polymerases with some of the domains of each labeled.

The compositions, methods and kits described herein relate to novel poly(A) polymerase termed PIP-PAPs. The PIP-PAPs have poly(A) polymerase activity which can be directly modulated by components of the phosphatidylinositol signaling pathway. Such components may include PIP kinases and phosphoinositide second messengers. For clarity and simplicity, an exemplary PIP-PAP, termed Star-PAP, is used to describe various aspects of the compositions, methods and kits. It will be understood by those skilled in the art that poly(A) polymerases may be identified as PIP-PAPs by performing substantially the same or similar analyses as described herein, and, once identified as a PIP-PAP, these poly(A) polymerases may be made and used as described.

The compositions, methods and kits described herein also relate to modulation of a PIP-PAP's poly(A) polymerase expression or activity for the treatment of disease, disorders, symptoms and conditions. Non-limiting, exemplary disease, disorders, symptoms and conditions are those which may be characterized by one or more of the following: (1) oxidative damage, oxidative stress, and inflammation; (2) an increase in the level or activity of HO-1; (3) treatable by increasing or decreasing the levels of Star-PAP expression or activity, and thereby increasing or decreasing levels of HO-1 expression or activity. By way of non-limiting example, such diseases, disorders, symptoms and conditions may include: neurodegenerative diseases such as Alzheimer's Disease and Parkinson's, cardiovascular disease such as atherosclerosis, inflammatory bowel disease, complications of sickle cell disease, graft-host rejection, septic shock, and Crohn's disease.

Other diseases may be characterized by the aberrant expression or function of one or more of the following genes: prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene, ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). Such a disease may be therapeutically treated by an agent which results in an increase or a decrease in Star-PAP expression or activity.

The present invention is described herein using several definitions, as set forth below and throughout the specification.

As used herein "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, unless otherwise stated, the singular forms "a," "an," and "the" includes plural reference. Thus, for example, a reference to "an oligonucleotide" includes a plurality of oligonucleotide molecules, and a reference to "a nucleic acid" is a reference to one or more nucleic acids.

As used herein, the term "subject" refers to an animal that may experience the benefit of the claimed methods, preferably a mammal, more preferably a human.

As used herein the term "isolated" or "purified" in reference to a nucleic acid molecule or a polypeptide refers to a nucleic acid molecule or polypeptide which is separated from the organisms and biological materials (e.g., blood, cells, serum, plasma, saliva, urine, stool, sputum, nasopharyngeal aspirates and so forth), which are present in the natural source of the nucleic acid molecule or polypeptide. An isolated nucleic acid molecule or an isolated polypeptide can be substantially free of other cellular material, or culture medium when produced by recombinant techniques, or substantially free of chemical precursors or other chemicals when chemically synthesized. Methods of nucleic acid isolation and polypeptide isolation are well known in the art and may include total nucleic acid isolation methods, RNA-specific isolation methods, or DNA-specific isolation methods, affinity purification methods, gel purification methods, antibody purification methods, etc.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin which may be single-stranded or double-stranded and may represent the sense or the antisense strand.

An oligonucleotide is a nucleic acid that includes at least two nucleotides. An oligonucleotide may be designed to function as a "primer." A "primer" is a short nucleic acid, usually a single-stranded DNA oligonucleotide, which may be annealed to a target polynucleotide by complementary basepairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which is used to detect identical, allelic or related nucleic acid sequences. Probes may include oligonucleotides which have been attached to a detectable label or reporter molecule. Typical labels include fluorescent dyes, quenchers, radioactive isotopes, ligands, scintillation agents, chemiluminescent agents, and enzymes.

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC.

A "mutation," or "mutant," or "variant" is meant to encompass at least a single nucleotide variation in a nucleic acid sequence relative to the normal sequence or wild-type sequence. A mutation may include a substitution, a deletion, an inversion or an insertion of one or more nucleotides compared to the normal or wild-type sequence.

With respect to an encoded polypeptide, a mutation may be "silent" and result in no change in the encoded polypeptide sequence. As is known in the art, the same amino acids may be encoded by a variety of different codons (i.e., a set of three nucleotides). Thus, multiple nucleic acid sequences may encode the same amino acid sequence—such nucleic acid variations may be characterized as "due to the degeneracy of the genetic code."

A mutation may also result in a change in the encoded polypeptide sequence. Such a change may be, for example, a frameshift, a deletion an insertion or a substitution. Amino acid substitutions may be conservative or non-conservative.

As used herein, a "conservative amino acid substitution" is one in which the replacement amino acid has similar chemical properties and/or structure to the original amino acid. A "non-conservative amino acid substitution" is one in which the replacement amino acid differs from the original amino acid in chemical property and/or structure.

Amino acids may be divided, for example, according to the chemical properties of their side chains (e.g., charge, hydrophobicity) into different groups such as acidic, basic, uncharged polar and non-polar. By way of non-limiting example one such grouping may be as follows: acidic amino acids may include aspartic acid and glutamic acid; basic amino acids may include lysine, arginine and histidine; uncharged polar amino acids may include glycine, asparagine, glutamine, cysteine, serine, threonine and tyrosine; non-polar amino acids may include alanine, valine, leucine, isoleucine, proline, phenylalanine, methionine, and tryptophan. In some embodiments, substitutions between amino acids in the same group may be considered conservative while substitutions between amino acids in different groups may be considered non-conservative. However, other groupings also exist and are known to those of skill in the art. For example, in some embodiments, substitutions between the following amino acids may also be considered conservative substitutions: glycine and alanine; phenylalanine, tryptophan and tyrosine. In still other embodiments the following groups of amino acids may be considered conservative substitutions for one another: 1) alanine, serine, threonine; 2) aspartic acid, glutamic acid; 3) asparagine, glutamine; 4) arginine, lysine; 5) isoleucine, leucine, methionine, valine; and 6) phenylalanine, tyrosine, tryptophan.

Exemplary regions of Star-PAP that are likely to tolerate amino acid variation include, without limitation amino acids 256-338 of SEQ ID NO: 2. Star-PAP is found only in vertebrates and is highly sequence conserved between humans and other mammals, but with lower conservation in other vertebrates such as zebrafish. The regions of low sequence identity such as between residues 256 and 338, the PRR (see FIG. 1) are thus likely to tolerate amino acid changes without eliminating protein function. This is the unique insert region of Star-PAP and mutations in this region may maintain PAP activity but change regulation. Such variants are likely to maintain some level of Star-PAP activity or function. Regions of Star-PAP that are likely less tolerant to amino acid sequence variation include the zinc finger domain (ZF) (amino acids 16-46 of SEQ ID NO: 2), the RNA recognition motif (RRM) (55-128), and the PAP associated domain (447-554) (FIG. 1). The region most likely to be sensitive to amino acid variations (e.g., PAP function would likely be affected) would be the PAP catalytic domain (residues 193-255, and 339-447).

As used herein the terms "peptide," "polypeptide" and "protein" are used interchangeably, and are understood to mean a molecule comprising two or more amino acids, where the alpha carboxyl group of one is bound to the alpha amino group of another. A peptide may have a C-terminus and an N-terminus, which relate to the carboxy portion of an amino acid on one end of the peptide chain and the amino portion of an amino acid on the other end of the peptide chain.

Figure 2:
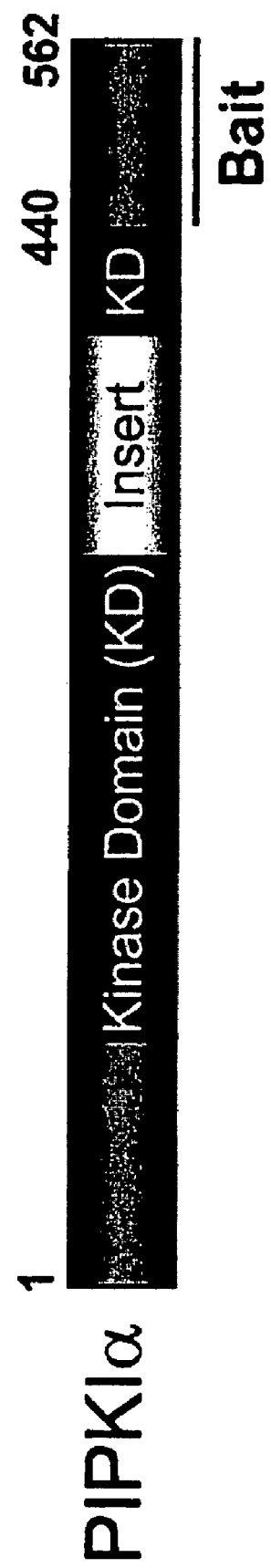
FIG. 2 shows a schematic of the PIPKIα protein, with C-terminal amino acids 440-562 labeled as "bait." This "bait" region was used in a two-hybrid screen to detect Star-PAP.

When referring to a polypeptide, the terms "C-terminus," "COOH end," "COOH terminus," "carboxy terminus" may be used interchangeably and are meant to include the carboxy portion of a polypeptide chain. Such a portion may include only one or a few amino acids from the C-terminus of the peptide, or may include up to one-fourth, one-third, one-half or more of the length of the polypeptide which includes the C-terminus. Similarly, the terms "N-terminus," "NH2 end," "amino terminus," may be used interchangeably and are meant to include the amino portion of a polypeptide chain. Such a portion may include only one or a few amino acids from the N-terminus of the peptide, or may include up to one-fourth, one-third, one-half or more of the length of the polypeptide which includes the N-terminus. An exemplary COOH-terminus comprises amino acids 440-562 of the PIP-KIα amino acid sequence (see e.g., FIG. 2 "bait"). An example of an amino terminus comprises amino acids 1-440 of PIPKIα (FIG. 2).

The term "protein domain" or "protein motif" is meant to include structurally and/or functionally defined regions of proteins. Proteins may have multiple domains. Exemplary domains include but are not limited to zinc finger motifs, nucleotidyl transferase sequence motifs, nucleic acid recognition and binding motif, protein/protein interaction motifs and enzyme motifs. One example of a protein domain is the nucleotidyltransferase motif from poly(A) polymerases, including Star-PAP. Some exemplary motifs are shown in FIG. 1 and FIG. 3.

As used herein, the term "functional fragment" of a polypeptide is one having an in vivo or in vitro biological activity which is characteristic of naturally occurring PIP-PAP polypeptides, such as Star-PAP, from which the fragment is derived. Fragments may arise from post-transcriptional processing, from translation of alternatively spliced RNAs, from the selective expression of a portion of the entire polypeptide, or the addition of a tag, linker, or other sequence to the N- or C-terminus of the protein. Fragments include those expressed in native or endogenous cells as well as those made in expression systems. Fragments of a nucleotide sequence may encode protein fragments that retain the biological activity of the native protein. Fragments may also include amino acid substitutions, insertions, or other sequence variation. Non-limiting examples of functional fragments include the COOH-terminus amino acids (amino acids 440-562) of the PIPKIα peptide. This fragment is sufficient to target to nuclear speckles. Additional, non-limiting examples of functional fragments of Star-PAP are provided in table 1 below.

TABLE 1

Exemplary Star-PAP fragments

| Star-PAP amino acids | Function |
|---|---|
| 1-547 | localizes in nuclei and enrichment at nuclear speckles |
| 1-328 | localizes in cytoplasm and disrupts normal Sm protein (snRNPs) localization in nuclear speckle; also disrupts PIPKIα targeting to nuclei and speckles |
| 557-874 | localizes in nuclei and at nuclear speckles |
| 16-46 | $C_2H_2$-zinc finger domain |
| 56-128 | RNA recognition motif |
| 197-221, 357-447 | split poly-A polymerase domain |
| 229-310 | proline rich region; important for phosphorylation by the protein kinase CKIalpha and functional modulation of gene specificity. |
| 575-587 | arginine/serine domain |
| 640-643, 659-662 | putative nuclear localization sequence |

Figure 24:
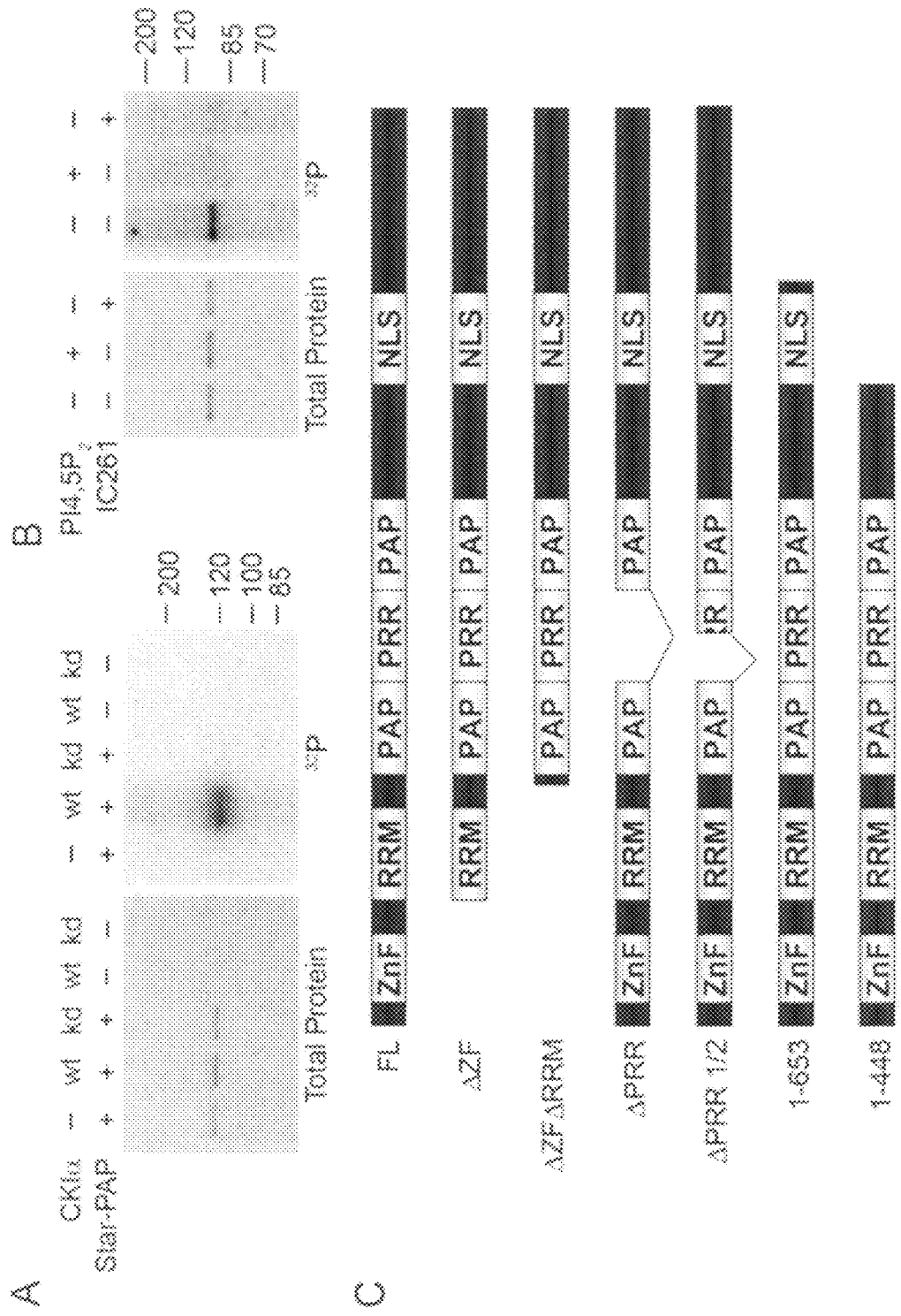
FIG. 24 illustrates that CKIa can directly phosphorylate Star-PAP within the proline rich region. (A) FLAG tagged wild type or K46R (kinase inactive) CKIα expressed in HEK 293 cells was purified and used to phosphorylate Star-PAP from the heat inactivated FLAG purified Star-PAP complex in an in vitro kinase assay. (B) The addition of 50 µM IC261 or $PI4,5P_2$ can block CKIα phosphorylation of Star-PAP. (C) A schematic diagram depicting the Star-PAP truncations used. (D) Flag-Star-PAP was expressed in HEK 293 cells, purified by immunoprecipitation with anti-FLAG M2 antibody and heat inactivated prior to being subjected to in vitro phosphorylation by purified CKIα as above. (E) An alignment of the CKIα phosphorylation regions in Star-PAP (amino acids 223-275) (SEQ ID NOS 69-73, respectively, in order of appearance) showing sequence conservation between mammalian species. Serine and threonine residues are denoted with (*) and consensus CKIα sites are boxed.

Other exemplary fragments are shown in FIG. 24. In some embodiments, the fragment is at least about 10%, at least about 20%, at least about 30%, at least about 40%, at least about 50%, at least about 60%, at least about 70%, at least about 80%, at least about 90%, at least about 95%, or at least about 98% or 99% of the length of the full length polypeptide.

As used herein the term "poly(A) polymerase" or "PAP" is meant to encompass all template-independent enzymes capable of polyadenylating the 3' end of a target nucleic acid sequence such as an RNA molecule, in vivo, in vitro or both. In some embodiments, poly(A) polymerases may have additional enzymatic functions and may not be limited to polyadenylation alone. Some poly(A) polymerases recognize and bind conserved sequence motifs. Such sequence motifs include, but are not limited to AAUAA (or slight variants of this) and (UAGGGA)n (SEQ ID NO: 19), where n is two or more. The term "canonical PAP" as used herein refers to the eukaryotic nuclear poly(A) polymerase (PAPα), responsible for the polyadenylation of newly transcribed mRNAs. Such a PAP is exemplified in SEQ ID NO: 3 and 4.

The term "poly(A) polymerase activity" is meant to include the enzymatic polyadenylation of a target sequence. A poly(A) polymerase activity may be enhanced (e.g., the poly(A) polymerase may show increased activity, processivity or both) as compared to another PAP or the same PAP under different conditions. Or, a poly(A) polymerase activity may be inhibited or reduced as compared to another PAP or the same PAP under different conditions. Poly(A) polymerase activity may be measured by methods known in the art.

As used herein, the term "phosphatidylinositol phosphate poly(A) polymerase," "PIP poly(A) polymerase" or "PIP-PAP" refers minimally, to a poly(A) polymerase which exhibits enhanced poly(A) polymerase activity in the presence of a phosphatidylinositol pathway second messenger. Such a second messenger may include phosphoinositides, such as the phospholipid $PI4,5P_2$, or PIP kinases such as PIPKIα or a functional fragment thereof. Such components may directly interact with a PIP-PAP. In some embodiments, the PIP-PAP may be localized to nuclear speckles in eukaryotic cells. In still other embodiments, a PIP-PAP may include one or more of the following: a split poly(A) polymerase domain linked by a proline rich region, a conserved transferase motif, a characteristic signature of the pol β superfamily of nucleotidyl transferases, a C2H2 zinc finger motif ("ZF"), an RNA recognition motif ("RRM"), short RS repeats (arginine/serine dipeptide repeats), and a nuclear localization sequence (NLS). One example of a PIP-PAP is "Speckle Targeting and PIPKIα Regulated Poly(A) Polymerase" or "Star-PAP," shown in FIG. 1 and at SEQ ID NOs: 1 and 2.

The term "having at least about 95% sequence identity" with reference to a nucleic acid sequence is meant to include a nucleic acid molecule which is from about 95% to about 100% identical to a reference sequence. In some embodiments, SEQ ID NO: 1 may be a reference sequence. Likewise, phrases having other amounts of sequence identity with respect to nucleic acid sequences are to be construed analogously.

With reference to an amino acid sequence, the term "having at least about 95% sequence identity" is meant to include a peptide sequence which is from about 95% to about 100% identical to a reference sequence. In some embodiments, SEQ ID NO: 2 may be a reference sequence. Likewise, phrases having other amounts of sequence identity with respect to polypeptide sequences are to be construed analogously.

By "recombinant" is meant that a protein, such as a poly(A) polymerase is not produced by a naturally-occurring nucleic acid but rather by a "recombinant nucleic acid," one that has been manipulated by one or more procedures to position that nucleic acid either within a vector or at a location in a genome in which it does not naturally occur. The recombinant protein may also be produced in a cell in which it does not naturally occur, purified after its production, and thus separated (e.g., purified) from contaminants such as cells, enzymes, other proteins, nucleic acids, etc.

As used herein, the term "antibody" encompasses monoclonal and polyclonal antibodies. Such an antibody can belong to any antibody class (IgG, IgM, IgA, etc.). The term "antibody" also includes intact molecules as well as fragments thereof, such as Fab, F(ab')2, Fv and single chain antibodies ("SCA") which are capable of binding the epitopic determinant. These antibody fragments retain some ability to selectively bind with the antigen. In some embodiments, the antibodies are chimeric antibodies. In other embodiments, the antibodies are human or humanized antibodies. In some embodiments, antibodies specifically bind to a PIP-PAP, such as Star-PAP. In other embodiments, antibodies bind to fragments and variants of Star-PAP. By way of example, but not by way of limitation, such fragments may be those shown above in Table 1. Again, by way of example but not by way of limitation, variants may be those shown in Table 2 below.

TABLE 2

| Exemplary Star-PAP mutants | |
|---|---|
| Star-PAP mutations | Function |
| Double point mutant: K640A, R641A | inhibits Star-PAP nuclear targeting |
| Multiple point mutant: Wild-type sequence: $_{575}$RSLQYQRRSSRGR$_{587}$ (SEQ ID NO: 20) mutant sequence: $_{575}$AALQYQAAAAAGA$_{587}$ (SEQ ID NO: 21) | diffuse nuclear localization; likely inhibits targeting to nuclear speckles |
| Double point mutant: K659A, R660A | inhibits nuclear targeting |
| Deletion mutant: 256-274 | lacks phosphorylation by the protein kinase CKIα |

As used herein, the term "epitope" means any antigenic determinant on an antigen to which an antibody binds. Epitopic determinants usually include chemically active surface groupings of molecules such as amino acids or sugar side chains and usually have specific three dimensional structural characteristics, as well as specific charge characteristics.

As used herein, the term "Star-PAP target" means a gene whose mRNA levels are modulated when Star-PAP levels or activity are altered. Star-PAP targets may be modulated directly or indirectly by Star-PAP. Exemplary, non-limiting Star-PAP targets include: prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). See also the targets listed in the tables presented in FIGS. 10 and 18.

I. EXAMPLES

These following examples and discussion are provided to aid the reader in understanding the invention and are not intended to be limiting. Those skilled in the art will understand that in some instances, methods, procedures, reagents, etc. may be substituted with others which will provide the same or similar results.

A. Methods to Identify and Characterize PIP-PAPs

The following experimental examples and discussion describe the identification and characterization of an exemplary PIP-PAP, termed Star-PAP. Star-PAP binds to the PIP kinase PIPKIα, and can be regulated by the phospholipid second messenger P4,5PI$_2$. It will be understood by those skilled in the art that the present methods may be applied to identify and characterize homologous PIP-PAPs in other organisms, variant PIP-PAPs, and PIP-PAPs that bind to other PIP kinases and that are modulated by other phosphoinositides. Additionally, because neither poly(A) polymerases nor PIP kinases are present only in the nucleus, screening and characterization methods similar to those described below may be used to identify PIP-PAPs that are localized to other regions of the cell.

1. Two Hybrid Screen

A novel poly(A) polymerase, termed Speckle Targeting and PIPKIα Regulated Poly(A) Polymerase, or Star-PAP, was identified via a yeast two-hybrid screen. Because PIPKIα targets to nuclear speckles via its COOH-terminus (amino acids 440-562, see e.g., FIG. 2), this region of PIPKIα was used as bait to identify other proteins which may localize at nuclear speckles. A yeast two-hybrid screen may be performed according to well-known methods (see e.g., James, et al. (1996) Genetics 144:1425 1436).

The yeast two-hybrid screen was performed at the Molecular Interaction Facility (University of Wisconsin Biotechnology Center) according to their protocols. Libraries screened were: mouse embryonic, human B cell, human breast, human prostate, human placenta, and mouse brain.

2. Cloning, Isolation and Expression of Star-PAP

Full length Star-PAP was cloned into expression vectors for expression in bacterial and mammalian cells. The Star-PAP open reading frame was amplified by PCR from *Homo sapiens* cDNA: FLJ222347 fis, clone HRC06188 (GenBank ACCESSION NO: NM_022830) using primers that incorporated a 5' EcoRI and 3' Sal I restriction site. The resulting PCR fragment was cloned into mammalian expression vectors pCMV-FLAG (Invitrogen), PCMV-HA, PCMV-Myc and PET28c (Novagen). The NH$_2$-terminus (1-328aa) of Star-PAP was amplified by PCR and cloned into pGEX-5X-2 (Amersham Biosciences). Subsequently full length His-Star-PAP was purified over a Ni$^{++}$ or glutathione columns under standard chromatography conditions, or as per manufacturer's instructions. full-length Star-PAP was also cloned into a pCMV4a vector, expressed in mammalian cells and full length Flag-Star-PAP was affinity purified over an a-M2 Flag agarose affinity column under standard chromatography conditions. The functional domain polynucleotide sequences such as the poly(A) polymerase domain and the zinc finger domain have been also cloned into a number of mammalian and *E. coli* expression vectors. (See e.g., Table 1, above).

3. Determining Star-PAP Structural Characteristics

The polypeptide of the exemplary PIP-PAP, Star-PAP, includes poly(A) polymerase catalytic and core domains, a poly(A) polymerase associated domain (FIG. 1, top panel), and ATP interacting residues. It also includes a conserved transferase motif, a characteristic signature of the pol β superfamily of nucleotidyl transferases (see e.g., FIG. 3).

The arrangement of Star-PAP domains shows clear differences when compared to both the canonical mammalian poly (A) polymerase (PAPα), responsible for the polyadenylation of newly transcribed mRNAs, and the non-canonical regulatory PAP GLD2, which modulates polyandenylation in the cytosol (FIG. 1).

Referring to FIG. 1, for example, Star-PAP contains a C$_2$H$_2$ zinc finger motif ("ZF") with homology to ZFs from other mRNA processing proteins at its NH$_2$-terminus followed by an RNA recognition motif ("RRM") that differs in both sequence and location from the RNA binding domain of PAPα. The RRM domain of Star-PAP appears to share the greatest identity with that of HnRNP A1, which has been shown to bind the conserved sequence motif (UAGGGA)$_n$ (SEQ ID NO: 19), where n=two or more.

Another distinguishing feature of Star-PAP from the canonical PAP is its split poly(A) polymerase domain that is linked by a proline rich region ("PRR"). This appears to be a unique characteristic of Star-PAP versus all other reported poly(A) polymerases. Following the PAP domain is the PAP associated domain, which is of unknown function but is also found in GLD2 and a related regulatory PAP Trf4/5p, but not PAPα suggesting that it serves a functional role specifically in regulatory PAPs.

Further, the COOH-terminus of Star-PAP contains a short RS repeat (arginine/serine dipeptide repeats), characteristic of splicing factors, and a nuclear localization sequence (NLS). These unique domains of Star-PAP may be important for interactions with molecular partners and for targeting to sub-cellular compartments. The presence of these additional domains and their unique architecture distinguish Star-PAP as a new class of poly(A) polymerase.

4. Identification of Star-PAP Homologues

Figure 4A:
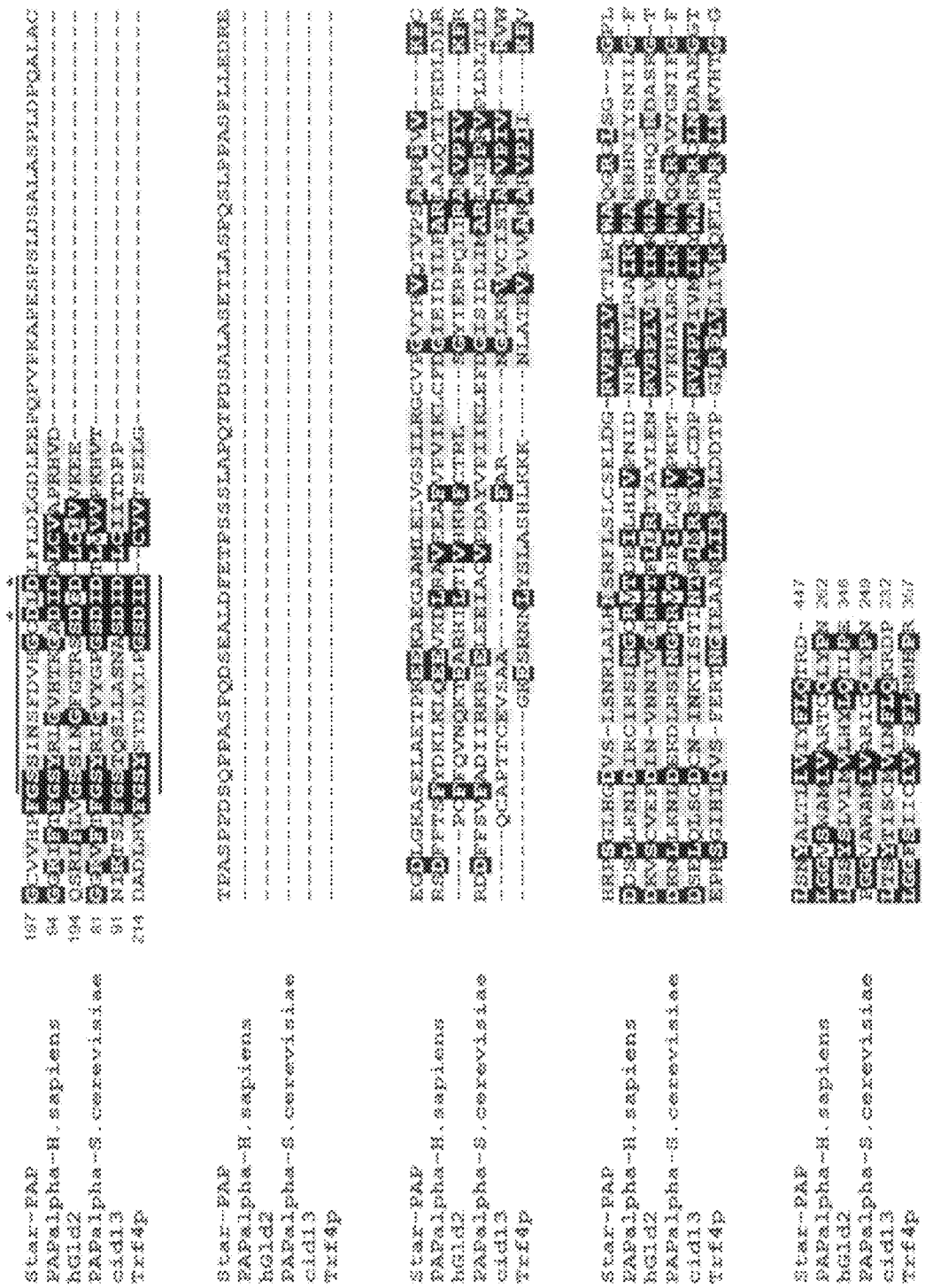
FIG. 4(A) shows a Clustal W sequence alignment of the complete catalytic domain from Star-PAP-H. sapiens (SEQ ID NO: 55) versus the complete catalytic domain from a number of reported poly(A) polymerases (SEQ ID NOS 56-60, respectively, in order of appearance). Accession numbers: Canonical H. sapiens gi_32490557; Canonical M. musculus gi_25090856; Canonical S. cerevisiae gi_3334283; GLD2 H. sapiens NM_173797; CID13 S. pompe gi_26392335; Trf4p S. cerevisiae NP_014100.
Figure 4B:
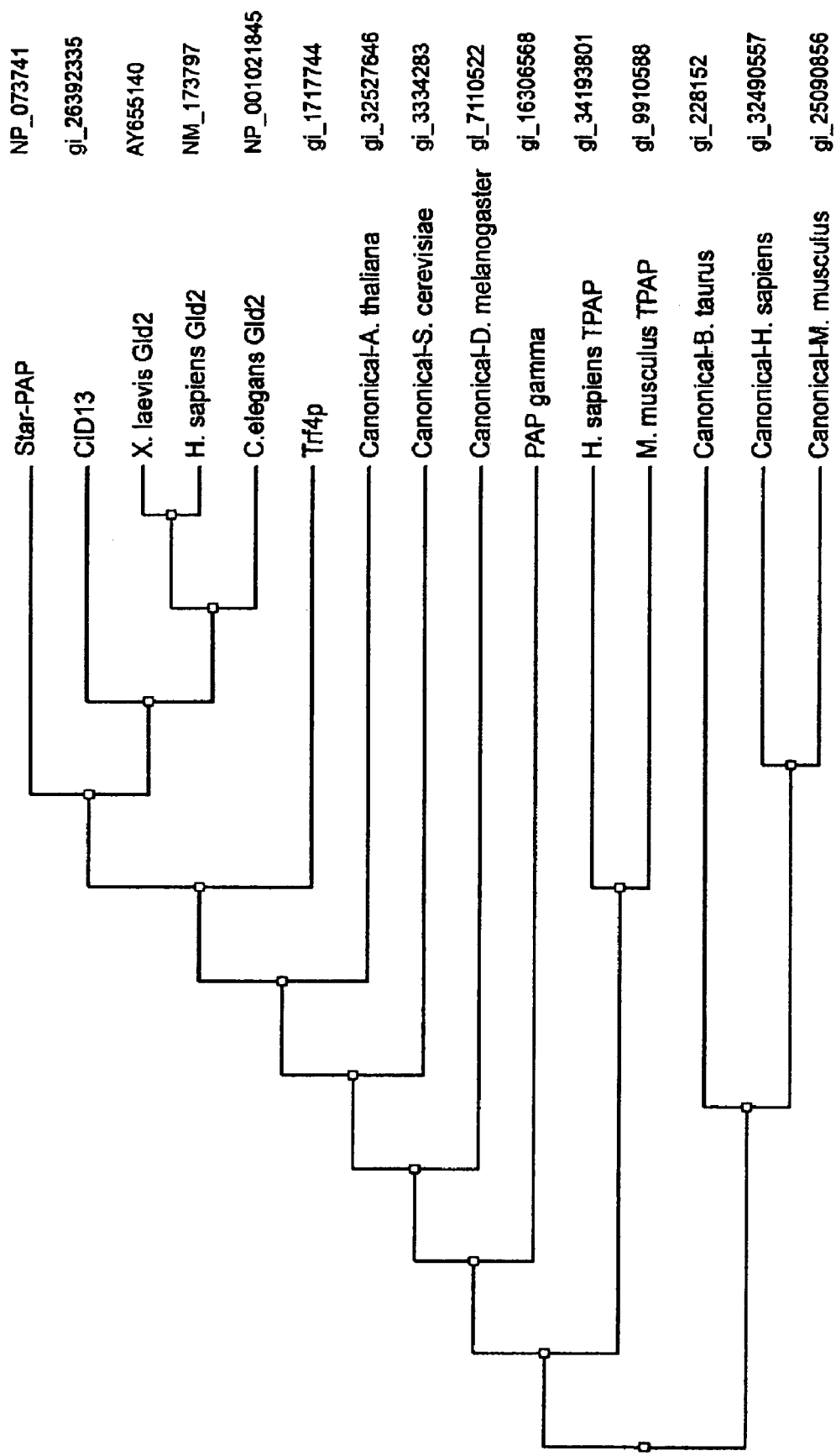
FIG. 4(B) shows an unrooted tree of Star-PAP and all known poly(A) polymerases based on a Standard ClustalX alignment. The polymerases present in the unrooted tree represent those which are most identical in sequence to Star-PAP. This tree was built using the catalytic and central domain sequence of Star-PAP, residues # 197-447, based on a ClustalW sequence alignment using Parsimony.
Figure 5:
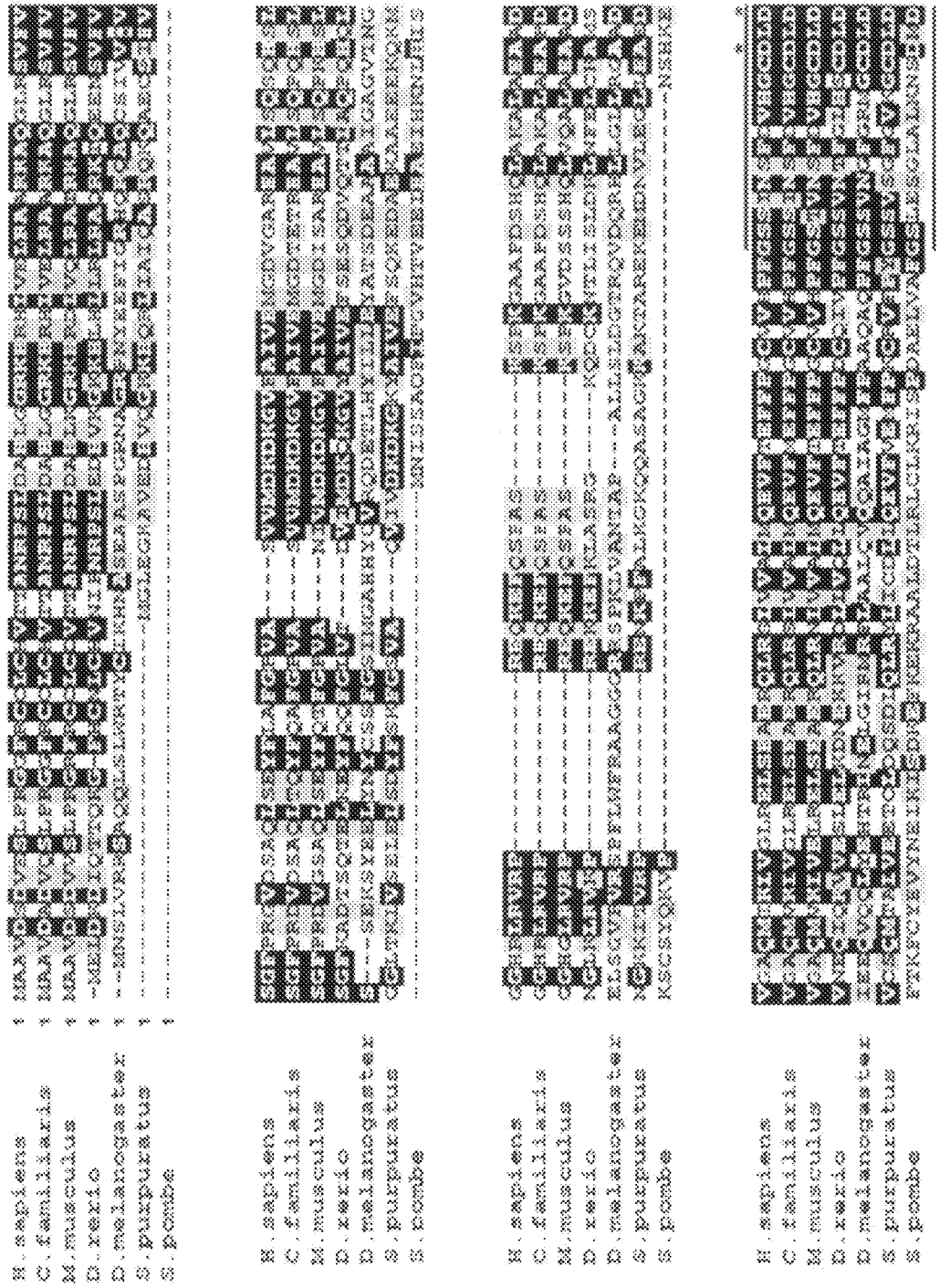
FIG. 5 shows a Clustal W sequence alignment of Star-PAP H. sapiens (SEQ ID NO: 61) against putative Star-PAP family members from various species (SEQ ID NOS 62-67, respectively, in order of appearance). Accession numbers: H. sapiens NP_073741; M. musculus NP_932110.1; C. familiaris XP_533266.2; D. rerio NP_001025359.1; D. melonogaster NP_569904; S. purpuratus XP_798256.1; S. pombe NP_594901. The alignment illustrates that vertebrates have identical functional domains. Canine Star-PAP may have an N-terminal extension as it contains 904 amino acids, compared to human with 874 amino acids, mouse with 869 amino acids and zebra fish with 797 amino acids.

Star-PAP homologues exist in a variety of species from *S. pombe* to *H. sapiens*, each with an intact catalytic domain (see e.g., FIGS. 4 and 5). Sequence conservation between the putative catalytic domain of Star-PAP and other known poly (A) polymerases is shown in FIG. 3.

5. Determining Cell-Type Expression and Tissue Localization of Star-PAPs

Antibodies to Star-PAP were generated by methods known in the art. Briefly, polyclonal Star-PAP antiserum was generated at Covance from rabbits boosted with the purified GST-tagged N terminus (residues 1-328) as the antigen and affinity purified over a column coupled with His-tagged Star-PAP N terminus (residues 1-328), or by using purified full-length GST-Star-PAP as antigen and affinity purified from precleared serum over a column coupled with GST-Star PAP. For northern blot analysis, a DNA probe representing base pairs 541-1046 of human Star-PAP was generated with the Strip-EZ PCR kit (Abmion) and used to probe the human multiple-tissue northern blot II membrane (Ambion) in accordance with the manufacturer's instructions. The blots were visualized with a Storm 840 phosphoimager (Molecular Dynamics).

Western blot analysis shows that endogenous Star-PAP protein is expressed in a number of cell lines such as HeLa, Human Embryonic Kidney HEK293, MCF7, U2OS, COS7 and MDCK (data not shown). Tissues from Northern blot analysis include brain, spleen, placenta, liver, small intestine, colon, pancreas, prostate, testes and ovary showed the expression of Star-PAP to be ubiquitous, with greatest expression in ovary and testis (data not shown).

6. Sub-Cellular Localization of Star-PAPs

Subcellular localization of a PIP-PAP protein, such as Star-PAP, can be determined via antibody staining of cell preparations by methods well known in the art. The following description provides one example.

Cells were cultured and transfected using the FuGENE 6 transfection reagent (Roche) according to the manufacturer's instructions. Transfections were carried out for 24 h. Immunofluorescence and confocal microscopy were performed by methods known in the art.

Figure 6:
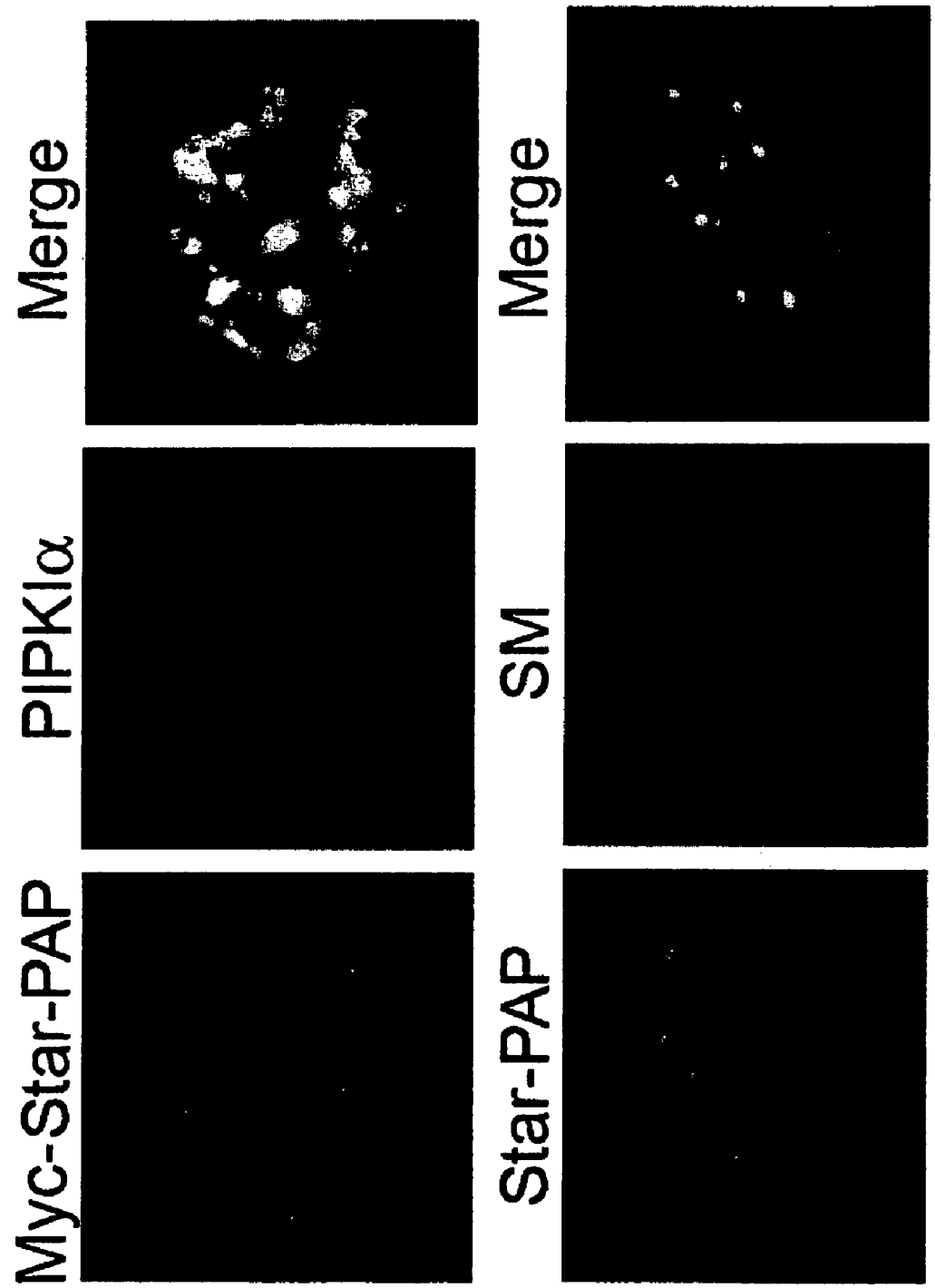
FIG. 6 shows maximum projections of deconvolved optical sections, demonstrating that Myc-tagged Star-PAP localizes at nuclear speckles with PIPKIα (top row) and with Sm proteins at nuclear speckles (bottom row).

Transiently expressed Star-PAP was detected via antibody staining in nuclear speckles, co-localized with PIPKIα (FIG. 6, upper panel) in HeLa, Human Embryonic Kidney HEK293, and COS7 cells. Endogenous Star-PAP, like PIPKIα and PI4,5P$_2$ was also detected at nuclear speckles and appear to co-localize with Sm proteins. (FIG. 6, lower panel). Nuclear speckles are not only the foci for storage factors with roles in mRNA processing but are also the sites of nuclear phospholipid metabolism. The presence of all three molecules in the same nuclear compartment suggests that Star-PAP may work with PIPKIα and PI4,5P$_2$ in the processing of pre-mRNA.

7. Star-PAP Interactions with Other Cellular Components

PIP-PAP interactions with a PIP kinase and/or other proteins may be detected and confirmed by in vivo and in vitro methods known in the art (e.g., western blot analysis, ELISA, gel shift analysis, co-immunoprecipitation assays, etc.). Exemplary methods are described below using Star-PAP, PIPKIα and the proteins of the poly(A) polymerase complex.

For immunoblotting and immunoprecipitation, HeLa and HEK 293 cells were lysed in IP buffer (100 mM KCL, 50 mM Tirs pH 7.4, 5 mM EDTA, 0.5% NP-40, 100 µg/ml RNase A, 200 mM NaVO$_4$, 50 mM L-glycerophosphate, 50 mM NaF and 1×EDTA free protease inhibitor cocktail (Roche)) with gentle sonication. Lysates were centrifuged at 40,000 g, the supernatant was incubated at 4° C. for 4 hours with 4 µg of specific antibody or control IgG as indicated, followed by incubation with a protein A-Spearose. Pellets were washed extensively with lysis buffer and analyzed.

For in vitro GST pulldown assays, PIPKIα and Star-PAP were expressed separately in *E. coli* and affinity purified. Briefly, pET28 constructs containing either His-tagged Star-PAP or GST-tagged PIPKIα were transformed into BL21 (DE3) (Novagen, Inc., Madison, Wis.). Proteins were expressed and purified using His- or glutathione-resin following the manufacturer's instructions (Novagen, Inc., Madison, Wis.).

His-Star-PAP bound to full-length GST-PIPKIα as well as GST-PIPKIα COOH-terminus (amino acids 440-562), but not GST alone indicating a direct interaction between Star-PAP and PIPKIα (data not shown).

To demonstrate that this interaction occurs in vivo, polyclonal antibodies to the NH$_2$-terminal region of Star-PAP, amino acids 1-328 of SEQ ID NO: 2 (FIG. 29), were generated by methods known in the art. Immunoprecipitation of endogenous Star-PAP from both HeLa and HEK 293 cell lysates with the NH$_2$-terminal polyclonal antibody resulted in co-immunoprecipitation of PIPKIα but not other PIPKI isoforms. Moreover, immunoprecipitation of HA-PIPKIα resulted in co-immunoprecipitation of Star-PAP, demonstrating that Star-PAP can form a stable interaction with PIPKIα in vivo (data not shown).

As another example of testing for PIP-PAP, such as Star-PAP, protein-protein interaction, proteins of the polyadenylation complex were evaluated. The in vivo polyadenylation of pre-mRNA by PAPα requires its association with a complex set of proteins, including Cleavage and Polyadenylation Specificity Factor subunits (CPSF$^{160, -100, -73 \& -30}$ and hFIP1), Cleavage-Stimulatory Factor subunits (CstF$^{77, -64 \& -50}$), and the scaffolding protein Symplekin and RNA Pol II.

Using the antibody binding methods described above, Star-PAP and CPSF$^{100}$ co-immunoprecipitated with Symplekin, indicating Star-PAP can form a stable complex with components of mRNA polyadenylation machinery.

Figure 7:
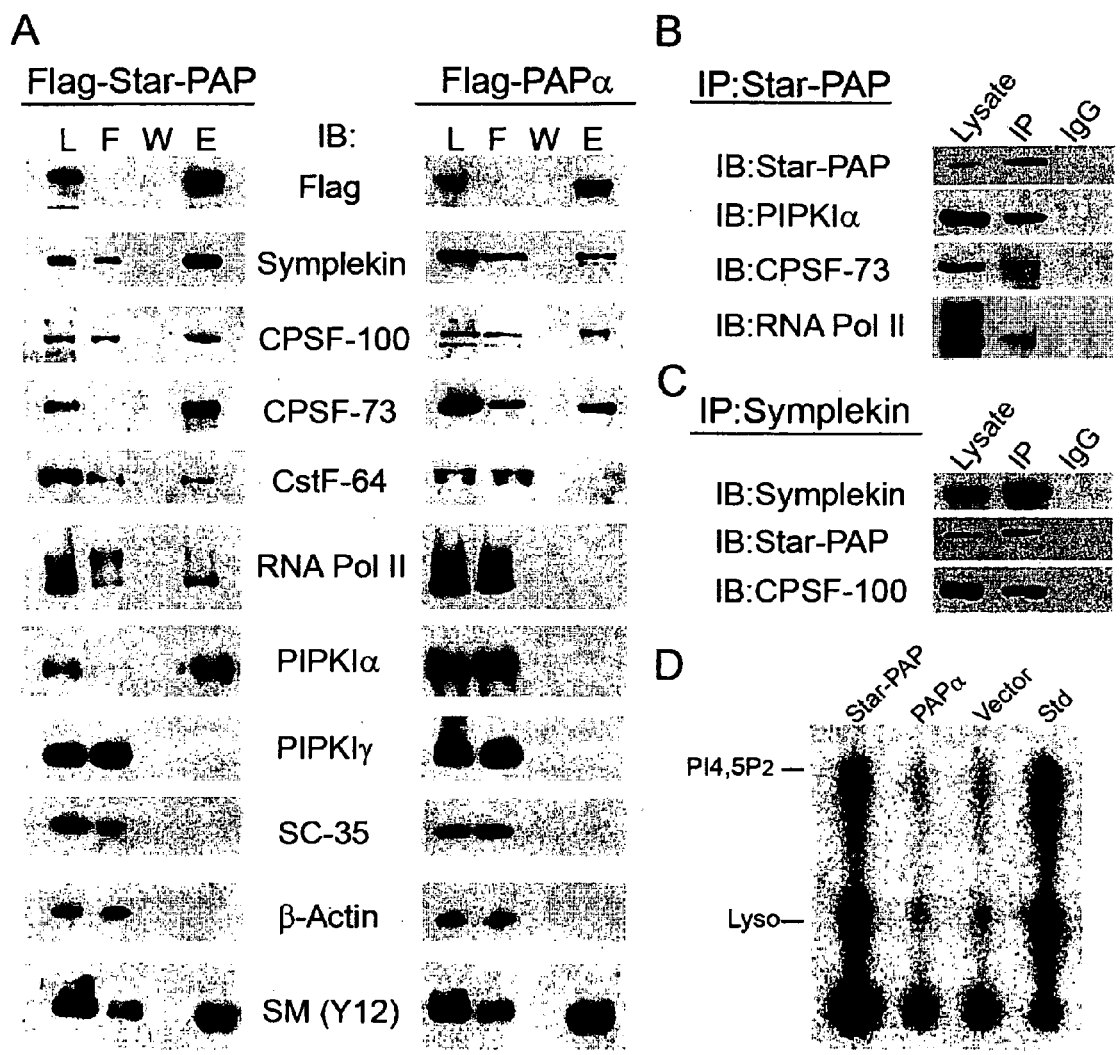
FIG. 7A-D show, via western blotting, that Star-PAP is associated with components of the canonical nuclear polyadenylation complex but is distinct from the canonical complex. T or L, total lysate; F, flow through; W, wash; E, eluate from the M2 flag-antibody column. PIPKIγ, SC-35 and β-actin were examined as controls for specificity (panel A). The figures show that endogenous Star-PAP is associated with proteins that modulate polyadenylation and with PIP kinase and PIP kinase activity.

Affinity purification of Flag-Star-PAP and Flag-PAPα and their associated complex of proteins in parallel allowed a comparison of the complexes formed by Star-PAP and PAPα in more detail. Flag tagged Star-PAP and PAPα were purified from HEK 293 cells stably expressing Flag-Star-PAP or Flag-PAPα (following manufacturer's instructions; Sigma-Aldrich) and the presence of endogenous symplekin, CPSF$^{100}$, CPSF$^{73}$, CstF$^{64}$, RNA Pol II, Sm protein (Y12) and PIPKIα was assessed by western blotting. Like Flag-PAPα, Flag-Star-PAP associates with symplekin, CPSF$^{100}$ and CPSF$^{73}$, further confirmation that Star-PAP may function in an mRNA polyadenylation complex (FIG. 7). Also detected with both PAPs was a faster migrating form of RNA Pol II and Sm protein (Y-12), a component of the spliceosome, which is consistent with reports that the machinery for splicing and polyadenylation are coupled.

Another difference between the Flag-tagged Star-PAP and PAPα complexes was the association of PIPKIα with Flag-Star-PAP but not Flag-PAPα (FIG. 7). Consistent with this observation, the Flag-Star-PAP complex contained lipid kinase activity that converted PI4P to PI4,5P$_2$ (data not shown). The fact that PIPKIα present in the Flag-Star-PAP polyadenylation complex generates PI4,5P$_2$ suggests that de novo PI4,5P$_2$ synthesis can occur in proximity to Star-PAP to regulate its activity in vivo. Other differences between the two protein complexes included the detection of RNA Pol II and CstF$^{64}$ in the Flag-Star-PAP complex but not in the Flag-PAPα complex even though PAPα is known to functionally associate with both CstF$^{64}$ and RNA Pol II. Additionally, protein kinase activity was also identified in the Star-PAP complex (see section 8, below).

Antibodies against full-length Star-PAP were also able to coimmunoprecipitate PIPKIα, CPSF-73, and RNA Pol II, demonstrating an in vivo association of Star-PAP with these enzymes. Endogenous Star PAP and CPSF-100 coimmunoprecipitated with Symplekin, further indicating that Star-PAP is in association with a polyadenylation complex known to act on mRNA.

The association of Star-PAP with polyadenylation components suggests that Star-PAP plays a role in the polyadenylation of mRNAs and may do so similarly to the canonical PAP.

Antibodies were obtained as follows: anti-HA and anti-Myc (Covance); anti-Flag M5 (Sigma); anti-SM (Y12) (Stratech); anti-5C-35 (BD Pharmingen); anti-symplekin (BD Transduction Laboratories); anti-CPSF-100 and RNA Pol II (N-20) (Santa Cruz Biotechnology); anti-RNA polymerase II antibody 8WG16 (Neoclone), and anti-β-actin acites (MB Biomedicals). All secondary antibodies were from Jackson Immunoresearch Laboratories.

8. The Star-PAP Complex Contains Protein Kinase Activity

As noted above in section 7, purification of FLAG-Star-PAP or FLAG-PAPα from HEK 293 cells resulted in the co-purification of a large protein complex. Also as noted above in section 7, protein kinase activity was identified in the Star-PAP complex. This activity was demonstrated as follows.

Figure 19:
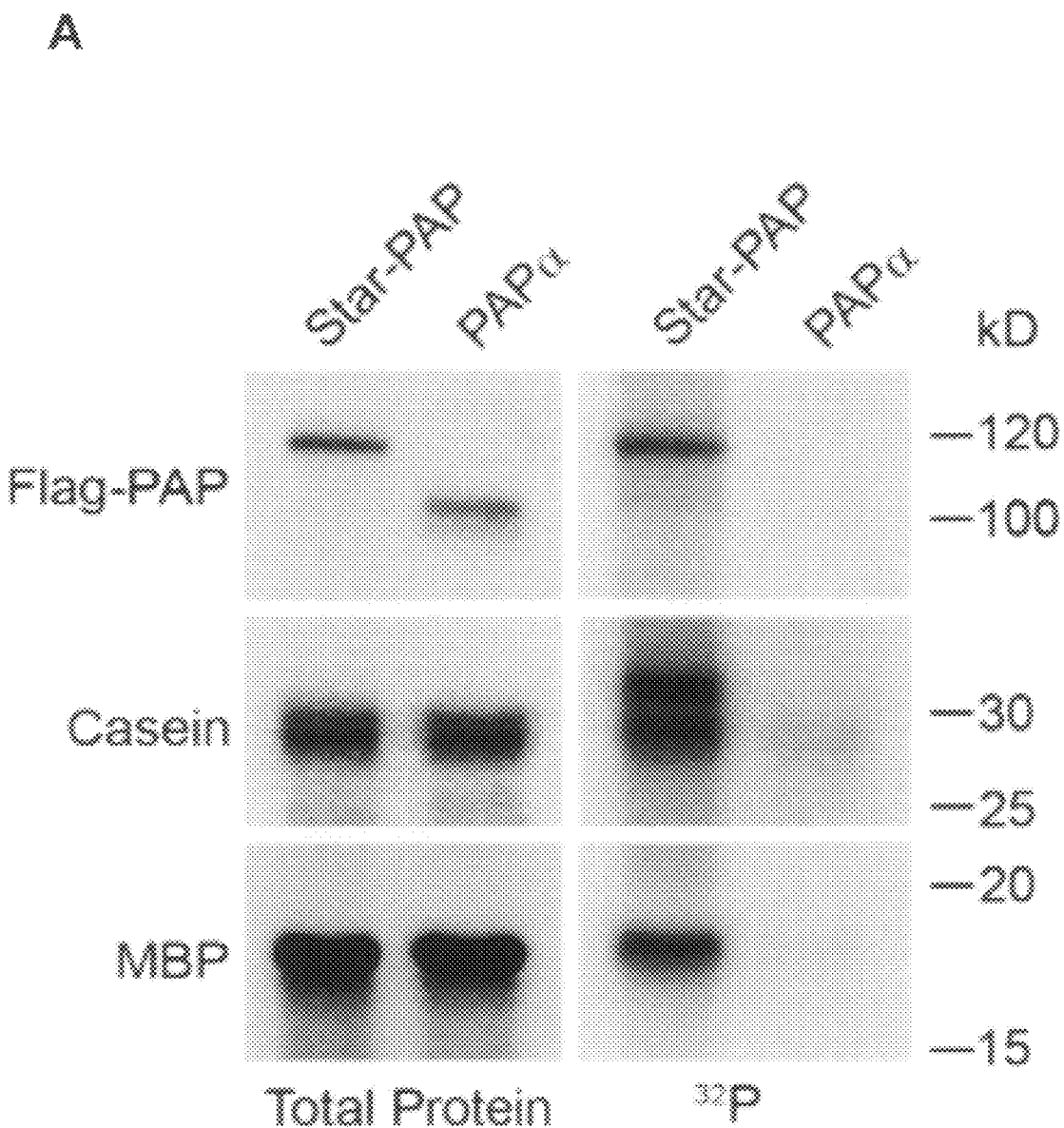
FIG. 19 compares the kinase activity of Star-PAP and PAPα. Flag-Star-PAP or PAPα was expressed in HEK 293 cells, purified by anti-FLAG M2 affinit chromatography and eluted in three consecutive fractions with a 3×FLAG peptide. (A) Fractions were collected and used in an in vitro kinase assay with no substrate (top), 100 µg/ml casein (middle) or MBP (bottom). (B) The FLAG-Star-PAP complex was incubated with 0, 1.5, 15, 50 or 100 µM PI4,5P2 micells for 45 minutes on ice prior to initiation of the kinase reaction by addition of ATP.

Flag-Star-PAP and FLAG-PAPα were expressed in HEK 293 cells and purified on anti-FLAG M2 resin. Purified PAP complexes were subject to an in vitro protein kinase assay as follows. Protein kinase assays were performed in 1× kinase buffer (50 mM Tris-HCl pH 7.5, 10 mM $MgCl_2$ and 0.5 mM EGTA). Assays were initiated by the addition of 10 μM ATP and 5 μCi $\gamma^{32}P$ ATP to the reaction mix. Substrates included 100 μg/ml of the generic protein kinase substrates myelin basic protein (MBP) or casein. Heat inactivation of the endogenous kinase activity in the Star-PAP complex was destroyed by heating for 15 minutes at 65° C. The Star-PAP purified complex contained protein kinase activity toward both MBP and casein while the PAPα complex contained almost no detectable protein kinase activity (FIG. 19).

9. Determining Star-PAP Polymerase Activity

The poly(A) polymerase activity of PIP-PAPs such as Star-PAP, natural or artificial variants, homologues or fragments thereof may be tested by methods known in the art. (See e.g., Kyriakopoulou et al., (2001) *J Biol Chem*, 276:33504-11).

When Star-PAP poly(A) polymerase activity was tested using a generic $A_{15}$ RNA primer (SEQ ID NO: 17), the purified protein was able to extend the generic primer with radio-labelled α-$^{32}P$-ATP in a dose dependent fashion demonstrating that Star-PAP has poly(A) polymerase activity.

Figure 8:
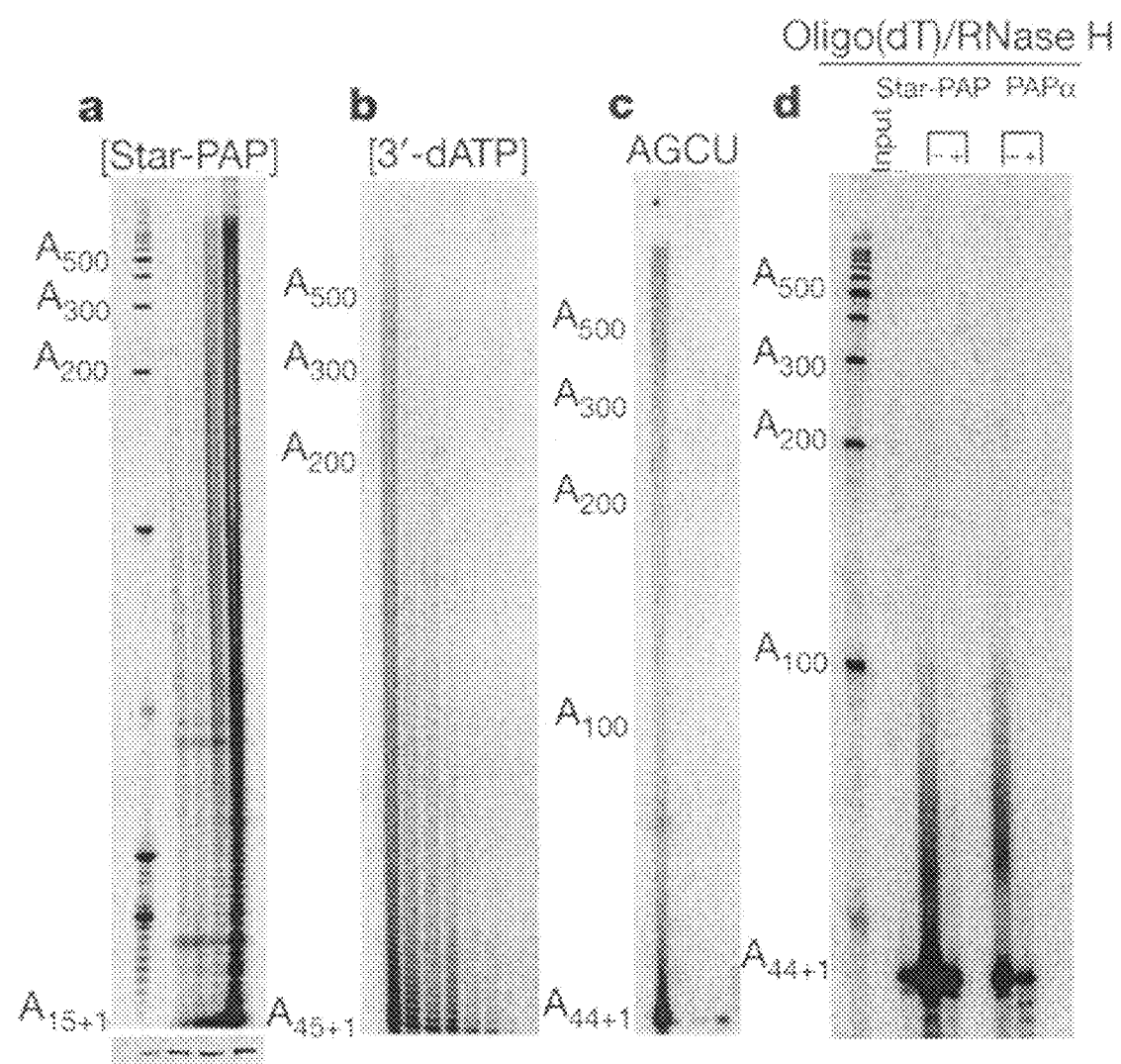
FIG. 8 discloses A$_{15+1}$ as SEQ ID NO: 74; A$_{300}$ as SEQ ID NO: 75; A$_{500}$ as SEQ ID NO: 76; A$_{45+1}$ as SEQ ID NO: 77; A$_{100}$ as SEQ ID NO: 78; A$_{44+1}$ as SEQ ID NO: 79.

As another example, a specific 45 nt RNA oligonucleotide (UAGGGA)$_5$A$_{15}$ (SEQ ID NO: 22) was designed to serve as an RNA substrate in the poly(A) polymerase assay. Using the (UAGGGA)$_5$A$_{15}$ primer (SEQ ID NO: 22), Star-PAP showed enhanced poly(A) polymerase, activity when compared to the $A_{15}$ RNA primer (SEQ ID NO: 17) (data not shown). Using this primer, Star-PAP activity was inhibited in a dose dependent fashion by the chain terminator cordycepin triphosphate, as was the yeast canonical poly(A) polymerase control (FIG. 8).

To demonstrate that the polymerase activity was specific for ATP and not GTP, CTP, or UTP, the nucleotide specificity of Star-PAP was tested. Replacement of ATP with any of the other three nucleotide triphosphates did not allow nucleotide incorporation into the RNA substrate by Star-PAP in this assay (FIG. 8). Additionally, tails generated in the presence of all four NTPs are susceptible to digestion with oligo (dT) and RNase H, indicating the extension of the RNA primer is primarily through the addition of AMP. Thus, it is likely that Star-PAP uses ATP exclusively for its polymerase activity in vivo. Oligo (dT)/RNase H digestions were performed with a [$\gamma^{32}$-P] ATP 5'-labeled L1 RNA primer at 4 μM and 1 mM unlabeled NTPs. Digestion of poly(A)$^+$ RNA was performed in 200 mM KCl, 1 mM EDTA, 20 mM Tris-HCl pH 8.0, 30 mM $MgCl_2$ and 20 U RNasin. Oligo (dT) (8 μM) was used for annealing to the RNA primer and digestion was performed at 37° C. for 90 minutes with 4 units of RNase H (Promega).

Additionally, both Star-PAP and PAPα showed greater non-specific in vitro poly(A) polymerase activity in the presence of $Mn^{2+}$ versus $Mg^{2+}$ (data not shown), a characteristic of PAPs. When poly(A) polymerase activity of Star-PAP was compared side-by-side with canonical PAPα, Star-PAP had a 1.3 fold greater specific activity than PAPα.

Because Star-PAP associates with the $PI4,5P_2$ generating enzyme PIPKIα; the effect of exogenous phosphoinositides on the in vitro poly(A) polymerase activity of Star-PAP was evaluated. Star-PAP was incubated in the presence of various phosphoinositides (PI, PI3P, PI4P, PI5P, $PI3,4P_2$, $PI3,5P_2$, $PI4,5P_2$ and $PI3,4,5P_3$) or buffer only as a control. Following a brief incubation period the remaining components of the assay were added and allowed to react. In the absence of any phosphoinositide species, Star-PAP was able to extend an RNA primer to generate a modest poly(A) tail. In the presence of $PI4,5P_2$ the incorporation of ATP into poly(A) tails was enhanced. This increase appeared to be concentrated above the 200 base range of the generated poly(A) tails, suggesting that $PI4,5P_2$ may both increase the activity and processivity of Star-PAP. This effect was specific for $PI4,5P_2$ as all other inositol phospholipids assayed had no effect on Star-PAP activity in this assay. Additionally, no phosphoinositides tested, including $PI4,5P_2$ stimulated the activity of PAPα (FIG. 8). These data indicate that $PI4,5P_2$ can specifically and directly modulate the activity of Star-PAP; however, it is understood that the activity of other PIP-PAPs may be modulated by different phosphoinositides such as PI, PI3P, PI4P, PI5P, $PI3,4P_2$, $PI3,5P_2$ and $PI3,4,5P_3$.

The stimulation of Star-PAP occurred in the presence of a number of mRNA substrates, at pH 7.4, 7.9 and 8.6 and in the presence of both metal cofactors $Mn^{2+}$ and $Mg^{2+}$ although at pH 7.4 the magnitude of PI4,5P2 stimulation was greater (data not shown).

Using the methods described above, mutations of Star-PAP were tested for poly(A) polymerase activity. Mutations were generated in conserved catalytic residues within the nucleotidyl transferase motif (D218A and DD216/218AA, see "*" at FIG. 3) by methods known in the art. Briefly, site-directed mutagenesis was performed by using PCR-primer overlap extension with mutagenic primers. Primers used were 5'-GTCCATGGCTGTGATCTTGCCCTCTTCT-TGGATCGGGTG-3' (SEQ ID NO: 23) and 5'-GTCCATG-GCTGTGCTCTTGCCCTCTTCTTGGATCTGGGTG-3' (SEQ ID NO: 24) for Star-PAP (D218A), and 5'-CACCCA-GATCCAAGAAGAGGGCAAGAGCACAGC-CATGGAC3' (SEQ ID NO: 25) for Star-PAP (D216A/D218A). These mutations abolished Star-PAP poly(A) polymerase activity (FIG. 8).

Star-PAP also includes terminal uridylyl transferase ("TUTase") activity. TUTase assays were performed with Star-PAP purified from *E. coli*. Under defined TUTase conditions (see e.g., Trippe, R. et al. *RNA* 12, 1494-504 (2006)), Star-PAP has the capacity to transfer UMP residues to total cellular RNA (data not shown). In cells, there is at least 10-fold greater concentration of ATP than UTP, and Star-PAP activity towards $\alpha^{32}$-P-labeled UTP was competed by the addition of five-fold excess cold ATP in dose-dependent manner. In contrast, $\alpha^{32}P$-ATP was not effectively competed by increasing concentrations of UTP. Nucleotide competition experiments under PAP assay conditions demonstrated the same effects (data not shown).

Additionally, nucleotide competition assays were performed under PAP conditions with the RNA primer L1 which contains the conserved AAUAAA and G/U-rich down stream consensus sequence elements present in mRNA. Here, Star-PAP showed weak poly(U) activity which was effectively competed with addition of excess cold ATP, and robust poly (A) activity which was unaffected by the addition of excess UTP (data not shown). Thus, although Star-PAP has TUTase activity, the data indicate that Star-PAP preferentially utilized ATP as a nucleotide substrate in vitro.

10. Star-PAP Function In Vivo

The correct polyadenylation of messages is critical for the stability of mRNAs. To identify messages which require PIP-PAP activity, such as Star-PAP activity, knockdown experiments were performed.

a. Star-PAP Knockdown and Microarray Analysis #1

In this example, HeLa cells were treated with control siRNA (Control: 5'-AGGUAGUGUAAU CGCCUUG-3' (SEQ ID NO: 26)) or siRNA specific for Star-PAP (Star-PAP sequence specific oligos: 5'-GUGUGU UUGUCAGUG-GCUU-3' (SEQ ID NO: 27); 5'-AACUACGAGCTGC-GAGAAA-3' (SEQ ID NO: 28)).

Briefly, HeLa cells were maintained in DMEM containing 10% FBS. The cells were passed into 60 mm dishes one day prior to transfection. The cells were then transfected with a PIPKIα specific siRNA oligonucleotide using Oligofectamine (Invitrogen, Madison, Wis.) transfection reagent. After 24 hours, the cells were transfected again in the same manner.

Figure 9A:
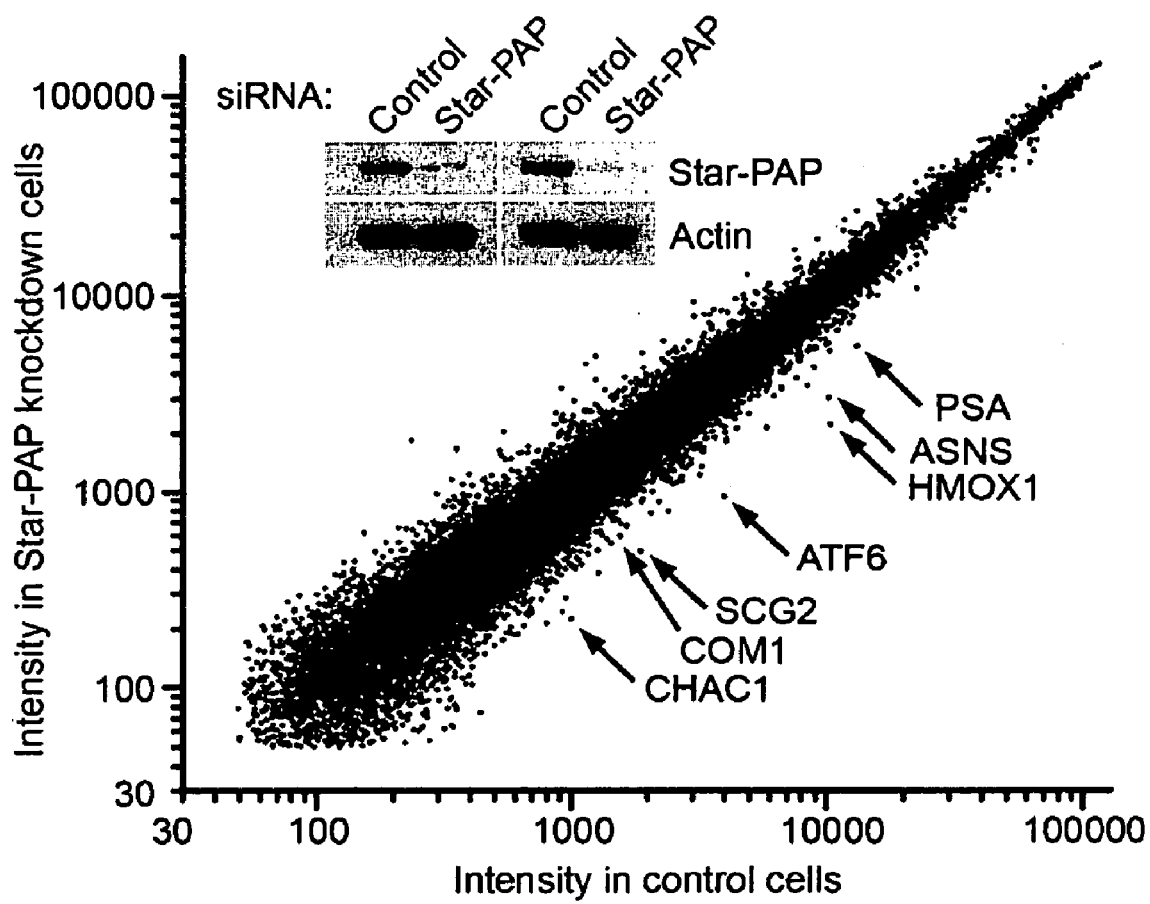
FIGS. 9A and B.

The knockdown of Star-PAP was confirmed using a Star-PAP specific polyclonal antibody (FIG. 9A insert). Microscopic evaluation showed that the Star-PAP knockdown cells had no obvious phenotypes, and the cells proliferated normally.

To identify potential Star-PAP targets, microarray analysis with RNA isolated from Star-PAP knock down and control cells was performed on Affymetrix U133 plus 2.0 human genome expression chips (Affymetrix, Santa Clara, Calif.). Total RNA was extracted using the RNeasy mini isolation kit (Qiagen). Probes for microarray hybridization were generated from the RNA using a poly d(T) primer and fluorescently labeled according to the manufacturer's instructions (Affymetrix). U133A plus 2.0 arrays (Affymetrix) were used for expression profiling; two each for Star-PAP and control siRNA generated cDNAs. The data from the control siRNA treatment were used as a baseline expression for comparison with the Star-PAP siRNA-treated samples. The changes in signal intensity of mRNAs in the Star-PAP knockdown cell versus control cells are shown in FIG. 9A.

The measurement of changes in expression were statistically analyzed using the empirical Bayes methodology EBarrays, which is implement in R, a publicly available statistical analysis environment. Posterior probabilities of differential expression (DE) were calculated assuming the log-normal (LNN) expression model. The threshold was determined with a direct posterior probability approach which seeks to control the conditional false discovery rate (cFDR) at a specific level. (See tables 1-4 in FIG. 10).

In this microarray analysis, of the approximately 47,000 features spotted on each chip, approximately 4500 features showed statistical changes in intensity in the Star-PAP knockdown versus controls. Statistical analysis indicated that ~100 mRNAs where highly significantly reduced by 5-fold or more in the microarray. These genes are involved in a wide array of cellular functions.

Figure 9B:
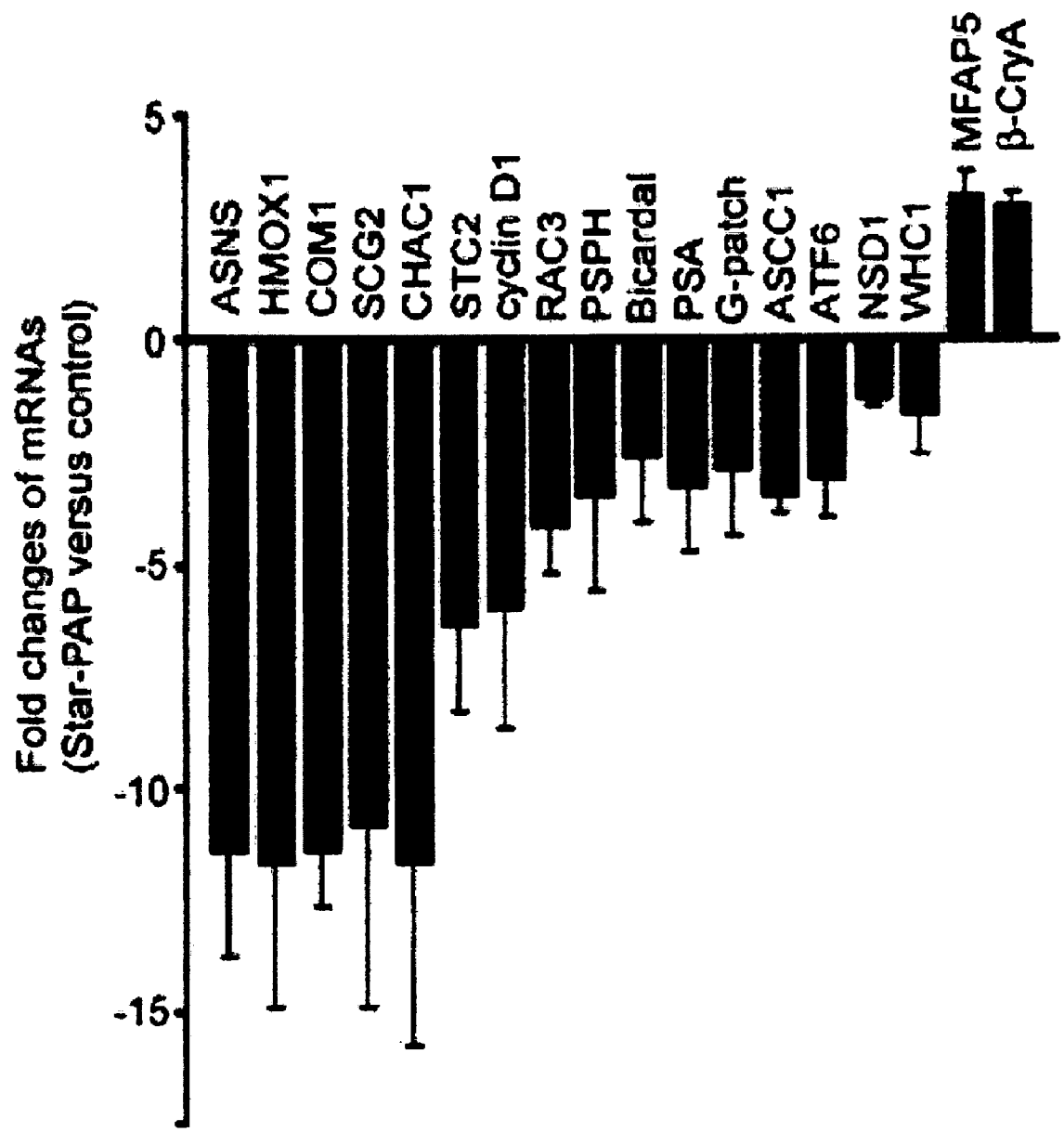
FIG. 9B) shows fold changes of selected mRNAs in Star-PAP knockdown versus control cells were validated by quantitative real-time RT-PCR. Data shown is mean fold changes for 5 independent experiments.

To confirm the microarray results, 18 targets were chosen for validation in a Star-PAP knockdown assay followed by quantitative real-time PCR (FIG. 9B). For quantitative RT-PCR, 2 μg of RNA was reverse transcribed using SuperScript III reverse transcriptase (Invitrogen) according to the manufacturer's instructions. Genes included ASNS, HO-1, COM1, SCG2, CHAC1, STC2, cyclin D1, RAC3, PSPH, bicardal, PSA, G-patch, ASCC1, ATF6, NSD1, WHSC1, MFAP5 and β-CryA. FIG. 9B represents mean fold changes for five independent experiments.

Star-PAP knockdown significantly decreases the mRNA level of 5 of the 18 messages, ASNS, COM1, SCG2, CHAC1, and HO-1, suggesting that Star-PAP is required to maintain appropriate levels of select messages.

b. Star-PAP Knockdown and Microarray Analysis #2

The Star-PAP knockdown, microarray evaluation and statistical analysis were repeated, and the measurement of changes in expression of mRNAs, as determined using the empirical Bayes methodology previously described, is shown in the tables of FIG. 18.

For the microarray analysis, total RNA was extracted from HEK-293 cells transfected with Star-PAP-specific or control siRNA oligonucleotides with the RNeasy mini-isolation kit (Qiagen) (n=3). Labeled probes for microarray hybridization were generated with MessageAmp II-Biotin Enhanced kit (Ambion) in accordance with the manufacturer's instructions. U133A plus 2.0 arrays (Affymetrix) were used for expression profiling. Labeling, hybridization, washing, scanning and analysis of gene chips were performed at the University of Wisconsin Gene Expression Center. The data from the control siRNA treatment were used as baseline expression for comparison with Star-PAP and PIPKIα siRNA-treated samples.

Statistical analysis was performed as describe above. In this microarray analysis, of the approximately 47,000 transcripts and variants, the LNN model identified 6,311 DE genes with threshold 0.888 to control cFDR at 0.01 for the Star-PAP knockdown. The fold change in the intensity signals were calculated in Microsoft Excel using the following formula: fold change=—[(average signal intensity in control group)/(average signal intensity in knockdown group)] or fold change=[(average signal intensity in knockdown group)/(average signal intensity in control group)].— A significant (conditional false discovery rate≦0.01%) change in transcript level compared with control cells (n=3) was detected for 4,481 genes with Star PAP RNAi knockdown.

Figure 20:
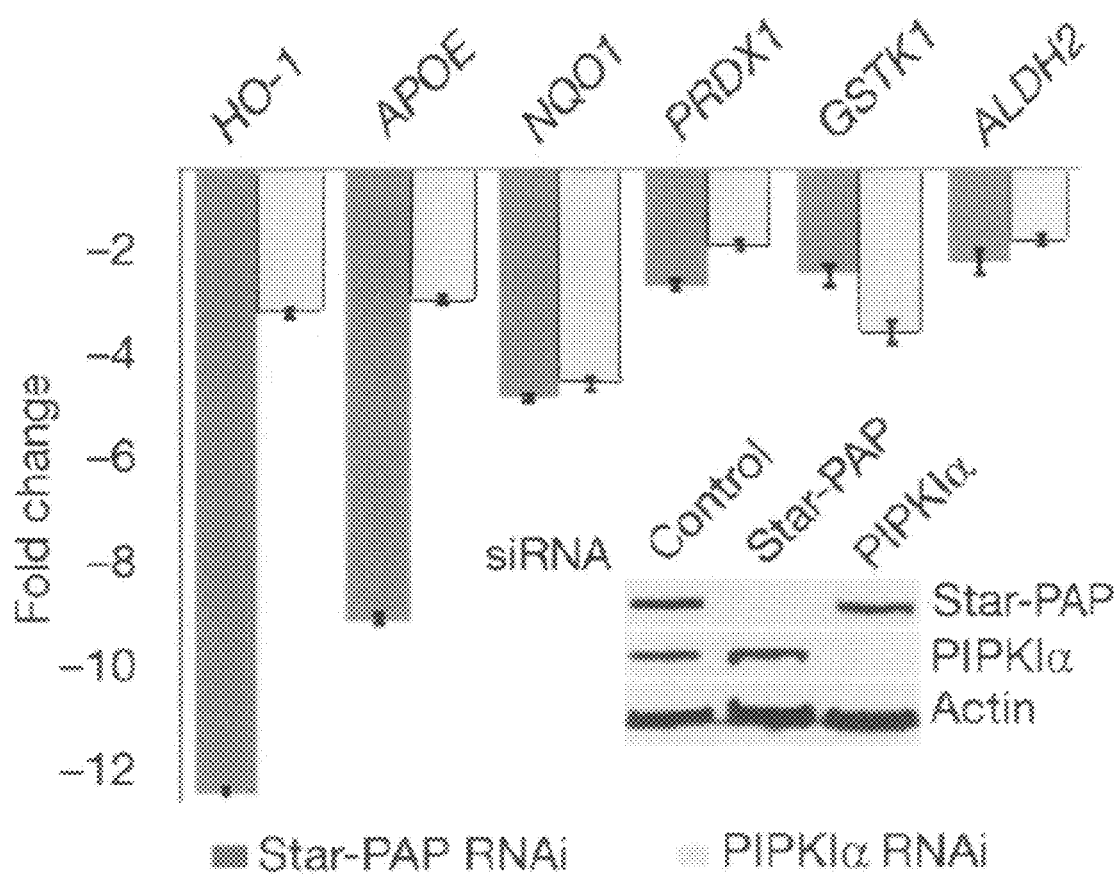
FIG. 20 shows the results of qRT-PCR analysis of select mRNAs (n=3). Error bars represent standard error of the mean (s.e.m.).

A confirmation of certain Star-PAP targets was performed using six different targets: HO-1, NQO1, APOE, PRDX1, GSTK1 and ALDH2. The targets were subject to quantitative real-time PCR. The expression levels of these candidate mRNAs were consistent with the microarray analysis, demonstrating that Star-PAP is required for the normal expression of at least these mRNAs. (FIG. 20). Primer used for real-time PCR analysis of these mRNA levels are presented in Table 3 below:

TABLE 3

Assay primers

| Primer | Sequence | SEQ ID NO: |
|---|---|---|
| ALDH2 fw | 5'-ACCTTCGTGCAGGAGGACAT-3' | 29 |
| ALDH2 rv | 5'-CGTGTTGATGTAGCCGAGGA-3' | 30 |
| APOE fw | 5'-CGTTGCTGGTCACATTCCTG-3' | 31 |
| APOE rv | 5'-CCTGCACCTGCTCAGACAGT-3' | 32 |
| GSTk1 fw | 5'-AAACAAGCCTCCAGGTCTGC-3' | 33 |
| GSTk1 rv | 5'-GGACGCTTTCTCCAGCATCT-3' | 34 |
| HO-1 fw | 5'-CCACCAAGTTCAAGCAGCTCTA-3' | 35 |
| HO-1 rv | 5'-GCTCCTGCAACTCCTCAAAGAG-3' | 36 |
| NQO1 fw | 5'-GAACTTCAATCCCATCATTTCCAG-3' | 37 |
| NQO1 rv | 5'-CAGCTTCTTTTGTTCAGCCACAAT-3' | 38 |

TABLE 3-continued

Assay primers

| Primer | Sequence | SEQ ID NO: |
|---|---|---|
| PRDX1 fw | 5'-TGCCAAGTGATTGGTGCTTC-3' | 39 |
| PRDX1 rv | 5'-AAAAGGCCCCTGAACGAGAT-3' | 40 | c. Determining Star-PAP Direct Interactions

To determine direct Star-PAP targets, the ability of Star-PAP to interact with CHAC1 and HO-1 mRNA was assessed using RNA immunoprecipitation. RNA immunoprecipitations were performed according to methods known in the art (see e.g., Im, et al., *Methods Mol Biol*, 284, 129-46 (2004); Gilbert et al., *Mol. Cell* 14: 457-464 (2004)) with the following modifications. After sonication, DNA was digested by adjusting the solution to 25 mM $MgCL_2$ and 5 mM $CaCl_2$ and 700 U/ml DNase I (Invitorgen) and incubating for 10 minutes at 37° C. Digestion was stopped by the addition of EDTA to a final concentration of 20 mM. Digested lysate was added to 6 µg of antibody and immune complexes were allowed to form overnight at 4° C. 20 µl protein A sepharose beads were added and incubated at 4° C. for an additional 60 minutes. Eluates were adjusted to 200 mM NaCl and 0.2 mg/ml proteinase K (Promega). Proteins were digested for 2 hours at 45° C. and the temperature was then raised to 67° C. for 4 hours to reverse crosslinking. All buffers contained 100 U/ml RNasin (Promega). RNA was purified from the immunoprecipitates with TRI reagent (Sigma) according to the manufacturer's instructions. RNA was analyzed by RT-PCR using the One Step RT-PCR kit (Qiagen) and specific gene primers listed in Table 1 above.

Figure 12:
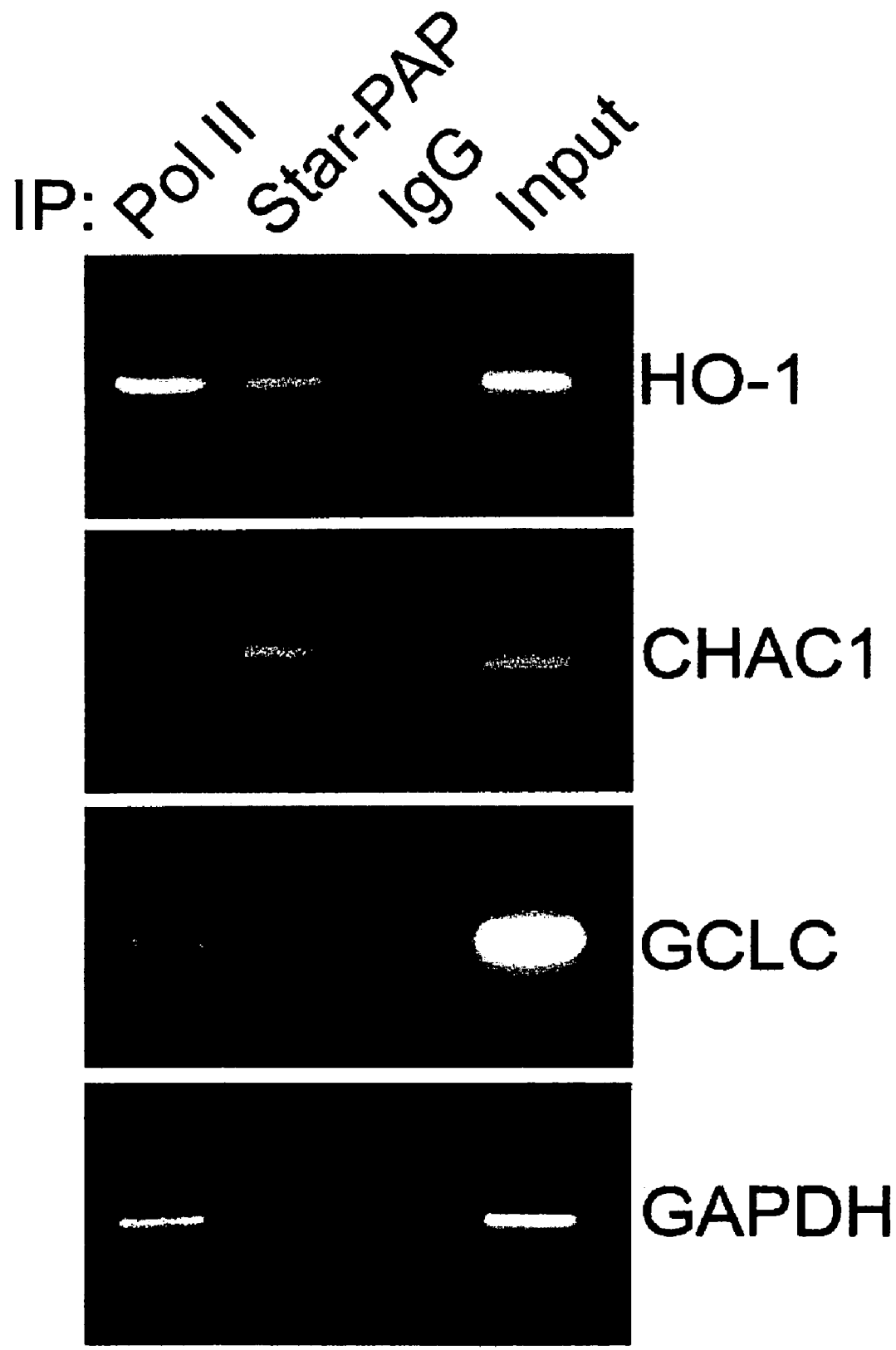
FIG. 12 shows that Star-PAP specifically interacts with its target messages. RNA polymerase II or Star-PAP were immunoprecipitated from nuclear extracts isolated from HEK293 cells cross-linked with 1% formaldehyde. The cross-links were reversed and total RNA was isolated from the immunoprecipitates and analyzed by reverse-transcriptase PCR with gene specific primers for the Star-PAP targets HO-1 and CHAC-1 as well as the non-targets GCLC and GAPDH. A non-specific rabbit IgG was used as a control. Primers are listed in Table 1.

Results are shown in Figure (FIG. 12). HO-1 and CHAC1 mRNA specifically interacted with Star-PAP while there was no such interaction with mRNAs of GCLC and GAPDH, providing evidence that HO-1 mRNA is a direct Star-PAP target.

HO-1 is an important component in the cellular response to oxidative stresses. HO-1 converts heme to potent signaling molecules, including biliverdin and carbon monoxide, which posses antioxidant, cytoprotective, and other protective properties. HO-1 also induces ferritin synthesis. Regulation of HO-1 is achieved primarily through regulation of HO-1 mRNA levels, and induction of HO-1 mRNA is a key cellular response to reactive oxygen species and other cellular stresses.

d. Star-PAP Knockdown Blocks HO-1 Stress-Related Induction

HO-1 mRNA expression can also be induced by compounds such as tert-butylhydroquinone (tBHQ) a compound which induces an antioxidant response in cells.

Star-PAP knockdown not only reduced basal levels of HO-1 but also blocked tertBHQ induction (100 µM t-butylhydroquinone treatment) of HO-1 mRNA (FIG. 21), indicating that Star-PAP may be required not only for maintaining of basal HO-1 mRNA levels, but also for inducible increase of the message.

e. Star-PAP 3'-Cleavage Function

Knockdown of Star-PAP did not cause a detectable change in the polyadenylation of HO-1 mRNA in vivo (data not shown). No differences in HO-1 mRNA levels were seen in Star-PAP knockdown cells when cDNA was generated using either (dT)20 (SEQ ID NO: 80) or random hexamer primers. Furthermore, no changes were observed in the length of HO-1 poly(A) tails after Star-PAP knockdown. Not wishing to be bound by theory, although Star-PAP may be functioning as a poly(A) polymerase in vivo, the reduced expression of Star-PAP target messages after Star-PAP knockdown may be due to the requirement of Star-PAP for the 3' cleavage reaction that precedes polyadenylation. Like canonical PAP, Star-PAP associates with the components required for 3' cleavage and may function similarly to canonical PAPs in the 3'-cleavage reaction. It would therefore be predicted that Star-PAP knockdown should result in a loss of 3'-cleavage of its target messages. The resulting messages would likely be rapidly degraded, resulting in an overall reduction in the level of Star-PAP target mRNAs.

Figure 13:
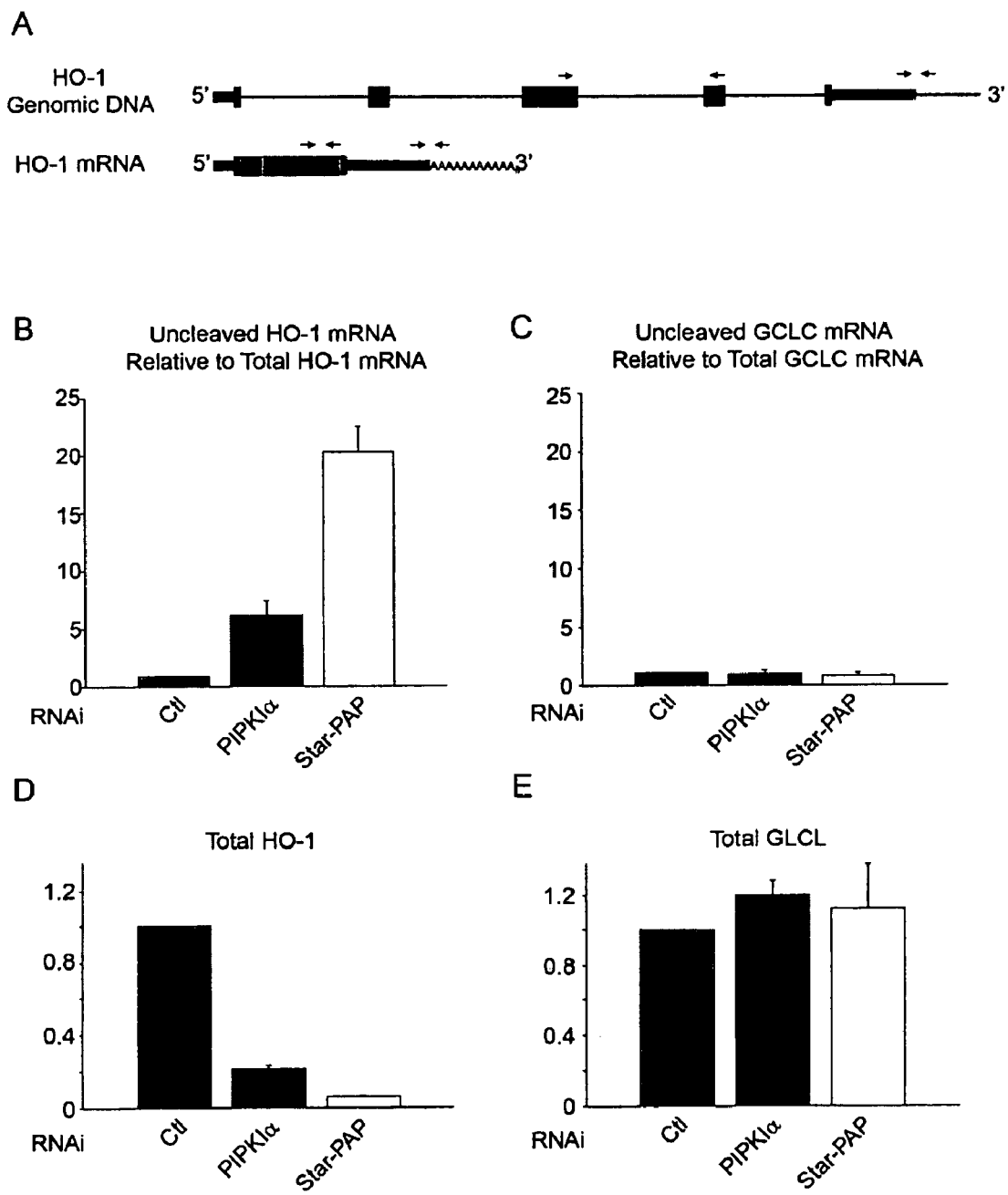
FIG. 13 shows that Star-PAP performs 3' cleavage of its target message. (A) a schematic diagram showing the position of the PCR primers (arrows) used for measurement of total and uncleaved mRNA. Total RNA was isolated from HEK293 cells treated with control (Ctl), PIPKIα, or Star-PAP siRNA oligos and reverse transcribed with random hexamer primers. The resulting cDNA was used to measure levels of total and uncleaved mRNA. Uncleaved HO-1 (B) and GCLC (C) mRNA levels were normalized to total HO-1 and GCLC levels respectively from the same cells (D) and (E). Data represents three independent experiments.

The amount of uncleaved HO-1 mRNA present after Star-PAP or PIPKIα knockdown was measured using quantitative real-time PCR. Total RNA was treated with DNaseI (Invitrogen) and then re-purified on RNeasy columns (Qiagen). Star-PAP knockdown resulted in a 20-fold increase in the quantity of uncleaved HO-1 pre-mRNA relative to total HO-1 mRNA. (FIG. 13). In contrast, the amount of uncleaved non-Star-PAP target mRNA GCLC was not changed by either Star-PAP or PIPKIα knockdown. Primers used for the cleavage analysis are presented in Table 4 as follows:

TABLE 4

Assay primers

| Primer | Sequence | SEQ ID NO: |
|---|---|---|
| HO-1 Clv fw | 5'-GGCACTGTGGCCTTGGTCTAA-3' | 41 |
| HO-1 Clv rv | 5'-TCCTACCGAGCACGCAAGAA-3' | 42 |
| GCLC Clv fw | 5'-ATGCCTGGTTTTCGTTTGCA-3' | 43 |
| GCLC Clv rv | 5'-AGCTGTGGAACTCACACACTCA-3' | 44 |

This is consistent with reports that poly(A) polymerase (PAP) is required for efficient 3' cleavage by the endonuclease CPSF-73 in vitro, and indicates that Star-PAP may be functioning as a PAP for the maturation of HO-1 mRNA. PIPKIα knockdown has a smaller effect on HO-1 mRNA cleavage, consistent with PIPKIα modifying Star-PAP function. The accumulation of unprocessed HO-1 mRNA on Star-PAP knockdown is consistent with Star-PAP functioning as a PAP in vivo, and demonstrates that Star-PAP participates in the 3' end formation of HO-1 mRNA.

f. PIPKIα Knockdown

PIPKIα knockdown (performed as described for Star-PAP, but using the following PIPKIα siRNAs: GGUGCCAUCCA-GUUAGGCA (SEQ ID NO: 45) and GAAGUUGGAG-CACUCUUGG[[A]] (SEQ ID NO: 46)) did not dramatically affect the amount of HO-1 pre-mRNA cleavage even though PIPKIα is required for HO-1 expression. Without wishing to be bound by theory, it may be that while Star-PAP knockdown may inhibit HO-1 expression by causing defects in cleavage, PIPKIα knockdown may be reducing HO-1 mRNA levels by affecting other aspects of 3' processing, such as assembly of the complex or reduced Star-PAP activity in the absence of PIPKIα generated $PIP4,5P_2$. This data is consistent with a model in which Star-PAP is required for efficient 3' processing of HO-1 mRNA, and the resulting unprocessed messages are rapidly degraded. It suggests that the decrease in HO-1 mRNA levels observed in Star-PAP knockdown cells is due to improper 3' processing.

Figure 22:
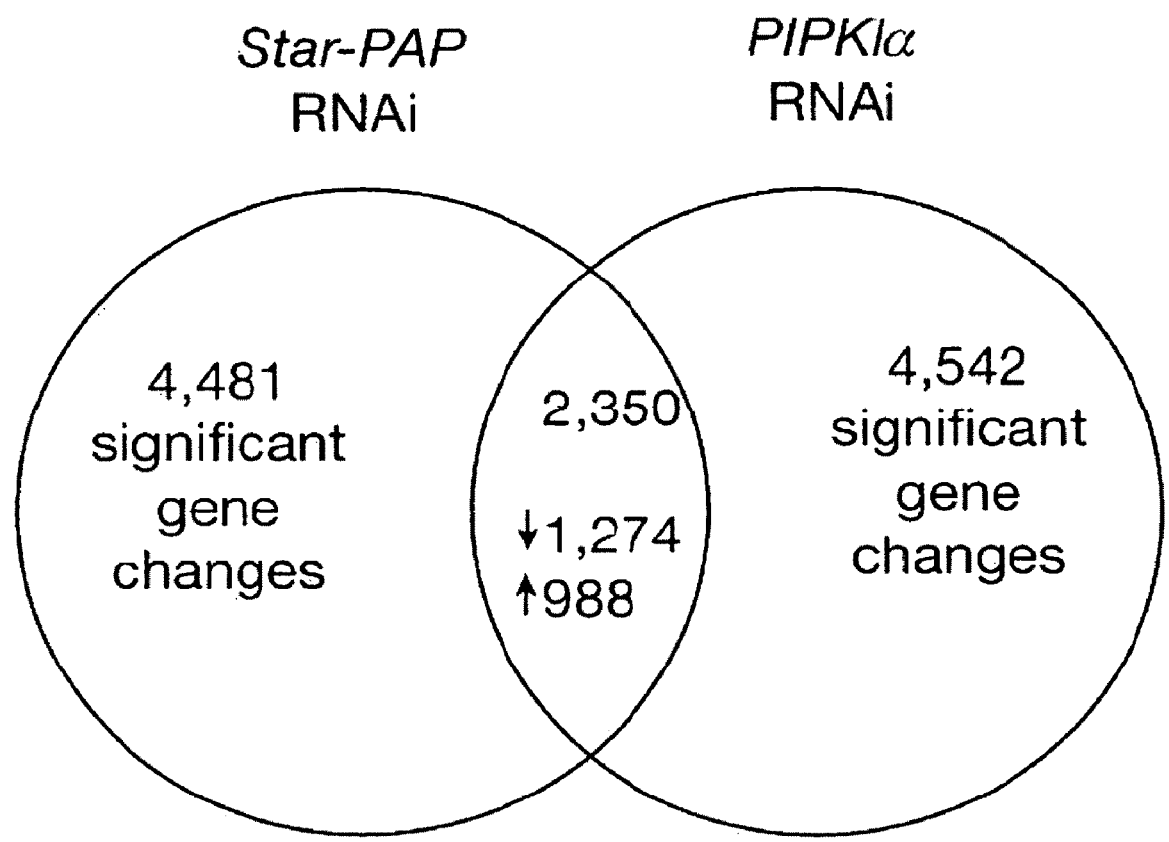
FIG. 22 shows a Venn diagram depicting mRNA expression profiles on Star-PAP or PIPKIα RNAi knockdown versus control.

To better understand the functional relationship between Star-PAP and PIPKIα, a microarray analysis was performed to compare the total polyadenylated mRNA from the Star- PAP knockdown and the PIPKIα knockdown. Statistical analysis was performed as described above for Star-PAP. In this experiment, a significant (conditional false discovery rate≦0.01) change in transcript level compared with control cells (n=3) was detected for 4,542 genes with PIPKIα knockdown. An overlap of 2,350 significant gene changes, of which 2,262 were in the same direction, were detected. (FIG. 22).

Knockdown of both Star-PAP and PIPKIα showed no additive effect on the loss of HO-1 or NQO1 mRNA.

Figure 21:
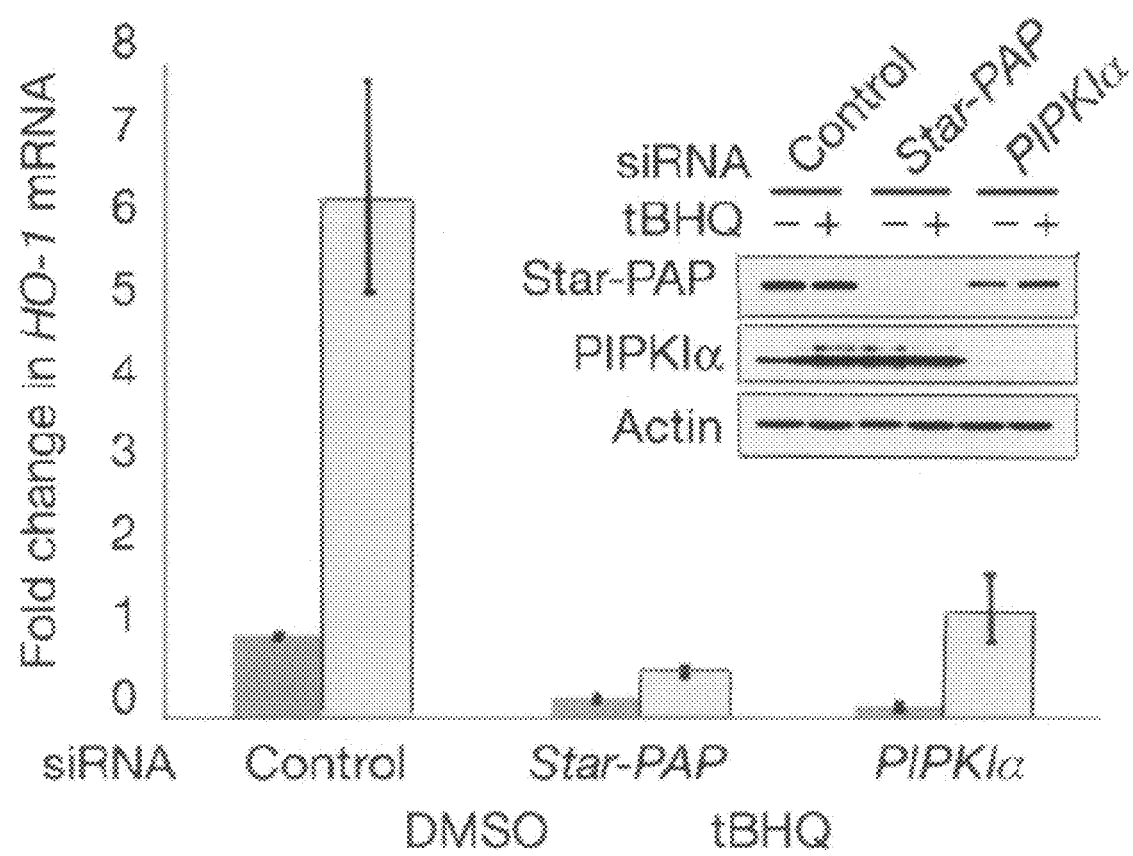
FIG. 21 shows the results of a qRT-PCR analysis of HO-1 mRNA levels from HEK-293 cells transfected with Star-PAP, PIPKIα or control siRNA oligonucleotides and treated with 100 µM tBHQ (n=3). DMSO, dimethylsulphoxide, vehicle control.

In addition, the PIPKIα knockdown was also able to block tBHQ induction of HO-1 mRNA while other mRNAs tested were not altered by PIPKIα knock down (FIG. 21). Thus, it appears that Star-PAP and PIPKIα both function in controlling basal HO-1 mRNA levels and induction HO-1 mRNA levels; indeed these proteins may synergize to maintain HO-1 levels in response to oxidative stress. Further, Star-PAP may play a role as a regulatory control in many cellular functions, and may not simply be a general polyadenylation enzyme.

Of the genes identified as Star-PAP targets, a number of these encode proteins involved in detoxification and/or oxidative stress response. Such genes include HO-1, NQO1, APOE, PRDX1, GSTK1 and ALDH2.

11. Determining Second Messenger Function In Vivo

Figure 11:
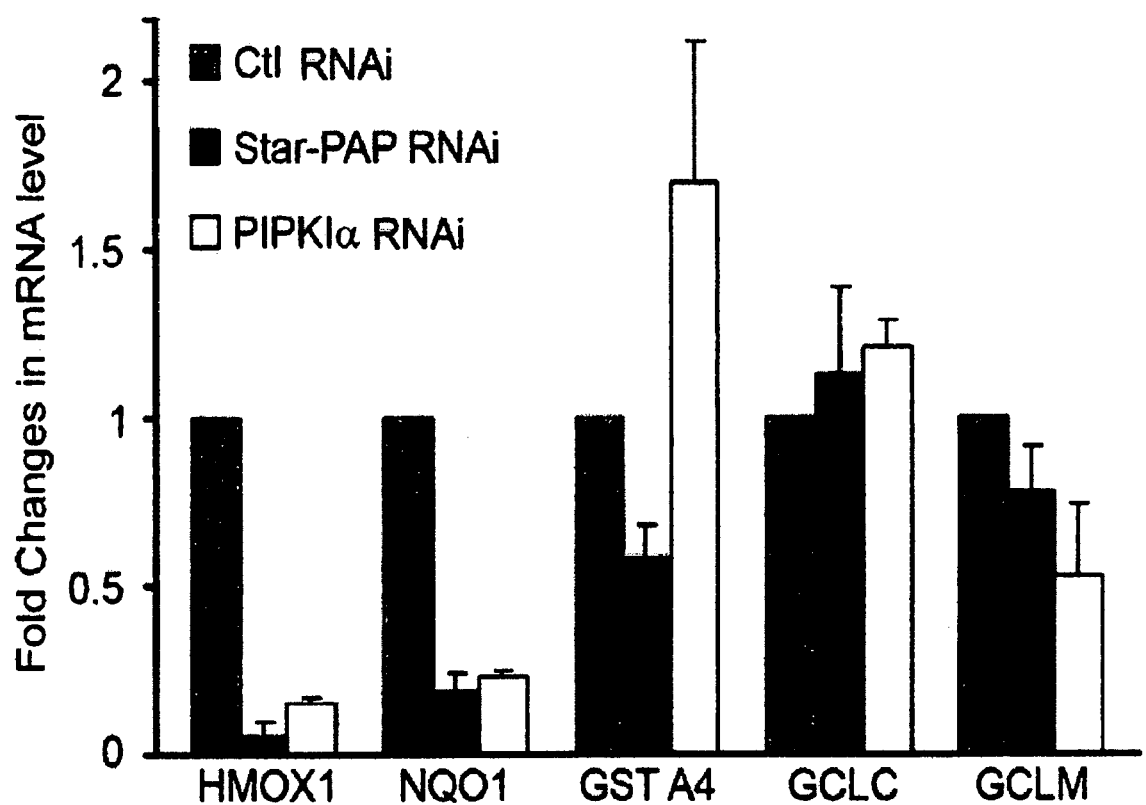
FIG. 11 shows a graph of fold change in mRNA level of five targets in Star-PAP knockdown, PIPKIα knockdown and control cells.

To demonstrate that $PI4,5P_2$ modulates Star-PAP in vivo, Star-PAP target mRNA level were evaluated in PIPKIα knockdown cells. (PIPKIa-1 siRNA sequences: 5'-GGUGCCAUCCAGUUAGGCA-3' (SEQ ID NO: 45); 5'-GAAGUUG-GAGCACUCUUGG-3' (SEQ ID NO: 46)). Message levels of five different sequences were compared in HEK293 cells containing either control siRNA or siRNA targeting PIPKIα. FIG. 11 shows that the PIPKIα knockdown cells produce a clearly reduced total amount of HO-1 mRNA and NQO1 mRNA, although to a lesser extent than Star-PAP knockdown.

Although Star-PAP is unique in its association with PIPKIα and its polymerase activity is regulated by $PI4,5P_2$, PIPKIα does not appear to be required for all Star-PAP dependent messages. Thus, the identification of Star-PAP as a nuclear poly(A) polymerase which selectively regulates specific messages adds an unexpected level of control to gene regulation.

12. Phosphorylation of Star-PAP by CKIα

As described in section 8 above, the Star-PAP complex includes kinase activity. In the assays to test the kinase activity of the Star-PAP complex, FLAG-Star-PAP was also phosphorylated (FIG. 19). The phosphorylation of FLAG-Star-PAP was inhibited by $PI4,5P_2$ at concentrations as low as 12.5 μM (FIG. 19) indicating that the associated kinase is sensitive to $PI4,5P_2$. Synthetic $PI4,5P_2$ (Echelon Biosciences Inc.) was resuspended in 50 mM Tris-HCL pH 7.9 at 2.5 mM and subjected to bath sonication to form micelles and used at final concentration of 12.5-100 μM.

Casein Kinase Iα (CKIα), is a protein kinase found in nuclear speckles; moreover, CKIα activity is inhibited by $PI4,5P_2$. To confirm that CKIα is present in Star-PAP complexes, an immunoblot of purified FLAG complexes with a CKIα specific antibody showed that CKIα co-purifies specifically with Star-PAP but not with PAPα (FIG. 23A). FLAG proteins were expressed and purified as follows. Human Star-PAP and rat CKIα cDNAs were cloned in to the pFLAG-1 mammalian expression vector (Sigma). For each FLAG purification, four 10 cm dishes each containing ~5×106 HEK 293 cells were transfected with 10 μg DNA and allowed to express for 48 hours. FLAG purifications were performed according to the manufacturer's directions.

In addition, immunoprecipitation (performed as described above) of endogenous Star-PAP from HEK 293 cells resulted in co-precipitation of endogenous CKIα (FIG. 23B).

To demonstrate that CKIα is involved in the phosphorylation of Star-PAP, the ability of CKI specific inhibitors to block the phosphorylation of FLAG purified Star-PAP by the associated kinase activity was evaluated.

The kinase assays were performed as described above in section 8 for the Star-PAP complexes. Except for inhibitor studies, all reaction components except ATP were incubated with inhibitors for 45 minutes on ice prior to starting the assay. The CKI inhibitors IC261 (Calbiochem) $IC_{50}$ 11 μM, and CKI-7 (Sigma) $IC_{50}$~6.0 μM, were resuspended in DMSO and used at final concentrations of 0.1-100 μM. Both inhibitors were able to block the phosphorylation of Star-PAP by the complex-associated kinase activity in a dose dependent fashion, suggesting that CKIα is responsible for at least some of the kinase activity contained in the Star-PAP complex (FIG. 23C, D)

To demonstrate direct phosphorylation of Star-PAP by CKIα, purified CKIα was used to phosphorylate FLAG-Star-PAP. Before the phosphorylation assay, endogenous kinase activity in the FLAG complex was destroyed by heat inactivation; no detectable phosphorylation activity was detected after heat inactivation. Purified FLAG-CKIα was able to directly phosphorylate heat inactivated Star-PAP while the catalytically inactivated CKIα mutant K46R was not (FIG. 24A). The K46R mutant was generated by PCR based mutagenesis using the following primers: 5-GAAGTG-GCAGTGAGACTAGAATCCCAG-3' (SEQ ID NO: 47) and 5'-CTGGGATTCTAGTCTCACTGCCACTCC-3' (SEQ ID NO: 48). Additionally, phosphorylation by CKIa was blocked by 50 μM IC261 or 50 μM $PI4,5P_2$. (FIG. 24B)

To determine CKIα phosphorylation sites on Star-PAP, a series of FLAG-Star-PAP truncation and deletion mutants (FIG. 24C) were expressed and purified from HEK 293 cells and subjected to the in vitro kinase assays described above.

Under these conditions, CKIα was able to phosphorylate all truncation mutants except those which lacked the first half of the proline rich region (ΔPRR ½, amino acids 223-274) that splits the catalytic domain of Star-PAP. (FIG. 24D). This region contains nine serine and threonine residues conserved among mammalian species, including two consensus CKIα sites and a number of acidic residues that could contribute to additional CKIα phosphorylation sites (FIG. 24E).

To determine whether the proline-rich region of Star-PAP is required for CKIα association with the Star-PAP complex, or for CKIα kinase activity, full-length and ΔPRR Star-PAP were expressed and purified from HEK 293 cells, and endogenous CKIα was found to be associated with both. (FIG. 25A) Furthermore, while FLAG purified Star-PAP ΔPRR was not phosphorylated by the associated kinases (FIG. 25B), the complex still contained activity towards both casein and MBP similar to that of full length Star-PAP demonstrating that the deletion of the PRR does not disrupt the association of protein kinase activity with the Star-PAP complex (FIG. 25C). These results indicate that the inability of CKIα to phosphorylate Star-PAP PRR deletion mutants is most likely due to a deletion of the phosphorylation site(s) and not a disruption of the Star-PAP/CKIα interaction.

13. Knockdown of CKIα and Effects on Star-PAP mRNA Targets

To determine whether CKIα plays a role in regulating the expression of Star-PAP targets identified in the Star-PAP knockdown experiments, CKIα knockdown experiments were performed.

HEK 293 cells were treated with a CKIα specific siRNA. The siRNAs were derived from an siGenome SMART Pool (Dharmacon) directed against CSNK1A1. Both HO-1 mRNA expression levels and NQO1 mRNA expression levels decreased, while other Star-PAP target mRNA levels appeared relatively unaffected. (FIG. 26).

The effects of PIPKIα knockdown compared to CKIα and Star-PAP knockdown on Star-PAP target mRNA levels were also evaluated. For PIPKIα, the following siRNAs were used: PIPKIα-1: 5'-GGUGCCAUCCAGUUAGGCA (SEQ ID NO: 45) and PIPKIα-3: 5'-GAAGUUGGAGCACUCUUGG (SEQ ID NO: 46). SiRNA oligonucleotides were transfected using calcium phosphate at a final concentration of 120 nM oligo/ml of growth media. Growth media was replaced 6 hours after transfection and the transfection was repeated 24 hours later. Cells were harvested for analysis 72 hours after the first transfection.

Figure 26:
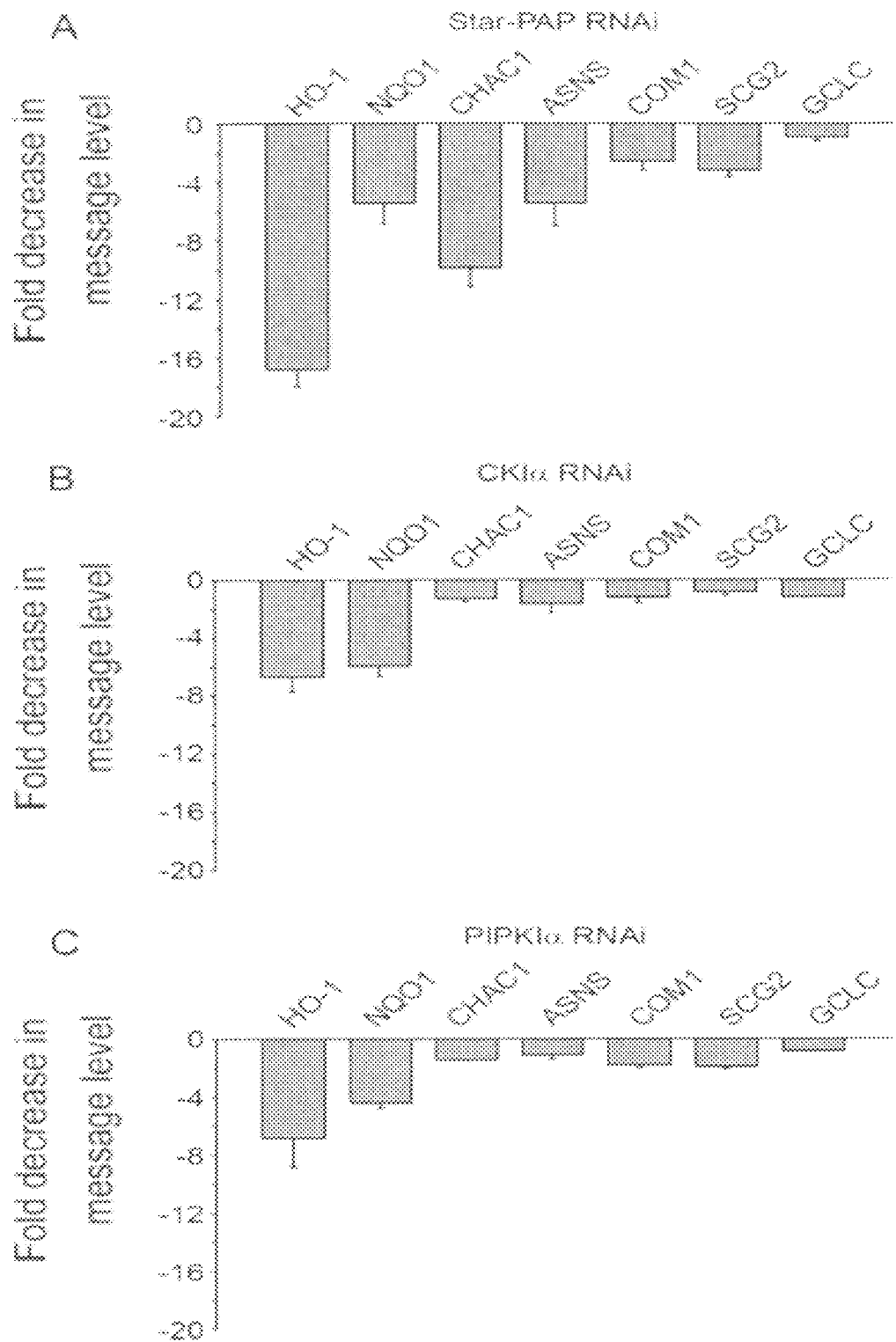
FIG. 26 shows that CKIα and PIPKIα are required for the maintenance of specific Star-PAP mRNAs. Quantitative real-time PCR analysis of mRNA expression levels after treatment with siRNA oligos specific for Star-PAP (B), CKIα (D), or PIPKIα (F), relative to treatment with control siRNA oligo. (A), (C) and (E) show immunoblotting results of representative protein levels from cells used in (B), (D) and (F) with Star-PAP antibodies, CKIα antibodies and PIPKIα antibodies, respectively. (G) Quantitative real-time PCR analysis of HO-1 message levels from cells treated with 100 µM tBHQ after 2.5 h pre-treatment with CKI inhibitors IC261 (50 µM) or CKI-7 (250 µM). (H) Quantitative real-time PCR analysis of HO-1 message levels from CKIα or PIPKIα knockdown cells treated with 100 µM tBHQ or DMSO (control) for four hours. Quantitative real-time PCR results are the average of three independent experiments. Error bars represent one standard deviation.

Of the mRNAs examined, treatment of cells with PIPKIα specific siRNA resulted in comparable decreases in the same Star-PAP target mRNAs as CKIα siRNA, namely HO-1 and NQO-1 (FIG. 26). Together, these data raise the possibility that PIPKIα and CKIα may be working to regulate specific Star-PAP target mRNAs.

Similar to Star-PAP and PIPKIα, a reduction in CKIα activity (achieved by pretreating HEK 293 cells with the CKI specific inhibitors CKI-7 and IC261) not only reduced the basal levels of HO-1 mRNA but also blocked HO-1 mRNA induction after exposure to 100 µM tBHQ (FIG. 26). The transcriptional anti-oxidant response in HEK 293 cells was induced by treatment with 100 µM tert-butylhydroquinone (Sigma) in DMSO for 4 hours. Control cells were treated with DMSO only.

Treatment of HEK 293 cells with CKIα siRNA did not block HO-1 induction by tBHQ. This suggests that other CKIα isoforms, or other protein kinases sensitive to CKI inhibitors are also involved in the induction of HO-1 mRNA.

Figure 16:
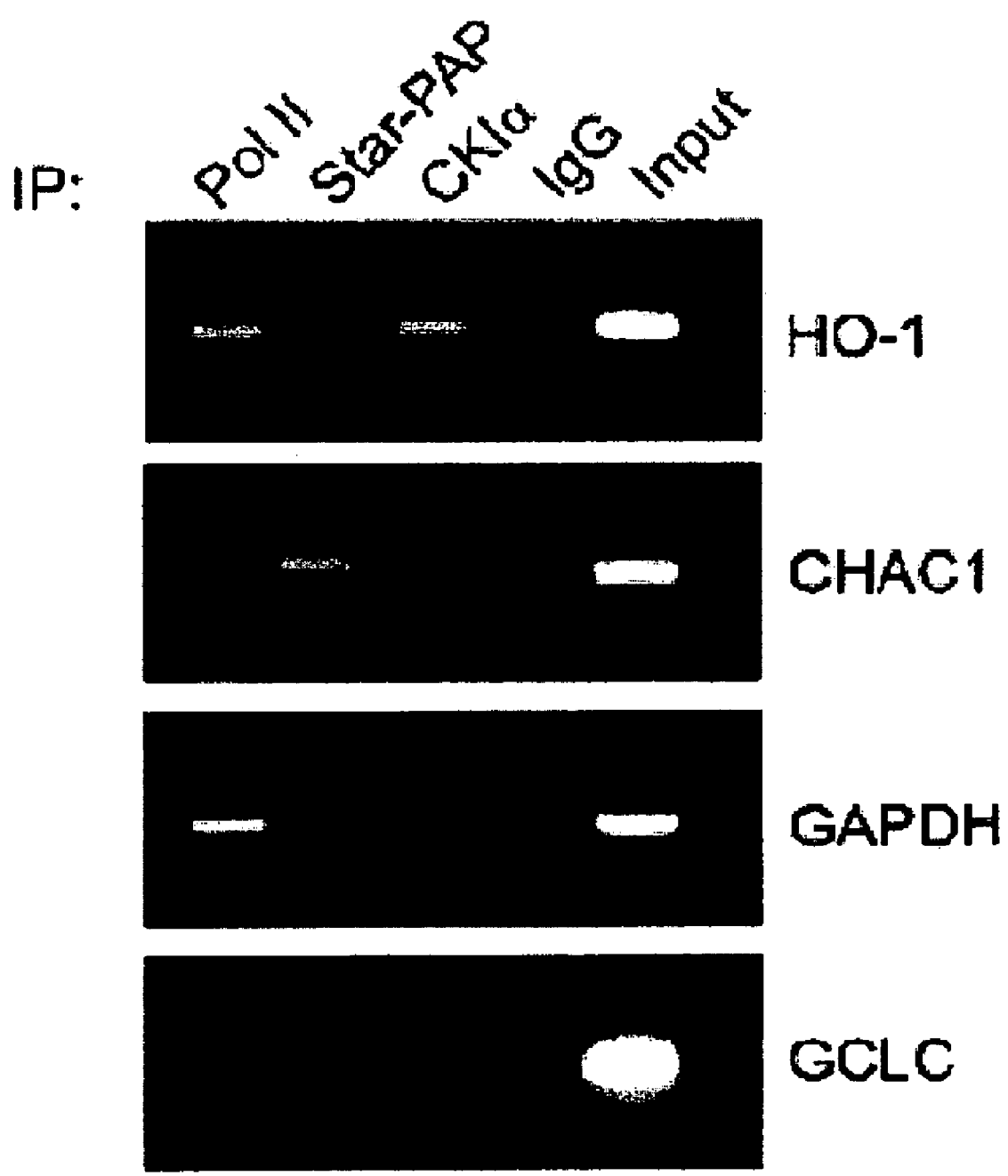
FIG. 16 shows that CKIα specifically interacts with some Star-PAP target messenger RNAs. RNA polymerase II, Star-PAP, or CKIα were immunoprecipitated from nuclear extracts isolated from HEK293 cells cross-linked with 1% formaldehyde. The cross-links were reversed and total RNA was isolated from the immunoprecipitates and analyzed by reverse-transcriptase PCR with gene specific primers for the Star-PAP targets HO-1 and CHAC-1 as well as the non-targets GCLC and GAPDH. A non-specific rabbit IgG was used as a control.
Figure 17:
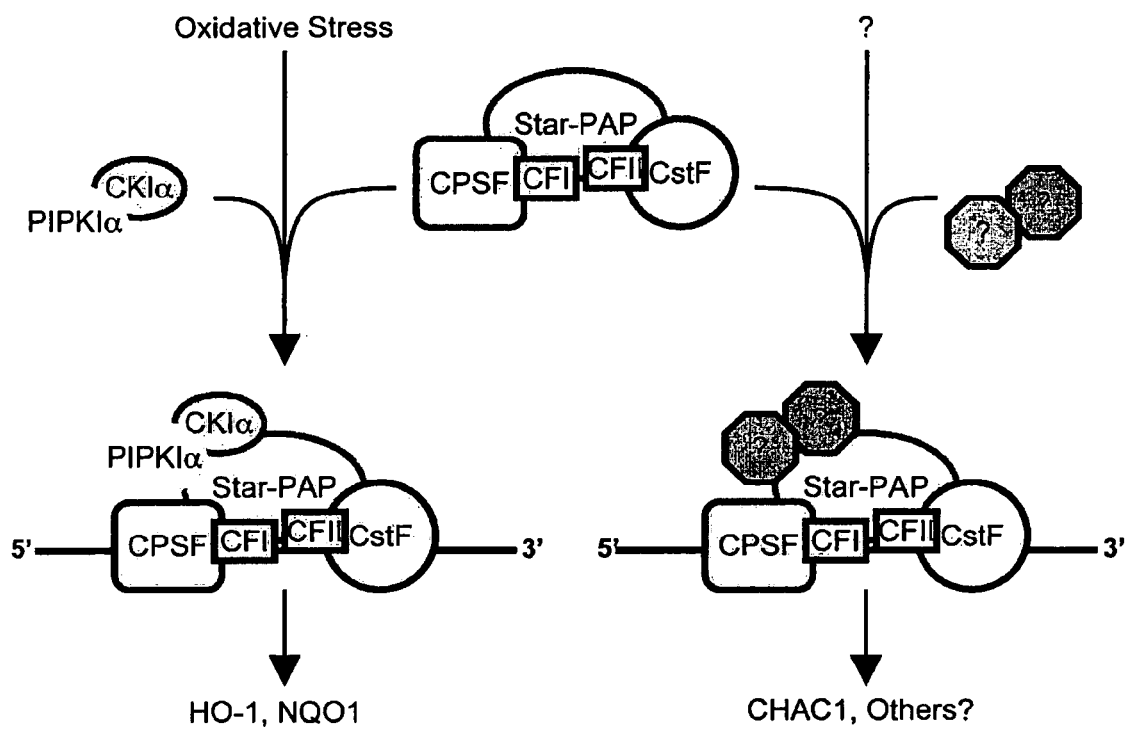
FIG. 17 shows a model of Star-PAP complex association defining target messages. A stimuli, such as oxidative stress, drives inclusion of the phosphoinositide signaling components PIPKIα and CKIα into the Star-PAP complex. The specific interactions of PIPKIα and CKIα with the Star-PAP complex is required for the regulation of specific target messages, in this case, those involved in response to oxidative stress. Alternatively, different stimuli could cause the assembly of a different complex, which regulates a different set of Star-PAP target messages.

To determine whether CKIα directly interacts with HO-1 mRNA, endogenous CKIα and Star-PAP were immunopurified from HEK 293 cells and total RNA was isolated from the immunoprecipitates. Specific mRNAs were then detected using reverse transcriptase PCR. Similar to Star-PAP, CKIα was specifically associated with its putative target mRNA HO-1 (FIG. 16). CKIα did not appear to interact with Star-PAP target mRNA CHAC1 whose expression does appear to require CKIα or PIPKIα. This suggests that the association of CKIα with the Star-PAP complex occurs only with specific target mRNAs and that CKIα is not a universal component of all Star PAP complexes.

14. Star-PAP Complex Activity is Enhanced in Cells Treated with tBHQ

Figure 27:
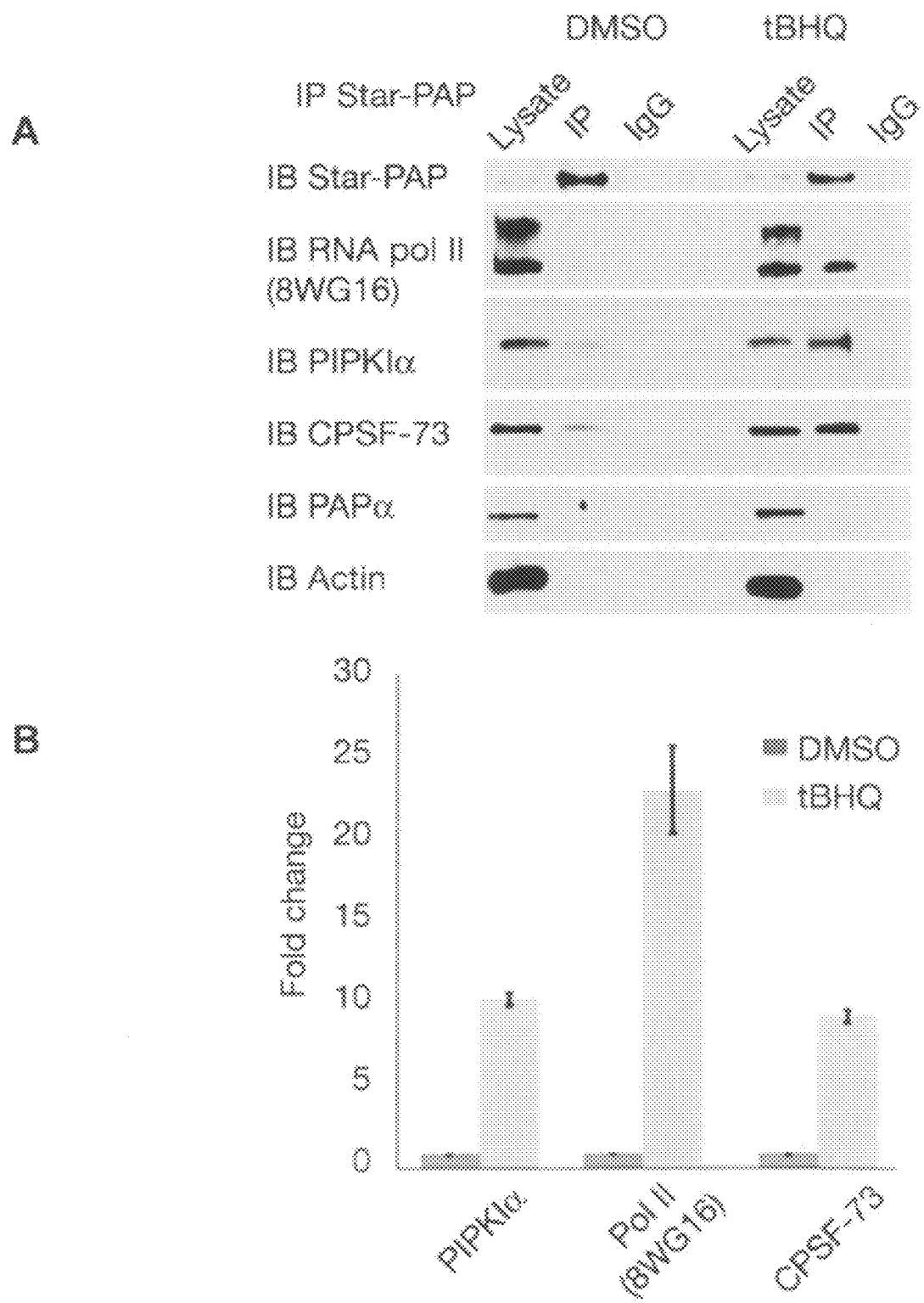
FIG. 27 (A) shows immunoprecipitation of Star-PAP and detection of associated proteins from HEK-293 cells after treatment with 100 µM tBHQ. IB=immunoblot. (B) Quantification of Star-PAP complex assembly from (A). (C) PAP assay with affinity purified FLAG-Star-PAP (WT) or FLAG-Star-PAP mutant (MT) from stably expressing HEK-293 cells subsequent to treatment with TBHQ and/or $PtdIns4,5P_2$. (D) Time course subsequent to treatment with tBHQ in (C) in the presence of $PtdIns4,5P_2$. (E) FLAG-PAPα activity after treatment with 100 µM tBHQ and/or the presence of $PtdIns4,5P_2$. All error bars represent s.e.m.

To explore the mechanism by which Star-PAP acts in the 3' processing of mRNA, the effect of stimulation of cells by tBHQ on Star-PAP complex assembly was evaluated. The association of endogenous Star-PAP with PIPKIα, CSPF-73 and RNA Pol II was enhanced by treatment with 100 µM tBHQ for 4 hours (FIGS. 27A, B). Further, Star-PAP complex purified from stably expressing cells treated with tBHQ showed a more than 15-fold increase in enzymatic activity over Star-PAP from control cells (FIG. 27C). Neither polymerase-inactive Star-PAP nor PAPα showed any increase in activity when isolated from tBHQ-treated cells (FIGS. 27C, E).

Treatment of cells with tBHQ caused a large increase in Star-PAP complex activity for the initiation of polyadenylation. When Star-PAP was isolated from tBHQ-treated cells, $PI4,5P_2$ stimulated Star-PAP processivity, increasing the length of the poly(A) tails, as can be seen over a time course (FIG. 27D). This demonstrates that tBHQ-induced signaling and $PI4,5P_2$ modulate Star-PAP activity in two distinct yet complementary manners. Not wishing to be bound by theory, these data suggest a model in which an antioxidant response induces the assembly of the Star-PAP complex, leading to a rapid initiation of 3' end formation and polyadenylation by the Star-PAP complex. $PI4,5P_2$ produced by PIPKIα in the complex may then control the processivity of Star-PAP, resulting in a lengthened poly(A) tail. In this manner Star-PAP may respond to oxidative stress signals, and potential other signals, to efficiently regulate the 3' end formation and polyadenylation by the Star-PAP complex.

B. Use of Star-PAP to Polyadenylate Target Sequences In Vitro and In Vivo

The novel PIP-PAP described herein can be used as molecular biology reagents to perform polyadenylation reactions in vitro, can be transformed or transfected alone or in conjunction with a PIP kinase into host cells to analyze the effects of polyadenylation of specific gene products in vivo, and may also be incorporated into the cells and tissues of a host organism, such as a mammal for therapeutic purposes. Additionally, nucleic acids may be used to detect or inhibit the expression of target sequences; recombinant techniques may be used to generate protein fusions or mutants with altered function or regulation; recombinant proteins may be used to generate antibodies to particular epitopes of a protein.

Methods for producing recombinant proteins or nucleic acids and variants thereof are well-known in the art. In general, nucleic acid sequences encoding PIP-PAPs such as Star-PAP may be incorporated into a recombinant expression vector in a form suitable for expression of the proteins in a host cell. A suitable form for expression provides that the recombinant expression vector includes one or more regulatory sequences operatively-linked to the nucleic acids encoding Star-PAP in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art.

A Star-PAP protein may be expressed not only directly, but also as a fusion protein with a heterologous polypeptide, e.g., a sequence to increase expression or solubility of the fusion protein, or to aid in the purification of the fusion protein by acting as a ligand in affinity purification, or to result in secretion. In other embodiments, the heterologous peptide may alter the function, targeting, regulation or protein-protein interactions of the protein of interest. For example, PIP-PAP functional domains may be used in conjunction with domains of other proteins to generate chimeric proteins with novel functions. Such a chimeric may include fusing the $PI4,5P_2$ regulatory domain of Star-PAP with the enzymatic functional domain of another protein to allow for a novel means of regulation and control of the enzymatic function of the other protein. The effect of the functional domain so targeted may prove therapeutic, for example, by providing enzymatic function to inhibit or to enhance a specific activity. Similarly the PIPKIα recognition/binding domain of Star-PAP could be fused to a protein of interest, thus allowing that protein to be targeted or modulated by PIPKIα.

C. Assays

Agents which modulate PIP-PAP activity (e.g., enhance, inhibit, alter target or substrate specificity, etc.) are also embodied herein. For clarity and simplicity, the following discussion describes the assay methods using Star-PAP and PIPKIα, as well as the HO-1 gene product. However, it will be understood by one skilled in the art that in some embodiments, other proteins may be used. Star-PAP activity may include but is not limited to (1) PIPKIα binding; (2) poly(A) polymerase activity; (3) enhanced poly(A) polymerase activity in the presence of $P4,5PI_2$; (4) modulation of the mRNA levels of one or more of the following: prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene, ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). In particular embodiments the mRNA levels of HO-1 and/or NQO1 may be evaluated for modulation.

Agents which modulate such activity may include but are not limited to: nucleic acid sequences such as siRNA and antisense oligonucleotides, proteins, antibodies, and organic and inorganic chemical compounds. These agents may be present in cells and tissues, or may be created, isolated or purified via synthetic means. Some test agents may be found to enhance or up-regulate PIP-PAP activity, while other may be found to diminish or decrease Star-PAP activity as compared to control sample (e.g., samples which includes no test compound). Activity may be evaluated before, during or after exposing the PIP-PAP to the test agent. As one skilled in the art would understand, the method of exposure may depend on the test agent. For example, "exposure" may include transfecting a cells with a nucleic acid encoding the agent if the agent is a protein or a nucleic acid, adding the agent to the cell medium if the agent is a chemical compound, etc.

Method for identifying agents which modulate such functions are known to those skilled in the art. For example, experimental example (8) describes testing for poly(A) polymerase activity in the presence or absence of various phosphoinositide second messengers. The same assay format could be used to test other compounds instead of second messengers. Moreover, the poly(A) polymerase activity of the PIP-PAP could also be evaluated with the test compound in the presence or absence of a second messenger. Additionally or alternatively, a host cell may be transformed with nucleic acid sequences encoding a PIP-PAP, or a PIP-PAP and a PIP kinase (or subunits thereof) in in vivo screening assays to determine whether a test agent modulates the activity of a PIP-PAP as compared to a control cell (e.g., a cell similarly transformed which has not been exposed to the test agent).

An in vitro or an in vivo assay can also be used to determine whether a test agent modulates the level (e.g., mRNA or protein level) of a Star-PAP target, e.g., prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene, ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"). In particular embodiments the levels of HO-1 and/or NQO1 may be evaluated for modulation.

An in vitro screening assay to identify an agent that modulates the binding of a PIP-PAP such as Star-PAP to a PIP kinase such as PIPKIα, can be carried out by detecting and measuring the binding (e.g., the affinity) of a PIP-PAP, such as Star-PAP or subunit thereof, to a PIP kinase or subunit thereof. The detection and measurement of this binding interaction will be dependent on the type of screening assay performed and the labels used. Such screening assays to detect binding between proteins in the presence of a test agent are well-known in the art, and methods for detecting and measuring binding between proteins are exemplified herein and may include but are not limited to GST pull-down, immunoprecipitation, ELISA, western blotting, gel shift analysis, etc. In an exemplary method, a test compound could be added to the GST or immunoprecipitation assay and compared with a control reaction (i.e., a reaction with no test agent). In other embodiments, a fluorescently labeled Star-PAP or PIPKIα peptide may be used in a binding assay with PIPKIα or a fragment thereof to identify agents which modulate the Star-PAP/PIPKIα interaction.

An in vivo assay can also be used to determine whether a test agent modulates the binding activity of a PIP-PAP with a PIP kinase. By way of illustration, a two-hybrid assay may be used, where the test agent is contacted with a cell expressing a PIP-PAP and a PIP kinase (or subunits thereof), where the PIP-PAP is fused to a DNA binding domain and the PIP kinase is fused to an activation domain. When the two fusion proteins can contact and bind each other on a reporter construct, reporter expression is induced. If the test agent disrupts the binding of the of the PIP-PAP and the PIP kinase, reporter protein expression is blocked.

Additionally, when assaying test agents, a control may also include a known agent which has a high affinity for binding and inhibiting the interaction between PIP-PAP and PIP kinase, or a known agent which has a low affinity for binding and inhibiting the interaction between a PIP-PAP and a PIP kinase.

D. Therapeutics

As described above, the modulation of a PIP-PAP can affect the expression levels of a specific subset of targets mRNAs. For example, down-modulation of Star-PAP poly (A) polymerase expression resulted in decreased mRNA expression of select target genes (e.g., prostate specific antigen ("PSA"), asparagine synthetase ("ASNS"), heme oxygenase (decycling) 1 ("HMOX1" or "HO-1"), active transcription factor 6 ("ATF6"), secretogranin II ("SCG2"), completion of meiotic recombination 1 ("COM1"), cation transport regulator-like 1 ("CHAC1"), stannioclacin 2 ("STC2"), cyclin D1, RAC3, phosphoserine phosphatase ("PSPH"), bicardal, G-Patch, activating signal cointegrator complex 1 ("ASCC1"), nuclear receptor binding SET domain protein 1 ("NSD1"), Wolf-Hirschhorn Syndrome Candidate 1 gene, ("WHSC1"), microfibrillar associated protein 5, ("MFAP5"), β-crystalline A, ("β-CryA"), NAD(P)H dehydrogenase, quinine 1, ("NQO1"), glutathione S-transferase A4, ("GSTA4"), glutamate cysteine ligase catalytic subunit, ("GCLC"), glutamate-cysteine ligase, modifier subunit, ("GCLM"), aldehyde dehydrogenase 1 family, member A3 ("ALDH1A3"), NADH dehydrogenase (ubiquinone) Fe—S protein 1, 75 kDa (NADH-coenzyme Q reductase) ("NDUFS1"), apolipoprotein E ("APOE"), cyclin A1 ("CCNA1"), amyloid beta (A4) precursor-like protein 1 ("APLP1"), ankyrin repeat domain 1 (cardiac muscle) ("ANKRD1"), cyclin E2 ("CCNE2"), peroxiredoxin 1 ("PRDX1"), glutathione s-transferase kappa 1 ("GSTK1") and aldehyde dehydrogenase 2 family (mitochondrial) ("ALDH2"), thereby resulting in decreased activity. Conversely, over-expression of Star-PAP or up-regulation of Star-PAP activity may have the effect of increasing expression levels, and thus the activity, of a select set of genes.

Numerous diseases, conditions and disorders have been found to be associated with non-wild-type expression levels of the genes shown to be affected by Star-PAP in the knockdown assays. For example, HO-1 expression is implicated in diseases and disorders such as adult onset Still's disease, hemophagocytic syndrome, septic shock, sickle-cell associated kidney injury and neurodegenerative disorders such as Alzheimer's Disease. It is contemplated that in some diseases, disorders or syndromes, enhanced expression of HO-1 may help alleviate symptoms. For example, early diagnosis of some types of cognitive disorders coupled with enhanced Star-PAP expression or activity, and thus enhanced HO-1 expression, could alleviate damage done to nervous tissue as the result of prolonged oxidative stress. Likewise, in a transplant patient, enhanced expression of Star-PAP and thus HO-1 could provide a longer interval between transplant and graft-host rejection complications.

Conversely, there are situations in which a down-modulation of Star-PAP, and thus HO-1 expression and activity would be therapeutic. In septic shock for example, a decrease in HO-1 expression could prolong the time to smooth muscle relaxation and hypotension, thereby providing caregivers extra minutes to provide fluids and other therapies to a patient at risk. Such therapeutic uses are described in more detail below.

An effective amount of an agent which modulates the activity of Star-PAP is an amount which prevents, eliminates or alleviates at least one sign or symptom of a condition, disorder or disease mediated by Star-PAP or a gene product whose expression or activity is modulated by Star-PAP. Exemplary conditions and disorders may be associated with oxidative damage, oxidative stress, and inflammation; such conditions diseases and disorders may additionally be characterized by an increase in the level or activity of HO-1 and may be treated by increasing or decreasing levels or activity of a PIP-PAP in a subject. By way of example, but not by way of limitation, such diseases, disorders and conditions may include: neurodegenerative diseases such as Alzheimer's Disease and Parkinson's, cardiovascular disease such as atherosclerosis, inflammatory bowel disease, complications of sickle cell disease, graft-host rejection, septic shock, and Crohn's disease. Signs or symptoms associated with such diseases, disorders and conditions vary but are well-known to the skilled clinician. The amount of the agent required to achieve the desired outcome of preventing, eliminating or alleviating a sign or symptom of such a disease, condition or disorder will be dependent on the pharmaceutical composition of the agent, the patient and the condition of the patient, the mode of administration, and the type of condition or disease being prevented or treated.

An agent which modulates the expression or activity of Star-PAP and is useful as a therapeutic agent for preventing or treating condition, disorder or disease may be identified using the screening assays provided herein. For example, Star-PAP activity or expression may be modulated by using antibodies, as discussed above, or inhibitory nucleic acids such as ribozymes, antisense RNA or DNA, RNAi, siRNA and the like. These RNA molecules may be designed to specifically interact with the nucleic acid sequences encoding Star-PAP to decrease the expression of Star-PAP thereby decreasing its capacity to polyadenlyate gene products such as HO-1 mRNA. As the RNA molecules encoding Star-PAP are unique from other PAP RNA molecules, inhibitory RNA molecules may be directed to these unique sequences.

It is further contemplated that an agent which modulates the activity of Star-PAP may be attached to a targeting moiety which delivers the agent to a cell-type or tissue of interest. This could potentially decrease harmful side-effects of modulating the activity of Star-PAP in all cell-types or tissues.

Gene therapy techniques are also contemplated. As described above, the enhanced or inhibited expression of Star-PAP may have therapeutic value in treating or preventing diseases, conditions or disorders. Target cell populations may be modified by introducing wild-type or altered forms of Star-PAP in order to modulate the expression of downstream proteins. For example, deletion or missense mutants of Star-PAP that retain the ability to polyadenylate a target but that show greater enhancement in the presence of $PI4,5P_2$ may be used to therapeutic advantage.

Exemplary uses of Star-PAP in treating specific diseases, conditions, disorders or symptoms follow.

1. Enhanced Expression or Activity of Star-PAP to Alleviate Sickle-Cell Symptoms Sickle cell disease, an inherited disorder, is characterized by malformed red blood cells ("sickle-shaped" cells) which carry an abnormal form of hemoglobin.

The abnormal hemoglobin, hemoglobin S, causes the red cells to become stiff and misshapen. The change in red blood cell shape and stiffness cause the cells to get stuck in the smaller blood vessels, cutting off the blood supply to downstream tissues. Not only are such vascular occlusions painful, they may also result in severe tissue and organ damage. Additionally, sickle cells die and break down more quickly than normal red blood cells, resulting in anemia and its related complications.

It has been demonstrated that HO-1 plays a protective role in ischemic/reperfusion injury, and that increasing HO-1 levels beyond the naturally enhanced levels has a beneficial effect in inhibiting sickle cell related symptoms and complications such as vascular inflammation and vaso-occlusion. Accordingly, administration of a therapeutic compound which results in increased Star-PAP activity will likely result in an increase in HO-1 levels. Such methods of HO-1 increase would provide a novel therapeutic approach to treat and inhibit the symptoms and complications experienced by sickle cell disease patients.

2. Enhanced Expression or Activity of Star-PAP to Treat Alzheimer's Disease, Age-Associated Cognitive Decline, Mild Cognitive Impairment In Alzheimer's Disease, a neurodegenerative disease which causes dementia, a patient progressively suffers loss of both mental function and control of bodily functions. It has recently been discovered that patients suffering from AD have a significantly lower concentration of heme oxygenase-1 (HO-1) in their lymphocytes and plasma. However, nervous tissue of AD patients appears to have high concentrations of HO-1 as compared to control tissue, and consistent co-localization of HO-1 to neurofibrillary tangles and senile plaques in the AD specimens has been demonstrated. Additionally, high levels of HO-1 protein were detected in protein extracts derived from AD temporal cortex and hippocampus, whereas HO-1 protein levels in control tissues were low or absent. These results indicate that HO-1 is significantly over-expressed in neurons and astrocytes of AD hippocampus and cerebral cortex relative to control brains and supports the contention that AD-affected tissues are experiencing chronic oxidative stress.

Accordingly, if Star-PAP expression were enhanced in these tissues, HO-1 expression levels would likely increase. Enhanced HO-1 level at the sites of oxidative stress in the brain may act therapeutically to alleviate some of the deleterious effects caused by the stress, thereby alleviating symptoms characteristic of deteriorating brain disorders such as Alzheimer's Disease.

3. Enhanced Expression of Star-PAP to Ameliorate Graft-Host Rejection

HO-1 expression is clearly associated with prolongation of xenograft survival as well as protection allograft blood vessels against arteriosclerosis.

The up-regulation of the HO-1 gene during graft rejection may represent the tissue response to immune-mediated injury. Due to its anti-inflammatory and anti-apoptotic roles, HO-1 might play a role, at least in part, to limit the extent of tissue injury from allograft rejection. It is also of interest to note that expression of HO-1 can be detected in the interstitial infiltrating cells. This suggests that HO-1 may actually promote the survival of pro-inflammatory cells as well. Because HO-1 is expressed in both the graft tissue and the infiltrating cells, expression of this gene can be measured in tissue biopsies as well as in fluid samples by methods well known in the art (e.g., antibody detection, nucleic acid hybridization assays, etc.).

Accordingly, it is contemplated to administer a therapeutic compound that will enhance Star-PAP activity and thereby increase the amount of HO-1 present at the site of the graft. The enhanced HO-1 levels may act to further alleviate or prolong graft-host rejection.

4. Decreased Expression or Activity of Star-PAP to Treat or Prevent Septic Shock Septic shock, the most common cause of death in intensive care units, is characterized by severe and often irreversible hypotension. Sepsis leading to shock is often caused by severe gram negative bacterial infection. Shock is initiated by the release of bacterial cell wall-derived lipopolysaccharide (LPS, also known as endotoxin) and the subsequent production of cytokines and vasoactive mediators that result in vascular smooth muscle cell relaxation and hypotension.

It has recently been discovered that inducible HO-1 transcription and enzymatic activity are markedly increased in response to LPS, suggesting that HO-1 generated carbon monoxide (CO), a potent vasodilator, contributes to the reduction in vascular tone and hypotension during sepsis. Inhibition of sepsis-induced hypotension can be achieved by inhibiting HO-1 expression, (e.g., transcription or translation) and/or enzymatic activity.

In both large blood vessels (aorta) and small resistance vessels (arterioles), the increase in HO-1 is localized to vascular smooth muscle cells and endothelial cells. Moreover, the induction of vascular smooth muscle cell-derived HO-1 in vitro occurred at the level of gene transcription. The marked induction of HO-1 enzymatic activity within vascular tissue suggests that the CO generated by this enzymatic activity contributes to the reduction in vascular tone during endotoxic shock. Thus, agents which selectively inhibit or reduce HO-1 levels can be administered to patients to prevent and treat sepsis-associated hypotension.

Sepsis-associated hypotension may be diagnosed in vivo by administering to a patient an HO-1 specific antibody linked to a detectable label and imaging where the label localizes in the patient. An elevated level of label in the vascular tissue of the patient compared to a normal control level indicates that the patient may be at risk of developing or is suffering from sepsis-associated hypotension.

Accordingly, administration of a therapeutic compound that will decrease Star-PAP activity will also result, as was shown above, in decreased HO-1 levels. Lowered levels of HO-1 will inhibit or prolong time to vascular relaxation, thus providing care givers additional time to treat a patient at risk of hypotension due to sepsis.

E. Kits

Any of the above described nucleic acids, antibodies or therapeutic compositions may be provided in kit form. For example, kits for determining the amount or level of Star-PAP that is present in a subject may be coupled with a kit for treating a conditions, disease or disorder. Such a kit may include one or more of the following: 1) an antibody, such as a monoclonal antibody, which binds to Star-PAP; 2) one or more nucleic acids that hybridize to Star-PAP nucleic acid; 3) control reagents; 4) instructions for carrying out the test procedure and for interpreting results; 5) a therapeutic agent to treat a subject tested and found in need.

What is claimed is:

1. A method for polyadenylating a target polynucleotide sequence comprising:
   combining in vitro at least the following components:
   i) the target polynucleotide sequence;
   ii) ATP;
   iii) an isolated polypeptide selected from the group consisting of: a polypeptide comprising SEQ ID NO: 2, a polypeptide that is at least about 95% identical to SEQ ID NO: 2, wherein the polypeptide comprises poly(A) polymerase activity; and
   iv) optionally $PI4,5P_2$;
   under conditions whereby the target polynucleotide sequence is polyadenylated by the polypeptide of iii).

2. The method of claim 1, comprising PI4,5P2, wherein the $PI4,5P_2$ is combined with components i)-iii), and wherein the poly(A) polymerase activity of the polypeptide is enhanced.

3. The method of claim 1, wherein the polypeptide comprises SEQ ID NO: 2.

4. The method of claim 1, wherein the polypeptide consists of SEQ ID NO: 2.

* * * * *

SEQUENCE LISTING

```
<160> NUMBER OF SEQ ID NOS: 80

<210> SEQ ID NO 1
<211> LENGTH: 2747
<212> TYPE: DNA
<213> ORGANISM: Homo sapiens

<400> SEQUENCE: 1
gaagtgggtt ccggtggtgg cagaggtgct tgtgtttttg tcggtacagg agagtcgcta      60
tggcggcggt ggattcggat gtcgaatcgc tgccgcgtgg ggggttccgc tgctgcctct     120
gccacgttac tacagccaac cgacccagcc ttgatgccca cttgggaggc agaaagcacc     180
```

```
ggcacctggt agaactacga gctgcgagaa aggcccaggg acttcgaagt gtgtttgtca    240
gtggctttcc caggggtgtg gattctgctc agctctctga gtacttccta gcatttgggc    300
ctgtggccag tgttgtcatg gacaaggaca agggagtgtt tgccattgtg gagatggggg    360
acgtgggtgc tcgagaggct gtcttgtcac agtcccagca cagcctggga ggacatcgcc    420
tgcgtgtccg cccacgggag cagaaggagt tccagagccc ggcctccaaa tcccccaaag    480
gagcggcccc cgacagtcac cagctggcca agcgctagc tgaggctgca gacgtggggg    540
cacaaatgat aaagcttgtg gggctgaggg agttgtccga ggccgagcgg cagcttcgca    600
gcctagtggt ggccctgatg caggaggtct tcacagagtt cttccctggc tgtgtggtcc    660
accctttggg ctcttccata aatagcttcg atgtccatgg ctgtgatctt gacctcttct    720
tggatctggg tgacttggaa gagccccagc cagtcccaaa ggctccagaa tctccatcgc    780
tggactcggc cctggcttcc ccactggacc tcaagccct ggcctgcacc ccagcttccc    840
ctccagattc acaacctcct gcttctcccc aggattctga agccctggac tttgaaaccc    900
cttcctcctc cctggcgccc caaactccgg actctgcctt ggcctccgag acccttgctt    960
ctccccagtc tctgcctcca gcttcaccac tgctagagga cagggaagag ggggacctgg   1020
ggaaggcctc ggaactagca gagaccccaa aggaggagaa agcagagggg gcagcaatgc   1080
tggagctggt gggatccatt tccggggct gtgtccctgg ggtgtatcga gtccaaactg    1140
tgccctctgc ccggcgccct gtggtcaagt tctgtcatcg gccttcaggt ctccacggtg   1200
atgtctccct cagtaaccgg ctggccctgc ataactcccg tttcctgagt ctctgctctg   1260
agctggatgg tcgagtccgg cccctcgtgt acaccctccg ctgctgggct cagggtcggg   1320
ggctgtcagg gagtggcccc cttctcagta actacgccct gaccttgctg gtgatctatt   1380
ttcttcagac cagggaccct cctgtgttgc ccactgtgtc ccagctcacc cagaaagcag   1440
gagaggggga acaggtggaa gtcgatggct gggactgcag tttccccagg gatgcctcaa   1500
gactggagcc cagcataaat gtggagcccc tcagttccct gctagcccag ttcttctcct   1560
gtgtatcttg ttgggatctt cgtggctccc tgctgtccct gcgggagggt caggcactgc   1620
ctgtggcagg gggcctgcct tctaatctct ggagggtct cgccttggc cccctgaatc    1680
tccaggaccc tttttgacctg agtcacaatg tcgcagccaa tgtgaccagc cgggtggctg   1740
ggcgcctaca gaactgctgc cgagcagcag ccaattactg ccgaagcctc cagtaccagc   1800
gccgttcctc ccggggtcgg gactggggc tgctccctct tctgcagccc agctccccca    1860
gctccctgct ctctgctacg ccgatccctt taccccttgc accttcacc cagctcactg    1920
ctgccctggt gcaggtattc agggaagcac tggggtgcca tatagaacag gcaaccaaga   1980
gaacgcggtc agaaggaggt ggaactgggg agtcctctca gggagggaca agcaaaagac   2040
tcaaagtaga tggacagaaa aactgctgtg aggaggggaa agaggagcag cagggatgtg   2100
caggggacgg tgggaagac agggtagaag agatggttat agaggttgga gagatggtgc   2160
aggactgggc catgcagagc cctgggcagc caggggacct gcccctgacc actggaaagc   2220
atggagcccc tggagaagag gggcagccca gccacgcagc cctggcagag cgggggccca   2280
agggacatga ggcagcccaa gaatggtctc agggtgaggc agggaagggg gcatccctgc   2340
cctcctcagc gagctggcgc tgtgccttgt ggcaccgagt gtggcaaggg cggcggcgag   2400
cccgtagacg cttgcagcag caaaccaagg agggagctgg aggtggcgct ggcacaagag   2460
cagggtggct ggcgactgag gctcaggtca cccaggagct gaaaggactg agtggtggcg   2520
aagagaggcc agaaactgag cccctgctga gctttgtggc gtctgtctcc ccggctgacc   2580
```

-continued

```
gaatgctcac tgtgaccccg ctccaggatc cccaaggcct gttccctgat ctccatcatt    2640
tcttacaggt tttcctccct caagcaattc gacatctcaa gtgaagacat ggcccctgaa    2700
gggcaataaa gctgctagtt tattaataca aaaaaaaaaa aaaaaaa                  2747
```

<210> SEQ ID NO 2
<211> LENGTH: 874
<212> TYPE: PRT
<213> ORGANISM: Homo sapiens

<400> SEQUENCE: 2

```
Met Ala Ala Val Asp Ser Asp Val Glu Ser Leu Pro Arg Gly Gly Phe
1               5                   10                  15

Arg Cys Cys Leu Cys His Val Thr Thr Ala Asn Arg Pro Ser Leu Asp
            20                  25                  30

Ala His Leu Gly Gly Arg Lys His Arg His Leu Val Glu Leu Arg Ala
        35                  40                  45

Ala Arg Lys Ala Gln Gly Leu Arg Ser Val Phe Val Ser Gly Phe Pro
    50                  55                  60

Arg Gly Val Asp Ser Ala Gln Leu Ser Glu Tyr Phe Leu Ala Phe Gly
65                  70                  75                  80

Pro Val Ala Ser Val Val Met Asp Lys Asp Lys Gly Val Phe Ala Ile
                85                  90                  95

Val Glu Met Gly Asp Val Gly Ala Arg Glu Ala Val Leu Ser Gln Ser
            100                 105                 110

Gln His Ser Leu Gly Gly His Arg Leu Arg Val Arg Pro Arg Glu Gln
        115                 120                 125

Lys Glu Phe Gln Ser Pro Ala Ser Lys Ser Pro Lys Gly Ala Ala Pro
    130                 135                 140

Asp Ser His Gln Leu Ala Lys Ala Leu Ala Glu Ala Ala Asp Val Gly
145                 150                 155                 160

Ala Gln Met Ile Lys Leu Val Gly Leu Arg Glu Leu Ser Glu Ala Glu
                165                 170                 175

Arg Gln Leu Arg Ser Leu Val Val Ala Leu Met Gln Glu Val Phe Thr
            180                 185                 190

Glu Phe Phe Pro Gly Cys Val Val His Pro Phe Gly Ser Ser Ile Asn
        195                 200                 205

Ser Phe Asp Val His Gly Cys Asp Leu Asp Leu Phe Leu Asp Leu Gly
    210                 215                 220

Asp Leu Glu Glu Pro Gln Pro Val Pro Lys Ala Pro Glu Ser Pro Ser
225                 230                 235                 240

Leu Asp Ser Ala Leu Ala Ser Pro Leu Asp Pro Gln Ala Leu Ala Cys
                245                 250                 255

Thr Pro Ala Ser Pro Pro Asp Ser Gln Pro Ala Ser Pro Gln Asp
            260                 265                 270

Ser Glu Ala Leu Asp Phe Glu Thr Pro Ser Ser Leu Ala Pro Gln
        275                 280                 285

Thr Pro Asp Ser Ala Leu Ala Ser Glu Thr Leu Ala Ser Pro Gln Ser
    290                 295                 300

Leu Pro Pro Ala Ser Pro Leu Leu Glu Asp Arg Glu Glu Gly Asp Leu
305                 310                 315                 320

Gly Lys Ala Ser Glu Leu Ala Glu Thr Pro Lys Glu Glu Lys Ala Glu
                325                 330                 335

Gly Ala Ala Met Leu Glu Leu Val Gly Ser Ile Leu Arg Gly Cys Val
            340                 345                 350
```

-continued

```
Pro Gly Val Tyr Arg Val Gln Thr Val Pro Ser Ala Arg Arg Pro Val
            355                 360                 365

Val Lys Phe Cys His Arg Pro Ser Gly Leu His Gly Asp Val Ser Leu
    370                 375                 380

Ser Asn Arg Leu Ala Leu His Asn Ser Arg Phe Leu Ser Leu Cys Ser
385                 390                 395                 400

Glu Leu Asp Gly Arg Val Arg Pro Leu Val Tyr Thr Leu Arg Cys Trp
                405                 410                 415

Ala Gln Gly Arg Gly Leu Ser Gly Ser Gly Pro Leu Leu Ser Asn Tyr
            420                 425                 430

Ala Leu Thr Leu Leu Val Ile Tyr Phe Leu Gln Thr Arg Asp Pro Pro
        435                 440                 445

Val Leu Pro Thr Val Ser Gln Leu Thr Gln Lys Ala Gly Glu Gly Glu
    450                 455                 460

Gln Val Glu Val Asp Gly Trp Asp Cys Ser Phe Pro Arg Asp Ala Ser
465                 470                 475                 480

Arg Leu Glu Pro Ser Ile Asn Val Glu Pro Leu Ser Ser Leu Leu Ala
                485                 490                 495

Gln Phe Phe Ser Cys Val Ser Cys Trp Asp Leu Arg Gly Ser Leu Leu
            500                 505                 510

Ser Leu Arg Glu Gly Gln Ala Leu Pro Val Ala Gly Gly Leu Pro Ser
        515                 520                 525

Asn Leu Trp Glu Gly Leu Arg Leu Gly Pro Leu Asn Leu Gln Asp Pro
    530                 535                 540

Phe Asp Leu Ser His Asn Val Ala Ala Asn Val Thr Ser Arg Val Ala
545                 550                 555                 560

Gly Arg Leu Gln Asn Cys Cys Arg Ala Ala Asn Tyr Cys Arg Ser
                565                 570                 575

Leu Gln Tyr Gln Arg Arg Ser Ser Arg Gly Arg Asp Trp Gly Leu Leu
            580                 585                 590

Pro Leu Leu Gln Pro Ser Ser Pro Ser Ser Leu Leu Ser Ala Thr Pro
        595                 600                 605

Ile Pro Leu Pro Leu Ala Pro Phe Thr Gln Leu Thr Ala Ala Leu Val
    610                 615                 620

Gln Val Phe Arg Glu Ala Leu Gly Cys His Ile Glu Gln Ala Thr Lys
625                 630                 635                 640

Arg Thr Arg Ser Glu Gly Gly Thr Gly Glu Ser Ser Gln Gly Gly
                645                 650                 655

Thr Ser Lys Arg Leu Lys Val Asp Gly Gln Lys Asn Cys Cys Glu Glu
            660                 665                 670

Gly Lys Glu Glu Gln Gln Gly Cys Ala Gly Asp Gly Gly Glu Asp Arg
        675                 680                 685

Val Glu Glu Met Val Ile Glu Val Gly Glu Met Val Gln Asp Trp Ala
    690                 695                 700

Met Gln Ser Pro Gly Gln Pro Gly Asp Leu Pro Leu Thr Thr Gly Lys
705                 710                 715                 720

His Gly Ala Pro Gly Glu Gly Gln Pro Ser His Ala Ala Leu Ala
                725                 730                 735

Glu Arg Gly Pro Lys Gly His Glu Ala Ala Gln Glu Trp Ser Gln Gly
            740                 745                 750

Glu Ala Gly Lys Gly Ala Ser Leu Pro Ser Ala Ser Trp Arg Cys
        755                 760                 765

Ala Leu Trp His Arg Val Trp Gln Gly Arg Arg Ala Arg Arg
    770                 775                 780
```

| Leu | Gln | Gln | Gln | Thr | Lys | Glu | Gly | Ala | Gly | Gly | Ala | Gly | Thr | Arg |
|---|---|---|---|---|---|---|---|---|---|---|---|---|---|---|
| 785 | | | | 790 | | | | 795 | | | | 800 | | |

| Ala | Gly | Trp | Leu | Ala | Thr | Glu | Ala | Gln | Val | Thr | Gln | Glu | Leu | Lys | Gly |
|---|---|---|---|---|---|---|---|---|---|---|---|---|---|---|---|
| | | | 805 | | | | 810 | | | | | 815 | | | |

| Leu | Ser | Gly | Gly | Glu | Glu | Arg | Pro | Glu | Thr | Glu | Pro | Leu | Leu | Ser | Phe |
|---|---|---|---|---|---|---|---|---|---|---|---|---|---|---|---|
| | | | 820 | | | | | 825 | | | | 830 | | | |

| Val | Ala | Ser | Val | Ser | Pro | Ala | Asp | Arg | Met | Leu | Thr | Val | Thr | Pro | Leu |
|---|---|---|---|---|---|---|---|---|---|---|---|---|---|---|---|
| | 835 | | | | | 840 | | | | | 845 | | | | |

| Gln | Asp | Pro | Gln | Gly | Leu | Phe | Pro | Asp | Leu | His | His | Phe | Leu | Gln | Val |
|---|---|---|---|---|---|---|---|---|---|---|---|---|---|---|---|
| | 850 | | | | | 855 | | | | 860 | | | | | |

| Phe | Leu | Pro | Gln | Ala | Ile | Arg | His | Leu | Lys |
|---|---|---|---|---|---|---|---|---|---|
| 865 | | | | | 870 | | | | |

<210> SEQ ID NO 3
<211> LENGTH: 4539
<212> TYPE: DNA
<213> ORGANISM: Homo sapiens

<400> SEQUENCE: 3

```
gaacgttgct gtggtagcgc tcgggcgcca tgttaggacg aaggggaagg aggagaagcg    60
cttaaagcgg cgggagcggt gcgggagagg ggttggaccc agggctgagg caggcccccc   120
cctccctccc gcctcagtgg atcatgccca gggcggcagc ggcggcggtt gcgggggga    180
agtgactggg cggtgccggc gccggagacg atgccgtttc cagttacaac acagggatca   240
caacaaacac aaccgccaca gaagcactat ggcattactt ctcctatcag cttagcagcc   300
cccaaggaga ctgactgcgt acttacacag aaactaattg agacattgaa accctttggg   360
gtttttgaag aggaagagga actgcagcgc aggattttaa ttttgggaaa actaaataac   420
ctggtaaaag agtggatacg agaaatcagt gaaagcaaga atcttccaca atctgtaatt   480
gaaaatgttg gaggaaaaat ttttacattt ggatcttaca gattaggagt gcatacaaaa   540
ggtgctgata ttgatgcgtt gtgtgttgca ccaagacatg ttgatcgaag tgacttttc    600
acctcattct atgataagtt gaaattacag gaagaagtaa aagatttaag agctgttgaa   660
gaggcattcg taccagttat taaactctgt tttgatggga tagagattga tattttgttt   720
gcaagattag cactgcagac aattcctgaa gatttggatc tacgagatga cagtctgcta   780
aaaaatttag atataagatg tataagaagt cttaacggtt gcagggtaac cgatgaaatt   840
ttacatctag taccaaacat tgacaacttc aggttaactc tgagagctat caaactatgg   900
gccaaacgcc acaacatcta ttccaatata ttaggtttcc tcggtggtgt ttcctgggct   960
atgctagtag caagaacttg ccagctttat ccaaatgcaa tagcatcaac tcttgtacat  1020
aaattttct tggtattttc taaatgggaa tggccaaatc cagtgctatt gaaacagcct  1080
gaagaatgca atcttaattt gcctgtatgg gacccaaggg taaacccag tgataggtac  1140
catcttatgc ctataattac accagcatac ccacaacaga actccacgta caatgtgtcc  1200
gtttcaacac ggatggtcat ggttgaggag tttaaacaag tcttgctat cacagatgaa  1260
attttgctga gtaaggcaga gtggtccaaa cttttgaag ctccaaactt ctttcaaaag  1320
tacaagcatt atattgtact tctagcaagt gcaccaacag aaaaacaacg cctggaatgg  1380
gtgggcttgg tggaatcaaa aatccgaatc ctggttggaa gcttgagaa gaatgaattt  1440
attacactgg ctcatgtgaa tcccccagtca tttccagcac ccaaagaaaa tcccgacaag  1500
gaagaatttc gcacgatgtg ggtgattggg ttagtgttta aaaaacaga aaactctgaa  1560
aacctcagtg ttgatctcac ctatgatatt cagtctttca cagatacagt ttataggcaa  1620
```

```
gcaataaaca gcaagatgtt tgaggtggat atgaaaattg ctgcaatgca tgtaaaaaga    1680
aagcaactcc atcaactact acctaatcat gtgcttcaga aaagaaaaa gcattcaaca     1740 gaaggtgtca aattgacagc tctcaatgac agcagcctcg acttgtctat ggacagtgat    1800
aacagcatgt ctgtgccttc acctactagt gctacgaaga ccagtccatt gaacagttct    1860
ggcagctctc agggcagaaa cagtcctgct ccagctgtaa cagcagcatc tgtgaccaac    1920
atacaggcta ctgaagtttc tgtgccacaa gtaaattcca gtgaaagctc aggggtaca    1980 tcgagtgaaa gcattcctca aactgccaca caaccagcca tttctccacc accaaagcct    2040
acggtctcca gagttgtttc ttcaacacgt ctggtaaacc caccacctag atcttcagga    2100
aatgcagcaa cttcaggaaa tgcagcaaca aaaatcaccta ctcctatagt aggagtcaag    2160
aggacatcct cacctcataa agaagagagt cccaagaaaa ccaaaacaga agaggatgaa    2220
acaagtgaag atgctaactg tcttgctttg agtggacatg ataaaacaga agcaaaggaa    2280
caacttgata cagagacaag tacaactcaa tcagaaacta ttcagacagc ggcttctctg    2340
ttggcctctc agaaaacatc cagtacagac ctttctgata tccctgctct ccctgcaaat    2400
cctattcctg ttatcaagaa ttcaataaaa ctgagattga atcggtaaaa acaaccttcag   2460 gggtccataa acaatatctg ccaactcaac ctgttgtctt caaatgctaa aaaaggagaa    2520
tggagggtac aagactagac atgactgaaa tggatttggg tttttggtg acctcccta     2580 ctgggctaat cagcacttga tcggaagtcc aggttagtat gtgaagccag gagtactatt    2640
attattgtgt tagcaacagt tgcattaact atttcaaaaa ttactgcctt taaaaaaaaac   2700 aacctcaagc tatatttgta ttcataattg acatctggat tgggtttatg tttgatgcat    2760
tgtttggaaa atttgcaata caaactggca taagaattac ttattctgat gatgcacttt    2820
tatgtatttt tcattagaaa gtagaactaa ttttagattt tcagcttgat ggattttcag    2880
tttttcctga agaattttct ttaccattag tcttcaaatt ggatactgtt gtgcagtggt    2940
gtactgttat acttcagaga aagggtaaga gtacatctag ttcagttcct atgaggtagc    3000
tgtaaccctt aaaaatgaaa cgtcaactct agggtacatt tgacattgaa agaatagtta    3060
ggaaataact tggttttgat agggtcatga ttaagaaatg atatattggt tttatttatg    3120
gaattgtttt atagtgcata caatcagcg atcagccagc aaatattttt ctttgagctt      3180
gtgaaagctc tgtgttcttt tgccttcaat ctgttgtctt caaaacaaac aaacaaaaaa    3240
agcttcttgc gcctttccct cccctgtttt cttcctttt cttttgctt gtatgcacaa     3300 ggtaggactt acttcgtaag aaacaaaatg ccagtatttt cttaagccat gatgtgaaac    3360
caatgaccct gtgaccacat ggcacagaac actaaatttt ggtcccatgg ctgaaacttg    3420
agggtgacta aaagtaatgc ctgtgaaaca tgatatctat ctgggatggc catttgatct    3480
ctaaaaggaa ttttgtacac tccacagaac tcctatctat agtaaaattg attttcagtt    3540
ttaaatgtgg gcaaaaaggc attttctcca agatttaaa actaattctt attttaaat     3600 ggtttaccaa aatttgtcag tacattttac gtgtagaagc attttaaaaa tcatttctag    3660
caagcacttg acatctagtc agctctctac tcctttattt tgttttatca aaagattaag    3720
agctcctttc tttgaataaa ataatttctc ataattaagc agtagaagat ctatcttcac    3780
aaagtatgag ggatgccaga tgttgataaa cttactcttt ctgaatctgg acaaagtcga    3840
cttaacagat ttttctgatg agcatgtttt atgaatcctc cattgtgctc cattctatca    3900
catgtgcatt tttcatgtta aactgcaatt acttaatctc ttcccctatc cttctaaatt    3960
aattttctga agttggagtg tagtctttc cccttaggc tatgcattaa tcgaagcttt      4020
```

```
cttttcacca tgactttata atgtctagta aacaatattt ctacttccca catctttgct    4080
ttacacagtc accttgccct tccttccacc accgaagaaa aagatggtc atactaacag     4140 gtgaaatgta caaggtgtct gtgtgttttg tgtagcttca gagttagatt gaaattacca    4200
ggcacagatt tagtcttgtc attttgttta cacattgggg aaaacaattc agtttattaa    4260
acgtttcatg taactgcacc caagttttgc caagctggaa acttggacct tttctgtgta    4320 gtgactttt aattatagtt ttcataacct ggagatcaga ctgttgcttt cgcatgatgt     4380
atgtagtgtc tcatgactgg agtttgcttt gttttatagt atctgtactc cttgtattt     4440 tcaagagcta ttttgtaaac agatgatgta tttctccatt gaaaacacaa taaaaaaaaa    4500
acagcacaaa aaaaaaaaaa aaaaaaaaaa aaaaaaaa                             4539
```

<210> SEQ ID NO 4
<211> LENGTH: 745
<212> TYPE: PRT
<213> ORGANISM: Homo sapiens

<400> SEQUENCE: 4

```
Met Pro Phe Pro Val Thr Thr Gln Gly Ser Gln Gln Thr Gln Pro Pro
1               5                   10                  15

Gln Lys His Tyr Gly Ile Thr Ser Pro Ile Ser Leu Ala Ala Pro Lys
            20                  25                  30

Glu Thr Asp Cys Val Leu Thr Gln Lys Leu Ile Glu Thr Leu Lys Pro
        35                  40                  45

Phe Gly Val Phe Glu Glu Glu Glu Leu Gln Arg Arg Ile Leu Ile
    50                  55                  60

Leu Gly Lys Leu Asn Asn Leu Val Lys Glu Trp Ile Arg Glu Ile Ser
65                  70                  75                  80

Glu Ser Lys Asn Leu Pro Gln Ser Val Ile Glu Asn Val Gly Lys
            85                  90                  95

Ile Phe Thr Phe Gly Ser Tyr Arg Leu Gly Val His Thr Lys Gly Ala
            100                 105                 110

Asp Ile Asp Ala Leu Cys Val Ala Pro Arg His Val Ser Arg Ser Asp
        115                 120                 125

Phe Phe Thr Ser Phe Tyr Asp Lys Leu Lys Leu Gln Glu Glu Val Lys
    130                 135                 140

Asp Leu Arg Ala Val Glu Glu Ala Phe Val Pro Val Ile Lys Leu Cys
145                 150                 155                 160

Phe Asp Gly Ile Glu Ile Asp Ile Leu Phe Ala Arg Leu Ala Leu Gln
                165                 170                 175

Thr Ile Pro Glu Asp Leu Asp Leu Arg Asp Asp Ser Leu Leu Lys Asn
            180                 185                 190

Leu Asp Ile Arg Cys Ile Arg Ser Leu Asn Gly Cys Arg Val Thr Asp
        195                 200                 205

Glu Ile Leu His Leu Val Pro Asn Ile Asp Asn Phe Arg Leu Thr Leu
    210                 215                 220

Arg Ala Ile Lys Leu Trp Ala Lys Arg His Asn Ile Tyr Ser Asn Ile
225                 230                 235                 240

Leu Gly Phe Leu Gly Gly Val Ser Trp Ala Met Leu Val Ala Arg Thr
                245                 250                 255

Cys Gln Leu Tyr Pro Asn Ala Ile Ala Ser Thr Leu Val His Lys Phe
            260                 265                 270

Phe Leu Val Phe Ser Lys Trp Glu Trp Pro Asn Pro Val Leu Leu Lys
        275                 280                 285
```

```
Gln Pro Glu Glu Cys Asn Leu Asn Leu Pro Val Trp Asp Pro Arg Val
    290                 295                 300

Asn Pro Ser Asp Arg Tyr His Leu Met Pro Ile Ile Thr Pro Ala Tyr
305                 310                 315                 320

Pro Gln Gln Asn Ser Thr Tyr Asn Val Ser Val Ser Thr Arg Met Val
                325                 330                 335

Met Val Glu Glu Phe Lys Gln Gly Leu Ala Ile Thr Asp Glu Ile Leu
            340                 345                 350

Leu Ser Lys Ala Glu Trp Ser Lys Leu Phe Glu Ala Pro Asn Phe Phe
        355                 360                 365

Gln Lys Tyr Lys His Tyr Ile Val Leu Leu Ala Ser Ala Pro Thr Glu
    370                 375                 380

Lys Gln Arg Leu Glu Trp Val Gly Leu Val Glu Ser Lys Ile Arg Ile
385                 390                 395                 400

Leu Val Gly Ser Leu Glu Lys Asn Glu Phe Ile Thr Leu Ala His Val
                405                 410                 415

Asn Pro Gln Ser Phe Pro Ala Pro Lys Glu Asn Pro Asp Lys Glu Glu
            420                 425                 430

Phe Arg Thr Met Trp Val Ile Gly Leu Val Phe Lys Lys Thr Glu Asn
        435                 440                 445

Ser Glu Asn Leu Ser Val Asp Leu Thr Tyr Asp Ile Gln Ser Phe Thr
    450                 455                 460

Asp Thr Val Tyr Arg Gln Ala Ile Asn Ser Lys Met Phe Glu Val Asp
465                 470                 475                 480

Met Lys Ile Ala Ala Met His Val Lys Arg Lys Gln Leu His Gln Leu
                485                 490                 495

Leu Pro Asn His Val Leu Gln Lys Lys Lys His Ser Thr Glu Gly
            500                 505                 510

Val Lys Leu Thr Ala Leu Asn Asp Ser Ser Leu Asp Leu Ser Met Asp
        515                 520                 525

Ser Asp Asn Ser Met Ser Val Pro Ser Pro Thr Ser Ala Thr Lys Thr
    530                 535                 540

Ser Pro Leu Asn Ser Ser Gly Ser Ser Gln Gly Arg Asn Ser Pro Ala
545                 550                 555                 560

Pro Ala Val Thr Ala Ala Ser Val Thr Asn Ile Gln Ala Thr Glu Val
                565                 570                 575

Ser Val Pro Gln Val Asn Ser Ser Glu Ser Ser Gly Gly Thr Ser Ser
            580                 585                 590

Glu Ser Ile Pro Gln Thr Ala Thr Gln Pro Ala Ile Ser Pro Pro Pro
        595                 600                 605

Lys Pro Thr Val Ser Arg Val Val Ser Thr Arg Leu Val Asn Pro
    610                 615                 620

Pro Pro Arg Ser Ser Gly Asn Ala Ala Thr Ser Gly Asn Ala Ala Thr
625                 630                 635                 640

Lys Ile Pro Thr Pro Ile Val Gly Val Lys Arg Thr Ser Ser Pro His
                645                 650                 655

Lys Glu Glu Ser Pro Lys Lys Thr Lys Thr Glu Glu Asp Glu Thr Ser
            660                 665                 670

Glu Asp Ala Asn Cys Leu Ala Leu Ser Gly His Asp Lys Thr Glu Ala
        675                 680                 685

Lys Glu Gln Leu Asp Thr Glu Thr Ser Thr Gln Ser Glu Thr Ile
    690                 695                 700

Gln Thr Ala Ala Ser Leu Leu Ala Ser Gln Lys Thr Ser Ser Thr Asp
```

| | | | | |
|---|---|---|---|---|
| 705 | | 710 | 715 | 720 |

Leu Ser Asp Ile Pro Ala Leu Pro Ala Asn Pro Ile Pro Val Ile Lys
             725                        730                     735

Asn Ser Ile Lys Leu Arg Leu Asn Arg
             740                        745

<210> SEQ ID NO 5
<211> LENGTH: 3713
<212> TYPE: DNA
<213> ORGANISM: Homo sapiens

<400> SEQUENCE: 5

| | |
|---|---|
| attaacaggc cgtggttagg aaggacggag aagggggcgtt cgctcctttg ggacttttca | 60 |
| tgcctcgttt ttttttcaga tgtggcttgg tctgggcgca aggtcccagc agccagctta | 120 |
| agcttactct tctgtgaaag ggaaagtat cccctgtgga aagcggttaa acttgtggag | 180 |
| ggggtgcggg acgtgagttc ttccccatgc caggcgaatg tgtggcctt gagctggtcc | 240 |
| aggagccggc tcgacgtgtc tgagggaggc ccggaggggg cggggaggtg gcccacagaa | 300 |
| cgcgggttct gtaaagagac gttgggaaga ttcgattccg agaagaggaa gaaccggatt | 360 |
| gaaagagagc caggccgctg aggggaggg ggctgctaag atggcgtcgg cctcctccgg | 420 |
| gccgtcgtct tcggtcggtt tttcatcctt tgatcccgcg gtcccttcct gtaccttgtc | 480 |
| ctcagcatct ggaatcaaga gacccatggc atctgaggtg ccttatgcct ctggcatgcc | 540 |
| catcaagaaa ataggccata gaagtgttga ttcctcagga gagacaacat ataaaaagac | 600 |
| aacctcatca gccttgaaag gtgccatcca gttaggcatt acccacactg tggggagcct | 660 |
| gagtaccaaa ccagagcgtg atgtcctcat gcaagatttc tacgtggttg agagtatctt | 720 |
| cttcccagt gaagggagca acctgacccc tgctcatcac tacaatgact ttcgtttcaa | 780 |
| gacctatgca cctgttgcct tccgctactt ccgggagcta tttggtatcc ggcccgatga | 840 |
| ttacttgtat tccctctgca gtgagccgct gattgaactc tgtagctctg gagctagtgg | 900 |
| ttccctattc tatgtgtcca gcgacgatga gttcattatt aagacagtcc aacataaaga | 960 |
| ggcggaattt ctgcagaagc tgcttccagg atactacatg aacctcaacc agaaccctcg | 1020 |
| gactttgctg cctaaattct atggactgta ctgtgtgcag gcaggtggca agaacattcg | 1080 |
| gattgtggtg atgaacaatc ttttaccaag atcggtaaaa atgcatatca aatatgacct | 1140 |
| caaaggctca acctacaaac ggcgggcttc ccagaaagag cgagagaagc ctcttcccac | 1200 |
| atttaaagac ctagacttct tacaagacat ccctgatggt ctttttttgg atgctgacat | 1260 |
| gtacaacgct ctctgtaaga ccctgcagcg tgactgtttg gtgctgcaga gcttcaagat | 1320 |
| aatggattac agcctcttga tgtcaatcca taatatagat catgcacaac gagagccctt | 1380 |
| aagcagtgaa acacagtact cagttgatac tcgaagaccg gcccccaaa aggctctgta | 1440 |
| ttccacagcc atggaatcca tcagggaga ggctcgacgg gtggtacca tggagactga | 1500 |
| tgaccatatg ggtggcatcc ctgcccggaa tagtaaaggg gaaaggcttc tgctttatat | 1560 |
| tggcatcatt gacattctac agtcttacag gtttgttaag aagttggagc actcttggaa | 1620 |
| agccctggta catgacggag acactgtctc agtgcatcgc ccaggcttct acgctgaacg | 1680 |
| gttccagcgc ttcatgtgca acacagtatt taagaagatt cccttgaagc cttctccttc | 1740 |
| caaaaagttt cggtctggct catctttctc tcggcgagca ggctccagtg caactcctg | 1800 |
| cattacttac cagccatcgg tctctgggga acacaaggca caagtgacaa caaaggcaga | 1860 |
| agtggagcca ggcgttcacc ttggtcgtcc tgatgtttta cctcagactc caccttttga | 1920 |

-continued

```
ggaaatcagt gagggctcgc ctattcctga ccccagtttc tcacctctag ttggagagac    1980
tttgcaaatg ctaactacaa gtacaacctt ggaaaagctt gaagttgcag agtcagagtt    2040
cacccattaa gcgcaaagcc tcagaagacc tggaacaaga ttctgccatc tctgtgatcc    2100
caagatgtca gcccttgccc cagcaatgct gaatttttct ctacttggtc atcaaaaaag    2160
gagtgtaata aagtgaggg gagctgctcc tccatcttct tcctgaagaa gaaccttctc    2220
tccttcctct tcctcatgaa tgggccttag tgcctcagag agttgaggac cgcagcatcc    2280
cctccactcc agagttgggt ggtacggatt tcaactggc caaccctttg cctccactat    2340 tgaattttt tcagacccc attcttcatg ctggaaatgg gattgctgga cttggcagct    2400
ttctttcccc tcgtctttga ctaggaaccg gactcttaat ttcctcagga cagactagct    2460
ggcacattat ccctacctta gttctttctc tctgactcct ggaagaatac tcctgtaatc    2520
tctgtaaagg ttttttgggg ataagggtgt ttaaccacct cccagctttc ttcttctttt    2580 tttttctga aaaaggaaa aagcacacag cacacaattt caagccattt tcagatcaga    2640
actccagaag tgttgacaag atgcctattc gtagagttcc ctcagaagag ccatggtgtt    2700
tatgaagaga agagtagtga ttgctctgcc agaagcagct cctctttaaa ctcctcctct    2760
cttgatgaat tcttaaggc tgaaggaatg aagagagtgg acatggggt aatctttatc    2820 ccttttgtta aaacaggagg cagccatggg ctgggagatc atagcccttc ctaggcagaa    2880
tcctgttcac tgccaggcta gtaattat tactatttg caatttgaaa tatattctgg    2940
ttgtttttct aaatgtgaag acttaccaaa tgaattttag atcattctcc agaggagatt    3000 tttttgctc ttctcatctt ttccaacagt gttctcctgt ttgtggagct aaggtaaaga    3060
ggggacactt ctgtctgttt aacagacagt ccatatctgt gaggccagca atatttct    3120 taaactcatg gggagacagc agattcttgc cttggtgagg tcattgctgt gccatatgtc    3180
ctacccccct gtcttcatgc agggaagttg gaaatgggg ctacatatgc cctctcctcc    3240
ccgtctacaa gagttgtggt tttccatctg atccttccac tcttgtcagg ggaagaaggg    3300
ggcctggtat ctcaggcaga ttgttgaatt cctgttctat cccttctcta tcccaccctg    3360
ccttgataat atgttagccc ataccccaaa taactgtcta tattagacac ccccagccag    3420
tttctggctg cctgtctttg ctgccatgtt ttttacaaga aggaaagaat tcttgctatt    3480
tttttttcat aatttactat ttatgatgta tttaagtgtt ttattaagga cagagttctg    3540
ttaggggtgg gagggaatat tgagggagg gctgggtctt agggaaagga atggggaagc    3600
aacattttta ttaagtgtta ctatttgcct ctactttgta ttgttcagaa atggcaaata    3660
caatataaaa gtgatatatg gttttaatgt aataaacttt aatgagttat tta           3713
```

<210> SEQ ID NO 6
<211> LENGTH: 549
<212> TYPE: PRT
<213> ORGANISM: Homo sapiens

<400> SEQUENCE: 6

```
Met Ala Ser Ala Ser Ser Gly Pro Ser Ser Val Gly Phe Ser Ser
1               5                   10                  15

Phe Asp Pro Ala Val Pro Ser Cys Thr Leu Ser Ser Ala Ser Gly Ile
                20                  25                  30

Lys Arg Pro Met Ala Ser Glu Val Pro Tyr Ala Ser Gly Met Pro Ile
            35                  40                  45

Lys Lys Ile Gly His Arg Ser Val Asp Ser Ser Gly Glu Thr Thr Tyr
        50                  55                  60
```

-continued

```
Lys Lys Thr Thr Ser Ser Ala Leu Lys Gly Ala Ile Gln Leu Gly Ile
 65                  70                  75                  80

Thr His Thr Val Gly Ser Leu Ser Thr Lys Pro Glu Arg Asp Val Leu
                 85                  90                  95

Met Gln Asp Phe Tyr Val Val Glu Ser Ile Phe Phe Pro Ser Glu Gly
            100                 105                 110

Ser Asn Leu Thr Pro Ala His His Tyr Asn Asp Phe Arg Phe Lys Thr
        115                 120                 125

Tyr Ala Pro Val Ala Phe Arg Tyr Phe Arg Glu Leu Phe Gly Ile Arg
    130                 135                 140

Pro Asp Asp Tyr Leu Tyr Ser Leu Cys Ser Pro Leu Ile Glu Leu
145                 150                 155                 160

Cys Ser Ser Gly Ala Ser Gly Ser Leu Phe Tyr Val Ser Ser Asp Asp
                165                 170                 175

Glu Phe Ile Ile Lys Thr Val Gln His Lys Glu Ala Glu Phe Leu Gln
            180                 185                 190

Lys Leu Leu Pro Gly Tyr Tyr Met Asn Leu Asn Gln Asn Pro Arg Thr
        195                 200                 205

Leu Leu Pro Lys Phe Tyr Gly Leu Tyr Cys Val Gln Ala Gly Gly Lys
    210                 215                 220

Asn Ile Arg Ile Val Met Asn Asn Leu Leu Pro Arg Ser Val Lys
225                 230                 235                 240

Met His Ile Lys Tyr Asp Leu Lys Gly Ser Thr Tyr Lys Arg Arg Ala
                245                 250                 255

Ser Gln Lys Glu Arg Glu Lys Pro Leu Pro Thr Phe Lys Asp Leu Asp
            260                 265                 270

Phe Leu Gln Asp Ile Pro Asp Gly Leu Phe Leu Asp Ala Asp Met Tyr
        275                 280                 285

Asn Ala Leu Cys Lys Thr Leu Gln Arg Asp Cys Leu Val Leu Gln Ser
    290                 295                 300

Phe Lys Ile Met Asp Tyr Ser Leu Leu Met Ser Ile His Asn Ile Asp
305                 310                 315                 320

His Ala Gln Arg Glu Pro Leu Ser Ser Glu Thr Gln Tyr Ser Val Asp
                325                 330                 335

Thr Arg Arg Pro Ala Pro Gln Lys Ala Leu Tyr Ser Thr Ala Met Glu
            340                 345                 350

Ser Ile Gln Gly Glu Ala Arg Arg Gly Gly Thr Met Glu Thr Asp Asp
        355                 360                 365

His Met Gly Gly Ile Pro Ala Arg Asn Ser Lys Gly Glu Arg Leu Leu
    370                 375                 380

Leu Tyr Ile Gly Ile Ile Asp Ile Leu Gln Ser Tyr Arg Phe Val Lys
385                 390                 395                 400

Lys Leu Glu His Ser Trp Lys Ala Leu Val His Asp Gly Asp Thr Val
                405                 410                 415

Ser Val His Arg Pro Gly Phe Tyr Ala Glu Arg Phe Gln Arg Phe Met
            420                 425                 430

Cys Asn Thr Val Phe Lys Lys Ile Pro Leu Lys Pro Ser Pro Ser Lys
        435                 440                 445

Lys Phe Arg Ser Gly Ser Ser Phe Ser Arg Arg Ala Gly Ser Ser Gly
    450                 455                 460

Asn Ser Cys Ile Thr Tyr Gln Pro Ser Val Ser Gly Glu His Lys Ala
465                 470                 475                 480

Gln Val Thr Thr Lys Ala Glu Val Glu Pro Gly Val His Leu Gly Arg
                485                 490                 495
```

Pro Asp Val Leu Pro Gln Thr Pro Leu Glu Glu Ile Ser Glu Gly
            500                 505                 510

Ser Pro Ile Pro Asp Pro Ser Phe Ser Pro Leu Val Gly Glu Thr Leu
        515                 520                 525

Gln Met Leu Thr Thr Ser Thr Thr Leu Glu Lys Leu Glu Val Ala Glu
    530                 535                 540

Ser Glu Phe Thr His
545

<210> SEQ ID NO 7
<211> LENGTH: 1550
<212> TYPE: DNA
<213> ORGANISM: Homo sapiens

<400> SEQUENCE: 7

| | | | | | |
|---|---|---|---|---|---|
| tcaacgcctg | cctcccctcg | agcgtcctca | gcgcagccgc | cgcccgcgga | gccagcacga | 60 |
| acgagcccag | caccggccgg | atggagcgtc | gcaacccga | cagcatgccc | caggatttgt | 120 |
| cagaggccct | gaaggaggcc | accaaggagg | tgcacaccca | ggcagagaat | gctgagttca | 180 |
| tgaggaactt | tcagaagggc | caggtgaccc | gagacggctt | caagctggtg | atggcctccc | 240 |
| tgtaccacat | ctatgtggcc | ctggaggagg | agattgagcg | caacaaggag | agcccagtct | 300 |
| tcgcccctgt | ctacttccca | gaagagctgc | accgcaaggc | tgccctggag | caggacctgg | 360 |
| ccttctggta | cgggccccgc | tggcaggagg | tcatccccta | cacaccagcc | atgcagcgct | 420 |
| atgtgaagcg | gctccacgag | gtggggcgca | cagagcccga | gctgctggtg | cccacgcct | 480 |
| acacccgcta | cctgggtgac | ctgtctgggg | gccaggtgct | caaaaagatt | gcccagaaag | 540 |
| ccctggacct | gcccagctct | ggcgagggcc | tggccttctt | caccttcccc | aacattgcca | 600 |
| gtgccaccaa | gttcaagcag | ctctaccgct | cccgcatgaa | ctccctggag | atgactcccg | 660 |
| cagtcaggca | gagggtgata | gaagaggcca | agactgcgtt | cctgctcaac | atccagctct | 720 |
| ttgaggagtt | gcaggagctg | ctgacccatg | acaccaagga | ccagagcccc | tcacgggcac | 780 |
| cagggcttcg | ccagcgggcc | agcaacaaag | tgcaagattc | tgcccccgtg | agactcccca | 840 |
| gagggaagcc | cccactcaac | acccgctccc | aggctccgct | tctccgatgg | gtccttacac | 900 |
| tcagctttct | ggtggcgaca | gttgctgtag | ggctttatgc | catgtgaatg | caggcatgct | 960 |
| ggctcccagg | gccatgaact | tgtccggtg | aaggccttc | tttctagaga | gggaattctc | 1020 |
| ttggctggct | tccttaccgt | gggcactgaa | ggctttcagg | gcctccagcc | ctctcactgt | 1080 |
| gtccctctct | ctggaaagga | ggaaggagcc | tatggcatct | tccccaacga | aaagcacatc | 1140 |
| caggcaatgg | cctaaacttc | agaggggcg | aaggggtcag | ccctgccctt | cagcatcctc | 1200 |
| agttcctgca | gcagagcctg | gaagacaccc | taatgtggca | gctgtctcaa | acctccaaaa | 1260 |
| gccctgagtt | tcaagtatcc | ttgttgacac | ggccatgacc | actttccccg | tgggccatgg | 1320 |
| caattttac | acaaacctga | aaagatgttg | tgtcttgtgt | ttttgtctta | tttttgttgg | 1380 |
| agccactctg | ttcctggctc | agcctcaaat | gcagtatttt | tgttgtgttc | tgttgttttt | 1440 |
| atagcagggt | tggggtggtt | tttgagccat | gcgtgggtgg | ggagggaggt | gtttaacggc | 1500 |
| actgtggcct | tggtctaact | tttgtgtgaa | ataataaaca | acattgtctg | | 1550 |

<210> SEQ ID NO 8
<211> LENGTH: 288
<212> TYPE: PRT
<213> ORGANISM: Homo sapiens

<400> SEQUENCE: 8

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65              70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
    275                 280                 285

<210> SEQ ID NO 9
<211> LENGTH: 2601
<212> TYPE: DNA
<213> ORGANISM: Homo sapiens

<400> SEQUENCE: 9
ccgcccttgt aggctgtcca cctcaaacgg gccggacagg atatataaga gagaatgcac    60
cgtgcactac acacgcgact cccacaaggt tgcagccgga gccgcccagc tcaccgagag   120
cctagttccg gccagggtcg ccccggcaac cacgagccca gccaatcagc gccccggact   180
gcaccagagc catggtcggc agaagagcac tgatcgtact ggctcactca gagaggacgt   240
ccttcaacta tgccatgaag gaggctgctg cagcggcttt gaagaagaaa ggatgggagg   300
tggtggagtc ggacctctat gccatgaact tcaatcccat catttccaga aaggacatca   360
caggtaaact gaaggaccct gcgaactttc agtatcctgc cgagtctgtt ctggcttata   420
aagaaggcca tctgagccca gatattgtgg ctgaacaaaa gaagctggaa gccgcagacc   480
ttgtgatatt ccagttcccc ctgcagtggt ttggagtccc tgccattctg aaaggctggt   540

```
ttgagcgagt gttcatagga gagtttgctt acacttacgc tgccatgtat gacaaaggac    600
ccttccggag taagaaggca gtgctttcca tcaccactgg tggcagtggc tccatgtact    660
ctctgcaagg gatccacggg gacatgaatg tcattctctg gccaattcag agtggcattc    720
tgcatttctg tggcttccaa gtcttagaac ctcaactgac atatagcatt gggcacactc    780
cagcagacgc ccgaattcaa atcctggaag gatggaagaa acgcctggag aatatttggg    840
atgagacacc actgtatttt gctccaagca gcctctttga cctaaacttc aggcaggat     900 tcttaatgaa aaagaggta caggatgagg agaaaaacaa gaaatttggc ctttctgtgg    960
gccatcactt gggcaagtcc atcccaactg acaaccagat caaagctaga aaatgagatt  1020
ccttagcctg gatttccttc taacatgtta tcaaatctgg gtatcttcc aggcttccct   1080 gacttgcttt agttttaag atttgtgttt ttctttttcc acaaggaata aatgagaggg   1140
aatcgactgt attcgtgcat ttttggatca tttttaactg attcttatga ttactatcat   1200
ggcatataac caaaatccga ctgggctcaa gaggccactt agggaaagat gtagaaagat   1260
gctagaaaaa tgttctttaa aggcatctac acaatttaat tcctctttttt agggctaaag   1320 ttttagggta cagtttggct aggtatcatt caactctcca atgttctatt aatcacctct   1380
ctgtagttta tggcagaagg gaattgctca gagaaggaaa agactgaatc tacctgccct   1440
aagggactta acttgtttgg tagttagcca tctaatgctt gtttatgata tttcttgctt   1500
tcaattacaa agcagttact aatatgccta gcacaagtac cactcttggt cagcttttgt   1560
tgtttatata cagtacacag ataccttgaa aggaagagct aataaatctc ttctttgctg   1620
cagtcatcta ctttttttt aattaaaaaa aatttttttt tgaagcagtc ttgctctgtt    1680
acccaggctg gagtgcagtg gtgtgatctc ggctcactgc aacctctgcc tcccaggttc    1740
cagcaattct cctgcctcag cctccctagt agctgggatg acaggcgcct gccatcatgc    1800
ctgactaatt tttgtatttt tagtagagac ggcgtttcac catgttggcc aggctggtct    1860
caaactcctg acctcaggtg atccgcctac ctcagcctcc caaagtgctg ggattacagg    1920
cgtgatccac cacacctggc ccttgcaatc ttctacttta aggtttgcag agataaacca    1980
ataaatccac accgtacatc tgcaatatga attcaagaaa ggaaatagta ccttcaatac    2040
ttaaaaatag tcttccacaa aaaatacttt atttctgatc tatacaaatt ttcagaaggt    2100
tattttcttt atcattgcta aactgatgac ttactatggg atggggtcca gtcccatgac    2160
cttggggtac aattgtaaac ctagagtttt atcaactttg gtgaacagtt ttggcataat    2220
agtcaatttc tacttctgga agtcatctca ttccactgtt ggtattatat aattcaagga    2280
gaatatgata aaacactgcc ctcttgtggt gcattgaaag aagagatgag aaatgatgaa    2340
aaggttgcct gaaaatggg agacagcctc ttacttgcca agaaaatgaa gggattggac     2400
cgagctggaa aacctccttt accagatgct gactggcact ggtggttttt gctctcgaca    2460
gtatccacaa tagctgacgg ctgggtgttt cagtttgaaa atattttgtt gccttcatct    2520
tcactgcaat tttgtgtaaa tttctcaaag atctgaatta aataaataaa attcatttct    2580
acagacccac aaaaaaaaaa a                                              2601
```

<210> SEQ ID NO 10
<211> LENGTH: 274
<212> TYPE: PRT
<213> ORGANISM: Homo sapiens

<400> SEQUENCE: 10

Met Val Gly Arg Arg Ala Leu Ile Val Leu Ala His Ser Glu Arg Thr

```
                 1               5                  10                 15
Ser Phe Asn Tyr Ala Met Lys Glu Ala Ala Ala Ala Leu Lys Lys
                20                 25                 30

Lys Gly Trp Glu Val Val Glu Ser Asp Leu Tyr Ala Met Asn Phe Asn
                35                 40                 45

Pro Ile Ile Ser Arg Lys Asp Ile Thr Gly Lys Leu Lys Asp Pro Ala
                50                 55                 60

Asn Phe Gln Tyr Pro Ala Glu Ser Val Leu Ala Tyr Lys Glu Gly His
65                 70                 75                 80

Leu Ser Pro Asp Ile Val Ala Glu Gln Lys Lys Leu Glu Ala Ala Asp
                85                 90                 95

Leu Val Ile Phe Gln Phe Pro Leu Gln Trp Phe Gly Val Pro Ala Ile
                100                105                110

Leu Lys Gly Trp Phe Glu Arg Val Phe Ile Gly Glu Phe Ala Tyr Thr
                115                120                125

Tyr Ala Met Tyr Asp Lys Gly Pro Phe Arg Ser Lys Lys Ala Val
                130                135                140

Leu Ser Ile Thr Thr Gly Gly Ser Gly Ser Met Tyr Ser Leu Gln Gly
145                150                155                160

Ile His Gly Asp Met Asn Val Ile Leu Trp Pro Ile Gln Ser Gly Ile
                165                170                175

Leu His Phe Cys Gly Phe Gln Val Leu Glu Pro Gln Leu Thr Tyr Ser
                180                185                190

Ile Gly His Thr Pro Ala Asp Ala Arg Ile Gln Ile Leu Glu Gly Trp
                195                200                205

Lys Lys Arg Leu Glu Asn Ile Trp Asp Glu Thr Pro Leu Tyr Phe Ala
                210                215                220

Pro Ser Ser Leu Phe Asp Leu Asn Phe Gln Ala Gly Phe Leu Met Lys
225                230                235                240

Lys Glu Val Gln Asp Glu Glu Lys Asn Lys Phe Gly Leu Ser Val
                245                250                255

Gly His His Leu Gly Lys Ser Ile Pro Thr Asp Asn Gln Ile Lys Ala
                260                265                270

Arg Lys
```

<210> SEQ ID NO 11
<211> LENGTH: 3149
<212> TYPE: DNA
<213> ORGANISM: Homo sapiens

<400> SEQUENCE: 11

```
cctttcccag agtgctctgc gccgtgaaga agcggctccc ggggactggg ggcattttgt    60
gttggctgga gctggagtaa caagatggcg tcgtccgcgg agtgacaggg gtccctctgg   120
gccggagccg gcggcagtgg tggcagcggt atcgccgccc tagctcaccg cgcccctttt   180
ccagcccgcg acgtcgccgc gcaagcgagg cagcggcggc cgccgagaaa caagtggccc   240
agcctggtaa ccgccgagaa gcccttcaca aactgcggcc tggcaaaaag aaacctgact   300
gagcggcggt gatcaggttc ccctctgctg attctgggcc ccgaaccccg gtaaaggcct   360
ccgtgttccg tttcctgccg ccctcctccg tagccttgcc tagtgtagga gccccgaggc   420
ctccgtcctc ttcccagagg tgtcggggct tggccccagc ctccatcttc gtctctcagg   480
atggcgagta gcagcggctc caaggctgaa ttcattgtcg agggaaaata taaactggta   540
cggaagatcg ggtctggctc cttcggggac atctatttgg cgatcaacat caccaacggc   600
```

```
gaggaagtgg cagtgaagct agaatctcag aaggccaggc atccccagtt gctgtacgag     660
agcaagctct ataagattct tcaaggtggg gttggcatcc cccacatacg gtggtatggt     720
caggaaaaag actacaatgt actagtcatg gatcttctgg gacctagcct cgaagacctc     780
ttcaatttct gttcaagaag gttcacaatg aaaactgtac ttatgttagc tgaccagatg     840
atcagtagaa ttgaatatgt gcatacaaag aattttatac acagagacat taaaccagat     900
aacttcctaa tgggtattgg gcgtcactgt aataagtgtt tagaatctcc agtggggaag     960
aggaaaagaa gcatgactgt tagtacttct caggacccat ctttctcagg attaaaccag    1020
ttattcctta ttgattttgg tttggccaaa aagtacagag acaacaggac aaggcaacac    1080
ataccataca gagaagataa aaacctcact ggcactgccc gatatgctag catcaatgca    1140
catcttggta ttgagcagag tcgccgagat gacatggaat cattaggata tgttttgatg    1200
tattttaata gaaccagcct gccatggcaa gggctaaagg ctgcaacaaa gaaacaaaaa    1260
tatgaaaaga ttagtgaaaa gaagatgtcc acgcctgttg aagttttatg taagggttt     1320 cctgcagaat ttgcgatgta cttaaactat tgtcgtgggc tacgctttga ggaagcccca    1380
gattacatgt atctgaggca gctattccgc attcttttca ggaccctgaa ccatcaatat    1440
gactacacat ttgattggac aatgttaaag cagaaagcag cacagcaggc agcctcttcc    1500
agtgggcagg gtcagcaggc ccaaaccccc acaggcaagc aaactgacaa aaccaagagt    1560
aacatgaaag gtttctaagc atgaattgag gaacagaaga agcagagcag atgatcggag    1620
cagcatttgt ttctccccaa atctagaaat tttagttcat atgtacacta gccagtggtt    1680
gtggacaacc atttacttgg tgtaaagaac ttaatttcag tataaactga ctctgggcag    1740
cattggtgat gctgtatcct gagttgtagc ctctgtaatt gtgaatatta actgagatag    1800
tgaaacatgg tgtccggttt tctattgcat tttttcaagt ggaaaagtta actaaatggt    1860
tgacacacaa aaattggtgg agaaattgtg catatgccaa ttttttgtta aaaccttttg    1920
ttttgaacta tactgctttg agatctcatt tcagaagaac ggcatgaaca gtcttcagcc    1980
acagttgtga tggttgttaa atgctcacaa ttgtgcattc ttagggtttt tccatccctg    2040
gggtttgcaa gttgttcact taaaacattc ttaaaatggt tggcttcttg tctgcaagcc    2100
agctgatatg gtagcaacca aagattccag tgtttgagca tatgaaagac tctgcctgct    2160
taattgtgct agaaataaca gcatctaaag tgaagactta agaaaaactt agtgactact    2220
agattatcct taggactctg cattaactct ataatgttct tggtattaaa aaaaaagcat    2280
atttgtcaca gaaatttagt taacatctta caactgaaca tgtatgtatg ttgcttagat    2340
aaatgtaatc actgtaaaca tctatatgat ctgggatttt gttttatttt tgaaatggga    2400
gcttttttgt ttacaagttc attaaaaact aaaaactgtt tctgtaagga aatgagattt    2460
tttttaaaca acaaaaaatg ccttgctgac tcactattaa ataaaaatct ccccaatttt    2520
ttgatagact acttcaagcc atttgttaca tggtattcct ttgcaagtca atttaggttt    2580
cgtgttataa cttttcctct ttttttaaga aaaatgaaaa aagtaattct tttgtctgaa    2640
ggggaaaggc attctttcat ttttttcttt tttttttttt tttttttatga cttgcaggca    2700 caatatctag tactgcaact gccagaactt ggtattgtag ctgctgcccg ctgactagca    2760
gctggactga ttttgaataa aaatgaaagc attaaagggt ttccctacaa acatttttc     2820 tttaaaatac ttttgaaatg gctataagca gttgactttc acccttggag agcatcacac    2880
tgtgtgaggt tcagtgattg ttgacccctcc ccagccctc ctgcttcttt aagttatctg    2940
tgtgcgtgcg cttcctctca atcttctttg cacgctcatt tcttttttctc tgacccatga    3000
```

```
gaaaggaaaa cttactgatg ataattttta aatagtgtaa tttattcatt tatagcatgt   3060
caggataaat taaagaaaca tttgtctgga aatgctgccg ggagcctatt gtgtaaatgt   3120
aggtattttg taaataaacc ttgaaattg                                     3149
```

<210> SEQ ID NO 12
<211> LENGTH: 365
<212> TYPE: PRT
<213> ORGANISM: Homo sapiens

<400> SEQUENCE: 12

```
Met Ala Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
130                 135                 140

Gly Ile Gly Arg His Cys Asn Lys Cys Leu Glu Ser Pro Val Gly Lys
145                 150                 155                 160

Arg Lys Arg Ser Met Thr Val Ser Thr Ser Gln Asp Pro Ser Phe Ser
                165                 170                 175

Gly Leu Asn Gln Leu Phe Leu Ile Asp Phe Gly Leu Ala Lys Lys Tyr
            180                 185                 190

Arg Asp Asn Arg Thr Arg Gln His Ile Pro Tyr Arg Glu Asp Lys Asn
        195                 200                 205

Leu Thr Gly Thr Ala Arg Tyr Ala Ser Ile Asn Ala His Leu Gly Ile
    210                 215                 220

Glu Gln Ser Arg Arg Asp Asp Met Glu Ser Leu Gly Tyr Val Leu Met
225                 230                 235                 240

Tyr Phe Asn Arg Thr Ser Leu Pro Trp Gln Gly Leu Lys Ala Ala Thr
                245                 250                 255

Lys Lys Gln Lys Tyr Glu Lys Ile Ser Glu Lys Lys Met Ser Thr Pro
            260                 265                 270

Val Glu Val Leu Cys Lys Gly Phe Pro Ala Glu Phe Ala Met Tyr Leu
        275                 280                 285

Asn Tyr Cys Arg Gly Leu Arg Phe Glu Glu Ala Pro Asp Tyr Met Tyr
    290                 295                 300

Leu Arg Gln Leu Phe Arg Ile Leu Phe Arg Thr Leu Asn His Gln Tyr
305                 310                 315                 320

Asp Tyr Thr Phe Asp Trp Thr Met Leu Lys Gln Lys Ala Ala Gln Gln
                325                 330                 335

Ala Ala Ser Ser Gly Gln Gly Gln Gln Ala Gln Thr Pro Thr Gly
            340                 345                 350
```

| Lys | Gln | Thr | Asp | Lys | Thr | Lys | Ser | Asn | Met | Lys | Gly | Phe |
|---|---|---|---|---|---|---|---|---|---|---|---|---|
| | | | 355 | | | | 360 | | | | | 365 |

<210> SEQ ID NO 13
<211> LENGTH: 3065
<212> TYPE: DNA
<213> ORGANISM: Homo sapiens

<400> SEQUENCE: 13

```
cctttcccag agtgctctgc gccgtgaaga agcggctccc ggggactggg ggcattttgt      60
gttggctgga gctggagtaa caagatggcg tcgtccgcgg agtgacaggg gtccctctgg     120
gccggagccg gcggcagtgg tggcagcggt atcgccgccc tagctcaccg cgccccttt     180
ccagcccgcg acgtcgccgc gcaagcgagg cagcggcggc cgccgagaaa caagtggccc     240
agcctggtaa ccgccgagaa gcccttcaca aactgcgggc tggcaaaaag aaacctgact     300
gagcggcggt gatcaggttc ccctctgctg attctgggcc ccgaacccg gtaaaggcct      360
ccgtgttccg tttcctgccg ccctcctccg tagccttgcc tagtgtagga gccccgaggc     420
ctccgtcctc ttcccagagg tgtcggggct tggccccagc ctccatcttc gtctctcagg     480
atggcgagta gcagcggctc caaggctgaa ttcattgtcg gagggaaata taaactggta     540
cggaagatcg ggtctggctc cttcggggac atctatttgg cgatcaacat caccaacggc     600
gaggaagtgg cagtgaagct agaatctcag aaggccaggc atcccagtt gctgtacgag      660
agcaagctct ataagattct tcaaggtggg gttggcatcc cccacatacg gtggtatggt     720
caggaaaaag actacaatgt actagtcatg gatcttctgg gacctagcct cgaagacctc     780
ttcaatttct gttcaagaag gttcacaatg aaaactgtac ttatgttagc tgaccagatg     840
atcagtagaa ttgaatatgt gcatacaaag aattttatac acagagacat aaaccagat      900
aacttcctaa tgggtattgg gcgtcactgt aataagttat ccttattga ttttggtttg      960
gccaaaaagt acagagacaa caggacaagg caacacatac catacagaga agataaaaac    1020
ctcactggca ctgcccgata tgctagcatc aatgcacatc ttggtattga gcagagtcgc    1080
cgagatgaca tggaatcatt aggatatgtt ttgatgtatt taatagaac cagcctgcca    1140
tggcaagggc taaaggctgc aacaaagaaa caaaaatatg aaaagattag tgaaaagaag    1200
atgtccacgc ctgttgaagt tttatgtaag gggtttcctg cagaatttgc gatgtactta    1260
aactattgtc gtgggctacg cttgaggaa gccccagatt acatgtatct gaggcagcta    1320
ttccgcattc ttttcaggac cctgaaccat caatatgact acacatttga ttggacaatg    1380
ttaaagcaga aagcagcaca gcaggcagcc tcttccagtg ggcagggtca gcaggcccaa    1440
accccccacag gcaagcaaac tgacaaaacc aagagtaaca tgaaaggttt ctaagcatga    1500
attgaggaac agaagaagca gagcagatga tcggagcagc atttgtttct ccccaaatct    1560
agaaattta gttcatatgt acactagcca gtggttgtgg acaaccattt acttggtgta    1620
aagaacttaa tttcagtata aactgactct gggcagcatt ggtgatgctg tatcctgagt    1680
tgtagcctct gtaattgtga atattaactg agatagtgaa acatggtgtc cggttttcta    1740
ttgcattttt tcaagtggaa aagttaacta aatggttgac acacaaaat tggtggagaa    1800
attgtgcata tgccaatttt ttgttaaaac cttttgtttt gaactatact gctttgagat    1860
ctcatttcag aagaacggca tgaacagtct tcagccacag ttgtgatggt tgttaaatgc    1920
tcacaattgt gcattcttag ggttttttcca tccctggggt ttgcaagttg ttcacttaaa    1980
acattcttaa aatggttggc ttcttgtctg caagccagct gatatggtag caaccaaga    2040
ttccagtgtt tgagcatatg aaagactctg cctgcttaat tgtgctagaa ataacagcat    2100
```

```
ctaaagtgaa gacttaagaa aaacttagtg actactagat tatccttagg actctgcatt   2160
aactctataa tgttcttggt attaaaaaaa aagcatattt gtcacagaaa tttagttaac   2220
atcttacaac tgaacatgta tgtatgttgc ttagataaat gtaatcactg taaacatcta   2280
tatgatctgg gattttgttt ttattttgaa atgggagctt ttttgtttac aagttcatta   2340
aaaactaaaa actgtttctg taaggaaatg agattttttt taaacaacaa aaaatgcctt   2400
gctgactcac tattaaataa aaatctcccc aattttttga tagactactt caagccattt   2460
gttacatggt attcctttgc aagtcaattt aggtttcgtg ttataacttt tcctcttttt   2520
ttaagaaaaa tgaaaaaagt aattcttttg tctgaagggg aaaggcattc tttcattttt   2580 ttctttttttt tttttttttt ttatgacttg caggcacaat atctagtact gcaactgcca   2640
gaacttggta ttgtagctgc tgcccgctga ctagcagctg gactgatttt gaataaaaat   2700
gaaagcatta aagggtttcc ctacaaaaca ttttttcttta aaatacttttt gaatggcta   2760 taagcagttg acttcaccc ttggagagca tcacactgtg tgaggttcag tgattgttga   2820
ccctccccag cccctcctgc ttctttaagt tatctgtgtg cgtgcgcttc ctctcaatct   2880
tctttgcacg ctcatttctt tttctctgac ccatgagaaa ggaaaactta ctgatgataa   2940
tttttaaata gtgtaatttta ttcatttata gcatgtcagg ataaattaaa agaacatttg   3000
tctgaaaatg ctgccgggag cctattgtgt aaatgtaggt attttgtaaa ataaccttga   3060
aattg                                                              3065
```

<210> SEQ ID NO 14
<211> LENGTH: 337
<212> TYPE: PRT
<213> ORGANISM: Homo sapiens

<400> SEQUENCE: 14

```
Met Ala Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
            20                  25                  30

Leu Ala Ile Asn Ile Thr Asn Gly Glu Glu Val Ala Val Lys Leu Glu
        35                  40                  45

Ser Gln Lys Ala Arg His Pro Gln Leu Leu Tyr Glu Ser Lys Leu Tyr
    50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
```

```
                195                 200                 205
Tyr Val Leu Met Tyr Phe Asn Arg Thr Ser Leu Pro Trp Gln Gly Leu
            210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
        290                 295                 300

Ala Ala Gln Gln Ala Ala Ser Ser Ser Gly Gln Gly Gln Gln Ala Gln
305                 310                 315                 320

Thr Pro Thr Gly Lys Gln Thr Asp Lys Thr Lys Ser Asn Met Lys Gly
                325                 330                 335

Phe

<210> SEQ ID NO 15
<211> LENGTH: 2544
<212> TYPE: DNA
<213> ORGANISM: Homo sapiens

<400> SEQUENCE: 15
cagcttttca cttcttcttg tagtcgcgac ttggagtttt gctaatgtct ccctcctttc        60
ctaagtgaca ttgaatccgt agggatgttg atgccatcat cccctctttc ccctgcagga       120
agtggcagtg aagctagaat ctcagaaggc caggcatccc cagttgctgt acgagagcaa       180
gctctataag attcttcaag gtggggttgg catcccccac atacggtggt atggtcagga       240
aaaagactac aatgtactag tcatggatct tctgggacct agcctcgaag acctcttcaa       300
tttctgttca agaaggttca caatgaaaac tgtacttatg ttagctgacc agatgatcag       360
tagaattgaa tatgtgcata caaagaattt tatacacaga gacattaaac cagataactt       420
cctaatgggt attgggcgtc actgtaataa gttattcctt attgattttg gtttggccaa       480
aaagtacaga gacaacagga caaggcaaca catacccatac agagaagata aaaacctcac      540
tggcactgcc cgatatgcta gcatcaatgc acatcttggt attgagcaga gtcgccgaga       600
tgacatggaa tcattaggat atgttttgat gtatttaat agaaccagcc tgccatggca       660
agggctaaag gctgcaacaa agaaacaaaa atatgaaaag attagtgaaa agaagatgtc       720
cacgcctgtt gaagttttat gtaagggggtt tcctgcagaa tttgcgatgt acttaaacta       780
ttgtcgtggg ctacgctttg aggaagcccc agattacatg tatctgaggc agctattccg       840 cattctttc aggaccctga accatcaata tgactacaca tttgattgga caatgttaaa        900
gcagaaagca gcacagcagg cagcctcttc cagtgggcag ggtcagcagg cccaaacccc       960
cacaggtttc taagcatgaa ttgaggaaca gaagaagcag agcagatgat cggagcagca      1020
tttgtttctc cccaaatcta gaaattttag ttcatatgta cactagccag tggttgtgga      1080
caaccattta cttggtgtaa agaacttaat ttcagtataa actgactctg gcagcattg       1140 gtgatgctgt atcctgagtt gtagcctctg taattgtgaa tattaactga gatagtgaaa      1200
catggtgtcc ggttttctat tgcattttt caagtggaaa agttaactaa atggttgaca       1260
cacaaaaatt ggtggagaaa ttgtgcatat gccaattttt tgttaaaacc ttttgttttg      1320
```

```
aactatactg ctttgagatc tcatttcaga agaacggcat gaacagtctt cagccacagt    1380
tgtgatggtt gttaaatgct cacaattgtg cattcttagg gttttttccat ccctgggggtt   1440 tgcaagttgt tcacttaaaa cattcttaaa atggttggct tcttgtctgc aagccagctg    1500
atatggtagc aaccaaagat tccagtgttt gagcatatga aagactctgc ctgcttaatt    1560
gtgctagaaa taacagcatc taaagtgaag acttaagaaa aacttagtga ctactagatt    1620
atccttagga ctctgcatta actctataat gttcttggta ttaaaaaaaa agcatatttg    1680
tcacagaaat ttagttaaca tcttacaact gaacatgtat gtatgttgct tagataaatg    1740
taatcactgt aaacatctat atgatctggg attttgtttt tattttgaaa tgggagcttt    1800
tttgtttaca agttcattaa aaactaaaaa ctgtttctgt aaggaaatga atttttttt     1860 aaacaacaaa aaatgccttg ctgactcact attaaataaa aatctcccca atttttgat    1920 agactacttc aagccatttg ttacatggta ttcctttgca agtcaattta ggtttcgtgt    1980
tataactttt cctcttttt taagaaaaat gaaaaaagta attcttttgt ctgaagggga    2040
aaggcattct ttcatttttt tcttttttt tttttttt tatgacttgc aggcacaata      2100
tctagtactg caactgccag aacttggtat tgtagctgct gcccgctgac tagcagctgg    2160
actgattttg aataaaaatg aaagcattaa agggtttccc tacaaaacat ttttctttaa    2220 aatactttg aaatggctat aagcagttga cttcaccct tggagagcat cacactgtgt     2280
gaggttcagt gattgttgac cctccccagc ccctcctgct tctttaagtt atctgtgtgc    2340
gtgcgcttcc tctcaatctt ctttgcacgc tcatttctttt ttctctgacc catgagaaag    2400
gaaaacttac tgatgataat ttttaaatag tgtaatttat tcatttatag catgtcagga    2460
taaattaaaa gaacatttgt ctggaaatgc tgccgggagc ctattgtgta aatgtaggta    2520
ttttgtaaaa taaccttgaa attg                                           2544
```

<210> SEQ ID NO 16
<211> LENGTH: 236
<212> TYPE: PRT
<213> ORGANISM: Homo sapiens

<400> SEQUENCE: 16

```
Met Asp Leu Leu Gly Pro Ser Leu Glu Asp Leu Phe Asn Phe Cys Ser
1               5                   10                  15

Arg Arg Phe Thr Met Lys Thr Val Leu Met Leu Ala Asp Gln Met Ile
            20                  25                  30

Ser Arg Ile Glu Tyr Val His Thr Lys Asn Phe Ile His Arg Asp Ile
        35                  40                  45

Lys Pro Asp Asn Phe Leu Met Gly Ile Gly Arg His Cys Asn Lys Leu
    50                  55                  60

Phe Leu Ile Asp Phe Gly Leu Ala Lys Lys Tyr Arg Asp Asn Arg Thr
65                  70                  75                  80

Arg Gln His Ile Pro Tyr Arg Glu Asp Lys Asn Leu Thr Gly Thr Ala
                85                  90                  95

Arg Tyr Ala Ser Ile Asn Ala His Leu Gly Ile Glu Gln Ser Arg Arg
            100                 105                 110

Asp Asp Met Glu Ser Leu Gly Tyr Val Leu Met Tyr Phe Asn Arg Thr
        115                 120                 125

Ser Leu Pro Trp Gln Gly Leu Lys Ala Ala Thr Lys Lys Gln Lys Tyr
    130                 135                 140

Glu Lys Ile Ser Glu Lys Lys Met Ser Thr Pro Val Glu Val Leu Cys
145                 150                 155                 160
```

-continued

```
Lys Gly Phe Pro Ala Glu Phe Ala Met Tyr Leu Asn Tyr Cys Arg Gly
            165                 170                 175
Leu Arg Phe Glu Glu Ala Pro Asp Tyr Met Tyr Leu Arg Gln Leu Phe
        180                 185                 190
Arg Ile Leu Phe Arg Thr Leu Asn His Gln Tyr Asp Tyr Thr Phe Asp
    195                 200                 205
Trp Thr Met Leu Lys Gln Lys Ala Ala Gln Ala Ala Ser Ser Ser
    210                 215                 220
Gly Gln Gly Gln Gln Ala Gln Thr Pro Thr Gly Phe
225                 230                 235

<210> SEQ ID NO 17
<211> LENGTH: 15
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 17
aaaaaaaaaa aaaaa                                                      15

<210> SEQ ID NO 18
<211> LENGTH: 200
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa                                                200

<210> SEQ ID NO 19
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: This region may or may not be present

<400> SEQUENCE: 19
uagggauagg ga                                                         12

<210> SEQ ID NO 20
<211> LENGTH: 13
<212> TYPE: PRT
<213> ORGANISM: Homo sapiens

<400> SEQUENCE: 20

Arg Ser Leu Gln Tyr Gln Arg Arg Ser Ser Arg Gly Arg
1               5                   10

<210> SEQ ID NO 21
<211> LENGTH: 13
<212> TYPE: PRT
<213> ORGANISM: Homo sapiens
```

-continued

<400> SEQUENCE: 21

Ala Ala Leu Gln Tyr Gln Ala Ala Ala Ala Gly Ala
1               5                   10

<210> SEQ ID NO 22
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uagggauagg gauagggaua gggauaggga aaaaaaaaaa aaaaa                45

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtccatggct gtgatcttgc cctcttcttg gatcgggtg                       39

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtccatggct gtgctcttgc cctcttcttg gatctgggtg                      40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cacccagatc caagaagagg gcaagagcac agccatggac                      40

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
agguagugua aucgccuug                                             19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 27
guguguuugu caguggcuu                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aacuacgagc tgcgagaaa                                                19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
accttcgtgc aggaggacat                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgtgttgatg tagccgagga                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgttgctggt cacattcctg                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cctgcacctg ctcagacagt                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
```
aaacaagcct ccaggtctgc                                           20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggacgctttc tccagcatct                                           20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccaccaagtt caagcagctc ta                                        22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gctcctgcaa ctcctcaaag ag                                        22

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaacttcaat cccatcattt ccag                                      24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagcttcttt tgttcagcca caat                                      24

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgccaagtga ttggtgcttc                                           20

```
<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aaaaggcccc tgaacgagat                                              20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggcactgtgg ccttggtcta a                                            21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcctaccgag cacgcaagaa                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atgcctggtt ttcgtttgca                                              20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agctgtggaa ctcacacaca ctca                                         24

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggugccaucc aguuaggca                                               19

<210> SEQ ID NO 46
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gaaguuggag cacucuugg                                              19

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaagtggcag tgagactaga atcccag                                     27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctgggattct agtctcactg ccactcc                                     27

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 49

Gly Ser Xaa Xaa Xaa Xaa Xaa Xaa Xaa Xaa Xaa Xaa Asp Xaa Asp
1               5                   10                  15

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Arg Leu Phe Leu Val Gly Ser Ser Leu Asn Gly Phe Gly Thr Arg
1               5                   10                  15

Ser Ser Asp Gly Asp Leu Cys Leu Val Val Lys
            20                  25

<210> SEQ ID NO 51
<211> LENGTH: 27
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 51

Cys Val Val His Pro Phe Gly Ser Ser Ile Asn Ser Phe Asp Val His
1               5                   10                  15

Gly Cys Asp Leu Asp Leu Phe Leu Asp Leu Gly
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Lys Ile Phe Thr Phe Gly Ser Tyr Arg Leu Gly Val His Thr Lys
1               5                   10                  15

Gly Ala Asp Ile Asp Ala Leu Cys Val Ala Pro Arg
            20                  25

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Lys Thr Ser Leu Phe Gly Ser Thr Gln Ser Leu Leu Ala Ser Asn
1               5                   10                  15

Ala Ser Asp Ile Asp Leu Cys Ile Ile Thr Asp
            20                  25

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Asp Leu His Val Phe Gly Ser Phe Ala Thr Asp Leu Tyr Leu Pro
1               5                   10                  15

Gly Ser Asp Ile Asp Cys Val Val Asn Ser
            20                  25

<210> SEQ ID NO 55
<211> LENGTH: 250
<212> TYPE: PRT
<213> ORGANISM: Homo sapiens

<400> SEQUENCE: 55

Gly Cys Val Val His Pro Phe Gly Ser Ser Ile Asn Ser Phe Asp Val
1               5                   10                  15

His Gly Cys Asp Leu Asp Leu Phe Leu Asp Leu Gly Asp Leu Glu Glu
            20                  25                  30

Pro Gln Pro Val Pro Lys Ala Pro Glu Ser Pro Ser Leu Asp Ser Ala
        35                  40                  45

```
Leu Ala Ser Pro Leu Asp Pro Gln Ala Leu Ala Cys Thr Pro Ala Ser
     50                  55                  60

Pro Pro Asp Ser Gln Pro Ala Ser Pro Gln Asp Ser Glu Ala Leu
 65                  70                  75                  80

Asp Phe Glu Thr Pro Ser Ser Leu Ala Pro Gln Thr Pro Asp Ser
                 85                  90                  95

Ala Leu Ala Ser Glu Thr Leu Ala Ser Pro Gln Ser Leu Pro Pro Ala
                100                 105                 110

Ser Pro Leu Leu Glu Asp Arg Glu Glu Gly Asp Leu Gly Lys Ala Ser
             115                 120                 125

Glu Leu Ala Glu Thr Pro Lys Glu Glu Lys Ala Glu Gly Ala Ala Met
130                 135                 140

Leu Glu Leu Val Gly Ser Ile Leu Arg Gly Cys Val Pro Gly Val Tyr
145                 150                 155                 160

Arg Val Gln Thr Val Pro Ser Ala Arg Arg Pro Val Val Lys Phe Cys
                165                 170                 175

His Arg Pro Ser Gly Leu His Gly Asp Val Ser Leu Ser Asn Arg Leu
            180                 185                 190

Ala Leu His Asn Ser Arg Phe Leu Ser Leu Cys Ser Glu Leu Asp Gly
        195                 200                 205

Arg Val Arg Pro Leu Val Tyr Thr Leu Arg Cys Trp Ala Gln Gly Arg
210                 215                 220

Gly Leu Ser Gly Ser Gly Pro Leu Leu Ser Asn Tyr Ala Leu Thr Leu
225                 230                 235                 240

Leu Val Ile Tyr Phe Leu Gln Thr Arg Asp
                245                 250

<210> SEQ ID NO 56
<211> LENGTH: 169
<212> TYPE: PRT
<213> ORGANISM: Homo sapiens

<400> SEQUENCE: 56

Gly Gly Lys Ile Phe Thr Phe Gly Ser Tyr Arg Leu Gly Val His Thr
 1               5                  10                  15

Lys Gly Ala Asp Ile Asp Ala Leu Cys Val Ala Pro Arg His Val Asp
             20                  25                  30

Arg Ser Asp Phe Phe Thr Ser Phe Tyr Asp Lys Leu Lys Leu Gln Glu
         35                  40                  45

Glu Val Lys Asp Leu Arg Ala Val Glu Glu Ala Phe Val Pro Val Ile
     50                  55                  60

Lys Leu Cys Phe Asp Gly Ile Glu Ile Asp Ile Leu Phe Ala Arg Leu
 65                  70                  75                  80

Ala Leu Gln Thr Ile Pro Glu Asp Leu Asp Leu Arg Asp Asp Ser Leu
                 85                  90                  95

Leu Lys Asn Leu Asp Ile Arg Cys Ile Arg Ser Leu Asn Gly Cys Arg
            100                 105                 110

Val Thr Asp Glu Ile Leu His Leu Val Pro Asn Ile Asp Asn Phe Arg
        115                 120                 125

Leu Thr Leu Arg Ala Ile Lys Leu Trp Ala Lys Arg His Asn Ile Tyr
130                 135                 140

Ser Asn Ile Leu Gly Phe Leu Gly Gly Val Ser Trp Ala Met Leu Val
145                 150                 155                 160

Ala Arg Thr Cys Gln Leu Tyr Pro Asn
                165
```

<210> SEQ ID NO 57
<211> LENGTH: 153
<212> TYPE: PRT
<213> ORGANISM: Homo sapiens

<400> SEQUENCE: 57

Gln Ser Arg Leu Phe Leu Val Gly Ser Ser Leu Asn Gly Phe Gly Thr
1               5                   10                  15

Arg Ser Ser Asp Gly Asp Leu Cys Leu Val Val Lys Glu Glu Pro Cys
                20                  25                  30

Phe Phe Gln Val Asn Gln Lys Thr Glu Ala Arg His Ile Leu Thr Leu
            35                  40                  45

Val His Lys His Phe Cys Thr Arg Leu Ser Gly Tyr Ile Glu Arg Pro
50                  55                  60

Gln Leu Ile Arg Ala Lys Val Pro Ile Val Lys Phe Arg Asp Lys Val
65                  70                  75                  80

Ser Cys Val Glu Phe Asp Leu Asn Val Asn Asn Ile Val Gly Ile Arg
                85                  90                  95

Asn Thr Phe Leu Leu Arg Thr Tyr Ala Tyr Leu Glu Asn Arg Val Arg
            100                 105                 110

Pro Leu Val Leu Val Ile Lys Lys Trp Ala Ser His His Gln Ile Asn
        115                 120                 125

Asp Ala Ser Arg Gly Thr Leu Ser Ser Tyr Ser Leu Val Leu Met Val
130                 135                 140

Leu His Tyr Leu Gln Thr Leu Pro Glu
145                 150

<210> SEQ ID NO 58
<211> LENGTH: 169
<212> TYPE: PRT
<213> ORGANISM: Saccharomyces cerevisiae

<400> SEQUENCE: 58

Gly Gly Lys Val Phe Thr Phe Gly Ser Tyr Arg Leu Gly Val Tyr Gly
1               5                   10                  15

Pro Gly Ser Asp Ile Asp Thr Leu Val Val Val Pro Lys His Val Thr
                20                  25                  30

Arg Asp Asp Phe Phe Ser Val Phe Ala Asp Ile Ile Arg Lys Arg Pro
            35                  40                  45

Glu Leu Glu Glu Ile Ala Cys Val Pro Asp Ala Tyr Val Pro Ile Ile
50                  55                  60

Lys Leu Glu Phe Asp Gly Ile Ser Ile Asp Leu Ile Met Ala Arg Leu
65                  70                  75                  80

Asn Ile Pro Arg Val Pro Leu Asp Leu Thr Leu Asp Asp Lys Asn Leu
                85                  90                  95

Leu Lys Asn Leu Asp Glu Lys Asp Leu Arg Ser Leu Asn Gly Thr Arg
            100                 105                 110

Val Thr Asp Glu Ile Leu Gln Leu Val Pro Lys Pro Thr Val Phe Lys
        115                 120                 125

His Ala Leu Arg Cys Ile Lys Leu Trp Ala Gln Gln Arg Ala Val Tyr
130                 135                 140

Gly Asn Ile Phe Gly Phe Pro Gly Gly Val Ala Trp Ala Met Leu Val
145                 150                 155                 160

Ala Arg Ile Cys Gln Leu Tyr Pro Asn
                165

<210> SEQ ID NO 59
<211> LENGTH: 142
<212> TYPE: PRT
<213> ORGANISM: Schizosaccharomyces pombe

<400> SEQUENCE: 59

```
Asn Ile Lys Thr Ser Leu Phe Gly Ser Thr Gln Ser Leu Leu Ala Ser
1               5                   10                  15

Asn Ala Ser Asp Ile Asp Leu Cys Ile Ile Thr Asp Pro Pro Gln Cys
            20                  25                  30

Ala Pro Thr Thr Cys Glu Val Ser Ala Ala Phe Ala Arg Asn Gly Leu
        35                  40                  45

Lys Lys Val Val Cys Ile Ser Thr Ala Lys Val Pro Ile Val Lys Val
    50                  55                  60

Trp Asp Ser Glu Leu Gln Leu Ser Cys Asp Cys Asn Ile Asn Lys Thr
65                  70                  75                  80

Ile Ser Thr Leu Asn Thr Arg Leu Met Arg Ser Tyr Val Leu Cys Asp
                85                  90                  95

Pro Arg Val Arg Pro Leu Ile Val Met Ile Lys Tyr Trp Ala Lys Arg
            100                 105                 110

Arg Cys Leu Asn Asp Ala Ala Glu Gly Gly Thr Leu Thr Ser Tyr Thr
        115                 120                 125

Ile Ser Cys Met Val Ile Asn Phe Leu Gln Lys Arg Asp Pro
    130                 135                 140
```

<210> SEQ ID NO 60
<211> LENGTH: 144
<212> TYPE: PRT
<213> ORGANISM: Saccharomyces cerevisiae

<400> SEQUENCE: 60

```
Asp Ala Asp Leu His Val Phe Gly Ser Tyr Ser Thr Asp Leu Tyr Leu
1               5                   10                  15

Pro Gly Ser Asp Ile Asp Cys Val Val Thr Ser Glu Leu Gly Gly Lys
            20                  25                  30

Glu Ser Arg Asn Asn Leu Tyr Ser Leu Ala Ser His Leu Lys Lys Lys
        35                  40                  45

Asn Leu Ala Thr Glu Val Glu Val Ala Lys Ala Arg Val Pro Ile
    50                  55                  60

Ile Lys Phe Val Glu Pro His Ser Gly Ile His Ile Asp Val Ser Phe
65                  70                  75                  80

Glu Arg Thr Asn Gly Ile Glu Ala Ala Lys Leu Ile Arg Glu Trp Leu
                85                  90                  95

Asp Asp Thr Pro Gly Leu Arg Glu Leu Val Leu Ile Val Lys Gln Phe
            100                 105                 110

Leu His Ala Arg Arg Leu Asn Asn Val His Thr Gly Gly Leu Gly Gly
        115                 120                 125

Phe Thr Ile Ile Cys Leu Val Phe Ser Phe Leu His Met His Pro Arg
    130                 135                 140
```

<210> SEQ ID NO 61
<211> LENGTH: 389
<212> TYPE: PRT
<213> ORGANISM: Homo sapiens

<400> SEQUENCE: 61

```
Met Ala Ala Val Asp Ser Asp Val Glu Ser Leu Pro Arg Gly Gly Phe
1               5                   10                  15
```

```
Arg Cys Cys Leu Cys His Val Thr Thr Ala Asn Arg Pro Ser Leu Asp
            20                  25                  30

Ala His Leu Gly Gly Arg Lys His Arg His Leu Val Glu Leu Arg Ala
        35                  40                  45

Ala Arg Lys Ala Gln Gly Leu Arg Ser Val Phe Val Ser Gly Phe Pro
 50                  55                  60

Arg Gly Val Asp Ser Ala Gln Leu Ser Glu Tyr Phe Leu Ala Phe Gly
 65                  70                  75                  80

Pro Val Ala Ser Val Val Met Asp Lys Asp Lys Gly Val Phe Ala Ile
            85                  90                  95

Val Glu Met Gly Asp Val Gly Ala Arg Glu Ala Val Leu Ser Gln Ser
            100                 105                 110

Gln His Ser Leu Gly Gly His Arg Leu Arg Val Arg Pro Arg Glu Gln
        115                 120                 125

Lys Glu Phe Gln Ser Pro Ala Ser Lys Ser Pro Lys Gly Ala Ala Pro
    130                 135                 140

Asp Ser His Gln Leu Ala Lys Ala Leu Ala Glu Ala Ala Asp Val Gly
145                 150                 155                 160

Ala Gln Met Ile Lys Leu Val Gly Leu Arg Glu Leu Ser Glu Ala Glu
                165                 170                 175

Arg Gln Leu Arg Ser Leu Val Val Ala Leu Met Gln Glu Val Phe Thr
            180                 185                 190

Glu Phe Phe Pro Gly Cys Val Val His Pro Phe Gly Ser Ser Ile Asn
        195                 200                 205

Ser Phe Asp Val His Gly Cys Asp Leu Asp Leu Phe Leu Asp Leu Gly
    210                 215                 220

Asp Leu Glu Glu Pro Gln Pro Val Pro Lys Ala Pro Gly Ser Pro Ser
225                 230                 235                 240

Leu Asp Ser Ala Leu Ala Ser Pro Leu Asp Pro Gln Ala Leu Ala Cys
                245                 250                 255

Thr Pro Ala Ser Pro Pro Asp Ser Gln Pro Pro Ala Ser Pro Gln Asp
            260                 265                 270

Ser Glu Ala Leu Asp Phe Glu Thr Pro Ser Ser Ser Leu Ala Pro Gln
    275                 280                 285

Thr Pro Asp Ser Ala Leu Ala Ser Glu Thr Leu Ala Ser Pro Gln Ser
290                 295                 300

Leu Pro Pro Ala Ser Pro Leu Leu Glu Asp Arg Glu Glu Gly Asp Leu
305                 310                 315                 320

Gly Lys Ala Ser Glu Leu Ala Glu Thr Pro Lys Glu Lys Ala Glu
                325                 330                 335

Gly Ala Ala Met Leu Glu Leu Val Gly Ser Ile Leu Arg Gly Cys Val
            340                 345                 350

Pro Gly Val Tyr Arg Val Gln Thr Val Pro Ser Ala Arg Arg Pro Val
        355                 360                 365

Val Lys Phe Cys His Arg Pro Ser Gly Leu His Gly Asp Val Ser Leu
    370                 375                 380

Ser Asn Arg Leu Ala
385

<210> SEQ ID NO 62
<211> LENGTH: 388
<212> TYPE: PRT
<213> ORGANISM: Canis familiaris

<400> SEQUENCE: 62
```

Met Ala Ala Val Asp Ala Asp Val Gln Ser Leu Pro Arg Gly Gly Phe
1               5                   10                  15

Arg Cys Cys Leu Cys His Val Thr Thr Ala Asn Arg Pro Ser Leu Asp
            20                  25                  30

Ala His Leu Gly Gly Arg Lys His Arg His Leu Val Glu Leu Arg Ala
        35                  40                  45

Ala Arg Lys Ala Gln Gly Leu Arg Ser Val Phe Val Ser Gly Phe Pro
    50                  55                  60

Arg Asp Val Asp Ser Ala Gln Leu Thr Gln Tyr Phe Gln Ala Phe Gly
65                  70                  75                  80

Pro Val Ala Ser Val Val Met Asp Lys Asp Lys Gly Val Phe Ala Ile
                85                  90                  95

Val Glu Met Gly Asp Thr Glu Thr Arg Glu Ala Val Leu Ser Gln Pro
                100                 105                 110

Gln His Ser Leu Gly Gly His Arg Leu Arg Val Arg Pro Arg Glu Gln
            115                 120                 125

Lys Glu Phe Gln Ser Pro Ala Ser Lys Ser Pro Lys Gly Ala Ala Pro
        130                 135                 140

Asp Ser His Gln Leu Ala Lys Ala Leu Ala Glu Ala Pro Asp Val Gly
145                 150                 155                 160

Ala Gln Met Val Lys Leu Val Gly Leu Arg Glu Leu Ser Glu Ala Glu
                165                 170                 175

Arg Gln Leu Arg Ser Leu Val Val Ala Leu Met Gln Glu Val Phe Met
            180                 185                 190

Glu Phe Phe Pro Gly Cys Val His Pro Phe Gly Ser Ser Ile Asn
        195                 200                 205

Ser Phe Asp Val His Gly Cys Asp Leu Asp Leu Phe Leu Asp Leu Gly
    210                 215                 220

Asp Leu Glu Glu Ser Gln Pro Ala Pro Lys Ala Pro Glu Ser Pro Ser
225                 230                 235                 240

Leu Asp Ser Ala Leu Ala Ser Pro Leu Asp Pro Gln Ala Leu Ala Cys
                245                 250                 255

Thr Pro Ala Ser Pro Pro Asp Ser Gln Pro Pro Ser Pro Pro Asp Ser
                260                 265                 270

Glu Ala Leu Asp Phe Glu Thr Pro Ser Ser Leu Ala Pro Gln Thr
        275                 280                 285

Pro Asp Ser Ala Leu Ala Ser Glu Thr Leu Ala Ser Pro Gln Ser Leu
    290                 295                 300

Pro Pro Ala Ser Pro Leu Gln Glu Asp Leu Gly Glu Gly Asn Leu Gly
305                 310                 315                 320

Lys Ala Leu Glu Leu Ala Glu Ala Leu Lys Gly Glu Lys Pro Glu Gly
                325                 330                 335

Ala Ala Met Leu Glu Leu Val Gly Ser Ile Leu Arg Gly Cys Val Pro
            340                 345                 350

Gly Val Tyr Arg Val Gln Thr Val Pro Ser Ala Arg Arg Pro Val Val
        355                 360                 365

Lys Phe Cys His Arg Pro Ser Gly Leu His Gly Asp Val Ser Leu Ser
    370                 375                 380

Asn Arg Leu Ala
385

<210> SEQ ID NO 63
<211> LENGTH: 392
<212> TYPE: PRT

<213> ORGANISM: Mus musculus

<400> SEQUENCE: 63

Met Ala Ala Val Asp Ser Asp Val Val Ser Leu Pro Arg Gly Arg Phe
1               5                   10                  15

Arg Cys Cys Leu Cys Asp Val Thr Thr Ala Asn Arg Pro Ser Leu Asp
            20                  25                  30

Ala His Leu Lys Gly Arg Lys His Arg Asp Leu Val Gln Leu Arg Ala
        35                  40                  45

Thr Arg Lys Ala Gln Gly Leu Arg Ser Val Phe Val Ser Gly Phe Pro
    50                  55                  60

Arg Asp Val Gly Ser Ala Gln Leu Ser Glu Tyr Phe Gln Thr Phe Gly
65                  70                  75                  80

Pro Val Ala Asn Ile Val Met Asp Lys Asp Lys Gly Val Phe Ala Ile
                85                  90                  95

Val Glu Met Gly Asp Ile Ser Ala Arg Glu Ala Val Leu Ser Gln Pro
            100                 105                 110

Lys His Ser Leu Gly Gly His Gly Leu Arg Val Arg Pro Arg Glu Gln
        115                 120                 125

Lys Glu Phe Gln Ser Pro Ala Ser Lys Ser Pro Lys Gly Val Asp Ser
    130                 135                 140

Ser Ser His Gln Leu Val Gln Ala Leu Ala Glu Ala Ala Asp Val Gly
145                 150                 155                 160

Ala Gln Met Val Lys Leu Val Glu Leu Arg Glu Leu Ser Glu Ala Glu
                165                 170                 175

Arg Gln Leu Arg Asn Leu Val Ala Leu Met Gln Glu Val Phe Thr
            180                 185                 190

Glu Phe Phe Pro Gly Cys Val Val His Pro Phe Gly Ser Thr Val Asn
        195                 200                 205

Ser Phe Asp Val His Gly Cys Asp Leu Asp Leu Phe Leu Asp Met Gly
    210                 215                 220

Asp Met Glu Glu Thr Glu Pro Asp Pro Lys Ala Pro Lys Val Pro Glu
225                 230                 235                 240

Thr Ser Ser Leu Asp Ser Ala Leu Ala Ser Ser Leu Asp Pro Gln Ala
                245                 250                 255

Leu Ala Cys Thr Pro Ala Ser Pro Leu Asp Ser Leu Ser Pro Thr Ser
            260                 265                 270

Val Gln Glu Ser Glu Ser Leu Asp Phe Asp Thr Pro Ser Ser Leu Ala
        275                 280                 285

Pro Gln Thr Pro Asp Ser Ala Leu Gly Ser Asp Thr Val Thr Ser Pro
    290                 295                 300

Gln Ser Leu Pro Pro Val Ser Pro Leu Gln Glu Asp Arg Lys Glu Gly
305                 310                 315                 320

Lys Gln Gly Lys Glu Leu Glu Leu Ala Glu Ala Ser Lys Asp Glu
                325                 330                 335

Lys Glu Glu Ala Ala Ala Val Leu Glu Leu Val Gly Ser Ile Leu Arg
            340                 345                 350

Gly Cys Val Pro Gly Val Tyr Arg Val Gln Thr Val Pro Ser Ala Arg
        355                 360                 365

Arg Pro Val Val Lys Phe Cys His Arg Pro Ser Gly Leu His Gly Asp
    370                 375                 380

Val Ser Leu Ser Asn Arg Leu Ala
385                 390

<210> SEQ ID NO 64
<211> LENGTH: 316
<212> TYPE: PRT
<213> ORGANISM: Danio rerio

<400> SEQUENCE: 64

Met Glu Leu Asp Lys Asp Ile Gln Thr Thr Gln Lys Gly Phe His Cys
1               5                   10                  15

Asn Leu Cys His Val Asn Ile Pro Asn Arg Pro Ser Leu Glu Asp His
            20                  25                  30

Val Lys Gly Lys Lys His Leu His Leu Leu Arg Leu Arg Ala Gln Arg
        35                  40                  45

Lys Thr Gln Glu Glu Asn Ser Val Phe Val Ser Gly Phe Lys Ala Asp
    50                  55                  60

Thr Ser Gln Thr Glu Leu Lys Glu Tyr Phe Gln Gln Phe Gly Leu Val
65                  70                  75                  80

Thr Asp Val Ile Met Asp Lys Gln Lys Gly Val Tyr Ala Ile Val Glu
                85                  90                  95

Phe Ser Glu Ser Gln Asp Val Gln Thr Thr Leu Ala Gln Pro Gln His
            100                 105                 110

Gln Leu Asn Gly Leu Lys Leu Arg Val Lys Pro Arg Glu Lys Lys Glu
        115                 120                 125

Phe Lys Leu Ala Ser Arg Gly Lys Gln Asp Cys Lys Asn Thr Leu Ile
    130                 135                 140

Ser Leu Asp Lys Leu Asn Phe Glu Leu Cys Lys Ala Met Ser Val Asn
145                 150                 155                 160

Glu Gln Ile Gln Lys Val Val Glu Ser Leu Glu Leu Lys Asp Asn Glu
                165                 170                 175

Lys Lys Val Arg Asp Leu Leu Val Gln Leu Leu Gln Glu Val Phe Thr
            180                 185                 190

Glu Phe Phe Pro Asp Cys Gln Ile Val Pro Phe Gly Ser Ser Val Asn
        195                 200                 205

Thr Phe Gly Leu His Ser Cys Asp Leu Asp Leu Phe Leu Asp Leu Glu
    210                 215                 220

Asn Thr Lys Val Phe Gln Ala Arg Ala Lys Ser Ser Glu Gln Thr Gly
225                 230                 235                 240

Glu Asn Gln Ser Glu Asp Cys Arg Ser Glu Asp Ser Ile Leu Ser Asp
                245                 250                 255

Ile Asp Leu Ser Thr Ala Ser Pro Ala Glu Ile Leu Glu Leu Val Ala
            260                 265                 270

Val Ile Leu Arg Lys Cys Val Pro Gly Val His Lys Val Gln Ala Leu
        275                 280                 285

Ser Thr Ala Arg Leu Pro Val Val Lys Phe Ser His Lys Glu Leu Asn
    290                 295                 300

Leu Gln Gly Asp Ile Thr Ile Asn Asn Arg Leu Ala
305                 310                 315

<210> SEQ ID NO 65
<211> LENGTH: 322
<212> TYPE: PRT
<213> ORGANISM: Drosophila melanogaster

<400> SEQUENCE: 65

Met Asn Ser Leu Val Arg Arg Ser Ala Gln Gln Leu Ser Leu Trp Arg
1               5                   10                  15

Thr Tyr Cys Ile Lys His Asn Ala Ser Glu Ala Ala Ser Pro Gly Arg
            20                  25                  30

```
Asn Ala Gly Arg Pro Asn Tyr Glu Glu Phe Ile Gly Arg His Gln Arg
             35                  40                  45

Gln Ala Gln Cys Ser Ile Val Val Gln Val Ser Ser Glu Lys Ser Tyr
 50                  55                  60

Glu Glu Leu Tyr Asn Tyr Cys Ser Ser Phe Gly Ser Ile Met Gly Ala
 65                  70                  75                  80

His His Tyr Cys Val Arg Gln Asp Glu Thr Leu His Tyr Ile Leu Leu
                 85                  90                  95

Glu Tyr Ala Thr Ser Asp Glu Ala Ala Ala Ile Gly Ala Gly Val
                100                 105                 110

Thr Asn Gly Glu Leu Ser Gly Val Pro Val Arg Ser Pro Phe Leu Trp
                115                 120                 125

Phe Arg Ala Ala Gly Gly Arg Arg Ser Pro Lys Leu Val Ala Asn
                130                 135                 140

Thr Ala Pro Ala Leu Leu Ser Leu Asp Gly Thr Arg Gln Val Asp Gln
145                 150                 155                 160

Arg His Leu Leu Gly Leu Leu Arg Gly Ala Ala Asp Ile Glu Glu Gln
                165                 170                 175

Val Gln Gln Leu Tyr Glu His Thr Arg Leu Asn Glu Leu Gly Ile Arg
                180                 185                 190

Met Arg Phe Leu Ala Ala Leu Gln Val Gln Gln Ala Ile Ala Gly Met
                195                 200                 205

Phe Pro Ala Ala Gln Ala Gln Pro Phe Gly Ser Ser Val Asn Gly Phe
                210                 215                 220

Gly Arg Met Gly Cys Asp Leu Asp Leu Ile Leu Arg Phe Asp Ser Asp
225                 230                 235                 240

Met Gly Ala Lys Ile Pro Leu Glu Ala Ala Val Pro Ser Arg Leu Val
                245                 250                 255

Tyr His Thr Lys Glu Asn Leu Ser Asn Gly Arg Ser Gln Thr Gln Arg
                260                 265                 270

His Met Glu Cys Phe Gly Asp Met Leu His Leu Phe Leu Pro Gly Val
                275                 280                 285

Cys His Val Arg Arg Ile Leu Gln Ala Arg Val Pro Ile Ile Lys Tyr
                290                 295                 300

His His Glu His Leu Asp Leu Gly Val Asp Leu Ser Met Ser Asn Leu
305                 310                 315                 320

Thr Gly

<210> SEQ ID NO 66
<211> LENGTH: 308
<212> TYPE: PRT
<213> ORGANISM: Strongylocentrotus purpuratus

<400> SEQUENCE: 66

Met Gly Leu Glu Gly Lys Ala Val Glu Asp His Val Gln Gly Lys Lys
 1               5                  10                  15

His Gln Arg Leu Ile Ala Ile Gln Ala Ser Arg Gln Lys Gln Ala Glu
                20                  25                  30

Cys Ser Ile Phe Val Gly Gly Leu Thr Lys Leu Val Ser Glu Leu Glu
                35                  40                  45

Leu Ser Asp Tyr Phe Ser Lys Phe Gly Ser Val Ala Gln Val Ile Val
 50                  55                  60

Asp Lys Asp Lys Gly Lys Tyr Ala Ile Val Glu Phe Ser Gln Lys Glu
65                  70                  75                  80
```

-continued

Asp Ala Glu Lys Ala Glu Glu Lys Gln Lys Met Asn Gly Lys
            85                  90                  95

Lys Ile Thr Val Arg Pro Arg Glu Asn Lys Pro Phe Ala Leu Lys Gly
            100                 105                 110

Lys Gln Gln Ala Ser Ala Gly Lys Lys Ala Lys Thr Ala Arg Glu Lys
            115                 120                 125

Glu Met Asp Asn Val Leu Glu Gly Leu Leu Glu Ala Glu Asp Val Cys
130                 135                 140

Ser Gln Met Thr Ala Leu Val Glu Glu Thr Cys Leu Asp Gln Ser Asp
145                 150                 155                 160

Leu Gln Leu Arg Tyr Leu Ile Cys Asp Leu Gln Glu Val Phe Val
                165                 170                 175

Glu Met Phe Pro Lys Cys Arg Val Phe Pro Tyr Gly Ser Ser Val Ser
            180                 185                 190

Gly Phe Gly Val Lys Gly Cys Asp Leu Asp Leu Gln Ile Asp Leu Gly
            195                 200                 205

Arg Asp Ser Glu Gln Tyr Lys Tyr Lys Phe Ala Ser Met Phe Pro Asp
            210                 215                 220

Glu Asp Met Glu Thr Asn Glu Glu Met Ala Ala Gly Thr Ser Asp
225                 230                 235                 240

Ala Asp Gly Thr Ser Ser Glu Gln Pro Glu Thr Ser Asn Met Thr His
            245                 250                 255

Glu Glu Ile Leu Gln Ile Leu Cys Arg Leu Leu Lys Gln Cys Val Pro
            260                 265                 270

Ser Cys Gln His Val Arg Val Ile Pro Ser Ser Arg Arg Pro Val Ile
            275                 280                 285

Lys Phe Ile His Lys Glu Ser Gly Leu His Cys Asp Leu Ser Leu Asp
            290                 295                 300

Asn Arg Leu Ala
305

<210> SEQ ID NO 67
<211> LENGTH: 168
<212> TYPE: PRT
<213> ORGANISM: Schizosaccharomyces pombe

<400> SEQUENCE: 67

Met Asn Ile Ser Ser Ala Gln Phe Ile Pro Gly Val His Thr Val Glu
1               5                   10                  15

Glu Ile Glu Ala Glu Ile His Lys Asn Leu His Ile Ser Lys Ser Cys
            20                  25                  30

Ser Tyr Gln Lys Val Pro Asn Ser His Lys Glu Phe Thr Lys Phe Cys
            35                  40                  45

Tyr Glu Val Tyr Asn Glu Ile Lys Ile Ser Asp Lys Glu Phe Lys Glu
50                  55                  60

Lys Arg Ala Ala Leu Asp Thr Leu Arg Leu Cys Leu Lys Arg Ile Ser
65                  70                  75                  80

Pro Asp Ala Glu Leu Val Ala Phe Gly Ser Leu Glu Ser Gly Leu Ala
            85                  90                  95

Leu Lys Asn Ser Asp Met Asp Leu Cys Val Leu Met Asp Ser Arg Val
            100                 105                 110

Gln Ser Asp Thr Ile Ala Leu Gln Phe Tyr Glu Glu Leu Ile Ala Glu
            115                 120                 125

Gly Phe Glu Gly Lys Phe Leu Gln Arg Ala Arg Ile Pro Ile Ile Lys
130                 135                 140

```
Leu Thr Ser Asp Thr Lys Asn Gly Phe Gly Ala Ser Phe Gln Cys Asp
145                 150                 155                 160

Ile Gly Phe Asn Asn Arg Leu Ala
                165
```

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Asp Glu Ala Asp
1
```

<210> SEQ ID NO 69
<211> LENGTH: 53
<212> TYPE: PRT
<213> ORGANISM: Homo sapiens

<400> SEQUENCE: 69

```
Asp Leu Gly Asp Leu Glu Glu Pro Gln Pro Val Pro Lys Ala Pro Glu
1               5                   10                  15

Ser Pro Ser Leu Asp Ser Ala Leu Ala Ser Pro Leu Asp Pro Gln Ala
                20                  25                  30

Leu Ala Cys Thr Pro Ala Ser Pro Pro Asp Ser Gln Pro Pro Ala Ser
            35                  40                  45

Pro Gln Asp Ser Glu
    50
```

<210> SEQ ID NO 70
<211> LENGTH: 53
<212> TYPE: PRT
<213> ORGANISM: Bos sp.

<400> SEQUENCE: 70

```
Asp Leu Gly Asp Leu Asp Glu Pro Gln Pro Ala Pro Lys Ala Pro Glu
1               5                   10                  15

Ser Pro Ser Leu Asp Ser Ala Leu Ala Ser Pro Leu Asp Pro Gln Ala
                20                  25                  30

Leu Ala Cys Thr Pro Ala Ser Pro Pro Asp Ser Gln Pro Pro Ala Ser
            35                  40                  45

Pro Gln Asp Ser Glu
    50
```

<210> SEQ ID NO 71
<211> LENGTH: 52
<212> TYPE: PRT
<213> ORGANISM: Canis familiaris

<400> SEQUENCE: 71

```
Asp Leu Gly Asp Leu Glu Glu Ser Gln Pro Ala Pro Lys Ala Pro Glu
1               5                   10                  15

Ser Pro Ser Leu Asp Ser Ala Leu Ala Ser Pro Leu Asp Pro Gln Ala
                20                  25                  30

Leu Ala Cys Thr Pro Ala Ser Pro Pro Asp Ser Gln Pro Pro Ser Pro
            35                  40                  45

Pro Asp Ser Glu
    50
```

-continued

<210> SEQ ID NO 72
<211> LENGTH: 56
<212> TYPE: PRT
<213> ORGANISM: Mus musculus

<400> SEQUENCE: 72

Asp Met Gly Asp Met Glu Glu Thr Glu Pro Asp Pro Lys Ala Pro Lys
1               5                   10                  15

Val Pro Glu Thr Ser Ser Leu Asp Ser Ala Leu Ala Ser Ser Leu Asp
            20                  25                  30

Pro Gln Ala Leu Ala Cys Thr Pro Ala Ser Pro Leu Asp Ser Leu Ser
        35                  40                  45

Pro Thr Ser Val Gln Glu Ser Glu
    50                  55

<210> SEQ ID NO 73
<211> LENGTH: 55
<212> TYPE: PRT
<213> ORGANISM: Rattus sp.

<400> SEQUENCE: 73

Asp Leu Gly Asp Met Glu Glu Pro Gln Pro Asp Pro Gln Thr Pro Lys
1               5                   10                  15

Leu Pro Glu Ala Ser Ser Leu Asp Ser Thr Leu Ala Ser Ser Leu Asp
            20                  25                  30

Pro Gln Val Leu Ala Cys Thr Pro Ala Ser Leu Asp Ser Leu Ser Pro
        35                  40                  45

Thr Ser Leu Gln Asp Ser Glu
    50                  55

<210> SEQ ID NO 74
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aaaaaaaaaa aaaaaa                                                           16

<210> SEQ ID NO 75
<211> LENGTH: 300
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
aaaaaaaaaa aaaaaaaaaa aaaaaaaaaa aaaaaaaaaa aaaaaaaaaa aaaaaaaaaa           60
aaaaaaaaaa aaaaaaaaaa aaaaaaaaaa aaaaaaaaaa aaaaaaaaaa aaaaaaaaaa          120
aaaaaaaaaa aaaaaaaaaa aaaaaaaaaa aaaaaaaaaa aaaaaaaaaa aaaaaaaaaa          180
aaaaaaaaaa aaaaaaaaaa aaaaaaaaaa aaaaaaaaaa aaaaaaaaaa aaaaaaaaaa          240
aaaaaaaaaa aaaaaaaaaa aaaaaaaaaa aaaaaaaaaa aaaaaaaaaa aaaaaaaaaa          300

<210> SEQ ID NO 76
<211> LENGTH: 500
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 76
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa                                                 500

<210> SEQ ID NO 77
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aaaaaaaaaa aaaaaaaaaa aaaaaaaaaa aaaaaaaaaa aaaaaa                     46

<210> SEQ ID NO 78
<211> LENGTH: 100
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                           100

<210> SEQ ID NO 79
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aaaaaaaaaa aaaaaaaaaa aaaaaaaaaa aaaaaaaaaa aaaaa                      45

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tttttttttt tttttttttt                                                  20